US009702005B2

(12) United States Patent
Bartholomeusz et al.

(10) Patent No.: US 9,702,005 B2
(45) Date of Patent: Jul. 11, 2017

(54) HEPATITIS B VIRAL VARIANTS WITH REDUCED SUSCEPTIBILITY TO NUCLEOSIDE ANALOGS AND USES THEREOF

(71) Applicant: ABL SA, Luxembourg ville (LU)

(72) Inventors: Angeline Ingrid Bartholomeusz, Carnegie (AU); Stephen Alister Locarnini, Balaclava (AU); Anna Ayres, Brunswick West (AU); Danielle Colledge, Bundoora (AU); Joseph John Sasadeusz, Camberwell (AU); Peter William Angus, East Ivanhoe (AU); William Sievert, Canterbury (AU)

(73) Assignee: ABL SA (LU)

( * ) Notice: Subject to any disclaimer, the term of this patent is extended or adjusted under 35 U.S.C. 154(b) by 26 days.

(21) Appl. No.: 14/090,808

(22) Filed: Nov. 26, 2013

(65) Prior Publication Data

US 2014/0296504 A1    Oct. 2, 2014

Related U.S. Application Data

(63) Continuation of application No. 12/791,621, filed on Jun. 1, 2010, now Pat. No. 8,592,143, which is a continuation of application No. 11/860,727, filed on Sep. 25, 2007, now Pat. No. 7,745,130, which is a continuation of application No. 11/166,004, filed on Jun. 24, 2005, now Pat. No. 7,384,747, which is a continuation of application No. 10/963,333, filed on Oct. 12, 2004, now abandoned, which is a continuation of application No. PCT/AU03/00432, filed on Apr. 11, 2003.

(30) Foreign Application Priority Data

Apr. 12, 2002  (AU) .................................. PS1710/02
Jun. 26, 2002  (AU) .................................. PS3224/02

(51) Int. Cl.
    *C07K 14/005*   (2006.01)
    *C12N 7/00*     (2006.01)
    *C12Q 1/68*     (2006.01)

(52) U.S. Cl.
    CPC .......... *C12Q 1/6876* (2013.01); *C07K 14/005* (2013.01); *C12N 7/00* (2013.01); *C12N 2730/10122* (2013.01)

(58) Field of Classification Search
    CPC ........ C12N 2730/10122; C12N 9/1276; C12Q 1/6876; C12Q 1/706
    See application file for complete search history.

(56) References Cited

U.S. PATENT DOCUMENTS

| | | | |
|---|---|---|---|
| 4,946,677 A | 8/1990 | Dorner et al. | |
| 5,237,053 A | 8/1993 | Dorner et al. | |
| 5,593,825 A | 1/1997 | Carman et al. | |
| 6,100,380 A | 8/2000 | Green et al. | |
| 6,436,391 B1 | 8/2002 | Foster et al. | |
| 6,555,311 B1 | 4/2003 | Locarnini et al. | |
| 6,969,583 B2* | 11/2005 | Delaney et al. ................. | 435/5 |
| 7,291,453 B1* | 11/2007 | Bartholomeusz et al. ....... | 435/5 |
| 7,384,747 B2 | 6/2008 | Bartholomeusz et al. | |
| 7,405,039 B2* | 7/2008 | Bartholomeusz et al. ....... | 435/5 |
| 7,422,848 B2 | 9/2008 | Bozdayi | |
| 7,431,933 B2* | 10/2008 | Bartholomeusz et al. | 424/227.1 |
| 7,745,130 B2 | 6/2010 | Bartholomeusz et al. | |
| 7,807,437 B2 | 10/2010 | Schildgen et al. | |
| 7,846,663 B2 | 12/2010 | Bartholomeusz et al. | |
| 7,887,813 B2 | 2/2011 | Bartholomeusz et al. | |
| 7,931,907 B2* | 4/2011 | Bartholomeusz et al. | 424/227.1 |
| 7,989,162 B2 | 8/2011 | Bartholomeusz et al. | |
| 8,211,443 B2 | 7/2012 | Bartholomeusz et al. | |
| 8,211,633 B2* | 7/2012 | Bartholomeusz et al. ....... | 435/5 |

(Continued)

FOREIGN PATENT DOCUMENTS

| | | |
|---|---|---|
| AU | 734831 B2 | 6/1998 |
| CA | 2270178 A1 | 5/1998 |

(Continued)

OTHER PUBLICATIONS

Nizokami et al. FEBS Letter, 1999, vol. 450, Issues 1-2, pp. 66-71.*
Kramvis et al. Vaccine 2005, vol. 23, pp. 2409-2423.*
ABI Prism Big Dye Terminator Cycle Sequencing Ready Reaction Kit, Prodction Bulletin Automated DNA Sequencing published by ABI at WWW/ Appliedbiosystems.com, 2000, pp. 1-4.*
Sipos, A., et al., "Cloning and sequencing of the genes coding for the 10- and 60-kDa heat shock proteins from Pseudomonas aeruginosa and mapping of a species-specific epitope", "Infection and Immunity", Sep. 1991, pp. 3219-3226, vol. 59, No. 9.
Stephens, R., et al., "Heparin binding to the urokinase kringle domain", "Biochemistry", 1992, pp. 7572-7579, vol. 31.
Stover, C., et al., "Complete genome sequence of Pseudomonas acruginosa PA01, an opportunistic pathogen", "Nature", Aug. 2000, pp. 959-964, vol. 406.

(Continued)

*Primary Examiner* — Bao Li
(74) *Attorney, Agent, or Firm* — Andrews Kurth Kenyon LLP; David Bradin

(57) ABSTRACT

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring antiviral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

3 Claims, 32 Drawing Sheets

(56) References Cited

U.S. PATENT DOCUMENTS

| | | | |
|---|---|---|---|
| 8,273,527 B2* | 9/2012 | Bartholomeusz et al. | ....... 435/5 |
| 8,367,317 B2 | 2/2013 | Bartholomeusz et al. | |
| 8,592,143 B2 | 11/2013 | Bartholomeusz et al. | |
| 2003/0124096 A1 | 7/2003 | Locarnini et al. | |
| 2004/0005541 A1 | 1/2004 | Bartholomeusz et al. | |
| 2004/0194155 A1 | 9/2004 | Delaney et al. | |
| 2006/0051743 A1 | 3/2006 | Bartholomeusz et al. | |
| 2007/0042356 A1 | 2/2007 | Schildgen et al. | |
| 2010/0075299 A1 | 3/2010 | Bartholomeusz et al. | |
| 2011/0236422 A1 | 9/2011 | Bartholomeusz et al. | |

FOREIGN PATENT DOCUMENTS

| | | | |
|---|---|---|---|
| CA | 2309379 A1 | 12/2001 | |
| CA | 2409983 A1 | 12/2001 | |
| EP | 0252064 A2 | 1/1988 | |
| EP | 0717106 A1 | 6/1996 | |
| WO | 9006696 A2 | 6/1990 | |
| WO | 9324636 A1 | 12/1993 | |
| WO | 9741234 A2 | 11/1997 | |
| WO | 9821317 A1 | 5/1998 | |
| WO | 0061758 A1 | 10/2000 | |
| WO | 0157244 A1 | 8/2001 | |
| WO | 0194559 A1 | 12/2001 | |
| WO | 03066841 A1 | 8/2003 | |
| WO | 03087351 A1 | 10/2003 | |
| WO | 2004031224 A2 | 4/2004 | |
| WO | 2005042733 A1 | 5/2005 | |
| WO | 2006034545 A1 | 4/2006 | |

OTHER PUBLICATIONS

Stuyver, L., et al., "Line probe assay for monitoring drug resistance in hepatitis B virus-infected patients during antiviral therapy", "Journal of Clinical Microbiology", Feb. 2000, pp. 702-707, vol. 38, No. 2.

Stuyver, L., et al., "Nomenclature for Antiviral-Resistant Human Hepatitis B Virus Mutations in the Polymerase Region", "Hepatology", Mar. 2001, pp. 751-757, vol. 33.

Summers, J., et al., "Replication of the genome of a hepatitis B-like virus by reverse transcription of an RNA intermediate", "Cell", Jun. 1982, pp. 403-415, vol. 29.

Suo, Z., et al., "Selective inhibition of HIV-1 reverse transcriptase by an antiviral", "The Journal of Biological Chemistry", Oct. 16, 1998, pp. 27250-27258, vol. 273, No. 42.

Tatti, K., et al., "Mutations in the conserved woodchuck hepatitis virus polymerase FLLA and YMDD regions conferring resistance to lamivudine", "Antiviral Research", Jul. 2002, pp. 141-150, vol. 55.

Tavis, J., et al., "The duck Hepatitis B virus polymerase is activated by its RNA packaging signal, epsilon", "Journal of Virology", Jul. 1998, pp. 5789-5796, vol. 72, No. 7.

Tenney, D., et al., "Clinical Emergence of Entecavir-Resistant Hepatitis B Virus Requires Additional Substitutions in Virus Already Resistant to Lamivudine", "Antimicrobial Agents and Chemotherapy", Sep. 2004, pp. 3498-3507, vol. 48, No. 9.

Toh, H., et al., "Sequence homology between retroviral reverse transcriptase and putative polymerases of Hepatitis B virus and cauliflower mosaic virus", "Nature", Oct. 27, 1983, pp. 827-829, vol. 305.

Torresi, J., "The virological and clinical significance of mutations in the overlapping envelope and polymerase genes of hepatitis B virus", "Journal of Clinical Virology", Aug. 2002, pp. 97-106, vol. 25.

Torresi, J., et al., "Restoration of Replication Phenotype of Lamivudine-Resistant Hepatitis B Virus Mutants by Compensatory Changes in the 'Fingers' Subdomain of the Viral Polymerase Selected as a Consequence of Mutations in the Overlapping S Gene", "Virology", Jul. 20, 2002, pp. 88-99, vol. 299.

Preisler-Adams, S., et al., "Hepatitis B virus (HBV), DNA polymerase, fragment", "UniProtKB/TrEMBL Accession No. Q67907", Jan. 1, 1998, pp. 1-2.

Urban, M., et al., "In vitro activity of Hepatitis B virus polymerase: requirement for distinct metal ions and the viral epsilon stem-loop", "Journal of General Virology", 1998, pp. 1121-1131, vol. 79.

Villeneuve, J., et al., "Selection of a hepatitis B virus strain resistant to adefovir in a liver transplantation patient", "Journal of Hepatology", Dec. 2003, pp. 1085-1089, vol. 39.

Westland, C., et al., "Week 48 Resistance Surveillance in Two Phase 3 Clinical Studies of Adefovir Dipivoxil for Chronic Hepatitis B", "Hepatology", Jul. 2003, pp. 96-103, vol. 38, No. 1.

Wrobel, J., et al., "A genetic approach for identifying critical residues in the fingers and palm subdomains of HIV-1 reverse transcriptase", "Proc. Natl. Acad. Sci. USA", Jan. 1998, pp. 638-645, vol. 95.

Wuelfing, C., et al., "An *Escherichia coli* protein consisting of a domain homologous to FK506-binding proteins (FKBP) and a new metal binding motif", "The Journal of Biological Chemistry", Jan. 28, 1994, pp. 2895-2901, vol. 269, No. 4.

Xiong, Y., et al., "Origin and evolution of retroelements based upon their reverse transcriptase sequences", "The EMBO Journal", 1990, pp. 3353-3362, vol. 9, No. 10.

Xiong, X., et al., "Mutations in hepatitis B DNA polymerase associated with resistance to lamivudine do not confer resistance to adefovir in vitro", "Hepatology", Dec. 1998, pp. 1669-1673, vol. 28, No. 6.

Xiong, X., et al., "In vitro evaluation of hepatitis B virus polymerase mutations associated with famciclovir resistance", "Hepatology", Jan. 2000, pp. 219-224, vol. 31, No. 1.

Xiong, S,. et al., "Resistance surveillance of HBeAg-chronic hepatitis B patients treated for 2 years with adefovir dipivoxil (ADV)", "Journal of Hepatology", Apr. 2003, p. 182 vol. 38, Supplement 2.

Yamanaka, G., et al., "Metabolic studies on BMS-200475, a new antiviral compound active against hepatitis B virus", "Antimicrobial Agents and Chemotherapy", Jan. 1999, pp. 190-193, vol. 43, No. 1.

Yeh, C., et al., "Clearance of the original hepatitis B virus YMDD-motif mutants with emergence of distinct lamivudine-resistant mutants during prolonged lamivudine therapy", "Hepatology", Jun. 2000, pp. 1318-1326, vol. 31, No. 6.

Ying, C., et al., "Inhibition of the replication of the DNA polymerase M550V mutation variant of human hepatitis B virus by adefovir, tenofovir, L-FMAU, DAPD, penciclovir and lobucavir", "Journal of Viral Hepatitis", 2000, pp. 161-165, vol. 7.

Ying, C., et al., "Lamivudine, adefovir and tenofovir exhibit long-lasting anti-hepatitis B virus activity in cell culture", "Journal of Viral Hepatitis", 2000, pp. 79-83, vol. 7.

Zhu, Y., et al., "Anti-Hepatitis B virus activity and metabolism of 2',3'-dideoxy-2',-3'-didehydro-beta-L(−)-5-fluorocytidine", "Antimicrobial Agents and Chemotherapy", Jul. 1998, pp. 1805-1810, vol. 42, No. 7.

Zurawski, S., et al., "Definition and spatial location of mouse interleukin-2 residues that interact with its heterotrimeric receptor", "The EMBO Journal", 1993, pp. 5113-5119, vol. 12, No. 13.

Severini, A., et al., "Mechanism of inhibition of duck hepatitis B virus polymerase by (−)-beta-L-2',3'-dideoxy-3'-thiacytidine", "Antimicrobial Agents and Chemotherapy", Jul. 1995, pp. 1430-1435, vol. 39, No. 7.

Database UniProt [Online], Jul. 1, 1993; "Protein P [Includes: DNA-directed DNA polymerase (EC<A HREF"http://srs.ebi.ac.uk/srsbin/cgi-bin/wgetz?[enzyme-ECNumber:2.7.7.49]+-e"&- gt;2.7.7</A); RNA-directed DNA polymerase (EC < A HREF="http://srs.ebi.ac.uk/srsbin/cig-bin/wgetz?[enzyme-ECNumber:2.7.7.49- ]+-e">2.7.7.49</A>); Ribonuclease H (EC <A".

Alestig, E., "Phylogenetic Origin of Hepatitis B Virus Strains", "Journal of Clinical Microbiology", Sep. 2001, pp. 3200-3203, vol. 39, No. 9.

Allen, M., et al.C, "Identification and Characterization of Mutations in Hepatitis B Virus Resistant to Lamivudine", "Hepatology", 1998, pp. 1670-1677, vol. 27, No. 6.

Angus, P., et al., "Resistance to Adefovir Dipivoxil Therapy Associated With the Selection of a Novel Mutation in the HBV Polymerase", "Gastroenterology", Aug. 2003, pp. 292-297, vol. 125.

Aye, T., et al., "Hepatitis B virus polymerase mutations during antiviral therapy in a patient following liver transplantation", "Journal of Hepatology", 1997, pp. 1148-1153, vol. 26.

(56) References Cited

OTHER PUBLICATIONS

Bartenschlager, R., et al., "Hepadnaviral assembly is initiated by polymerase binding to the ecapsidation signal in the viral RNA genome", "The EMBO Journal", 1992, pp. 3413-3420, vol. 11, No. 9.

Bartholomeusz, A., et al., "Clinical Experience with Famciclovir Against Hepatitis B Virus", "Intervirology", 1997, pp. 337-342, vol. 40.

Bartholomeusz, A., et al., "Significance of mutations in the hepatitis B virus polymerase selected by nucleoside analogues and implications for controlling chronic disease", "Viral Hepatitis", 1998, pp. 167-187, vol. 4, No. 3.

Bartholomeusz, A., et al., "Mutations in the hepatitis B virus polymerase gene that are associated with resistance to famciclovir and lamivudine", "International Antiviral News", 1997, pp. 123-124, vol. 5, No. 8.

Bartholomew, M., et al., "Hepatitis-B-Virus resistance to lamivudine given for recurrent infection after orthotopic liver transplant action", "Lancet", 1997, pp. 20-22, vol. 349.

Benhamou, Y., et al., "Safety and efficacy of adefovir dipivoxil in patients co-infected with HIV-1 and lamivudine-resistant hepatitis B virus: an open-label pilot study", "Lancet", Sep. 1, 2001, pp. 718-723, vol. 358.

Benzaria, S., et al., "Synthesis, in vitro antiviral evaluation, and stability studies of bis(S-acyl-2-thioethyl) ester derivatives of 9-[2-(phosphonomethoxy)ethyl]adenine (PMEA) as potential PMEA prodrugs with improved oral bioavailability", "J. Med. Chem.", 1996, pp. 4958-4965, vol. 39.

Bisacchi, G., et al., "BMS-200475, a novel carbocyclic 2'-deoxyguanosine analog with potent and selective anti-hepatitis B virus activity in vitro", "Bioorganic and Medicinal Chemistry Letters", 1997, pp. 127-132, vol. 7, No. 2.

Bock, C., et al., "Selection of Hepatitis B Virus Polymerase Mutants With Enhanced Replication by Lamivudine Treatment After Liver Transplantation", "Gastroenterology", Feb. 2002, pp. 264-273, vol. 122.

Bowie, J., et al., "Deciphering the message in protein sequences: tolerance to amino acid substitutions", "Science", Mar. 16, 1990, pp. 1306-1310, vol. 247, No. 4948.

Boyd, M., et al., "Antiherpesvirus activity of 9-(4-hydroxy-3-hydroxymethylbut-l-yl) guanine (BRL 39123) in animals", "Antimicrobial Agents and Chemotherapy", Mar. 1988, pp. 358-363, vol. 32, No. 3.

Brown, S., et al., "Cloning and characterization of the katB gene of Pseudomonas aeruginosa encoding a hydrogen peroxide-inducible catalase: purification of KatB, cellular localization, and demonstration that it is essential for optimal resistance to hydrogen peroxide", "Journal of Bacteriology", Nov. 1995, pp. 6536-6544, vol. 177, No. 22.

Burgess, W., et al., "Possible dissociation of the heparin-binding and mitogenic activities of heparin-binding (acidic fibroblast) growth factor-1 from its receptor-binding activities by site-directed mutagenesis of a single lysine residue", "The Journal of Cell Biology", Nov. 1990, pp. 2129-2138, vol. 111.

Calio, R., et al., "Enhancement of natural killer activity and interferon induction by different acyclic nucleoside phosphonates", "Antiviral Research", 1994, pp. 77-89, vol. 23.

Cane, P., et al., "Analysis of hepatitis B virus quasispecies changes during emergence and reversion of lamivudine resistance in liver transplantation", "Antiviral Therapy", 1999, pp. 7-14, vol. 4.

Chang, L., et al., "Mechanism of translation of the Hepadnaviral polymerase (P) gene", "Proc. Natl. Acad. Sci. USA", Jul. 1990, pp. 5158-5162, vol. 87.

Chen, W., et al., "Human hepatitis B virus mutants: Significance of molecular changes", "FEBS Letters", 1999, pp. 237-242, vol. 453.

Chotiyaputta, W., et al., "Hepatitis B virus variants", "Nature Reviews: Gastroenterology and Hepatology", Aug. 2009, pp. 453-462, vol. 6.

Coates, J., et al., "(--)-2'-deoxy-3'-thiacytidine is a potent, highly selective inhibitor of human immunodeficiency virus type 1 and type 2 replication in vitro", "Antimicrobial Agents and Chemotherapy", Apr. 1992, pp. 733-739, vol. 36, No. 4.

Colonno, R., et al., "Long-term entecavir treatment results in sustained antiviral efficacy and prolonged life span in the woodchuck model of chronic hepatitis infection", "The Journal of Infectious Diseases", Oct. 29, 2001, pp. 1236-1245, vol. 184.

Das, K., et al., "Molecular Modeling and Biochemical Characterization Reveal the Mechanism of Hepatitis B Virus Polymerase Resistance to Lamivudine (3TC) and Emtricitabine (FTC)", "Journal of Virology", May 2001, pp. 4771-4779, vol. 75, No. 10.

"Definition of Codon", "Mosby's Medical Dictionary: 8th Edition Online", Dec. 2008, p. 1, Publisher: Elsevier Health Sciences.

Delaney IV, W., et al., "Hepatitis B Virus Replication in Human HepG2 Cells Mediated by Hepatitis B Virus Recombinant Baculovirus", "Hepatology", Oct. 1998, pp. 1134-1146, vol. 28, No. 4.

Delaney, IV, W., et al., "Cross-resistance testing of antihepadnaviral compounds using novel recombinant baculoviruses which encode drug-resistant strains of hepatitis B virus", "Antimicrobial Agents and Chemotherapy", Jun. 2001, pp. 1705-1713, vol. 45, No. 6.

Dienstag, J., et al., "A preliminary trial of lamivudine for chronic hepatitis B infection", "The New England Journal of Medicine", Dec. 21, 1995, pp. 1657-1661, vol. 333, No. 25.

Dienstag, J., et al., "Lamivudine as initial treatment for chronic Hepatitis B in the United States", "The New England Journal of Medicine", Oct. 21, 1999, pp. 1256-1263, vol. 341, No. 17.

Doong, S., et al., "Inhibition of the replication of Hepatitis B virus in vitro by 2',3'-dideoxy-3'-thiacytidine and related analogues", "Proc. Natl. Acad. Sci. USA", Oct. 1991, pp. 8495-8499, vol. 88.

Yeh, C., "Hepatitis B virus mutant polymerase gene, partial cds.", "EMBL-EBI Accession No. AF156492", Jun. 28, 2000.

Yamamoto, T., et al., "Woodchuck hepatitis B virus isolate 331 type IV mutant polymerase gene, complete cds.", "EMBL-EBI Accession No. AF410856", Sep. 20, 2001.

Estacio, R., et al., "Nucleotide sequence of a hepatitis B virus genome of subtype adw isolated from a Philippino: Comparison with the reported three genomes of the same subtype", "Journal of Gastroenterology and Hepatology", 1988, pp. 215-222, vol. 3.

Farrell, G., "Clinical Potential of Emerging New Agents in Hepatitis B", "Drugs", Oct. 2000, pp. 701-710, vol. 60, No. 4.

Fiser, A., et al., "Modeling of loops in protein sturctures", "Protein Science", 2000, pp. 1753-1773, vol. 9.

Frick, L., et al., "Pharmacokinetics, oral bioavailability, and metabolic disposition in rats of (−)-cis-5-fluoro-1-[2-(hydroxymethyl)-1,3-oxathiolan-5-yl] cytosine, a nucleoside analog active against human immunodeficiency virus and hepatitis B virus", "Antimicrobial Agents and Chemotherapy", Nov. 1993, pp. 2285-2292, vol. 37, No. 11.

Gaillard, R., et al., "Kinetic analysis of wild-type and YMDD mutant hepatitis B virus polymerases and effects of deoxyribonucleotide concentrations on polymerase activity", "Antimicrobial Agents and Chemotherapy", Apr. 2002, pp. 1005-1013, vol. 46, No. 4.

Gardsvoll, H., et al., "Mapping part of the functional epitope for ligand binding on the receptor for urokinase-type plasminogen activator by site-directed mutagenesis", "Journal of Biological Chemistry", Dec. 31, 1999, pp. 37995-38003, vol. 274, No. 53.

Renbao, G., et al., "Hepatitis B virus, complete genome", "NCBI Genbank Accession No. M38454", Mar. 6, 1995, pp. 1-3.

Stover, C., et al., "Complete genome sequence of Pseudomonas aeruginosa PA01, an opportunistic pathogen", "NCBI Genbank Accession No. NP_252926", Aug. 31, 2000, pp. 16.

Genovesi, E., et al., "Efficacy of the carbocyclic 2'-deoxyguanosine nucleoside BMS-200475 in the woodchuck model of hepatitis B virus infection", "Antimicrobial Agents and Chemotherapy", Dec. 1998, pp. 3209-3217, vol. 42, No. 12.

Georgiadis, M., et al., "Mechanistic implications from the structure of a catalytic fragment of Moloney murine leukemia virus reverse transcriptase", "Structure", Sep. 1995, pp. 879-892, vol. 3.

Gilson, R., et al., "A placebo-controlled phase I/II study of adefovir dipivoxil in patients with chronic hepatitis B virus infection", "Journal of Viral Hepatitis", 1999, pp. 387-395, vol. 6.

(56) References Cited

OTHER PUBLICATIONS

Greenberg, E., "Pump up the Versatility", "Nature", Aug. 31, 2000, pp. 947-948, vol. 406.
Guenther, S., et al., "Analysis of hepatits B virus populations in an interferon-alpha-treated patient reveals predominant mutations in the C-Gene and changing e-Antigenicity", "Virology", 1998, pp. 146-160, vol. 244.
Heathcote, E., et al., "Loss of serum HBV DNA and HBeAg and seroconversion following short term (12 weeks) Adefovir Dipivoxil therapy in in chronic hepatitis B: two placebo-controlled phase II studies", "Hepatology", 1998, p. A620, vol. 28.
Hendricks, D., et al., "Quantitation of HBV DNA in human serum using a branched DNA (bDNA) signal amplification assay", "Clinical Microbiology and Infectious Diseases", Nov. 1995, pp. 537-546, vol. 104, No. 5.
Hess, G., et al., "Inhibition of Hepatitis B Virus Specific DNA Polymerase by Intercalating Agents", "Med. Microbiol. Immunol.", 1980, pp. 25-34, vol. 168.
Hodge, R., et al., "Famciclovir and penciclovir. The mode of action of famciclovir including its conversion to peciclovir", "Antiviral Chemistry & Chemotherapy", 1993, pp. 67-84, vol. 4, No. 2.
Hoyer-Hansen, G., et al., "The intact urokinase receptor is required for efficient vitronectin binding: receptor cleavage prevents ligand interaction", "FEBS Letters", 1997, pp. 79-85, vol. 420.
Innaimo, S., et al., "Identification of BMS-200475 as a potent and selective inhibitor of hepatitis B virus", "Antimicrobial Agents and Chemotherapy", Jul. 1997, pp. 1444-1448, vol. 41, No. 7.
Jarvis, B., et al., "Lamivudine: A review of its therapeutic potential in chronic Hepatitis B", "Drugs", Jul. 1999, pp. 101-141, vol. 58, No. 1.
Khan, S., et al., "The functional analysis of directed amino-acid alterations in ZntR from *Escherichia coli*", "Biochem Biophys Res Commun", Dec. 6, 2002, pp. 438-445, vol. 299, No. 3.
Krueger, M., et al., "Famciclovir treatment of hepatitis B virus recurrence after orthotopic liver transplantation—a pilot study", "Hepatology", Oct. 10, 1995, p. 219A (Abstract), vol. 22, No. 4.
Kukor, J., et al., "Cloning and expression of the catA and catBC gene clusters from Pseudomonas aeruginosa PAO", "Journal of Bacteriology", Oct. 1988, pp. 4458-4465, vol. 170, No. 10.
Lanford, R., et al., "Mapping of the Hepatitis B virus reverse transcriptase TP and RT domains for transcomplementation for nucleotide priming and by protein-protein interaction", "Journal of Virology", Mar. 1999, pp. 1885-1893, vol. 73, No. 3.
Lazar, E. et al., "Transforming growth factor alpha: mutation of aspartic acid 47 and leucine 48 results in different biological activities", "Molecular and Cellular Biology", Mar. 1988, pp. 1247-1252, vol. 8, No. 3.
Lesburg, C., et al., "Crystal structure of the RNA-dependent RNA polymerase from Hepatitis C virus reveals a fully encircled active site", "Nature Structural Biology", Oct. 1999, pp. 937-943, vol. 6, No. 10.
Liaw, Y., et al., "Acute exacerbation and Hepatitis B virus clearance after emergence of YMDD motif mutation during lamivudine therapy", "Hepatology", Aug. 1999, pp. 567-572, vol. 30, No. 2.
Ma, J., et al., "Bacterioferritin a modulates catalase A (KatA) activity and resistance to hydrogen peroxide in Pseudomonas aeruginosa", "Journal of Bacteriology", Jun. 1999, pp. 3730-3742, vol. 181, No. 12.
Mack, D., et al., "Hepatitis B virus particles contain a polypeptide encoded by the largest open reading frame: a putative reverse transcriptase", "Journal of Virology", Dec. 1988, pp. 4786-4790, vol. 62, No. 12.
Main, J., et al., "A double blind, placebo-controlled study to assess the effect of famciclovir on virus replication in patients with chronic hepatitis B virus infection", "Journal of Viral Hepatitis", 1996, pp. 211-215, vol. 3, No. 211.
Miller, M., et al., "Adefovir and tenofovir susceptibilities of HIV-1 after 24 to 48 weeks of adefovir dipivoxil therapy: genotypic and phenotypic analyses of study GS-96-408", "JAID Journal of Acquired Immune Deficiency Syndrome", Aug. 15, 2001, pp. 450-458, vol. 27, No. 5.
Nakamura, T., et al., "Telomerase Catalytic Subunit Homologs from Fission Yeast and Human", "Science", Aug. 15, 1997, pp. 955-959, vol. 277.
Ngo, J., et al., "Unit 14: Computational complexity, protein structure prediction, and the Levinthal Paradox", "The Protein Folding Problem and Tertiary Structure Prediction (Ed.: Merz, Jr., K., et al.)", 1994, pp. 433 and 492-495, Publisher: Birkhauser, Published in: Boston, MA.
Norder, H., et al., "Genetic relatedness of hepatitis B viral strains of diverse geographical origin and natural variations in the primary structure of the surface antigen", "Journal of General Virology", 1993, pp. 1341-1348, vol. 74.
Ogata, N., et al., "Novel Patterns of Amino Acid Mutations in the Hepatitis B Virus Polymerase in Association With Resistance to Lamivudine Therapy in Japanese Patients With Chronic Hepatitis B", "Journal of Medical Virology", 1999, pp. 270-276, vol. 59.
Ono, S., et al., "The polymerase L528M mutation cooperates with nucleotide binding-site mutations, increasing hepatitis B virus replication and drug resistance", "J. Clin. Invest", Feb. 2001, pp. 449-455, vol. 107.
Ono-Nita, S., et al., "YMDD motif in hepatitis B virus DNA polymerase influences on replication and lamivudine resistance: A study by in vitro full-length viral DNA transfection", "Hepatology", Mar. 1999, pp. 939-945, vol. 29, No. 3.
Oon, C., et al., "Hepatitis B virus variants with lamivudine-related mutations in the DNA polymerase and the 'a' epitope of the surface antigen are sensitive to ganciclovir", "Antiviral Research", 1999, pp. 113-118, vol. 41.
Perrillo, R., et al., "Adefovir dipivoxil for the treatment of lamivudine-resistant hepatitis B mutants", "Hepatology", Jul. 2000, pp. 129-134, vol. 32, No. 1.
Peters, M., et al., "Fulminant hepatic failure resulting from lamivudine-resistant hepatitis B virus in a renal transplant recipient: durable response after orthotopic liver transplantation on adefovir dipivoxil and hepatitis B immune globulin", "Transplantation", Dec. 1999, pp. 1912-1914, vol. 68, No. 12.
Ploug, M., et al., "Ligand interaction between urokinase-type plasminogen activator and its receptor probed with 8-anilino-1-naphthalenesulfonate. Evidence for a hydrophobic binding site exposed only on the intact receptor", "Biochemistry", 1994, pp. 8991-8997, vol. 33.
Ploug, M., et al., "Chemical modification of the urokinase-type plasminogen activator and its receptor using tetranitromethane. Evidence for the involvement of specific tyrosine residues in both molecules during receptor-ligand interaction", "Biochemistry", 1995, pp. 12524-12534, vol. 34.
Ploug, M., "Identification of specific sites involved in ligand binding by photoaffinity labeling of the receptor for the urokinase-type plasminogen activator. Residues located at equivalent positions in uPAR domains I and III participate in the assembly of a Composite Ligand-Binding Site", "Biochemistry", 1998, pp. 16494-16505, vol. 37.
Ploug, M., et al., "Photoaffinity labeling of the human receptor for urokinase-type plasminogen activator using a decapeptide antagonist. Evidence for a composite ligand-binding site and a short interdomain separation", "Biochemistry", 1998, pp. 3612-3622, vol. 37.
Poch, O., et al., "Identification of four conserved motifs among the RNA-dependent polymerase encoding elements", "The EMBO Journal", 1989, pp. 3867-3874, vol. 8, No. 12.
Preisler-Adams, S., et al., "Sequence analysis of hepatitis B virus DNA in immunologically negative infection", "Arch Virol", 1993, pp. 385-396, vol. 133.
Price, P., et al., "Inhibition of the replication of hepatitis B virus by the carbocyclic analogue of 2'-deoxyguanosine", "Proc. Natl. Acad. Sci. USA", Nov. 1989, pp. 8541-8544, vol. 86.
Radziwill, G., et al., "Mutational analysis of the Hepatitis B virus P gene product: domain structure and RNase H activity", "Journal of Virology", Feb. 1990, pp. 613-620, vol. 64, No. 2.

(56) References Cited

OTHER PUBLICATIONS

Ren, S., et al., "Hepatitis B virus (HBV) virion and covalently closed circular DNA formation in primary tupaia hepatocytes and human hepatoma cell lines upon HBV genome transduction with replication-defective adenovirus vectors", "Journal of Virology", Feb. 2001, pp. 1104-1116, vol. 75, No. 3.

Rodgers, D., et al., "The structure of unliganded reverse transcriptase from the human immunodeficiency virus type 1", "Proc. Natl. Acad. Sci. USA", Feb. 1995, pp. 1222-1226, vol. 92.

Sali, A., et al., "Comparative protein modelling by satisfaction of spatial restraints", "J. Mol. Biol.", 1993, pp. 779-815, vol. 234.

Sarafianos, S., et al., "Structures of HIV-1 reverse transcriptase with pre- and post-translocation AZTMP-terminated DNA", "The EMBO Journal", Dec. 2, 2002, pp. 6614-6624, vol. 21, No. 23.

Sawaya, M., et al., "Crystal structure of rat DNA polymerase beta: Evidence for a common polymerase mechanism", "Science", Jun. 24, 1994, pp. 1930-1935, vol. 264.

Schildgen, O., et al., "Successful therapy of hepatits B with tenofovir in HIV-infected patients failing previous adefovir and lamivudine treatment", "AIDS", Nov. 19, 2004, pp. 2325-2341, vol. 18.

Seifer, M., et al., "In Vitro Inhibition of Hepadnavirus Polymerases by the Triphosphates of BMS-200475 and Lobucavir", "Antimicrobial Agents and Chemotherapy", Dec. 1998, pp. 3200-3208, vol. 42, No. 12.

Seigneres, B., et al., "Evolution of Hepatitis B Virus Polymerase Gene Sequence during Famciclovir Therapy for Chronic Hepatitis B", "The Journal of Infectious Diseases", Apr. 2000, pp. 1221-1233, vol. 181.

\* cited by examiner

Figure 4

```
                                                                                     [SEQ ID NO:8]
                                                                                     [SEQ ID NO:9]
                                                                                     [SEQ ID NO:10]
                                                                                     [SEQ ID NO:11]

ILA1 F, A-E   781 TGGCTCAGTTTACTAGTGCCATTTGTTCAGTGGTTCGTAGGGCTTTCCCCACTGTTTGGCTTTCAGTTATATGGATGATGTGGTATTGGGGGCCAAGTC  880
ILA 2 F, A-E  789 TGGCTCAGTTTACTAGTGCCATTTGTTCAGTGGTTCGTAGGGCTTTCCCCACTGTTTGGCTTTCAGTTATATGGATGATGTGGTATTGGGGGCCAAGTC  888
ILA 3 F, A-E  801 TGGCTCAGTTTACTAGTGCCATTTGTTCAGTGGTTCGTAGGGCTTTCCCCACTGTTTGGCTTTCAGTTATATGGATGATGTGGTATTGGGGGCCAAGTC  900
ILA 4 F, A-E  774 TGGCTCAGTTTACTAGTGCCATTTGTTCAGTGGTTCGTAGGGCTTTCCCCACTGTTTGGCTTTCAGTTATATGGATGATGTGGTATTGGGGGCCAAGTC  873

ILA1 F, A-E   881 TGTAYAGCAYCTTGAGTCCCTTTTTACCGCTGTTACCAATTTCTTTTGTCTTTGGGTATACATTTAAACCTAACAAAACTAAAAGATGGGTTACTCT    980
ILA 2 F, A-E  889 TGTACAGCATCTTGAGTCCCTTTTTACCGCTGTTACCAATTTCTTTTTGTCTTTGGGTATACATTTAAACCTAACAAAACAAAGAGATGGGTTACTCT   988
ILA 3 F, A-E  901 TGTACAGCATCTTGAGTCCCTTTTTACCGCTGTTACCAATTTCTTTTGTCTTTGGGTATACATTTAAACCTAACAAAACAAAACAAAGATGGGTTACTCT 1000
ILA 4 F, A-E  874 TGTACAGCATCTTGAGTCCCTTTTTACCGCTGTTACCAATTTCTTTTGTCTTTGGGCATACATTTAAACCCTAACAAAACTAAAAGATGGGTTACTCT   973

ILA1 F, A-E   981 TTACATTTCATGGGNTATGTCATTGGATGTTATGGGTCATTGCCAAGATCACATCATACAGAAAATCAAAGATGGTTT 1060
ILA 2 F, A-E  989 CTAAATTTTATGGGTTATGTCATTGGATGTTATGGGTTATGGGTCTTTG                             1030
ILA 3 F, A-E 1001 CTAAATTTTATGGGTTATGTCATTGGATGTTATGGGTTATGGGTCTTGCCACAAGAACACATCATACAAAAATCAAAGAATG 1077
ILA 4 F, A-E  974 TTAAATTTCATGGGATATGTCATTGGATGGTATGGG                                          1010
```

Figure 4 (continued)

Patient A polymerase amino acid sequence alignment

```
Pol Trans Pre 1       KLASKSASSIXQSPVRKAAYPAVSTFEKHSSSGHAVEXHNLPPNSXRSQERPVFPCWMLQFRNSKPCSDYCLSHIVANLLEDWGPCAEHGEHH    93  [SEQ ID NO:12]
Pol Trans 2   1       HTTNFASKSASCLHQSPVRKAAYPAVSTFEKHSSSGHAVEFHNLPPNSARSQSERPVFPCWMLQFRNSKPCSDYCLSLIVNLLEDWGPCAEHGEHH   96  [SEQ ID NO:13]
Pol Trans 3   1  LACGILQNFASKSASCLHQSPVRKAAYPAVSTFEKHSSSGHAVEFHNLPPNSARSQSERPVFPCWMLQFRNSKPCSDYCLSLIVNLLEDWGPCAEHGEHH  100  [SEQ ID NO:14]
Pol Trans 4   1            ASKSASSIYQSPVGTAAYPAVSTXEKHSSSGHAVELHNLPPNSERSQGERPVFPCWMLQFRNSKPCSDYCLSHIVNLLEDWGPCAEHGEHH   91  [SEQ ID NO:15]

Pol Trans Pre  94     IRIPRTPXRVTGGVFLVDKNPHNTAESRLVVDFSQFSRGNYRVSWPKFAVPNLQSLTNLLSSNLSWLSLDVSAAFYHLPLHPAAMPHLLVGSSGLSRYVA  193
Pol Trans 2    97     IRIPRTPSRVTGGVFLVDKNPHNTAESRLVVDFSQFSRGNYRVSWPKFAVPNLQSLTNLLSSNLSWLSLDVSAAFYHLPLHPAAMPHLLVGSSGLSRYVA  196
Pol Trans 3   101     IRIPRTPSRVTGGVFLVDKNPHNTAESRLVVDFSQFSRGNYRVSWPKFAVPNLQSLTNLLSSNLSWLSLDVSAAFYHLPLHPAAMPHLLVGSSGLSRYVA  200
Pol Trans 4    92     IRIPRTPARVTGGVFLVDKNPHNTAESRLVVDFSQFSRGNYRVSWPKFAVPNLQSLITNLLSSNLSWLSLDVSAAFYHLPLHPAAMPHLLVGSSGLSRYVA  191

Pol Trans Pre 194     RLSSNSRIFNHQRGXMQNLHDYCSRNLYVSLLLLYQTFGRKLHLYSHPIILGFRKIPMGVGLSPFLLAQFTSAICSVVRRAFPHCLAFSYMDDVVLGAKS  293
Pol Trans 2   197     RLSSNSRILNNQHGTMPDLHDYCSRNLYVSLLLLYQTFGRKLHLYSHPIILGFRKIPMGVGLSPFLLAQFTSAICSVVRRAFPHCLAFSYMDDVVLGAKS  296
Pol Trans 3   201     RLSSNSRILNNQHGTMPDLHDYCSRNLYVSLLLLYQTFGRKLHLYSHPIILGFRKIPMGVGLSPFLLAQFTSAICSVVRRAFPHCLAFSYMDDVVLGAKS  300
Pol Trans 4   192     RLSSNSRIFNHQRGNMQNLHDCCSRNLYVSLLLLYQTFGRKLHLYSHPIILGFRKIPMGVGLSPFLLAQFTSAICSVVRRAFPHCLAFSYMDDVVLGAKS  291

Pol Trans Pre 294     VXHLESLFTAVTNFLLSLGIHLNPNKTKRWGYSLHFMGYVIGC    336
Pol Trans 2   297     VQHLESLFTAVTNFLLSLGIHLNPNKTKRWGYSLNFMGYVIGCY   340
Pol Trans 3   301     VQHLESLFTAVTNFLLSLGIHLNPNKTKRWGYSLNFMGYVIGCY   344
Pol Trans 4   292     VQHLESLFTAVTNFLLSLGIHLNPNKTKRWGYSLNFMGYVIGWYG  336
```

Figure 5

Patient A HBsAg Amino acid alignment

```
HBsAg Trans of Pre1    1                                                                               MENITSGFLGPLLVLQA  17   [SEQ ID NO:16]
HBsAg Trans of 2       1   PPPASTNRQSGRQPTPLSPPLRNTHPQAMQWNSTTFHQTLQDPRVRGLYFPAGGSSSGTVNPVLTTASPLSSIFSRIGDPALNMENITSGFLGPLLVLQA 100  [SEQ ID NO:17]
HBsAg Trans of 3       1   PPPASTNRQSGRQPTPLSPPLRNTHPQAMQWNSTTFHQTLQDPRVRGLYFPAGGSSSGTVNPVLTTASPLSSIFSRIGDPALNMENITSGFLGPLLVLQA 100  [SEQ ID NO:18]
HBsAg Trans of 4       1   PPPPSTNRQSGRQPTPLSPPXRNTHPQAMQWNSTTFHQTLLDPRVXGLYFPAGGSSGTVNPVPTTASPISSIFSRIGDPALNMENITSGFLGPLLVLQA 100  [SEQ ID NO:19]

HBsAg Trans of Pre1   18   GFFLLTRILTITPQSLDSWNTSLMFLGGTTVCLGQNSQSPTSNHSPTSCPPTCPGYRWMCLRRFIIFLFILLLCLIFLLVLLDYQGMLPVCPLIPGSSTTS 117
HBsAg Trans of 2     101   GFFLLTRILITIPQSLDSWNTSLMFLGGTTVCLGQNSQSPTSNHSPTSCPPTCPGYRWMCLRRFIIFLFILLLCLIFLLVLLDYQGMLPVCPLIPGSSTTS 200
HBsAg Trans of 3     101   GFFLLTRILITIPQSLDSWNTSLMFLGGTTVCLGQNSQSPTSNHSPTSCPPTCPGYRWMCLRRFIIFLFILLLCLIFLLVLLDYQGMLPVCPLIPGSSTTS 200
HBsAg Trans of 4     101   GFFILTRIIIIPQSLDSWNTSLMFLGGTTVCLGQNSQSPTSNHSPTSCPPTCPGYRWMCLRRFTIFLFILLLCLIFLLVLLDYQGMLPVCPLIPGSSTTS 200

HBsAg Trans of Pre1  118   AGXCRTCTTTAQGTSMYPSCCCTKPSDGNCTCIPIPSSWAFGKFLMEWASARFSWLSLLIVPFVQWFVGLSPTVWLSPIVWMNYWGPSLYSXLSPFLPLLP 217
HBsAg Trans of 2     201   TGPCRTCMTTAQGTSMYPSCCCTKPSDGNCTCIPIPSSWAFGKFLMEWASARFSWLSLLIVPFVQWFVGLSPTVWLSPIVWMNYWGPSLYSILSPFLPLLP 300
HBsAg Trans of 3     201   TGPCRTCMTTAQGTSMYPSCCCTKPSDGNCTCIPIPSSWAFGKFLMEWASARFSWLSLLIVPFVQWFVGLSPTVWLSPIVWMNYWGPSLYSILSPFLPLLP 300
HBsAg Trans of 4     201   AGTCRTCTTAAQGTSMYPSCCCCTKPSDGNCTCIPIPSSWAFGKFLMEWASARFSWLSLLIVPFVQWFVGLSPTVWLSVIWMNYWGPSLYSILSPFLPLLP 300

HBsAg Trans of Pre1  218   IFFCLMVYI 226
HBsAg Trans of 2     301   IFFCLMVYI 309
HBsAg Trans of 3     301   IFFCLMVYI 309
HBsAg Trans of 4     301   IFFCLMAYI 309
```

Figure 6

```
              10         20         30         40         50
S0                                                                    [SEQ ID NO:20]
S6                                                                    [SEQ ID NO:21]
S8                                                                 T  [SEQ ID NO:22]
S12  TTTTGGGGAGCCCTCAGGCTCAGGGCATATTACAAACTCTGCCAGCAAAT                [SEQ ID NO:23]
S15                                  TACAAACTTTGCCAGCAAAT             [SEQ ID NO:24]

60         70         80         90        100
S0
S6
S8   GCCCCTTCTGCCTCCACCAATCGCCAGTCAGGAAGGCAGCCTACCCCGCT
S12  CCACCTCCTGCCTCCACCAATCGCCAGTCAGGAAGGCAGCCTACCCCGCT
S15  CCACCTCCTGCCTCCACCAATCGCCAGTCAGGAAGGCAGCCTACCCCGCT 110        120        130        140        150
S0
S6
S8   GTCTCCACCTTTGAGAGACACTCATCCTCAGGCCATGCAGTGGAACTCAA
S12  GTCTCCACCTTTGAGAGACACTCATCCTCAGGCCATGCAGTGGAACTCAA
S15  GTCTCCACCTTTGAGAGACACTCATCCTCAGGCCATGCAGTGGAACTCAA 160        170        180        190        200
S0
S6
S8   CAACCTTCCACCAAACTCTGCAAGATCCCAGAGTGAAAGGCCTGTATTTC
S12  CAACCTTCCACCAAACTCTGCAAGATCCCAGAGTGAAAGGCCTGTATTTC
S15  CAACCTTCCACCAAACTCTGCAAGATCCCAGAGTGAAAGGCCTGTATTTC 210        220        230        240        250
S0
S6
S8   CCTGCTGGTGGCTCCAGTTCAGGAACAGTAAACCCTGTTCCGACTACTGC
S12  CCTGCTGGTGGCTCCAGTTCAGGAACAGTAAACCCTGTTCCGACTACTGC
S15  CCTGCTGGTGGCTCCAGTTCAGGAACAGTAAACCCTGTTCCGACTACTGC 260        270        280        290        300
S0
S6
S8   CTCTCACTCATCGTCAATCTTCTCGAGGATTGGGGTCCCTGCGCTGAACA
S12  CTCTCACTCATCGTCAATCTTCTCGAGGATTGGGGTCCCTGCGCTGAACA
S15  CTCTCACTCATCGTCAATCTTCTCGAGGATTGGGGTCCCTGCGCTGAACA
```

Figure 7

```
              310         320         330        340         350
S0
S6
S8    TGGAGAACATCACATCAGGACTCCTAGGACCCCTTCTCGTGTTACAGGCG
S12   TGGAGAACATCACATCAGGACTCCTAGGACCCCTTCTCGTGTTACAGGCG
S15   TGGAGAACATCACATCAGGACTCCTAGGACCCCTTCTCGTGTTACAGGCG 360         370         380        390         400
S0                                                CGCAGAGTCTAGACTC
S6
S8    GGGTTTTTCTTGTTGACAAGAATCCTCACAATACCGCAGAGTCTAGACTC
S12   GGGTTTTTCTTGTTGACAAGAATCCTCACAATACCGCAGAGTCTAGACTC
S15   GGGTTTTTNTTGTTGACAAGAATCCTCACAATACCGCAGAGTCTAGACTC 410         420         430        440         450
S0    GTGGTGGACTTCTCTCAATTTTCGAGGGGGGACTACCGTGTGTCTTGGCC
S6
S8    GTGGTGGACTTCTCTCAATTTTCGAGGGGGGACTACCGTGTGTCTTGGCC
S12   GTGGTGGACTTCTCTCAATTTTCGAGGGGGGACTACCGTGTGTCTTGGCC
S15   GTGGTGGACTTCTCTCAATTTTCGAGGGGGGACTACCGTGTGTCTTGGCC 460         470         480        490         500
S0    AAAATTCGCAGTCCCCAACCTCCAATCACTCACCAACCTCCTGTCCTCCA
S6                                TTACTCACCNACCTCCTGTCCTCCA
S8    AAAATTCGCAGTCCCCAACCTCCAATCACTCACCAACCTCCTGTCCTCCA
S12   AAAATTCGCAGTCCCCAACCTCCAATCACTCACCAACCTCCTGTCCTCCA
S15   AAAATTCGCAGTCCCCAACCTCCAATCACTCACCAACCTCCTGTCCTCCA 510         520         530        540         550
S0    ACTTGTCCTGGTTATCGCTGGATGTGTCTGCGGCGTTTTATCATCTTCCT
S6    ACTTGTCCTGGTTATCGCTGGATGTGTCTGCGGCGTTTTATCATCTTCCT
S8    ACTTGTCCTGGTTATCGCTGGATGTGTCTGCGGCGTTTTATCATCTTCCT
S12   ACTTGTCCTGGTTATCGCTGGATGTGTCTGCGGCGTTTTATCATCTTCCT
S15   ACTTGTCCTGGTTATCGCTGGATGTGTCTGCGGCGTTTTATCATCTTCCT 560         570         580        590         600
S0    CTTCATCCTGCTGCTATGCCTCATCTTCTTGTTGGTTCTTCTGGACTGTC
S6    CTTCATCCTGCTGCTATGCCTCATCTTCTTGTTGGTTCTTCTGGACTGTC
S8    CTTCATCCTGCTGCTATGCCTCATCTTCTTGTTGGTTCTTCTGGACTGTC
S12   CTTCATCCTGCTGCTATGCCTCATCTTCTTGTTGGTTCTTCTGGACTGTC
S15   CTTCATCCTGCTGCTATGCCTCATCTTCTTGTTGGCTCTACTGGACTGTC 610         620         630        640         650
S0    AAGGTATGTTGCCCGTTTGTCCTCTAATTCCAGGATCCTCAACCACCAGC
S6    AAGGTATGTTGCCCGTTTGTCCTCTAATTCCAGGATCCTCAACCACCAGC
S8    AAGGTATGTTGCCCGTTTGTCCTCTAATTCCAGGATCCTCAACCACCAGC
S12   AAGGTATGTTGCCCGTTTGTCCTCTAATTCCAGGATCCTCAACCACCAGC
S15   AAGGTATGTTGCCCGTTTGTCCTCTAATTCCAGGATCCTCAACCACCAGC
```

Figure 7 (continued)

```
            660        670        680        690        700
S0   ACGGGACCATGCCGAACCTGCACGACTCCTGCTCAAGGAACCTCTACGGT
S6   AGGGGACCATGCCGAACCTGCACGACTCCTGCTCAAGGAACCTCTACGGT
S8   AGGGGACCATGCCGAACCTGCACGACTCCTGCTCAAGGAACCTCTACGGT
S12  AGGGGACCATGCCGAACCTGCACGACTCCTGCTCAAGGAACCTCTACGGT
S15  AGGGGACCATGCCGAACCTGCACGACTCCTGCTCAAGGAACCTCTACGGT 710        720        730        740        750
S0   TCCCTCATGTTGCTGTACCAAACCTTCGGACGGAAATTGCACCTGTATTC
S6   TCCCTCATGTTGCTGTACCAAACCTTCGGACGGAAATTGCACCTGTATTC
S8   TCCCTCATGTTGCTGTACCAAACCTTCGGACGGAAATTGCACCTGTATTC
S12  TCCCTCATGTTGCTGTACCAAACCTTCGGACGGAAATTGCACCTGTATTC
S15  TCCCTCATGTTGCTGTACCAAACCTTCGGACGGAAATTGCACCTGTATTC 760        770        780        790        800
S0   CCATCCCATCATCCTGGGCTTTCGGAAAATTCCTATGGGAGTGGGCCTCA
S6   CCATCCCATCATCCTGGGCTTTCGGAAAATTCCTATGGGAGTGGGCCTCA
S8   CCATCCCATCATCCTGGGCTTTCGGAAAATTCCTATGGGAGTGGGCCTCA
S12  CCATCCCATCATCCTGGGCTTTCGGAAAATTCCTATGGGAGTGGGCCTCA
S15  CCATCCCATCATCCTGGGCTTTCGGAAAATTCCTATGGGAGTGGGCCTCA 810        820        830        840        850
S0   GCCCGTTTCTCCTGGCTCAGTTTACTAGTGCCATTTGTTCAGTGGTTCGT
S6   GCCCGTTTCTCATGGCTCAGTTTACTAGTGCCATTTGTTCAGTGGTTCGT
S8   GCCCGTTTCTCATGGCTCAGTTTACTAGTGCCATTTGTTCAGTGGTTCGT
S12  GCCCGTTTCTCATGGCTCAGTTTACTAGTGCCATTTGTTCAGTGGTTCGT
S15  GCCCGTTTCTCATGGCTCAGTTTACTAGTGCCATTTGTTCAGTGGTTCGT 860        870        880        890        900
S0   AGGGCTTTCCCCCACTGTCTGGCTTTTAGTTATATGGATGATGTGGTATT
S6   AGGGCTTTCCCCCACTGTCTGGCTTTTGGTTATGTGGATGATGTGGTATT
S8   AGGGCTTTCCCCCACTGTCTGGCTTTTGGTTATGTGGATGATGTGGTATT
S12  AGGGCTTTCCCCCACTGTCTGGCTTTTGGTTATGTGGATGATGTGGTATT
S15  AGGGCTTTCCCCCACTGTCTGGCTTTTGGTTATGTGGATGATGTGGTATT 910        920        930        940        950
S0   GGGGGCCAAGTCTGTATCGCATCTTGAGTCCCTTTTTACCGCTGNTACCA
S6   GGGGGCCAAGTCTGTATCGCATCTTGAGTCCCTTTTTACCGCTGTTACCA
S8   GGGGGCCAAGTCTGTATCGCATCTTGAGTCCCTTTTTACCGCTGTTACCA
S12  GGGGGCCAAGTCTGTATCGCATCTTGAGTCCCTTTTTACCGCTGTTACCA
S15  GGGGGCCAAGTCTGTATCGCATCTTGAGTCCCTTTTTACCGCTGTTACCA 960        970        980        990       1000
S0   ATTTTCTTTTGTCTTTGGGTATACATTTAAACCCTAACAAAACAAAAAGA
S6   ATTTTCTTTTGTCTTTGGGTATACATTTAAATCCTAACAAAACAAAAAGA
S8   ATTTTCTTTTGTCTTTGGGTATACATTTAAATCCTAACAAAACAAAAAGA
S12  ATTTTCTTTTGTCTTTGGGTATACATTTAAATCCTAACAAAACAAAAAGA
S15  ATTTTCTTTTGTCTTTGGGTATNCATTTAAATCCTAACAAAACAAAAAGA 1010       1020       1030       1040       1050
```

Figure 7 (continued)

```
S0   TGGGGTTACTCCCTACATTTTATGGGCTATGTCATTGGAT
S6   TGGGGTTACTCCCTACATTTTATGGGCTATGTCATTGGATGTCATGGGTC
S8   TGGGGTTACTCCCTACATTTTATGGGCTATGTCATTGGATGTCATGGGTC
S12  TGGGGTTACTCCCTACATTTTATGGGCTATGTCATTGGATGTCATGGGTC
S15  TGGGGTTACTCCCTACA 1060      1070      1080      1090      1100
S0
S6   CTTGCCACAAGAACACATCAGACAAAAAATCAAAGAATGTTTTAGAAAAC
S8   CTTGCCACAAGAACACATCAGACAAAAAATCA
S12  CTTGCCACAAGAACACATCAGACAAAAAATCAAAGAATGTTTTAGAAAAC
S15
```

Figure 7 (continued)

Patient B Am

```
            260        270        280        290        300
S0    SGHTTNFASKSTSCLHQSPVRKAAYPAVSTFERHSSSGHAVELNNLPPNS    [SEQ ID NO:25]
S6                                                         [SEQ ID NO:26]
S8             CPFCLHQSPVRKAAYPAVSTFERHSSSGHAVELNNLPPNS    [SEQ ID NO:27]
S12   SGHITNSASKSTSCLHQSPVRKAAYPAVSTFERHSSSGHAVELNNLPPNS    [SEQ ID NO:28]
S15          TNFASKSTSCLHQSPVRKAAYPAVSTFERHSSSGHAVELNNLPPNS [SEQ ID NO:29]

310        320        330        340        350
S0    ARSQSERPVFPCWWLQFRNSKPCSDYCLSLIVNLLEDWGPCAEHGEHHIR
S6
S8    ARSQSERPVFPCWWLQFRNSKPCSDYCLSLIVNLLEDWGPCAEHGEHHIR
S12   ARSQSERPVFPCWWLQFRNSKPCSDYCLSLIVNLLEDWGPCAEHGEHHIR
S15   ARSQSERPVFPCWWLQFRNSKPCSDYCLSLIVNLLEDWGPCAEHGEHHIR 360        370        380        390        400
S0    TPRTPSRVTGGVFLVDKNPHNTAESRLVVDFSQFSRGDYRVSWPKFAVPN
S6
S8    TPRTPSRVTGGVFLVDKNPHNTAESRLVVDFSQFSRGDYRVSWPKFAVPN
S12   TPRTPSRVTGGVFLVDKNPHNTAESRLVVDFSQFSRGDYRVSWPKFAVPN
S15   TPRTPSRVTGGVFXVDKNPHNTAESRLVVDFSQFSRGDYRVSWPKFAVPN 410        420        430        440        450
S0    LQSLTNLLSSNLSWLSLDVSAAFYHLPLHPAAMPHLLVGSSGLSRYVARL
S6            SNLSWLSLDVSAAFYHLPLHPAAMPHLLVGSSGLSRYVARL
S8    LQSLTNLLSSNLSWLSLDVSAAFYHLPLHPAAMPHLLVGSSGLSRYVARL
S12   LQSLTNLLSSNLSWLSLDVSAAFYHLPLHPAAMPHLLVGSSGLSRYVARL
S15   LQSLTNLLSSNLSWLSLDVSAAFYHLPLHPAAMPHLLVGSTGLSRYVARL 460        470        480        490        500
S0    SSNSRILNHQHGTMPNLHDSCSRNLYGSLMLLYQTFGRKLHLYSHPIILG
S6    SSNSRILNHQQGTMPNLHDSCSRNLYGSLMLLYQTFGRKLHLYSHPIILG
S8    SSNSRILNHQQGTMPNLHDSCSRNLYGSLMLLYQTFGRKLHLYSHPIILG
S12   SSNSRILNHQQGTMPNLHDSCSRNLYGSLMLLYQTFGRKLHLYSHPIILG
S15   SSNSRILNHQQGTMPNLHDSCSRNLYGSLMLLYQTFGRKLHLYSHPIILG 510        520        530        540        550
S0    FRKIPMGVGLSPFLLAQFTSAICSVVRRAFPHCLAFSYMDDVVLGAKSVS
S6    FRKIPMGVGLSPFLMAQFTSAICSVVRRAFPHCLAFGYVDDVVLGAKSVS
S8    FRKIPMGVGLSPFLMAQFTSAICSVVRRAFPHCLAFGYVDDVVLGAKSVS
S12   FRKIPMGVGLSPFLMAQFTSAICSVVRRAFPHCLAFGYVDDVVLGAKSVS
S15   FRKIPMGVGLSPFLMAQFTSAICSVVRRAFPHCLAFGYVDDVVLGAKSVS 560        570        580        590        600
S0    HLESLFTAXTNFLLSLGIHLNPNKTKRWGYSLHFMGYVIGCHGSXPQEHI
S6    HLESLFTAVTNFLLSLGIHLNPNKTKRWGYSLHFMGYVIG
S8    HLESLFTAVTNFLLSLGIHLNPNKTKRWGYSLHFMGYVIGCHGSLPQEHI
S12   HLESLFTAVTNFLLSLGIHLNPNKTKRWGYSLHFMGYVIG
S15   HLESLFTAVTNFLLSLGXHLNPNKTKRWGYSL
```

Figure 8

|        | 10 | 20 | 30 | 40 | 50 | |
|--------|----|----|----|----|----|---|
| S0  |                                                      | [SEQ ID NO:30] |
| S6  |                                                      | [SEQ ID NO:31] |
| S8  |                                                      | [SEQ ID NO:32] |
| S12 | LGSPQAQGILQTLPANPPPASTNRQSGRQPTPLSPPLRDTHPQAMQWNST   | [SEQ ID NO:33] |
| S15 |             PPPASTNRQSGRQPTPLSPPLRDTHPQAMQWNST       | [SEQ ID NO:34] |

```
              60        70        80        90        100
S0
S6
S8
S12  TFHQTLQDPRVKGLYFPAGGSSSGTVNPVPTTASHSSSIFSRIGVPALNM
S15  TFHQTLQDPRVKGLYFPAGGSSSGTVNPVPTTASHSSSIFSRIGVPALNM 110       120       130       140       150
S0                                 QSLDSWWTSLNFRGGTTVCLGQ
S6
S8
S12  ENITSGLLGPLLVLQAGFFLLTRILTIPQSLDSWWTSLNFRGGTTVCLGQ
S15  ENITSGLLGPLLVLQAGFFLLTRILTIPQSLDSWWTSLNFRGGTTVCLGQ 160       170       180       190       200
S0   NSQSPTSNHSPTSCPPTCPGYRWMCLRRFIIFLFILLLCLIFLLVLLDCQ
S6                  PPTCPGYRWMCLRRFIIFLFILLLCLIFLLVLLDCQ
S8                   PTCPGYRWMCLRRFIIFLFILLLCLIFLLVLLDCQ
S12  NSQSPTSNHSPTSCPPTCPGYRWMCLRRFIIFLFILLLCLIFLLVLLDCQ
S15  NSQSPTSNHSPTSCPPTCPGYRWMCLRRFIIFLFILLLCLIFLLALLDCQ 210       220       230       240       250
S0   GMLPVCPLIPGSSTTSTGPCRTCTTPAQGTSTVPSCCCTKPSDGNCTCIP
S6   GMLPVCPLIPGSSTTSRGPCRTCTTPAQGTSTVPSCCCTKPSDGNCTCIP
S8   GMLPVCPLIPGSSTTSRGPCRTCTTPAQGTSTVPSCCCTKPSDGNCTCIP
S12  GMLPVCPLIPGSSTTSRGPCRTCTTPAQGTSTVPSCCCTKPSDGNCTCIP
S15  GMLPVCPLIPGSSTTSRGPCRTCTTPAQGTSTVPSCCCTKPSDGNCTCIP 260       270       280       290       300
S0   IPSSWAFGKFLWEWASARFSWLSLLVPFVQWFVGLSPTVWLLVIWMMWYW
S6   IPSSWAFGKFLWEWASARFSWLSLLVPFVQWFVGLSPTVWLLVMWMMWYW
S8   IPSSWAFGKFLWEWASARFSWLSLLVPFVQWFVGLSPTVWLLVMWMMWYW
S12  IPSSWAFGKFLWEWASARFSWLSLLVPFVQWFVGLSPTVWLLVMWMMWYW
S15  IPSSWAFGKFLWEWASARFSWLSLLVPFVQWFVGLSPTVWLLVMWMMWYW 310       320
S0   GPSLYRILSPFLPLXPIFFCLWVYI
S6   GPSLYRILSPFLPLLPIFFCLWVYI
S8   GPSLYRILSPFLPLLPIFFCLWVYI
S12  GPSLYRILSPFLPLLPIFFCLWVYI
S15  GPSLYRILSPFLPLLPIFFCLWVXI
```

Figure 9

SEQ ID NO: 42

```
         10         20         30         40         50         60         70         80         90        100
TACTACAAACTTGCCAGCAAATCCGCCTCCTGCCTCTACCAATCGCCAGTCAGGAAGGCAGCCTACCCCTCTGACTCCACCTTTGAGAAACACTCATCC 110        120        130        140        150        160        170        180        190        200
TCAGGCCATGCAGTGGAACTTCCACAAACTTCCACCGAACTCTACAGATCCCAGAGTGAAAGGCCTGTATCTCCCTGCTGGTGGCTCCAGTTCAGGAACA 210        220        230        240        250        260        270        280        290        300
GTAAACCCTGTCCAGTACTGTCTCTCACACATCGTCAATCTTATCGAGGATTGGGACCCTGCACTGCACATGAACATCACATCAGGATTCCTAG 310        320        330        340        350        360        370        380        390        400
GACCCCTGCTGTGTTACAGGCGGGGTTTTTCTTGTTGACAAGAATCCTCACAATACCGCAGAGTCTAGACTCGTGGTGGACTTCTCCTCAATTTTCTAGG 410        420        430        440        450        460        470        480        490        500
GGGGACCACCGTGTGCCTTGGCCAAAATTCGCAGTCCCCAAACCTCCAATCACTCACCAACTTGTCCTGTCCTCCAACTTGTCCTGGTTATCGCTGGATGTGT 510        520        530        540        550        560        570        580        590        600
CTGCGGCCGTTTTATCATATTCCTCTTCATCCTGCTGCTATGCCTCATCTTCTTGTTTGGTTCTTCTGGACTATCAAGGTATGTTGCCCGTTTGCCCTCTAA 610        620        630        640        650        660        670        680        690        700
TTCCAGGATCCTCAACCACCAGCACGGGACCATGCAGAGACCTGCACGACTCCTGCTCAAGGAACCTCTWTGTATCCCTCATGTTGCTGTACCAAACCTWC 710        720        730        740        750        760        770        780        790        800
GGMCGSAAATTGCACCTGTATTCCCATCCATCATCCTGGGCTTTCGGAAAATTCCTATGGGAGTGGGCCTCAGCCCGTTTCCTGACTCAGTTTACTA 810        820        830        840        850        860        870        880        890        900
GTGCCATTTGTTCTTCAGTGGTTCGTAGGGCTTTCCCCACTGTTTGGCTTTCAGTTATATGGATGATGTGGTATTGGGGGCCAGTTCTGTACAGCATCGTGA 910        920        930        940        950        960        970        980        990       1000
GGCCCTTTTTACCGCTGTACCAATTTCTTTTGTCTCTGGGTATACATTTAACCCCGGACAAAACAAAAAGATGGGGTTACTCTTTACATTTCATTTCATGGGC 1010       1020       1030
TATGTCATTGGATGTTATGGGTCATTGCCAC
```

Figure 10

SEQ ID NO.: 43

```
         10         20         30         40         50         60         70         80         90        100
TTNLASKSASCLYQSPVRKAAYPSDSTFEKHSSSGHAVELHKLPPNSTRSQSERPVSPCWWLQFRNSKPCSDYCLSHIVNLIEDWGPCTEHGEHHIRIPR
        110        120        130        140        150        160        170        180        190        200
TPARVTGGVFLVDKNPHNTAESRLVVDFSQFSRGDHRVPWPKFAVPNLQSLTNLLSSNLSWLSLDVSAAFYHIPLHPAAMPHLLVGSSGLSRYVARLPSN
        210        220        230        240        250        260        270        280        290        300
SRILNHQHGTMQNLHDSCSRNLY/FVSLMLLYQTF/TGRKLHLYSHPIILGFRKIPMGVGLSPFLLTQFTSAICSVVRRAPPHCLAFSYMDDVVLGARSVQ
        310        320        330        340
HREALFTAVTNFLLSLGIHLTPDKTKRWGYSLHFMGYVIGCYGSLP
```

Figure 11

SEQ ID NO.: 44

```
         10         20         30         40         50         60         70         80         90        100
LQTLPANPPASTNRQSGRQPTPLITPPLRNTHPQAMQWNSTNFHRTLQDPRVKGLYLPAGGSSSGTVNPVPTTVSHTSSILSRIGDPALMENITSGFLG
        110        120        130        140        150        160        170        180        190        200
PLLVLQAGFFLLTRILTIPQSLDSWWTSLNFLGGTTVCLGQNSQSPTSNHSPTSCPPTCPGYRWMCLRRFIIFLFILLLCLIFLLVLLDYQGMLPVCPLI
        210        220        230        240        250        260        270        280        290        300
PGSSTTSTGPCRICTTPAQGTSM/LYPSCCCTKPS/TAANCTCIPIPSSWAFGKFLWEWASARFS*LSLLVPFVQWFVGLSPTVWLSVIWMMWYNGPGLYS
IVR.
```

Figure 12

SEQ ID NO.: 45

```
         10         20         30         40         50         60         70         80         90        100
TGGTCACAGTGCCAACAGTTCCTCCTCCTGCCTCCACCAATCGGCAGTCAGGAGGCAGCCTACTCCCATCTCTCCACCTCTAAGAGACAGTCATCCTCA 110        120        130        140        150        160        170        180        190        200
GGCCATGGTGGCTCAGCCTGCTGGTGCTCCAGTTCAGGAACACTCAACCCTGTTCCCAATATTGCCTCTCACATCTCGTCAATCTCCTTGAGGACTGGG 210        220        230        240        250        260        270        280        290        300
GACCCTGCGCCGAACATGGAGAACATCACATCAGGATTCCTAGGACCCCTGCTCGTTGTTACAGGCGGGTTTTCTTGTTGACAAGAATCCTCACAATAC 310        320        330        340        350        360        370        380        390        400
CGCAGAGTCTAGACTCGTGGTTGGACTTCTCTCCAGTTTTCTAGGGGGATCACCCCGTGTGCTTGGCCAAAATTCGCAGTCCCCAACCTCCAATCACTCACC 410        420        430        440        450        460        470        480        490        500
AACCTCCTGTCCTCCAATTTGACCTGGTTATCGCTGGATATGTCTGCGGCGTTTTATCATATTCCTCTTCATCCTGCCGCTATGCCTCATCTTCTTATTG 510        520        530        540        550        560        570        580        590        600
GTTCTTCTGGATTATCAAGGTATGTTGCCCGTTTGTCCTCTAATTCCAGGATCCACAACCAGTGCGGGACCCTGCAAAACCTGCACGACTCCTGCTC 610        620        630        640        650        660        670        680        690        700
AAGGCAACTCTATGTTTCCCTCATGTTGCTGTACAAAACCTACGGATGGAAATTGCACCTGTATTCCCATCCCATCATCTTGGGCTTTCGCAAAATACCT 710        720        730        740        750        760        770        780        790        800
ATGGGAGTGGGCCTCAGTGCCGTTCTCTTGGCTCCTCAGTTACTAGTGCCATTTGTTCAGTGATTCGTAGGGCTTTCCCCACTGTTTGGCTTTCAGCTATA 810        820        830        840        850        860        870        880
TTGATGATGTGGTACTGGGGGCCAAGTCTGCACAACATCTTGAGTCCCTTTATACCGTGTTACCAATTTCTTTGTCTTTGGGTAT
```

Figure 13

SEQ ID NO.: 46

```
         10         20         30         40         50         60         70         80         90        100
GHSANSSSSCLHQSAVREAAYSHLSTSKRQSSSGHGGSACWMLQFRNTQPCSQYCLSHLVNLLEDWGPCAEHGEHHIRIPRTPARVTGGVFLVDKNPHNT
        110        120        130        140        150        160        170        180        190        200
AESRLVVDFSQFSRGITRVSWPKFAVPNLQSLTNLLSSNLTWLSLDMSAAFYHIPLHPAAMPHLLIGSSGLSRYVARLSSNSRIHNNQCGTLQNLHDSCS
        210        220        230        240        250        260        270        280        290
RQLYVSLMLLYKTYGWKLHLYSHPIILGFRKIPMGVGLSPFLLAQFTSAICSVIRRAFPHCLAFSYIDDVVLGAKSAQHLESLYTAVTNFLLSLG
```

Figure 14

SEQ ID NO.: 47

```
         10         20         30         40         50         60         70         80         90        100
VTVPTVPPASTNRQSGRQPTPISPPLRDSHPQAMVAQPAGGSSSGTLNPVPNIASHISSISLRTGDPAPNMENITSGFLGPLLIVLQAGFFLLTRILTIP
        110        120        130        140        150        160        170        180        190        200
QSLDSWNTSLSFLGGSPVCLGQNSQSPTSNHSPTSCPPI*PGYRWICLRRFIIFLFILPLCLIFLLVLLDYQGMLPVCPLIPGSTTTSAGPCKTCTTPAQ
        210        220        230        240        250        260        270        280        290
GNSMFPSCCCTKPTDGNCTCIPIPSSWAFAKYLWEWASVRFSWLSLLVPFVQ*FVGLSPTVWLSAILMMWYWGPSLHNILSPFIPLLPIFFCLWV
```

Figure 15

```
         10        20        30        40        50
TCCTGTCCTCCAATTTGTCCTGGTTATCGCTGGATGTGTCTGCGGCGTTT 60        70        80        90       100
TATGATATTCCTCTTCATCCTGCTGCTATGCCTCATCTTCTTATTGGTTC 110       120       130       140       150
TTCTGGATTATCAAGGTATGTTGCCCGTCTGTCCTCTAATTCCAGGATCA 160       170       180       190       200
ACAACAACCAGTACGGGACCATGCAAAACCAAAACCTGCACGACTCCTGC 210       220       230       240       250
TCAAGGCAACTCTATGTTTCCCTCATGTTGCTGTACAAAACCTACGGATG 260       270       280       290       300
GAAATTGCACCTGTATTCCCATCCCATCGTCCTGGGCTTTCGCAAAATTC 310       320       330       340       350
CTATGGGAGTGGGCCTCAGTCCGTTTCTCTTGGCTCAGTTTACTAGTGCC 360       370       380       390       400
ATTTGTTCAGTGGTTCGTAGGGCTTTCCCCCACTGTTTGGCTTTCAGCTA 410       420       430       440       450
TATGGATGATGTGGTATTGGGGGCCAAGTCTGTACAGCATCGTGAGGCCC 460       470       480       490       500
TTTATACAGCTGTTACCAATTTTCTTTTGTCTCTGGGTATACATTTAAAC 510       520       530       540       550
CCTAACAAAACAAAAAGATGGGGTTATTCCCTAAACTTCATGGGTTACAT 560       570       580       590
AATTGGAAGTTGGGGAACATTGCCACAGGATCATATTGTAC
```

SEQ ID NO.: 48

Figure 16

```
          10        20        30        40        50
SNLSWLSLDVSAAFYDIPLHPAAMPHLLIGSSGLSRYVARLSSNSRINNN 60        70        80        90       100
QYGTMQNQNLHDSCSRQLYVSLMLLYKTYGWKLHLYSHPIVLGFRKIPMG 110       120       130       140       150
VGLSPFLLAQFTSAICSVVRRAFPHCLAFSYMDDVVLGAKSVQHREALYT 160       170       180
AVTNFLLSLGIHLNPNKTKRWGYSLNFMGYIIGSWG
```

SEQ ID NO.: 49

Figure 17

```
         10        20        30        40        50
SCPPICPGYRWMCLRRFMIFLFILLLCLIFLLVLLDYQGMLPVCPLIPGS 60        70        80        90       100
TTTSTGPCKTKTCTTPAQGNSMFPSCCCTKPTDGNCTCIPIPSSWAFAKF 110       120       130       140       150
LWEWASVRFSWLSLLVPFVQWFVGLSPTVWLSAIWMMWYWGPSLYSIVRP

160
FIQLLPIFFCLWVYI
```

SEQ ID NO.: 50

Figure 18

```
          10         20         30         40         50
AATCCTCACAATACCGCAGAGTCTAGACTTCGTGGTGACTTCTCTCAATT 60         70         80         90        100
TTCTAGGGGACCACCCGTGTGTCTTGGCCAAAATTCGCAGTCCCCAACCT 110        120        130        140        150
CCAATCACTCACCAACCTCTTGTCCTCCAATTTGTCCTGGTTATCGCTGG 160        170        180        190        200
ATGTGTCTGCGGCGTTTTATCATATCCCTCTTCATCCTGCTGCTATGCCT 210        220        230        240        250
CATCTTCTTATTGGTTCTTCTGGATTATCAAGGTATGTTGCCCGTTTGTC 260        270        280        290        300
CTCTAATTCCAGGATCCACAACAACCAGTACGGGACCCTGCAAAACCTGC 310        320        330        340        350
ACGACTCCTGCTCAAGGCAACTCTATGTTTCCCTCATGTTGCTGTACAAA 360        370        380        390        400
ACCTACGGATGGAAATTGCACMTGTATTCCCATCCCATCATCTTGGGCTT 410        420        430        440        450
TCGCAAAATACCTATGGGAGTGGGCCTCAGTCCGTTTCTCTTGGTTCAGT 460        470        480        490        500
TTACTAGTGCCATTTGTTCAGTGGTTCGTAGGGCTTTCCCCCACTGTTTG 510        520        530        540        550
GCTTTCAGCTATATGGATGATATTGTACTGGGGGCCAAGTCTGTACAACA 560        570        580        590        600
TCTTGAGTCCCTTTATACCGCTGTTACCAATTTTCTTTTGTCTTTGGGTA 610        620        630        640        650
TACATTTAACCCCTAACAAAACAAAGAGATGGGGTTATTCCCTGAATTTC

660
ATGGGTTATGTAATTGGAA
```

SEQ ID NO.: 51

Figure 20

SEQ ID NO.: 52

```
         10        20        30        40        50
SNLSWLSLDVSAAFYHIPLHPAAMPHLLIGSSGLSRYVARLSSNSRIHNN 60        70        80        90       100
QYGTLQNLHDSCSRQLYVSLMLLYKTYGWKLHXYSHPIILGFRKIPMGVG 110       120       130       140       150
LSPFLLVQFTSAICSVVRRAFPHCLAFSYMDDIVLGAKSVQHLESLYTAV 160       170       180
TNFLLSLGIHLTPNKTKRWGYSLNFMGYVIG
```

Figure 21

SEQ ID NO.: 53

```
        10        20        30        40        50
PICPGYRWMCLRRFIISLFILLLCLIFLLVLLDYQGMLPVCPLIPGSTTT 60        70        80        90       100
STGPCKTCTTPAQGNSMFPSCCCTKPTDGNCTCIPIPSSWAFAKYLWEWA 110       120       130       140       150
SVRFSWFSLLVPFVQWFVGLSPTVWLSAIWMILYWGPSLYNILSPFIPLL

160
PIFFCLWVYI
```

Figure 22

```
        10         20         30         40         50
TCCAATTTGTCCTGGGTATCGCTGGATGTGTCTGCGGCGTTTTATCATAT 60         70         80         90        100
TCCTCTTCATCCTGCTGCTATGCCTCATCTTCTTGTTGGTTCTTCTGGAC 110        120        130        140        150
TATCAAGGTATGTTGCCCGTTTGTCCTCTACTTCCAGGAACATCAACTAC 160        170        180        190        200
CAGCACGGGACCATGCAAGACCTGCACGACTCCTGCTCAAGGAACCTCTA 210        220        230        240        250
TGTTTCCCTCTTGTTGCTGTACAAAACCTTCGGACGGAAATTGCACTTGT 260        270        280        290        300
ATTCCCATCCCATCGTCTTGGGCTTTCGCAAGATTCCTATGGGAGTGGGC 310        320        330        340        350
CTCAGTCCGTTTCTCTTGGCTCARTTTACTAGTGCCATTTGTTCAGTGGT 360        370        380        390        400
TCGTAGGGCTTTCCCCCACTGTTTGGCTTTCAGTTATATTGATGATGTGG 410        420        430        440        450
TATTGGGGGCCAAGTCTGTACAACATCTTGAATCCCTTTTTACCTCTATT 460        470        480        490        500
ACCAATTTTCTTATGTCTTTGGGTATACATTTAAACCCTAAGAAAACCAA 510        520        530        540        550
ACGTTGGGGCTACTCCCTTAACTTCATGGGATATGTAATTGGAAGTTGGG

GTAC
```

SEQ ID NO.: 54

Figure 23

SEQ ID NO.: 55

```
          10        20        30        40        50
SNLSWVSLDVSAAFYHIPLHPAAMPHLLVGSSGLSRYVARLSSTSRNINY 60        70        80        90       100
QHGTMQDLHDSCSRNLYVSLLLLYKTFGRKLHLYSHPIVLGFRKIPMGVG 110       120       130       140       150
LSPFLLAQFTSAICSVVRRAFPHCLAFSYIDDVVLGAKSVQHLESLFTSI 160       170       180
TNFLMSLGIHLNPKKTKRWGYSLNFMGYVIGSWG
```

Figure 24

```
          10        20        30        40        50
PICPGYRWMCLRRFIIFLFILLLCLIFLLVLLDYQGMLPVCPLLPGTSTT 60        70        80        90       100
STGPCKTCTTPAQGTSMFPSCCCTKPSDGNCTCIPIPSSWAFARFLWEWA 110       120       130       140       150
SVRFSWLXLLVPFVQWFVGLSPTVWLSVILMMWYWGPSLYNILNPFLPLL

160
PIFLCLWVYI
```

SEQ ID NO.: 56

Figure 25

SEQ ID NO.: 57

```
         10        20        30        40        50
CAGCAAATCCGCCTCCTGCCTCTACCAATCGCCAGTCAGGAAGGCAGCCT
         60        70        80        90       100
ACCCCTCTGTCTCCACCTTTGRGAAACACTCATCCTCAGGCCATGCAGTG
        110       120       130       140       150
GAACTCCACAACCTTCCACCAAACTCTGCWAGATCCCAGAGTGAGAGGCC
        160       170       180       190       200
TGTATTTCCTGCTGGTGGCTCCAGTTCAGGAACAGTAAACCCTGTTCCG
        210       220       230       240       250
ACTTCTGTCTCTCACACATCGTCAATCTTCTCGAGGATTGGGGWCCCTGC
        260       270       280       290       300
GCTGAACATGGAGAACATCACATCAGGATTCCTAGGACCCCTGCTCGTGT
        310       320       330       340       350
TACAGGCGGGGTTTTTCTTGTTGACAAGAATCCTCACAATACCGCAGAGT
        360       370       380       390       400
CTAGACTCGTGGTGGACTTCTCTCAATTTTCTAGGGGAACTACCGTGTG
        410       420       430       440       450
TCTTGGCCAAAATTCGCAGTTCCCAACCTCCAATCACTCACCAACCTCCT
        460       470       480       490       500
GTCCTCCAACTTGWCCTGGTTATCGCTGGATGTRCTGCGGCGTTTTATC
        510       520       530       540       550
ATCTTCCTCTTCATCCTGCTGCTATGCCTCATCTTCTTGTTGGTTCTTCT
        560       570       580       590       600
GGACTATCAAGGTATGTTGCCCGTTTGTCCTCTARTTCCAGGATCTTCAA
        610       620       630       640       650
CCACCAGCACGGGACCATGCAGAACCTGCACGACTCCTGCTCAAGGAAMC
        660       670       680       690       700
TCTATGAATCCCTCCTGTTGCTGTACCAAACCTTCGGACGGAAATTGCAC
        710       720       730       740       750
CTGTATTCCCATCCCATCATCCTGGGCTTTCGGAAAATTCCTATGGGAGT
        760       770       780       790       800
GGGCCTCAGCCCGTTTCTCCTGRCTCAGTTTACTAGTGCCATTTGTTCAG
        810       820       830       840       850
TGGTTCGTAGGGCTTTCCCCCACTGTTTGGCTTTCAGTTATATGGATGAT
        860       870       880       890       900
GTGGTATTGGGGGCCAAGTCTGTAYMGCATCTTRAGTCCCTTTTTACCGC
        910       920       930       940       950
TGTTACCAATTTTCTTTTGTCTYTGGGTATACATTTAAACCCTMACAAAA
        960       970       980       990      1000
CAAAAAGATGGGGTTACTCTTTACATTTCATGGGCTATGTCATTGGATGT
       1010      1020      1030      1040
TATGGGTCATTGCCACAAGATCACATCAGACAGAAAATCAAAGAA
```

Figure 26

SEQ ID NO.: 58

```
         10         20         30         40         50
SKSASCLYQSPVRKAAYPSVSTFXKHSSSGHAVELHNLPPNSARSQSERP 60         70         80         90        100
VFPCWWLQFRNSKPCSDFCLSHIVNLLEDWGPCAEHGEHHIRIPRTPARV 110        120        130        140        150
TGGVFLVDKNPHNTAESRLVVDFSQFSRGNYRVSWPKFAVPNLQSLTNLL 160        170        180        190        200
SSNLXWLSLDVSAAFYHLPLHPAAMPHLLVGSSGLSRYVARLSSXSRIFN 210        220        230        240        250
HQHGTMQNLHDSCSRXLYESLLLLYQTFGRKLHLYSHPIILGFRKIPMGV 260        270        280        290        300
GLSRFLLXQFTSAICSVVRRAFPHCLAFSYMDDVVLGAKSVXHLXSLFTA 310        320        330        340
VTNFLLSLGIHLNPXKTKRWGYSLHFMGYVIGCYGSLPQDHIRQKIKE
```

Figure 27

SEQ ID NO.: 59

```
         10         20         30         40         50
ANPPPASTNRQSGRQPTPLSPPLXNTHPQAMQWNSTTFHQTLXDPRVRGL 60         70         80         90        100
YFPAGGSSSGTVNPVPTSVSHTSSIFSRIGXPALNMENITSGFLGPLLVL 110        120        130        140        150
QAGFFLLTRILTIPQSLDSWWTSLNFLGGTTVCLGQNSQFPTSNHSPTSC 160        170        180        190        200
PPTXPGYRWMXLRRFIIFLFILLLCLIFLLVLLDYQGMLPVCPLXPGSST 210        220        230        240        250
TSTGPCRTCTTPAQGXSMNPSCCCTKPSDGNCTCIPIPSSWAFGKFLWEW 260        270        280        290        300
ASARFSXLSLLVPFVQWFVGLSPTVWLSVIWMMWYWGPSLYXILSPFLPL

310
LPIFFCLWVYI
```

Figure 28

HEPATITIS B VIRAL VARIANTS WITH REDUCED SUSCEPTIBILITY TO NUCLEOSIDE ANALOGS AND USES THEREOF

FIELD OF THE INVENTION

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring antiviral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

CROSS-REFERENCE TO RELATED APPLICATIONS

This application is a continuation under 35 USC 120 of U.S. patent application Ser. No. 12/791,621 filed Jun. 1, 2010, which is a continuation under 35 USC 120 of U.S. patent application Ser. No. 11/860,727 filed on Sep. 25, 2007 and issued as U.S. Pat. No. 7,745,130 on Jun. 29, 2010, which is a continuation under 35 USC 120 of U.S. patent application Ser. No. 11/166,004 filed on Jun. 24, 2005 and issued as U.S. Pat. No. 7,384,747 on Jun. 10, 2008, which is a continuation under 35 USC 120 of U.S. patent application Ser. No. 10/963,333 filed on Oct. 12, 2004, now abandoned, which is a continuation under 35 USC 120 of International Patent Application No. PCT/AU03/00432 filed on Apr. 11, 2003, which in turn claims priority of Australian Patent Application No. PS 1710/02 filed Apr. 12, 2002 and Australian Patent Application No. PS 3224/02 filed on Jun. 26, 2002. The disclosures of all such applications are hereby incorporated herein by reference in their respective entireties, for all purposes.

BACKGROUND OF THE INVENTION

The present invention relates generally to viral variants exhibiting reduced sensitivity to particular agents and/or reduced interactivity with immunological reagents. More particularly, the present invention is directed to hepatitis B virus (HBV) variants exhibiting complete or partial resistance to nucleoside or nucleotide analogs and/or reduced interactivity with antibodies to viral surface components including reduced sensitivity to these antibodies. The present invention further contemplates assays for detecting such viral variants, which assays are useful in monitoring antiviral therapeutic regimens and in developing new or modified vaccines directed against viral agents and in particular HBV variants. The present invention also contemplates the use of the viral variants to screen for and/or develop or design agents capable of inhibiting infection, replication and/or release of the virus.

DESCRIPTION OF THE PRIOR ART

Bibliographic details of the publications referred to in this specification are also collected at the end of the description.

The reference to any prior art in this specification is not, and should not be taken as, an acknowledgment or any form of suggestion that that prior art fowls part of the common general knowledge in any country.

Hepatitis B virus (HBV) can cause debilitating disease conditions and can lead to acute liver failure. HBV is a DNA virus which replicates via an RNA intermediate and utilizes reverse transcription in its replication strategy (Summers and Mason, Cell 29: 403-415, 1982). The HBV genome is of a complex nature having a partially double-stranded DNA structure with overlapping open reading frames encoding surface, core, polymerase and X genes. The complex nature of the HBV genome is represented in FIG. 1. The polymerase consists of four functional regions, the terminal protein (TP), spacer, reverse transcriptase (rt) and ribonuclease (RNAse).

The polymerase gene of RSV overlaps the envelope gene, mutations in the catalytic domain of the polymerase gene can also affect the nucleotide and the deduced amino acid sequence of the envelope protein and vice versa. In particular, the genetic sequence for the neutralization domain of HBV known as the 'a' determinant, which is found within the HBsAg and located between amino acids 99 and 169, actually overlaps the major catalytic regions of the viral polymerase protein and in particular domains A and B.

The presence of an HBV DNA polymerase has led to the proposition that nucleoside or nucleotide analogs could act as effective anti-viral agents. Examples of nucleoside analogs currently being tested are penciclovir and its oral form (FCV) [Vere Hodge, Antiviral Chem Chemother 4: 67-84, 1993; Boyd et al., Antiviral Chem Chemother. 32: 358-363, 1987; Kruger et al., Hepatology 22: 219A, 1994; Main et al., J. Viral Hepatitis 3: 211-215, 1996], Lamivudine[(−)-.beta.-2'-deoxy-3'-thiacytidine]; (3TC or LMV) [Severin et al., Antimicrobial Agents Chemother. 39: 430-435, 1995; Dienstag et al., New England J Med 333: 1657-1661, 1995]. New nucleoside or nucleotide analogs which have already progressed to clinical trials include the pyrimidines Emtricitabine, ((−)-(.beta.-L-2'-3'-dideoxy-5-fluoro-3'-thiacydidine; FTC), the 5-fluoro derivative of 3TC, and Clevudine (1-(2-fluoro-5-methyl-(1-L-arabino-furanosyl) uracil; L-FMAU), a thymidine analog: Like 3TC, these are pyrimidine derivatives with an unnatural "L"-configuration. Several purine derivatives have also progressed to clinical trials; they include Entecavir (BMS-200, 475; ETV), a carbocyclic deoxyguanosine analog, diaminopurine dioxolane (DAPD), an oral pro-drug for dioxolane guanine ((−)-3-D-2-aminopurine dioxolane; DXG) and Adefovir dipivoxil, an oral pro-drug for the acyclic deoxyadenosine monophosphate nucleoside analog Adefovir (9-[phosphonyl-methoxyethyl] adenine; PMEA). Other drugs in pre-clinical and clinical trials include FLG [Medivir], ACH-126,443 (L-d4C) [Archillion Pharmaceuticals], ICN 2001-3 (ICN) and Racivir (RCV) [Pharmassett]. Whilst these agents are highly effective in inhibiting HBV DNA synthesis, there is the potential for resistant mutants of HBV to emerge during long term antiviral chemotherapy. In patients on prolonged LMV therapy, key resistance mutations are selected in the rt domain within the polymerase at rtM204I/V+/−rtL180M as well as other mutations. The nomenclature used for the polymerase mutations is in accordance with that proposed by Stuyver et al., 2001, supra. LMV is a nucleoside analog that has been approved for use against chronic HBV infection. LMV is a particularly potent inhibitor of HBV replication and reduces HBV DNA titres in the sera of chronically infected patients after orthotopic liver transplantation (OLT) by inhibiting viral DNA synthesis. LMV monotherapy seems unlikely to be able to control HBV replication in the longer term. This is because emergence of LMV-resistant strains of HBV seems almost inevitable during monotherapy.

Adefovir dipivoxil (ADV: formerly, bis-pom PMEA) is an orally available prodrug of the acyclic deoxyadenosine monophosphate analog adefovir (formerly, PMEA) (FIG. 2). ADV is also a potent inhibitor of HBV replication and has recently been given FDA approval for use against chronic HBV infection. Adefovir dipivoxil differs from other agents in this class in that it is a nucleotide (vs. nucleoside) analog and as such bypasses the first phosphorylation reaction during drug activation. This step is often rate-limiting. Adefovir dipivoxil has demonstrated clinical activity against both wild-type and lamivudine-resistant strains of HBV and is currently in phase III clinical Testing (Gilson et al, J Viral Hepat 6: 387-395, 1999; Perrino et al., Hepatology 32: 129-134, 2000; Peters et al., Transplantation 68: 1912-1914, 1999; Benhamou et al., Lancet 358: 718-723, 2001). During phase II studies a 30 mg daily dose of adefovir dipivoxil resulted in a mean 4 $\log_{10}$ decrease in viremia over 12 weeks (Heathcote et al., Hepatology 28: A620, 1998).

ADV is a substituted acyclic nucleoside phosphonate. This class of compounds also includes tenofovir disoproxil fumarate (also referred to as tenofovir DF, or tenofovir, or (TFV) or 9-R-(2-phosphonomethoxypropyl)adenine (PMPA) and is marketed as Viread by Gilead sciences).

TFV has antiviral activity against both HBV and HIV (Ying et al., J Viral Hepat. 7(2): 161-165, 2000; Ying et al., J. Viral Hepat. 7(1): 79-83, 2000; Suo et al., J Biol Chem. 273(42): 27250-27258. 1998).

FTC has activity against HBV and HIV (Frick et al., Antimicrob Agents Chemother 37: 2285-2292, 1993).

Nucleoside or nucleotide analog therapy may be administered as monotherapy or combination therapy where two or more nucleoside or nucleotide analogs may be administered. The nucleoside or nucleotide analogs may also be administered in combination with other antiviral agents such as interferon or hepatitis B immunoglobulin (HBIG).

There is a need to monitor for the emergence of nucleoside/nucleotide-analog- or antibody-resistant strains of HBV and to develop diagnostic protocols to detect these resistant viruses and/or to use them to screen for and/or develop or design agents having properties making them useful as anti-viral agents. Defective forms of these resistant strains or antigenic components therefrom are also proposed to be useful in the development of therapeutic vaccine compositions as are antibodies directed to viral surface components.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

Specific mutations in an amino acid sequence are represented herein as "$Xaa_{1n}Xaa_2$" where $Xaa_1$ is the original amino acid residue before mutation, n is the residue number and $Xaa_2$ is the mutant amino acid. The abbreviation "Xaa" may be the three letter or single letter (i.e. "X") code. An "rt" before "$Xaa_{1n}Xaa_2$" means "reverse transcriptase". An "s" means an envelope gene. The amino acid residues for HBV DNA polymerase are numbered with the residue methionine in the motif Tyr Met Asp Asp (YMDD) being residue number 204 (Stuyver et al., Hepatology 33: 751-757, 2001). The amino acid residues for hepatitis B virus surface antigen are number according to Norder et al. (J. Gen. Virol. 74: 341-1348, 1993). Both single and three letter abbreviations are used to define amino acid residues and these are summarized in Table 2.

In accordance with the present invention, the selection of HBV variants is identified in patients (Patient A, C and D) with chronic HBV infection treated with ADV and liver transplant patients (Patients B and E) treated with both ADV and LMV post-OLT or ADV post-transplant. HBV variants from Patients F, G and H were also identified following similar treatments. Variants of HBV are identified during ADV or combination ADV and LMV treatment with mutations in the HBV DNA polymerase gene which reduce the sensitivity of HBV to this nucleoside analog. Consequently, HBV rt variants are contemplated which are resistant to, or which exhibit reduced sensitivity to, ADV, LMV, TFV, FTC, ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combinations thereof. Corresponding mutations in the surface antigen also occur. The identification of these HBV variants is important for the development of assays to monitor ADV, LMV, FTC and/or TFV resistance and/or resistance to other nucleoside or nucleotide analogs or other anti-HBV agents or combinations thereof and to screen for agents which are useful as alternative therapeutic agents.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release.

The detection of such HBV variants is particularly important in the management of therapeutic protocols including the selection of appropriate agents for treating HBV infection. The method of this aspect of the present invention is predicated in part on monitoring the development in a subject of an increased HBV load in the presence of a nucleoside or nucleotide analog or other anti-HBV agents or combinations thereof. The clinician is then able to modify an existing treatment protocol or select an appropriate treatment protocol accordingly.

Accordingly, one aspect of the present invention is directed to an isolated HBV variant comprising a nucleotide mutation in a gene encoding a DNA polymerase resulting in at least one amino acid addition, substitution and/or deletion to the DNA polymerase and which exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combinations thereof. The variant HBV comprises a mutation in an overlapping open reading frame in its genome in a region defined by one or more of domains F and G and domain A through to E of HBV DNA polymerase.

Another aspect of the present invention provides an isolated HBV variant comprising a nucleotide mutation in the S gene resulting in at least one amino acid addition, substitution and/or deletion to the surface antigen and which exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, or ADV and FTC and LMV and TFV, ADV and LMV and FTC, and/or optionally other nucleoside or nucleotide analogs or other anti-HBV agents or combinations thereof.

Useful mutants in the rt region include, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235UM; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; and in yet another embodiment, rtH90D and rtL/F108L; and in still a further embodiment, rtL157L/M, rtA181V and rtV207I and in yet a further embodiment, rtL80V, rtP109S, rtI163V, rtL229M and rtN/H/A/S/Q238K; and in another embodiment, rtS78S/T, rtN118N/S, rtN139N/K, rtV142E, rtA181A/T, rtI204M, rtQ/P/S/Stop215Q, rtE218K/E and rtN238N/H or a combination thereof or an equivalent mutation.

Other HBV variants are also contemplated with mutations in rt at rtK32, rtN33, rtP34, rtH35 and rtT37 (these are upstream of the F domain of the DNA polymerase), rtP59, rtK60, rtF61, rtA62 and rtV63 (these are located between the F and A domains), rtD83, rtV84, rtS85, rtA86, rtY89, rtH90 and rtI/L91 (these are located within the A domain and the region immediately prior to and following), rtP177, rtF178, rtL179, rtL180, rtA181, rtQ182, rtF183 and rtT184 (these are located in the B domain), rtM204 and rtY203 (these are located in the C domain), rt235, rt236, rt237, rt238 and rt239 (these are located in the D domain) and rt247, rt248, rt249, rt250 and rt251 (these are located in the E domain) or a combination thereof or an equivalent mutation.

Useful mutants are provided below (see also Tables 16 and 17):

K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion; and V251A/R/N/D/C/Q/E/G/H/I/L/K/M/F/P/S/T/W/Y/deletion.

Reference above to "deletion" means that the first mentioned amino acid before the residue number has been deleted.

Useful mutations in the S gene include, in one embodiment, sP120T, sM125T and sT127A; in another embodiment, T118R, sM133T, sF134V sI195M, sS207R and sY225Y/C; in a further embodiment, sS126T, sM133L/M, sS143S/T, sD144A sG145A and sW172Stop; in yet a further embodiment, sN40S, sC69 Stop, sM75I, sL88P, sT118A, sW182stop, sW196L, sY206H and sY225F; and in yet another embodiment, sI81M and sP214Q; and in still another embodiment, sF83S, sL173F and sW199L; and in still yet another embodiment, sI126T, sK160R, sS174N, sA184V, sW196L, sS210N, sF/C220L and sY221C; and in yet another embodiment, sC69 Stop/C, sC76Y sI110V/I, sY134N, sW172Stop/W, sW196Stop and sS207R or a combination thereof or an equivalent mutation.

The present invention further contemplates a method for determining the potential for an HBV to exhibit reduced sensitivity to ADV, LMV, TFV, or FTC, or ADV and LMV, ADV and TFV, LMV and TFV, FTC and ADV, FTC TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof by isolating DNA or corresponding mRNA from the HBV and screening for a mutation in the nucleotide sequence encoding HBV DNA polymerase resulting in at least one amino acid substitution, deletion and/or addition in any one or more of domains F and G and domains A through to E or a region proximal thereto of the DNA polymerase and associated with resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. The presence of such a mutation is an indication of the likelihood of resistance to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The present invention also provides a composition comprising a variant HBV resistant to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, or ADV and FTC and LMV and TFV, ADV and LMV and FTC, and/or optionally other nucleoside or nucleotide analogs or other anti-HBV agents or combination thereof or an HBV surface antigen from the variant HBV or a recombinant or derivative form thereof or its chemical equivalent and one or more pharmaceutically acceptable carriers and/or diluents.

Yet another aspect of the present invention provides a use of the aforementioned composition or a variant HBV comprising a nucleotide mutation in a gene encoding a DNA polymerase resulting in at least one amino acid addition, substitution and/or deletion to the DNA polymerase and a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof in the manufacture of a medicament for the treatment and/or prophylaxis of hepatitis B virus infection.

The present invention also contemplates a method for determining whether an HBV strain exhibits reduced sensitivity to a nucleoside or nucleotide analog or other anti-HBV agents or by isolating DNA or corresponding mRNA from the HBV and screening for a mutation in the nucleotide sequence encoding the DNA polymerase wherein the presence of the following mutations in the rt region: in one embodiment, rtS21A, rtL122F, rtN124H, rtH126R, rtT28N, rtP130Q, rtD131N and rtY135C; in another embodiment, rt/N/S/T/1/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtL212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L, in even yet another embodiment, rtL157L/M, rtA181V and rtV207I; in still yet another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, rtK32, rtN33, rtP34, rtH35 and rtT37; in yet another embodiment, rtP59, rtK60, rtF61, rtA62 and rtV63; in still another embodiment, rtD83, rtV84, rtS85, rtA86, rtY89, rtH90 and rtI/L91; in even yet another embodiment, rtP177, rtF178, rtL179, rtL180, rtA181, rtQ182, rtF183 and rtT184; in still yet another embodiment, rtM204 and rtY203; in another embodiment, rt235, rt236, rt237, rt238 and rt239; in a further embodiment, rt247, rt248, rt249, rt250 and rt251 or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

Still a further methodology comprises screening for a mutation in the nucleotide sequence encoding the envelope genes (s) wherein the presence of the following mutations in the S gene: in one embodiment, sP120T, sM125T and sT127A; in another embodiment, sT118R, sM133T, SF134V, sI195M, sS207R and sY225Y/C; in a further embodiment, sS126T, sM133L/M, sS143S/T, sD144A, sG145A and sW172Stop in yet another embodiment, sN40S, sC69Stop, sM75I, sL88P, sT118A, sW182Stop, sW196L, sY206H and sY225F; in still yet another embodiment, sI81M and sP214Q; in another embodiment, sF83S, sL173F and sW199L; in a further aspect, sI126T, sK160R, sS174N, sA184V, sW196L, sS210N, sF/C220L and sY221C; in a further embodiment, sC69Stop/C, sC76Y, sI110V/I, sY134N, sW172Stop/W, sW196Stop and sS207R or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV, and/or optionally other nucleoside or nucleotide analogs or other anti-HBV agents or combination thereof.

Preferably, the variants are in an isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCBs). The term "bodily fluid" includes any fluid derived from the blood, lymph, tissue or organ systems including serum, whole blood, biopsy and biopsy fluid, organ explants and organ suspension such as liver suspensions.

Another aspect of the present invention is directed to a variant HBV comprising a surface antigen having an amino acid sequence with a single or multiple amino acid substitution, addition and/or deletion or a truncation compared to a surface antigen from a reference or wild type HBV and wherein an antibody generated to the reference or wild type surface antigen exhibits an altered immunological profile relative to the HBV variant. One altered profile includes a reduced capacity for neutralizing the HBV. More particularly, the surface antigen of the variant HBV exhibits an altered immunological profile compared to a pre-treatment HBV where the variant HBV is selected for by a nucleoside or nucleotide analog or other anti-HBV agents of the HBV DNA polymerase. The variant HBV of this aspect of the invention may also comprise a nucleotide sequence comprising a single or multiple nucleotide substitution, addition and/or deletion compared to a pre-treatment HBV.

The present invention extends to an isolated HBsAg or a recombinant form thereof or derivative or chemical equivalent thereof corresponding to the variant HBV. Generally, the HBsAg or its recombinant or derivative form or its chemical equivalent comprises an amino acid sequence with a single or multiple amino acid substitution, addition and/or deletion or a truncation compared to an HBsAg from a reference HBV and wherein an antibody directed to a reference HBV exhibits an altered immunological profile to an HBV carrying said variant HBsAg. In one embodiment, the altered immunological profile comprises a reduction in the ability to neutralize the variant HBV.

Another aspect of the present invention contemplates a method for detecting an agent which exhibits inhibitory activity to an HBV by generating a genetic construct comprising a replication competent-effective amount of the genome from the HBV contained in a plasmid vector and then transfecting said cells with said construct, contacting the cells, before, during and/or after transfection, with the agent to be tested, culturing the cells for a time and under conditions sufficient for the HBV to replicate, express genetic sequences and/or assemble and/or release virus or virus-like particles if resistant to said agents; and the subjecting the cells, cell lysates or culture supernatant fluid to viral- or viral-component-detection means to determine whether or not the virus has replicated, expressed genetic material and/or assembled and/or been released in the presence of the agent. In a preferred embodiment, the plasmid vector in a baculovirus vector and the method comprises generating a genetic construct comprising a replication competent-effective amount of the genome from the HBV contained in or fused to an amount of a baculovirus genome effective to infect cells and then infecting said cells with said construct, contacting the cells, before, during and/or after infection, with the agent to be tested, culturing the cells for a time and under conditions sufficient for the HBV to replicate, express genetic sequences and/or assemble and/or release virus or virus-like particles if resistant to said agent and then subjecting the cells, cell lysates or culture supernatant fluid to viral- or viral-component-detection means to determine whether or not the virus has replicated, expressed genetic material and/or assembled and/or been released in the presence of the agent.

In connection with these methods, the plasmid vector may include genes encoding part or all of other viral vectors such as baculovirus vectors or adenovirus vectors (see Ren and Nassal, J. Virol. 75(3): 1104-1116, 2001).

In an alternative embodiment, the method comprises generating a continuous cell line comprising an infectious copy of the genome of the HBV in a replication competent effective amount such that said infectious HBV genome is stably integrated into said continuous cell line such as but not limited to the 2.2.15 or AD cell line, contacting the cells with the agent to be tested, culturing the cells for a time and under conditions sufficient for the HBV to replicate, express genetic sequences and/or assemble and/or release virus or virus-like particles if resistant to the agent and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., Antimicrob Agents Chemother. 46(4): 1005-1013, 2002; Xiong et al., Hepatology. 28(6): 1669-73, 1998). The HBV polymerase may be a wild-type or reference HBV polymerase or mutant HBV polymerase.

The identification of viral variants enables the production of vaccines comprising particular recombinant viral components such as polymerases or envelope genes PreS 1, PreS2, S encoding for L, M, S proteins as well as therapeutic vaccines comprising defective HBV variants. Rational drug design may also be employed to identify or generate therapeutic molecules capable of interacting with a polymerase or envelope genes PreS1, PreS2, S encoding for L, M, S proteins or other component of the HBV. Such drugs may also have diagnostic potential. In addition, defective HBV variants may also be used as therapeutic compositions to generate an immune response against the same, similar or homologous viruses. Alternatively, antibodies generated to the HBV variants or surface components thereof may be used in passive immunization of subjects against infection by HBV variants or similar or homologous viruses. Furthermore, agents such as nucleoside or nucleotide analogs, RNAi or siRNA molecules, antisense or sense oligonucleotides, chemical or proteinaceous molecules having an ability to down-regulate the activity of a component of HBV and inhibit replication, maintenance, infection, assembly or release are contemplated by the present invention.

A summary of the abbreviations used throughout the subject specification are provided in Table 3.

A summary of sequence identifiers used throughout the subject specification is provided in Table 1.

TABLE 1

Summary of sequence identifiers

| SEQUENCE ID NO: | DESCRIPTION |
|---|---|
| 1 | Formula I |
| 2 | Formula II |
| 3 | OS1 primer |
| 4 | TTA3 primer |
| 5 | JM primer |
| 6 | TTA4 primer |
| 7 | OS2 primer |
| 8 | sense primer |
| 9 | antisense primer |
| 10 | internal regions primer |
| 11 | internal regions primer |
| 12 | PC1 forward primer |
| 13 | PC2 reverse primer |
| 14 | HBV-specific molecular beacon primer |
| 15 | ILA 1 F, A-E (FIG. 4) |
| 16 | ILA 2 F, A-E (FIG. 4) |
| 17 | ILA 3 F, A-E (FIG. 4) |
| 18 | ILA 4 F, A-E (FIG. 4) |
| 19 | Pol Trans Pre 1 (FIG. 5) |
| 20 | Pol Trans 2 (FIG. 5) |
| 21 | Pol Trans 3 (FIG. 5) |
| 22 | Pol Trans 4 (FIG. 5) |
| 23 | HBsAg Trans of Pre 1 (FIG. 6) |
| 24 | HBsAg Trans of 2 (FIG. 6) |
| 25 | HBsAg Trans of 3 (FIG. 6) |
| 26 | HBsAg Trans of 4 (FIG. 6) |
| 27 | S0 (FIG. 7) |
| 28 | S6 (FIG. 7) |
| 29 | S8 (FIG. 7) |
| 30 | S12 (FIG. 7) |
| 31 | S15 (FIG. 7) |
| 32 | Pol Trans S0 (FIG. 8) |
| 33 | Pol Trans S6 (FIG. 8) |
| 34 | Pol Trans S8 (FIG. 8) |
| 35 | Pol Trans S12 (FIG. 8) |
| 36 | Pol Trans S15 (FIG. 8) |
| 37 | HBsAg Trans of S0 (FIG. 9) |
| 38 | HBsAg Trans of S6 (FIG. 9) |
| 39 | HBsAg Trans of S8 (FIG. 9) |
| 40 | HBsAg Trans of S12 (FIG. 9) |
| 41 | HBsAg Trans of S15 (FIG. 9) |
| 42 | Nucleotide sequence Patient C (FIG. 10) |
| 43 | POL Trans of Patient C (FIG. 11) |
| 44 | HBsAg Trans of Patient C ( FIG. 12) |
| 45 | Nucleotide sequence of Patient D (FIG. 13) |
| 46 | Pol Trans of Patient D (FIG. 14) |
| 47 | HBsAg Trans of Patient D (FIG. 15) |
| 48 | Nucleotide sequence of Patient E (FIG. 16) |
| 49 | Pol Trans of Patient E (FIG. 17) |
| 50 | HBsAg Trans of Patient E (FIG. 18) |
| 51 | Nucleotide sequence of Patient F (FIG. 20) |
| 52 | Deduced sequence of DNA polymerase of Patient F (FIG. 21) |
| 53 | HBsAg Trans of Patient F (FIG. 22) |
| 54 | Nucleotide sequence of Patient G (FIG. 23) |
| 55 | Deduced sequence of DNA polymerase of Patient G (FIG. 24) |
| 56 | HBsAg Trans of Patient G (FIG. 25) |
| 57 | Nucleotide sequence of Patient H (FIG. 26) |
| 58 | Deduced sequence of DNA polymerase of Patient H (FIG. 27) |
| 59 | HBsAg Trans of Patient H (FIG. 28) |

TABLE 2

Single and three letter amino acid abbreviations

| Amino Acid | Three-letter Abbreviation | One-letter symbol |
|---|---|---|
| Alanine | Ala | A |
| Arginine | Arg | R |
| Asparagine | Asn | N |
| Aspartic acid | Asp | D |
| Cysteine | Cys | C |
| Glutamine | Gln | Q |
| Glutamic acid | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | The | T |
| Tryptophan | Trp | W |
| Tyrosine | Tyr | Y |
| Valine | Val | V |
| Any residue | Xaa | X |

A list of abbreviations used throughout the subject specification are provided in Table 3.

TABLE 3

Abbreviations

| ABBREVIATION | DESCRIPTION |
|---|---|
| 3TC | (LMV); (-)-β-2'-deoxy-3'-thiacytidine |
| ADV | adefovir dipivoxil |
| DAPD | diaminopurine dioxalone |
| DXG | dioxolane guanine |
| ETV | entecavir |
| FAM | famciclovir |
| FCV | famciclovir |
| FTC | emtricitabine |
| HBIG | hepatitis B immunoglobulin |
| HBsAg | hepatitis B surface antigen |
| HBV | hepatitis B virus |
| LMV | lamividuine |
| PMEA | 9-[phosphonyl-methoxyethyl]-adenine; adefovir |
| PMPA | 9-R-(2-phosphonomethoxypropyl)adenine |
| RNase | ribonuclease |
| rt ("rt" before "$Xaa_1nXaa_2$" means reverse transcriptase) | reverse transcriptase |
| s (as used in a mutation, e.g. sF134V) | envelope gene |
| TFV | tenofovir disoproxil fumarate |
| YMDD | Tyr Met Asp Asp-a motif in the polymerase protein; where the Met residue is designated residue number 204 of the reverse transcriptase |

BRIEF DESCRIPTION OF THE FIGURES

FIG. 4 is a representation showing comparison of the HBV nucleotide sequence encoding the catalytic region of the polymerase gene in sequential samples from Patient A during ADV treatment.

FIG. 5 is a representation showing comparison of the deduced amino acid sequence of the catalytic region of the polymerase gene in sequential samples from Patient A during ADV therapy.

FIG. 6 is a representation showing comparison of the deduced amino acid sequence of the envelope gene in sequential samples from Patient A during ADV therapy.

FIG. 7 is a representation showing comparison of the HBV nucleotide sequence encoding the catalytic region of the polymerase gene in sequential samples from Patient B during ADV and LMV treatment.

FIG. 8 is a representation showing comparison of the deduced amino acid sequence of the catalytic region of the polymerase gene in sequential samples from Patient B during ADV and LMV therapy.

FIG. 9 is a representation showing comparison of the deduced amino acid sequence of the envelope gene in sequential samples from Patient B during ADV and LMV therapy.

FIG. 10 is a representation showing comparison of the HBV nucleotide sequence encoding the catalytic region of the polymerase gene in sequential samples from Patient C during ADV treatment.

FIG. 11 is a representation showing comparison of the deduced amino acid sequence of the catalytic region of the polymerase gene in sequential samples from Patient C during ADV therapy.

FIG. 12 is a representation showing comparison of the deduced amino acid sequence of the envelope gene in sequential samples from Patient C during ADV therapy.

FIG. 13 is a representation showing comparison of the HBV nucleotide sequence encoding the catalytic region of the polymerase gene in sequential samples from Patient D during ADV treatment.

FIG. 14 is a representation showing comparison of the deduced amino acid sequence of the catalytic region of the polymerase gene in sequential samples from Patient D during ADV therapy.

FIG. 15 is a representation showing comparison of the deduced amino acid sequence of the envelope gene in sequential samples from Patient D during ADV therapy.

FIG. 16 is a representation showing comparison of the HBV nucleotide sequence encoding the catalytic region of the polymerase gene in sequential samples from Patient E during ADV treatment.

FIG. 17 is a representation showing comparison of the deduced amino acid sequence of the catalytic region of the polymerase gene in sequential samples from Patient E during ADV therapy.

FIG. 18 is a representation showing comparison of the deduced amino acid sequence of the envelope gene in sequential samples from Patient E during ADV therapy.

FIG. 20 is a representation showing the nucleotide sequence of envelope/rt region of an HBV isolated from Patient F having ADV therapy.

FIG. 21 is a representation showing the deduced amino acid sequence of DNA polymerase encoded by the nucleotide sequence shown in FIG. 20.

FIG. 22 is a representation showing the deduced amino acid sequence of HBsAg encoded by the nucleotide sequence shown in FIG. 20.

FIG. 23 is a representation showing the nucleotide sequence of envelope/rt region of an HBV isolated from Patient G having ADV therapy.

FIG. 24 is a representation showing the deduced amino acid sequence of DNA polymerase encoded by the nucleotide sequence shown in FIG. 23.

FIG. 25 is a representation showing the deduced amino acid sequence of HBsAg encoded by the nucleotide sequence shown in FIG. 23.

FIG. 26 is a representation showing the nucleotide sequence of envelope/rt region of an HBV isolated from Patient H having ADV therapy.

FIG. 27 is a representation showing the deduced amino acid sequence of DNA polymerase encoded by the nucleotide sequence shown in FIG. 26.

FIG. 28 is a representation showing the deduced amino acid sequence of HBsAg encoded by the nucleotide sequence shown in FIG. 26.

DETAILED DESCRIPTION OF THE INVENTION

Figure 1:
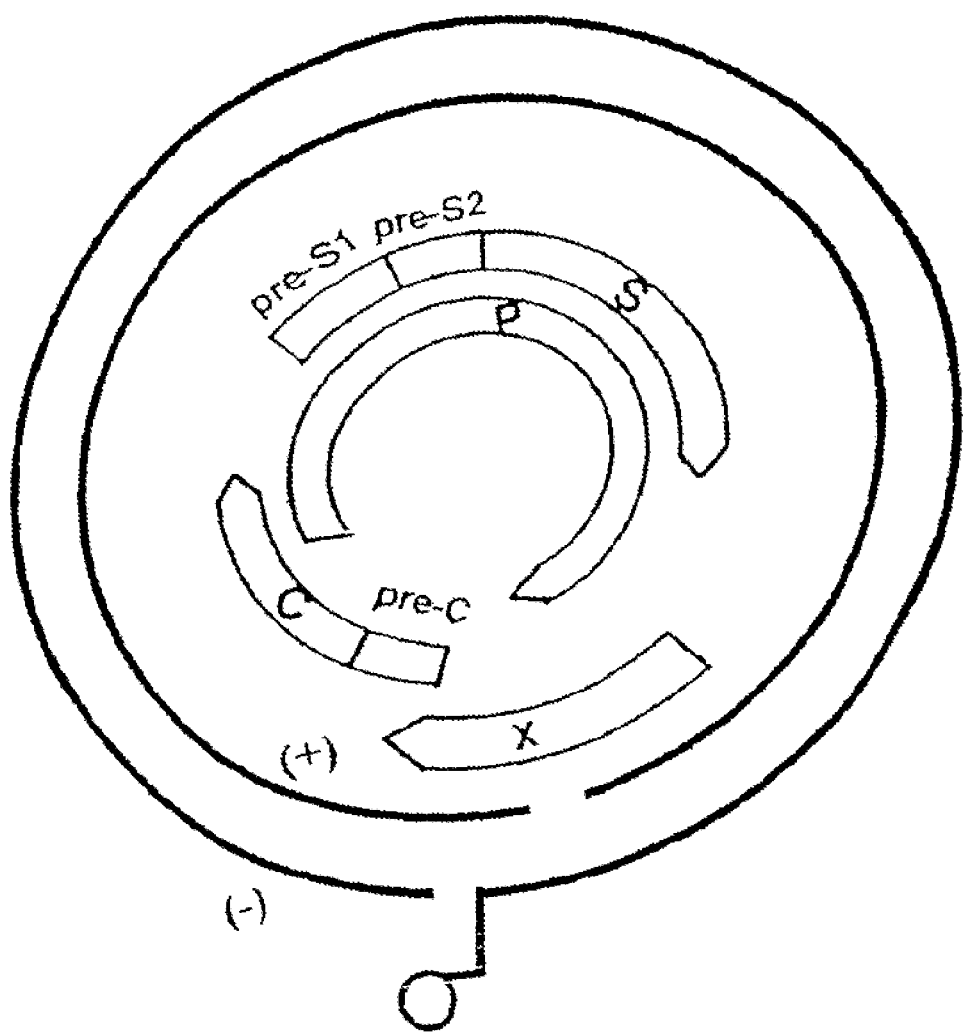
FIG. 1 is a diagrammatic representation showing the partially double stranded DNA HBV genome showing the overlapping open reading frames encoding surface (S), core (C), polymerase (P) and X gene.

The present invention is predicated in part on the identification and isolation of nucleoside or nucleotide analog-resistant variants of HBV following treatment of patients with either ADV or LMV or more particularly ADV and LMV, or optionally other nucleoside analogs or nucleotide analogs or other anti-HBV agents such as TFV or FTC. In particular, ADV or ADV and LMV treated patients gave rise to variants of HBV exhibiting decreased or reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV. Reference herein to "decreased" or "reduced" in relation to sensitivity to ADV and/or LMV and/or FTC and/or TFV includes and encompasses a complete or substantial resistance to the nucleoside or nucleotide analog or other anti-HBV agents as well as partial resistance and includes a replication rate or replication efficiency which is more than a wild-type in the presence of a nucleoside or nucleotide analog or other anti-HBV agents. In one aspect, this is conveniently measured by an increase in viral load during treatment, or alternatively, there is no substantial decrease in HBV DNA viral load from pre-treatment HBV DNA levels during treatment (i.e., non-response to treatment).

Before describing the present invention in detail, it is to be understood that unless otherwise indicated, the subject invention is not limited to specific formulations of components, manufacturing methods, dosage regimens, or the like, as such may vary. It is also to be understood that the terminology used herein is for the purpose of describing particular embodiments only and is not intended to be limiting.

It must be noted that, as used in the subject specification, the singular forms "a", "an" and "the" include plural aspects unless the context clearly dictates otherwise. Thus, for example, reference to "a nucleoside or nucleotide analog" includes a single analog, as well as two or more analogs; reference to "an HBV variant" includes reference to two or more HBV variants; and so forth.

In describing and claiming the present invention, the following terminology is used in accordance with the definitions set forth below.

The terms "analog", "compound", "active agent", "pharmacologically active agent", "medicament", "active" and "drug" are used interchangeably herein to refer to a chemical compound that induces a desired effect such as inhibit viral replication, infection, maintenance, assembly and/or the function of an enzyme such as HBV DNA polymerase. The terms also encompass pharmaceutically acceptable and pharmacologically active ingredients of those active agents specifically mentioned herein including but not limited to salts, esters, amides, prodrugs, active metabolites, analogs and the like. When the terms "analog", "compound", "active agent", "pharmacologically active agent", "medicament", "active" and "drug" are used, then it is to be understood that this includes the active agent per se as well as pharmaceutically acceptable, pharmacologically active salts, esters, amides, prodrugs, metabolites, analogs, etc.

The present invention contemplates, therefore, compounds useful in inhibiting HBV replication, infection, maintenance, assembly and/or the function of an enzyme such as HBV DNA polymerase. Reference to an "analog", "compound", "active agent", "pharmacologically active agent", "medicament", "active" and "drug" such as ADV, LMV, FTC and/or TFV includes combinations of two or more actives such as ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV. A "combination" also includes a two-part or more such as a multi-part anti-HBV therapeutic composition where the agents are provided separately and given or dispensed separately or admixed together prior to dispensation.

The terms "effective amount" and "therapeutically effective amount" of an agent as used herein mean a sufficient amount of the agent to provide the desired therapeutic or physiological effect of inhibiting HBV replication, infection, maintenance, assembly and/or the function of an enzyme such as HBV DNA polymerase. Furthermore, an "effective HBV-inhibiting amount" or "effective symptom-ameliorating amount" of an agent is a sufficient amount of the agent to directly or indirectly inhibit replication, infection, maintenance, assembly and/or the function of an enzyme such as HBV DNA polymerase. Undesirable effects, e.g. side effects, are sometimes manifested along with the desired therapeutic effect; hence, a practitioner balances the potential benefits against the potential risks in determining what is an appropriate "effective amount". The exact amount required will vary from subject to subject, depending on the species, age and general condition of the subject, mode of administration and the like. Thus, it may not be possible to specify an exact "effective amount". However, an appropriate "effective amount" in any individual case may be determined by one of ordinary skill in the art using only routine experimentation.

By "pharmaceutically acceptable" carrier, excipient or diluent is meant a pharmaceutical vehicle comprised of a material that is not biologically or otherwise undesirable, i.e. the material may be administered to a subject along with the selected active agent without causing any or a substantial adverse reaction. Carriers may include excipients and other additives such as diluents, detergents, coloring agents, wetting or emulsifying agents, pH buffering agents, preservatives, and the like.

Similarly, a "pharmacologically acceptable" salt, ester, emide, prodrug or derivative of a compound as provided herein is a salt, ester, amide, prodrug or derivative that this not biologically or otherwise undesirable.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage in relation to HBV infection. Thus, for example, "treating" a patient involves prevention of HBV infection as well as treatment of a clinically HBV symptomatic individual by inhibiting HBV replication, infection, maintenance, assembly and/or the function of an enzyme such as HBV DNA polymerase. Thus, for example, the present method of "treating" a patient with HBV infection or with a propensity for one to develop encompasses both prevention of HBV infection as well as treating HBV infection or symptoms thereof. In any event, the present invention contemplates the treatment or prophylaxis of HBV infection.

"Patient" as used herein refers to an animal, preferably a mammal and more preferably a primate including a lower primate and even more preferably, a human who can benefit from the formulations and methods of the present invention. A patient regardless of whether a human or non-human animal may be referred to as an individual, subject, animal, host or recipient. The compounds and methods of the present invention have applications in human medicine, veterinary medicine as well as in general, domestic or wild animal husbandry. For convenience, an "animal" includes an avian species such as a poultry bird (including ducks, chicken, turkeys and geese), an aviary bird or game bird. The condition in a non-human animal may not be a naturally occurring HBV infection but HBV-like infection may be induced.

As indicated above, the preferred animals are humans, non-human primates such as marmosets, baboons, orangutans, lower primates such as tupia, livestock animals, laboratory test animals, companion animals or captive wild animals. A human is the most preferred target. However, non-human animal models may be used.

Examples of laboratory test animals include mice, rats, rabbits, guinea pigs and hamsters. Rabbits and rodent animals, such as rats and mice, provide a convenient test system or animal model as do primates and lower primates. Livestock animals include sheep, cows, pigs, goats, horses and donkeys. Non-mammalian animals such as avian species, zebrafish, amphibians (including cane toads) and *Drosophila* species such as *Drosophila melanogaster* are also contemplated. Instead of a live animal model, a test system may also comprise a tissue culture system.

Accordingly, one aspect of the present invention is directed to an isolated HBV variant wherein said variant comprises a nucleotide mutation in a gene encoding a DNA polymerase resulting in at least one amino acid addition, substitution and/or deletion to said DNA polymerase and wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, or ADV and LMV and FTC, ADV and FTC and LMV and TFV and/or optionally other nucleoside or nucleotide analogs or other anti-HBV agents or combination thereof.

HBV is a member of the Hepadnaviridae that includes also avian hepatitis viruses such as Duck hepatitis B virus (DHBV) and hepatitis viruses from mammals such as woodchuck hepatitis virus (WHV). These viruses have similarity to HBV and may be used in in vitro and in vivo or animal model systems to investigate the equivalent HBV mutants and anti-viral sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV, An "anti-HBV agent" includes a nucleoside or nucleotide analog, protein, chemical compound, RNA or DNA or RNAi or siRNA oligonucleotide.

Preferably, the decreased sensitivity is in respect of ADV. Alternatively, the decreased sensitivity is in respect of LMV. Alternatively, the decreased sensitivity is in respect of TFV. Alternatively, the decreased sensitivity is in respect of FTC. Alternatively, the decreased sensitivity is in respect of ADV and LMV. Alternatively, the decreased sensitivity is in respect of ADV and TFV. Alternatively, the decreased sensitivity is in respect of LMV and TFV. Alternatively, the decreased sensitivity is in respect of ADV and FTC. Alternatively, the decreased sensitivity is in respect to FTC and TFV. Alternatively, the decreased sensitivity is in respect of FTC and LMV. Alternatively, the decreased sensitivity is in respect of ADV and LMV and TFV. Alternatively, the decreased sensitivity is in respect to ADV and TFV and FTC. Alternatively, the decreased sensitivity is in respect to LMV and TFV and FTC. Alternatively, the decrease sensitivity is in respect of ADV and LMV and FTC. Alternatively, the decreased sensitivity is in respect of ADV and FTC and TFV and LMV.

Reference herein to "anti-HBV agents" includes nucleoside and nucleotide analogs as well as immunological reagents (e.g. antibodies to HBV surface components) and chemical, proteinaceous and nucleic acid agents which inhibit or otherwise interfere with viral replication, maintenance, infection, assembly or release. Reference herein to "nucleic acid" includes reference to a sense or antisense molecule, RNA or DNA, oligonucleotides and RNAi and siRNA molecules and complexes containing same.

In addition to a mutation in the gene encoding DNA polymerase, due to the overlapping nature of the HBV genome (FIG. 1), a corresponding mutation may also occur in the gene encoding the S gene encoding the surface antigen (HBsAg) resulting in reduced interactivity of immunological reagents such as antibodies and immune cells to HBsAg. The reduction in the interactivity of immunological reagents to a viral surface component generally includes the absence of immunological memory to recognize or substantially recognize the viral surface component. The present invention extends, therefore, to an HBV variant exhibiting decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, and/or ADV and FTC and LMV and TFV or a reduced interactivity of an immunological reagent to HBsAg wherein the variant is selected for following ADV and/or LMV combination or sequential treatment. The term "sequential" in this respect means ADV followed by LMV and/or TFV, and/or FTC, LMV followed by ADV and/or TFV, and/or FTC, or multiple sequential administrations of each of ADV, LMV and/or TFV, and/or FTC.

A viral variant may, therefore, carry mutation only in the DNA polymerase gene or both in the DNA polymerase gene and the S gene. The term "mutation" is to be read in its broadest context and includes multiple mutations.

The present invention extends to a Mutation and any domain of the HBV DNA polymerase and in particular regions F and G, and domains A through to E provided said mutation leads to decreased sensitivity to ADV and/or LMV and/or TFV or combinations thereof. Regions F and G of the HBV DNA polymerase is defined by the amino acid sequence set forth in Formula I below [SEQ ID NO:1]:

```
FORMULA I
L, X1, X2, D, W, G, P, C, X3, X4, H, G, X5, H, X6, I, R, B7, P, R, T, P, X8,

R, V, X9, G, G, V, F, L, V, D, K, N, P, H, N, T, X10, E, S, X11, L, X12, V, D, F, S, Q,

F, S, R, G, X13, X14, X15, V, P, K, F, A, V, P, N, L, X16, S, L, T, N, L, L, S*
``` wherein:
X$_1$ is L, or R, or I
X$_2$ is E, or D
X$_3$ is T, or D, or A, or N, or Y
X$_4$ is E, or D
X$_5$ is E, or K, or Q
X is H, or R, or N,
X$_7$ is I, or T
X$_2$ is A, or S
X$_9$ is T or R
X$_{10}$ is A, or T, or S
X$_{11}$ is R, or T
X$_{12}$ is V, or G
X$_{13}$ is S, or I, or T, or N, or V
X$_{14}$ is T, or S, or H, or Y
X$_{15}$ is R, or H, or K, or Q
X$_{16}$ is Q, or P;
and wherein S* is designated as amino acid 74.

In this specification, reference is particularly made to the conserved regions of the DNA polymerase as defined by domains A to E. Regions A to E are defined by the amino acid sequence set forth in Formula II below [SEQ ID NO:2] (and in Australian Patent No. 734831):

```
FORMULA II
S X1 L S W L S L D V S AA F Y H X2 P L H P AA M P H L L X3 G S S

G L X4 R Y V A R L S S X5 S X6 X7 X N X8 Q X9 X10 X X X X11 L H X12 X13 C S R X14

L Y V S L X15 L L Y X16 T X17 G X18 K L H L X19 X20 H P I X21 L G F R K X22 P M G

X23 G L S P F L L A Q F T S A I X24 X25 X26 X27 X28 R A F X29 H C X30 X31 F X32 Y

M* D D X33 V L G A X34 X35 X36 X37 H X38 E X39 L X40 X41 X42 X43 X44 X45 X46 L L

X47 X48 G I H L N P X49 K T K R W G Y S L N F M G Y X50 I G
``` wherein: X is any amino acid
X$_1$ is N or D;
X$_2$ is 1 or 1';
X$_3$ is I or V;

$X_4$ is S or D;
$X_5$ is T or N;
$X_6$ is R or N;
$X_7$ is N or I;
$X_8$ is N or Y or H;
$X_9$ is H or Y;
$X_{10}$ is G or R;
$X_{11}$ is D or N;
$X_{12}$ is D or N;
$X_{13}$ is S or Y;
$X_{14}$ is N or Q;
$X_{15}$ is L or M;
$X_{16}$ is K or Q;
$X_{17}$ is Y or F;
$X_{18}$ is R or W;
$X_{19}$ is Y or L;
$X_{20}$ is or A;
$X_{21}$ is I or V;
$X_{22}$ is I or L;
$X_{23}$ is V or G;
$X_{24}$ is C or L;
$X_{25}$ is A or S;
$X_{26}$ is V or M;
$X_{27}$ is V or T;
$X_{28}$ is R or C;
$X_{29}$ is F or P;
$X_{30}$ is L or V;

```
FORMULA I
L, X₁, X₂, D, W, G, P, C, X₃, X₄, H, G, X₅, H, X₆, I, R, X₇, P, R, T,

P, X₈, R, V, X₉, G, G, V, F, L, V, D, K, N, P, H, N, T, X₁₀, E, S, X₁₁, L, X₁₂, V,

D, F, S, Q, F, S, R, G, X₁₃, X₁₄, X₁₅, V, S, W, P, K, F, A, V, P, N, L, X₁₆, S, L,

T, N, L, L, S*
```

$X_{31}$ is A or V;
$X_{32}$ is S or A;
$X_{33}$ is V or L or M;
$X_{34}$ is K or R;
$X_{35}$ is S or T;
$X_{36}$ is V or G;
$X_{37}$ is Q or E;
$X_{38}$ is L or S or R;
$X_{39}$ is S or F;
$X_{40}$ is F or Y;
$X_{41}$ is T or A;
$X_{42}$ is A or S;
$X_{43}$ is V or I;
$X_{44}$ is T or C;
$X_{45}$ is N or S;
$X_{46}$ is F or V;
$X_{47}$ is S or D;
$X_{48}$ is L or V;

$X_{49}$ is N or Q;
$X_{50}$ is V or I; and
M* is amino acid 204; and wherein the first S is designated as amino acid 75.

Preferably, the mutation results in an altered amino acid sequence in any one or more of domains F and G, and domains A through to E or regions proximal thereto of the HBV DNA polymerase.

Another aspect of the present invention provides an HBV variant comprising a mutation in an overlapping open reading frame in its genome wherein said mutation is in a region defined by one or more of domains F and G, and domains A through to E of HBV DNA polymerase and wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents.

In a related embodiment, there is provided an HBV variant comprising a mutation in the nucleotide sequence encoding a DNA polymerase resulting in an amino acid addition, substitution and/or deletion in said DNA polymerase in one or more amino acids as set forth in Formula I [SEQ ID NO:1] and/or Formula II [SEQ ID NO:2]:

wherein:
$X_1$ is L, or R, or I
$X_2$ is E, or D
$X_3$ is T, or D, or A, or N, or Y
$X_4$ is E, or D
$X_5$ is E, or K, or Q
$X_6$ is H, or R, or N,
$X_7$ is I, or T
$X_8$, is A, or S
$X_9$ is T or R
$X_{10}$ is A, or T, or S
$X_{11}$ is R, or T
$X_{12}$ is V, or G
$X_{13}$ is S, or I, or T, or N, or V
$X_{14}$ is T, or S, or H, or Y
$X_{15}$ is R, or H, or K, or Q
$X_{16}$ is Q, or P;
and

```
FORMULA II
S X₁ L S W L S L D V S AA F Y H X₂ P L H P AA M P H L L X₃ G S S

G L X₄ R Y V A R L S S X₅ X₆ X₇ X N X₈ Q X₉ X₁₀ X X X X₁₁ L H X₁₂ X₁₃ C S R X₁₄

L Y V S L X₁₅ L L Y X₁₆ T X₁₇ N G X₁₈ K L H L X₁₉ X₂₀ H P I X₂₁ L G F R K X₂₂ P M G

X₂₃ G L S P F L L A Q F T S A I X₂₄ X₂₅ X₂₆ X₂₇ X₂₈ R A F X₂₉ H C X₃₀ X₃₁ F X₃₂ Y

M* D D X₃₃ V L G A X₃₄ X₃₅ X₃₆ X₃₇ H X₃₈ X₃₉ L X₄₀ X₄₁ X₄₂ X₄₃ X₄₄ X₄₅ X₄₆ L L X₄₇

X₄₈ G I H L N P X₄₉ K T K R W G Y S L N F M G Y X₅₀ I G
``` wherein: X is any amino acid
$X_1$ is N or D;
$X_2$ is I or P;
$X_3$ is or V;
$X_4$ is S or D;
$X_5$ is T or N;
$X_6$ is R or N;
$X_7$ is N or I;
$X_8$ is N or Y or H;
$X_9$ is H or Y;
$X_{10}$ is G or R;
$X_{11}$ is D or N;
$X_{12}$ is D or N;
$X_{13}$ is S or Y;
$X_{14}$ is N or Q;
$X_{15}$ is L or M;
$X_{16}$ is K or Q;
$X_{17}$ is Y or F;
$X_{18}$ is R or W;
$X_{19}$ is Y or L;
$X_{20}$ is S or A;
$X_{21}$ is I or V;
$X_{22}$ is I or L;
$X_{23}$ is V or G;
$X_{24}$ is C or L;
$X_{25}$ is A or S;
$X_{26}$ is V or M;
$X_{27}$ is V or T;
$X_{28}$ is R or C;
$X_{29}$ is F or P;
$X_{30}$ is L or V;
$X_{31}$ is A or V;
$X_{32}$ is S or A;
$X_{33}$ is V or L or M;
$X_{34}$ is K or R;
$X_{35}$ is S or T;
$X_{36}$ is V or G;
$X_{37}$ is Q or E;
$X_{38}$ is L or S or R;
$X_{39}$ is S or F;
$X_{40}$ is F or Y;
$X_{41}$ is T or A;
$X_{42}$ is A or S;
$X_{43}$ is V or I;
$X_{44}$ is T or C;
$X_{45}$ is N or S;
$X_{46}$ is F or V;
$X_{47}$ is S or D;
$X_{48}$ is L or V;
$X_{49}$ is N or Q;
$X_{50}$ is V or I; and M* is amino acid 204; and wherein S* in Formula I is designated as amino acid 74 and the first S in Formula II is designated as amino acid 75; and wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. Preferably, the decreased sensitivity is to ADV or to both ADV and LMV or to one or both of ADV and/or LMV and/or TFV and for FTC.

Another preferred aspect of the present invention contemplates an HBV variant comprising a mutation in the nucleotide sequence encoding HBsAg resulting in an amino acid addition, substitution and/or deletion in said HBsAg in a region corresponding to the amino acid sequence set forth in Formulae I and II wherein said variant exhibits decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

More particularly, the present invention provides a variant HBV comprising a surface antigen having an amino acid sequence with a single or multiple amino acid substitution, addition and/or deletion or a truncation compared to a surface antigen from a reference or wild-type HBV and wherein an antibody generated to the reference or wild-type surface antigen exhibits reduced capacity for neutralizing said HBV variant, said variant selected by exposure of a subject to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The term "combination therapy" means that both combinations of ADV, LMV, FTC and/or TFV are co-administered in the same composition or simultaneously in separate compositions. The term "sequential therapy" means that the two agents are administered within seconds, minutes, hours, days or weeks of each other and in either order. Sequential therapy also encompasses completing a therapeutic course with one or other of ADV, LMV, FTC or TFV and then completing a second or third or subsequent therapeutic courses with the other of ADV, LMV, FTC or TFV.

Accordingly, another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and LMV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and TFV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to LMV and TFV therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV and FTC therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to TFV and FTC therapy or therapy by one or more other nucleoside or nucleotide analogs or other anti-HBV agents.

Still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC and LMV therapy or therapy by one or more other nucleoside or nucleotide analogs or other anti-HBV agents.

Even yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV therapy or therapy by one or more other nucleoside or nucleotide analogs or other anti-HBV agents.

Even still another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and TFV therapy or therapy by one or more other nucleoside or nucleotide analogs or other anti-HBV agents.

A further aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV and FTC therapy or therapy by one or more other nucleoside or nucleotide analogs or other anti-HBV agents.

Another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to FTC, LMV and TFV therapy or therapy by one or more other nucleoside or nucleotide analogs or other anti-HBV agents.

Yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, FTC and TFV therapy or therapy by one or more other nucleoside or nucleotide analogs or other anti-HBV agents.

Still yet another aspect of the present invention contemplates an HBV variant comprising a surface antigen having an amino acid sequence with a single or multiple amino acid substitution, addition and/or deletion or truncation compared to the pretreatment HBV and wherein the surface antigen of the variant HBV exhibits an altered immunological profile compared to the pretreatment HBV where the said variant HBV is selected for by exposure of a subject to ADV, LMV, FTC and TFV therapy or therapy by one or more other nucleoside or nucleotide analogs or other anti-HBV agents.

Preferably, the variants are in isolated form such that they have undergone at least one purification step away from naturally occurring body fluid. Alternatively, the variants may be maintained in isolated body fluid or may be in DNA form. The present invention also contemplates infectious molecular clones comprising the genome or parts thereof from a variant HBV. Furthermore, the present invention provides isolated components from the variant HBVs such as but not limited to an isolated HBsAg. Accordingly, the present invention provides an isolated HBsAg or a recombinant form thereof or derivative or chemical equivalent thereof, said HBsAg being from a variant HBV selected by exposure of a subject to one or more of ADV, LMV, FTC and/or TFV or optionally one or more nucleoside or nucleotide analogs or other anti-HBV agents.

More particularly, yet another aspect of the present invention is directed to an isolated variant HBsAg or a recombinant or derivative form thereof or a chemical equivalent thereof wherein said HBsAg or its recombinant or derivative form or its chemical equivalent exhibits an altered immunological profile compared to an HBsAg from a reference HBV, said HBsAg being from a variant HBV selected by exposure of a subject to one or more of ADV, LMV, FTC and/or TFV or optionally one or more nucleoside or nucleotide analogs or other anti-HBV agents.

Even more particularly, the present invention provides an isolated variant HBsAg or a recombinant or derivative form thereof or a chemical equivalent thereof wherein said HBsAg or its recombinant or derivative form or its chemical equivalent comprises an amino acid sequence with a single or multiple amino acid substitution, addition and/or deletion or a truncation compared to an HBsAg from a reference HBV and wherein a neutralizing antibody directed to a reference HBV exhibits no or reduced neutralizing activity to an HBV carrying said variant HBsAg, said HBsAg being from a variant HBV selected by exposure of a subject to one or more of ADV, LMV, FTC and/or TFV or optionally one or more nucleoside or nucleotide analogs or other anti-HBV agents.

Preferred mutations in the HBV DNA polymerase include variants selected from patients with HBV recurrence following ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV treatment. Nucleoside or nucleotide analog or other anti-HBV agents treatment may occur in relation to a transplantation procedure (e.g. bone marrow transplantation (BMT) or OLT) or following treatment of patients diagnosed with hepatitis. Following selection of variants, viral loads are obtainable at levels similar to pre-treatment levels or are increasing while on therapy.

Preferred mutations include, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D, and rtL/F108L; in even yet another embodiment, rtL157L/M, rtA181V and rtV207I; in still yet another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/F/S/Stop215Q, rtE218K/E and rtN238N/H; in a further embodiment, rtK32, rtN33, rtP34, rtH35 and rtT37; in yet another embodiment, rtP59, rtK60, rtF61, rtA62 and rtV63; in still another embodiment, rtD83, rtV84, rtS85, rtA86, rtY89, rtH90 and rtI/L91; in even yet another embodiment, rtP177, rtF178, rtL179, rtL180, rtA181, rtQ182, rtF183 and rtT184; in still yet another embodiment, rtM204 and rtY203; in another embodiment, rt235, rt236, rt237, rt238 and rt239; in a further embodiment, rt247, rt248, rt249, rt250 and rt251; in yet another embodiment.

K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/N/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E; and
V251A/R/N/D/C/Q/E/G/H/I/L/K/M/F/P/S/T/W/Y.

Reference above to "deletion" means that the first mentioned amino acid before the residue number has been deleted.

Such HBV variants are proposed to exhibit a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. It should be noted that the nomenclature system for amino acid positions is based on the methionine residues in the YMDD motif being designated codon rtM204. This numbering system is different to that iii Australian Patent No. 734831 where the methionine residue in the YMDD motif within the polymerase gene is designated codon 550. In this regard, rtL180M and rtM204V correspond to L526M and M550V, respectively, in Australian Patent No. 734831. Corresponding mutations may also occur in envelope genes such as in one or more of PreS1, PreS2 and S. The mutations in S gene encoding HBsAg at sT118R, sP120T, sS143S/T, sD144A or sI195M also result in mutation in the in the polymerase gene rtY126C, rtT128N, rtF151S/F or rtM204V respectively.

Another potential mode of action of ADV and other acyclic nucleoside phosphonates is that of immune stimulation (Calio et al., Antiviral Res. 23: 77-89, 1994). A number of mutations resulted in changes in the envelope gene detected in HBV variants which may be associated with immune escape. These changes include sT118R, sP120T, sS126T, sM133T, sM133L/M, sF134V, sS143S/T, sD144A, sG145A and/or sW172STOP.

HBV encoding the mutation at codon sG145R is a well characterized vaccine escape mutant, although the envelope protein from HBV encoding the mutation at sG145A does not have the same antigen/antibody binding characteristics as the sG145R. This mutation was detected in HBV isolated from patient C in conjunction with mutations at codons 143 and 144.

The identification of the variants of the present invention permits the generation of a range of assays to detect such variants. The detection of such variants may be important in identifying resistant variants to determine the appropriate form of chemotherapy and/or to monitor vaccination protocols, or develop new or modified vaccine preparations.

Still another aspect of the present invention contemplates a method for determining the potential for an HBV to exhibit reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and A domains through to E or a region proximal thereto of said DNA polymerase and associated with resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents wherein the presence of such a mutation is an indication of the likelihood of resistance to said ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents.

Preferably, the assay detects one or more of the following mutations: in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L; in even yet another embodiment, sP120T, sM125T and sT127A; in still yet another embodiment, sT118R, sM133T, SF134V, sI195M, sS207R and sY225Y/C; in another embodiment, sS126T, sM133L/M, sS143S/T, sD144A, sG145A and sW172Stop; in a further embodiment, sN40S, sC69STOP, sM75I, sL88P, sT118A, sW182Stop, sW196L, sY206H and sY225F; in yet another embodiment, s181M and sP214Q; in still another embodiment, sF83S, sL173F and sW199L; in yet another embodiment, sI126T, sK160R, sS174N, sA184V, sW196L, sS210N, sF/C220L and sY221C; in still another embodiment, sC69Stop/C, sC76Y, sI110V/I, sY134N, sW172Stop/W, sW196Stop, sS207R; in even still another embodiment, rtK32, rtN33, rtP34, rtH35 and rtT37); in another embodiment, rtP59, rtK60, rtF61, rtA62 and rtV63); in a further embodiment, rtD83, rtV84, rtS85, rtA86, rtY89, rtH90 and rtI/L91); in yet another embodiment, rtP177, rtF178, rtL179, rtL180, rtA181, rtQ182, rtF183 and rtT184; in still another embodiment, rtM204 and rtY203; in even yet another embodiment, rt235, rt236, rt237, rt238 and rt239 and in even still another embodiment, rt247, rt248, rt249, rt250 and rt251 and in another embodiment, K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M//deletionF;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H23SI/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion;
and
V251A/R/N/D/C/Q/E/G/H/I/L/K/M/F/P/S/T/W/Y/deletion or combinations thereof or an equivalent one or more other mutation is indicative of a variant wherein said variant exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

Accordingly, another aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rt212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L; in even yet another embodiment, sP120T, sM125T and sT127A; in still yet another embodiment, sT118R, sM133T, SF134V, sI195M, sS207R and sY225Y/C; in another embodiment, sS126T, sM133L/M, sS143S/T, sD144A, sG145A and sW172Stop; in a further embodiment, sN40S, sC69STOP, sM75I, sL88P, sT118A, sW182Stop, sW196L, sY206H and sY225F; in yet another embodiment, s181M and sP214Q; in still another embodiment, sF83S, sL173F and sW199L; in yet another embodiment, sI126T, sK160R, sS174N, sA184V, sW196L, sS210N, sF/C220L and sY221C; in still another embodiment, sC69Stop/C, sC76Y, sI110V/I, sY134N, sW172Stop/W, sW196Stop, sS207R; in even still another embodiment, rtK32, rtN33, rtP34, rtH35 and rtT37); in another embodiment, rtP59, rtK60, rtF61, rtA62 and rtV63); in a further embodiment, rtD83, rtV84, rtS85, rtA86, rtY89, rtH90 and rtI/L91); in yet another embodiment, rtP177, rtF178, rtL179, rtL180, rtA181, rtQ182, rtF183 and rtT184; in still another embodiment, rtM204 and rtY203; in even yet another embodiment, rt235, rt236, rt237, rt238 and rt239 and in even still another embodiment, rt247, rt248, rt249, rt250 and rt251; and in another embodiment, K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion;
and
V251A/R/N/D/C/Q/E/G/H/I/L/K/M/F/P/S/T/W/Y/deletion or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

A further aspect of the present invention produces a method for determining whether an HBV strain exhibits reduced sensitivity to a nucleoside or nucleotide analog or other anti-HBV agents, said method comprising isolating DNA or corresponding mRNA from said HBV and screening for a mutation in the nucleotide sequence encoding the DNA polymerase and/or a corresponding region of the S gene, wherein the presence of a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment, rtH90D and rtL/F108L; in even yet another embodiment, sP120T, sM125T and sT127A; in still yet another embodiment, sT118R, sM133T, SF134V, sI195M, sS207R and sY225Y/C; in another embodiment, sS126T, sM133L/M, sS143S/T, sD144A, sG145A and sW172Stop; in a further embodiment, sN40S, sC69STOP, sM75I, sL88P, sT118A, sW182Stop, sW196L, sY206H and sY225F; in yet another embodiment, s181M and sP214Q; in still another embodiment, sF83S, sL173F and sW199L; in yet another embodiment, sI126T, sK160R, sS174N, sA184V, sW196L, sS210N, sF/C220L and sY221C; in still another embodiment, sC69Stop/C, sC76Y, sI110V/I, sY134N, sW172Stop/W, sW196Stop, sS207R; in even still another embodiment, rtK32, rtN33, rtP34, rtH35 and rtT37); in another embodiment, rtP59, rtK60, rtF61, rtA62 and rtV63); in a further embodiment, rtD83, rtV84, rtS85, rtA86, rtY89, rtH90 and rtI/L91); in yet another embodiment, rtP177, rtF178, rtL179, rtL180, rtA181, rtQ182, rtF183 and rtT184; in still another embodiment, rtM204 and rtY203; in even yet another embodiment, rt235, rt236, rt237, rt238 and rt239 and in even still another embodiment, rt247, rt248, rt249, rt250 and rt251; and in another embodiment,
K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion; and
V251A/R/N/D/C/Q/E/G/H/I/L/K/M/F/P/S/T/W/Y/deletion or combinations thereof or an equivalent one or more other mutation is indicative of a variant which exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The detection of HBV or its components in cells, cell lysates, cultured supernatant fluid and bodily fluid may be by any convenient means including any nucleic acid-based detection means, for example, by nucleic acid hybridization techniques or via one or more polymerase chain reactions (PCRs). The term "bodily fluid" includes any fluid derived from the blood, lymph, tissue or organ systems including serum, whole blood, biopsy and biopsy fluid, organ explants and organ suspension such as liver suspensions. The invention further encompasses the use of different assay formats of said nucleic acid-based detection means, including restriction fragment length polymorphism (RFLP), amplified fragment length polymorphism (AFLP), single-strand chain polymorphism (SSCP), amplification and mismatch detection (AMD), interspersed repetitive sequence polymerase chain reaction (IRS-PCR), inverse polymerase chain reaction (iPCR) and reverse transcription polymerase chain reaction (RT-PCR), amongst others. Other forms of detection include Northern blots, Southern blots, PCR sequencing, antibody procedures such as ELISA, Western blot and immunohistochemistry. A particularly useful assay includes the reagents and components required for immobilized oligonucleotide- or oligopeptide-mediated detection systems.

One particularly useful nucleic acid detection system is the reverse hybridization technique. In this technique, DNA from an HBV sample is amplified using a biotin or other ligand-labeled primer to generate a labeled amplificon. Oligonucleotides immobilized to a solid support such as a nitrocellulose film are then used to capture amplified DNA by hybridization. Specific nucleic acid fragments are identified via biotin or the ligand. Generally, the labeled primer is specific for a particular nucleotide variation to be detected. Amplification occurs only if the variation to be detected is present. There are many forms of the reverse hybridization assay and all are encompassed by the present invention.

Detecting HBV replication in cell culture is particularly useful.

This and other aspects of the present invention is particularly amenable to microarray analysis such as to identify oligonucleotides including sense and antisense molecules, RNAi or siRNA molecules or DNA or RNA-binding molecules which down-regulate genomic sequences or transcripts of HBV. Microarray analysis may also be used to identify particular mutations in the HBV genome such as within the HBV DNA polymerase-coding region or the HBsAg-coding region.

Another aspect of the present invention contemplates a method for detecting an agent which exhibits inhibitory activity to an HBV by:

generating a genetic construct comprising a replication competent-effective amount of the genome from the HBV contained in a plasmid vector and then transfecting said cells with said construct;

contacting the cells, before, during and/or after transfection, with the agent to be tested;

culturing the cells for a time and under conditions sufficient for the HBV to replicate, express genetic sequences and/or assemble and/or release virus or virus-like particles if resistant to said agents; and then subjecting the cells, cell lysates or culture supernatant fluid to viral- or viral-component-detection means to determine whether or not the virus has replicated, expressed genetic material and/or assembled and/or been released in the presence of the agent.

In a preferred embodiment, the plasmid vector may include genes encoding part or all of other viral vectors such as baculovirus or adenovirus (Ren and Nassal, 2001, supra) and the method comprises:

generating a genetic construct comprising a replication competent-effective amount of the genome from the HBV contained in or fused to an amount of a baculovirus genome or adenovirus genome effective to infect cells and then infecting said cells with said construct;

contacting the cells, before, during and/or after infection, with the agent to be tested;

culturing the cells for a time and under conditions sufficient for the HBV to replicate, express genetic sequences and/or assemble and/or release virus or virus-like particles if resistant to said agent; and then subjecting the cells, cell lysates or culture supernatant fluid to viral- or viral-component-detection means to determine whether or not the virus has replicated, expressed genetic material and/or assembled and/or been released in the presence of the agent.

In an alternative embodiment, the method comprises:

generating a continuous cell line comprising an infectious copy of the genome of the HBV in a replication competent effective amount such that said infectious HBV genome is stably integrated into said continuous cell line such as but not limited to 2.2.15 or AD;

contacting the cells with the agent to be tested;

culturing the cells for a time and under conditions sufficient for the HBV to replicate, express genetic sequences and/or assemble and/or release virus or virus-like particles if resistant to the agent; and then subjecting the cells, cell lysates or culture supernatant fluid to viral- or viral-component-detection means to determine whether or not the virus has replicated, expressed genetic material and/or assembled and/or been released in the presence of the agent.

The above-mentioned methods are particularly useful in identifying or developing agents against HBV variants such as those carrying mutations, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235UM; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, sI81M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion; N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion;
K239M/F/P/S/T/W/Y/V/A/R/N/D/C/Q/E/G/H/I/L/deletion;
L247K/M/F/P/S/T/W/Y/V/A/R/N/D/C/Q/E/G/H/I/deletion;
N248D/C/Q/E/G/H/I/L/K/M/F/P/S/T/W/Y/V/A/R/deletion;
H248I/L/K/M/F/P/S/T/W/Y/V/A/R/N/D/C/Q/E/G/deletion;
F249P/S/T/W/Y/V/A/R/N/D/C/Q/E/G/H/I/L/K/M/deletion;
M250F/P/S/T/W/Y/V/A/R/N/D/C/Q/E/G/H/I/L/K/deletion;
G251H/I/L/K/M/F/P/S/T/W/Y/V/A/R/N/D/C/Q/E/deletion; and
V251A/R/N/D/C/Q/E/G/H/I/L/K/M/F/P/S/T/W/Y/deletion.

Accordingly, another aspect of the present invention contemplates a method for determining whether an HBV strain exhibits reduced sensitivity to a nucleoside or nucleotide analog or other potential anti-HBV agent, said method comprising isolating DNA or corresponding mRNA from said HBV and screening for a mutation in the nucleotide sequence of the envelope genes or DNA polymerase gene selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and 11251; and in even yet another embodiment,
K32M/F/P/S/T/W/Y/V/A/R/N/D/C/Q/E/G/H/I/L/deletion;
N33D/C/Q/E/G/H/I/L/K/M/F/P/S/T/W/Y/V/A/R/deletion;
P34S/T/W/Y/V/A/R/N/D/C/Q/E/G/H/I/L/K/M/F/deletion;
H35I/L/K/M/F/P/S/T/W/Y/V/A/R/N/D/C/Q/E/G/deletion;
T37W/Y/V/A/R/N/D/C/Q/E/G/H/I/L/K/M/F/P/S/deletion;
P59S/T/W/Y/V/A/R/N/D/C/Q/E/G/H/I/L/K/M/F/deletion;
K60M/F/P/S/T/W/Y/V/A/R/N/D/C/Q/E/G/H/I/L/deletion;
F61P/S/T/W/Y/V/A/R/N/D/C/Q/E/G/H/I/L/K/M/deletion;
A62R/N/D/C/Q/E/G/H/I/L/K/M/F/P/S/T/W/Y/V/deletion;
V63A/R/N/D/C/Q/E/G/H/I/L/K/M/F/P/S/T/W/Y/deletion;
D83C/Q/E/G/H/I/L/K/M/F/P/S/T/W/Y/V/A/R/N/deletion;
V84A/R/N/D/C/Q/E/G/H/I/L/K/M/F/P/S/T/W/Y/deletion;
S85T/W/Y/V/A/R/N/D/C/Q/E/G/H/I/L/K/M/F/P/deletion;
A86R/N/D/C/Q/E/G/H/I/L/K/M/F/P/S/T/W/Y/V/deletion;
Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237 S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C;
K239M/F/P/S/T/W/Y/V/A/R/N/D/C/Q/E/G/H/I/L;
L247K/M/F/P/S/T/W/Y/V/A/R/N/D/C/Q/E/G/H/I;
N248D/C/Q/E/G/H/I/L/K/M/F/P/S/T/W/Y/V/A/R;
H248I/L/K/M/F/P/S/T/W/Y/V/A/R/N/D/C/Q/E/G;
F249P/S/T/W/Y/V/A/R/N/D/C/Q/E/G/H/I/L/K/M;
M250F/P/S/T/W/Y/V/A/R/N/D/C/Q/E/G/H/I/L/K;
G251H/I/L/K/M/F/P/S/T/W/Y/V/A/R/N/D/C/QE; and
V251A/R/N/D/C/Q/E/G/H/I/L/K/M/F/P/S/T/W/Y/deletion
or combinations thereof or an equivalent one or more other mutation is indicative of a variant wherein said variant exhibits a decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof.

The detection of amino acid variants of DNA polymerase is conveniently accomplished by reference to the amino acid sequence shown in Formulae I and II. The polymorphisms shown represent the variations shown in various databases for active pathogenic HBV strains. Where an HBV variant comprises an amino acid different to what is represented, then such an isolate is considered a putative HBV variant having an altered DNA polymerase activity.

The present invention further contemplates agents which inhibit ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV resistant HBV variants. Such agents are particularly useful if long term treatment by ADV, LMV, FTC and/or TFV and/or optionally other nucleoside analogs or nucleotide analogs such as TFV is contemplated by the clinician. The agents may be DNA or RNA or proteinaceous or non-proteinaceous chemical molecules. Natural product screening such as from plants, coral and microorganisms is also contemplated as a useful potential source of masking agents as is the screening of combinatorial or chemical libraries. The agents may be in isolated fowl or in the form of a pharmaceutical composition or formulation and may be administered in place of or sequentially or simultaneously with a nucleoside or nucleotide analog. Furthermore, rationale drug design is contemplated including solving the crystal or NMR structure of, for example, HBV DNA polymerase and designing agents which can bind to the enzyme's active site. This approach may also be adapted to other HBV components.

Accordingly, another aspect of the present invention contemplates a method for detecting an agent which exhibits inhibitory activity to an HBV which exhibits resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof, said method comprising:

generating a genetic construct comprising a replication competent-effective amount of the genome from said HBV contained in a plasmid vector and then transfecting said cells with said construct;

contacting said cells, before, during and/or after transfection, with the agent to be tested;

culturing said cells for a time and under conditions sufficient for the HBV to replicate, express genetic sequences and/or assemble and/or release virus or virus-like particles if resistant to said agent; and subjecting the cells, cell lysates or culture supernatant fluid to viral- or viral-component-detection means to determine whether or not the virus has replicated, expressed genetic material and/or assembled and/or been released in the presence of said agent.

Still another aspect of the present invention provides a method for detecting an agent which exhibits inhibitory activity to an HBV which exhibits resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof, said method comprising:

generating a genetic construct comprising a replication competent-effective amount of the genome from said HBV contained in or fused to an amount of a baculovirus genome effective to infect cells and then infecting said cells with said construct;

contacting said cells, before, during and/or after infection, with the agent to be tested;

culturing said cells for a time and under conditions sufficient for the HBV to replicate, express genetic sequences and/or assemble and/or release virus or virus-like particles if resistant to said agent;

subjecting the cells, cell lysates or culture supernatant fluid to viral- or viral-component-detection means to determine whether or not the virus has replicated, expressed genetic material and/or assembled and/or been released in the presence of said agent.

Preferably, the HBV genome is stably integrated into the cells' genome.

Particularly useful cells are 2.2.15 cells (Price et al., Proc. Natl. Acad. Sci, USA 86(21): 8541-8544, 1989 or AD cells (also known as HepAD32 cells or HepAD79 cells [Ying et al., Viral Hepat. 7(2): 161-165, 2000.

Whilst the baculovirus vector is a particularly useful in the practice of the present invention, the subject invention extends to a range of other vectors such as but not limited to adenoviral vectors.

The present invention further extends to cell lines (e.g. 2.2.15 or AD cells) carrying genetic constructs comprising all or a portion of an HBV genome or a gene or part of a gene therefrom.

The present invention also provides for the use of the subject HBV variants to screen for anti-viral agents. These anti-viral agents inhibit the virus. The term "inhibit" includes antagonizing or otherwise preventing infection, replication, assembly and/or release or any intermediate step. Preferred anti-viral agents include nucleoside or nucleotide analogs or anti-HBV agents, however, the present invention extends to non-nucleoside molecules.

In addition, rational drug design is also contemplated to identify or generate chemical molecules which either mimic a nucleoside or which interact with a particular nucleotide sequence or a particular nucleotide. Combinatorial chemistry and two hybrid screening are some of a number of techniques which can be employed to identify potential therapeutic or diagnostic agents.

In one example, the crystal structure or the NMR structure of polymerase or the surface antigen is used to rationally design small chemical molecules likely to interact with key regions of the molecule required for function and/or antigenicity. Such agents may be useful as inhibitors of polymerase activity and/or may alter an epitope on the surface antigen.

Several models of the HBV polymerase have been prepared due to the similarity with reverse transcriptase from HIV (Das et al., J. Virol. 75(10): 4771-4779, 2001; Bartholomeusz et al., Intervirology 40(5-6): 337-342 1997; Allen et al., Hepatology 27(6): 1670-1677, 1998). The models of the HBV polymerase can be used for the rational drug design of new agents effective against HBV encoding the resistant mutations as well as wild type virus. The rational drug that is designed may be based on a modification of an existing antiviral agent such as the agent used in the selection of the HBV encoding the mutations associated with resistance. Viruses or clones expressing HBV genomic material encoding the mutations may also be used to screen for new antiviral agents.

In an alternative embodiment, the present invention also contemplates a method for detecting an agent which exhibits inhibitory activity to an HBV polymerase in an in vitro polymerase assay. The HBV polymerase activity can be examined using established assays (Gaillard et al., Antimicrob Agents Chemother. 46(4): 1005-1013, 2002; Xiong et al., Hepatology 28(6): 1669-1673, 1998).

As indicated above, microarray technology is also a useful means of identifying agents which are capable of interacting with defined HBV internal or external components. For example, arrays of HBV DNA polymerase or peptide fragments thereof carrying different amino acid variants may be used to screen for agents which are capable of binding or otherwise interacting with these molecules. This is a convenient way of determining the differential binding patterns of agents between HBV variants. Arrays of antibodies may also be used to screen for altered HBsAg molecules. Microarrays are also useful in proteomic analysis to identify molecules such as antibodies, interferons or cytokines which have an ability to interact with an HBV component. Microarrays of DNA and RNA molecules may also be employed to identify sense and antisense molecules for genetic regions on the HBV genome or transcripts thereof.

The above methods are particularly useful in identifying an inhibitor of an HBV resistant to or exhibiting reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof. The present invention extends, therefore, to compositions of the inhibitors. The inhibitors may also be in the form of antibodies or genetic molecules such as ribozymes, antisense molecules and/or sense molecules for co-suppression or the induction of RNAi or may be other nucleoside or nucleotide analogs or other anti-HBV agents or derivatives of known analogs. Reference to RNAi includes reference to short, interfering RNAs (siRNA).

The term "composition" includes a "pharmaceutical composition" or a formulation.

The inhibitor is referred to below as an "active ingredient" or "active compound" and may be selected from the list of inhibitors given above.

The composition may include an antigenic component of the HBV, a defective HBV variant or an agent identified through natural product screening or rational drug design (including combinatorial chemistry).

Pharmaceutically acceptable carriers and/or diluents include any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient; use thereof in the therapeutic compositions is contemplated. Supplementary active ingredients can also be incorporated into the compositions.

The pharmaceutical composition may also comprise genetic molecules such as a vector capable of transfecting target cells where the vector carries a nucleic acid molecule capable of encoding an aspartyl protease inhibitor. The vector may, for example, be a viral vector.

Pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various antibacterial and anti-fungal agents, for example, parabens, chlorobutanol, phenol, sorbic acid, thirmerosal and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

When the active ingredient is suitably protected, it may be orally administered, for example, with an inert diluent or with an assimilable edible carrier, or it may be enclosed in hard or soft shell gelatin capsule, or it may be compressed into tablets. For oral therapeutic administration, the active ingredient may be incorporated with excipients and used in the form of ingestible tablets, buccal tablets, troches, capsules, elixirs, suspensions, syrups, wafers and the like. Such compositions and preparations should contain at least 1% by weight of active compound. The percentage of the compositions and preparations may, of course, be varied and may conveniently be between about 5 to about 80% of the weight of the unit. The amount of active compound in such therapeutically useful compositions is such that a suitable dosage will be obtained. Preferred compositions or preparations according to the present invention are prepared so that an oral dosage unit form contains between about 0.1 µg and 200 mg of active compound. Alternative dosage amounts include from about 1 µg to about 1000 mg and from about 10 µg to about 500 mg. These dosages may be per individual or per kg body weight. Administration may be per hour, day, week, month or year.

The tablets, troches, pills, capsules and the like may also contain the components as listed hereafter. A binder such as gum, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavouring agent such as peppermint, oil of wintergreen or cherry flavouring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and a flavouring. Of course, any material used in preparing any dosage unit form should be pharmaceutically pure and substantially non-toxic in the amounts employed. In addition, the active compound(s) may be incorporated into sustained-release preparations and formulations.

As stated above, the present invention further extends to an isolated HBsAg from the HBV variants herein described. More particularly, the present invention provides an HBsAg or a recombinant form thereof or derivative or chemical equivalent thereof. The isolated surface component and, more particularly, isolated surface antigen or its recombinant, derivative or chemical equivalents are useful in the development of biological compositions such as vaccine formulations.

Yet another aspect of the present invention provides a composition comprising a variant HBV resistant to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or an HBV surface antigen from said variant HBV or a recombinant or derivative form thereof or its chemical equivalent and one or more pharmaceutically acceptable carriers and/or diluents. Such a composition may be regarded as a therapeutic composition and is useful in generating an immune response including a humoral response. Generally, the HBV variants are "defective" and in themselves are unable to cause a sustained infection in a subject.

As indicated above, antibodies may be generated to the mutant HBV agents and used for passive or direct vaccination against infection by these viruses. The antibodies may be generated in humans or non-human animals. In the case of the latter, the non-human antibodies may need to be deimmunized or more specifically humanized prior to use. Deimmunized may include, for example, grafting complementarity determining regions (CDRs) from the variable region of a murine or non-human animal anti-HBV antibody onto a human consensus fragment antibody binding (Fab) polypeptide. Alternatively, amino acids defining epitopes in the variable region of the antibody may be mutated so that the epitopes are no longer recognized by the human MHC H complex.

Insofar as ribozyme, antisense or co-suppression (RNAi) or siRNA or complexes thereof repression is concerned, this is conveniently aimed at post-transcription gene silencing. DNA or RNA may be administered or a complex comprising RNAi or a chemical analog thereof specific for HBV mRNA may be employed.

All such molecules may be incorporated into pharmaceutical compositions.

In another embodiment, the present invention provides a biological composition comprising a variant HBV or an HBsAg or L, M or S proteins from said variant HBV or a recombinant or derivative form thereof or its chemical equivalent.

Generally, if an HBV is used, it is first attenuated. The biological composition according to this aspect of the present invention generally further comprises one or more pharmaceutically acceptable carriers and/or diluents.

The biological composition may comprise HBsAg or like molecule from one HBV variant or the composition may be a cocktail of HbsAgs or L, M or S proteins or like molecules from a range of ADV- and/or LMV- and/or, FTC- and/or TFV-resistant HBV variants. Similar inclusions apply where the composition comprises an HBV.

The present invention is further directed to the use of defective HBV variants in the manufacture of therapeutic vaccines to vaccinate individuals against infection by HBV strains having a particular nucleotide sequence or encoding a particular polymerase or surface antigen or L, M or S proteins.

Examples of suitable vaccine candidates are defective forms of HBV variants comprising a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124I-1, rtV134D, rtY141Y/F, rtL145M, rtF151F/Y, rtA181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rtI163V, rtL229M and rtN/H/A/S/Q238K; in another embodiment, rtS78S/T, rtN118N/S, rtN139N/K, rtV142E, rtA181A/T, rtI204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144S, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and sW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt238 and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion; N33D/C/Q/E/G/H/I/L/K/M/F/P/S/T/W/Y/V/A/R/deletion; P34S/T/W/Y/V/A/R/N/D/C/Q/E/G/H/I/L/K/M/F/deletion; H35I/L/K/M/F/P/S/T/W/Y/V/A/R/N/D/C/Q/E/G/deletion; T37W/Y/V/A/R/N/D/C/Q/E/G/H/I/L/K/M/F/P/S/deletion; P59S/T/W/Y/V/A/R/N/D/C/Q/E/G/H/I/L/K/M/F/deletion; K60M/F/P/S/T/W/Y/V/A/R/N/D/C/Q/E/G/H/I/L/deletion; F61P/S/T/W/Y/V/A/R/N/D/C/Q/E/G/H/I/L/K/M/deletion; A62R/N/D/C/Q/E/G/H/I/L/K/M/F/P/S/T/W/Y/V/deletion; V63A/R/N/D/C/Q/E/G/H/I/L/K/M/F/P/S/T/W/Y/deletion; D83C/Q/E/G/H/I/L/K/M/F/P/S/T/W/Y/V/A/R/N/deletion; V84A/R/N/D/C/Q/E/G/H/I/L/K/M/F/P/S/T/W/Y/deletion; S85T/W/Y/V/A/R/N/D/C/Q/E/G/H/I/L/K/M/F/P/deletion; A86R/N/D/C/Q/E/G/H/I/L/K/M/F/P/S/T/W/Y/V/deletion; Y89V/A/R/N/D/C/Q/E/G/H/I/L/K/M/F/P/S/T/W/deletion; H90I/L/K/M/F/P/S/T/W/Y/V/A/R/N/D/C/Q/E/G/deletion; I/L91K/M/F/P/S/T/W/Y/V/A/R/N/D/C/Q/E/G/deletion; P177S/T/W/Y/V/A/R/N/D/C/Q/E/G/H/I/L/K/M/F/deletion; F178P/S/T/W/Y/V/A/R/N/D/C/Q/E/G/H/I/L/K/M/deletion; L179K/M/F/P/S/T/W/Y/V/A/R/N/D/C/Q/E/G/H/I/deletion; L180K/M/F/P/S/T/W/Y/V/A/R/N/D/C/Q/E/G/H/I/deletion; A181R/N/D/C/Q/E/G/H/I/L/K/M/F/P/S/T/W/Y/V/deletion; Q183E/G/H/I/L/K/M/F/P/S/T/W/Y/V/A/R/N/D/C/deletion; F183P/S/T/W/Y/V/A/R/N/D/C/Q/E/G/H/I/L/K/M/deletion; T184W/Y/V/A/R/N/D/C/Q/E/G/H/I/L/K/M/F/P/S/deletion; Y203V/A/R/N/D/C/Q/E/G/H/I/L/K/M/F/P/S/T/W/deletion; M204F/P/S/T/W/Y/V/A/R/N/D/C/Q/E/G/H/I/L/K/deletion; L235K/M/F/P/S/T/W/Y/V/A/R/N/D/C/Q/E/G/H/I/deletion; N236D/C/Q/E/G/H/I/L/K/M/F/P/S/T/W/Y/V/A/R/deletion; T237W/Y/V/A/R/N/D/C/Q/E/G/H/I/L/K/M/F/P/S/deletion; P237S/T/W/Y/V/A/R/N/D/C/Q/E/G/H/I/L/K/M/F/deletion; N238D/C/Q/E/G/H/I/L/K/M/F/P/S/T/W/Y/V/A/R/deletion; H238I/L/K/M/F/P/S/T/W/Y/V/A/R/N/D/C/Q/E/G/deletion; A238R/N/D/C/Q/E/G/H/I/L/K/M/F/P/S/T/W/Y/V/deletion; S239T/W/Y/V/A/R/N/D/C/Q/E/G/H/I/L/K/M/F/P/deletion; Q238E/G/H/I/L/K/M/F/P/S/T/W/Y/V/A/R/N/D/C/deletion; K239M/F/P/S/T/W/Y/V/A/R/N/D/C/Q/E/G/H/I/L/deletion; L247K/M/F/P/S/T/W/Y/V/A/R/N/D/C/Q/E/G/H/I/deletion; N248D/C/Q/E/G/H/I/L/K/M/F/P/S/T/W/Y/V/A/R/deletion; H248I/L/K/M/F/P/S/T/W/Y/V/A/R/N/D/C/Q/E/G/deletion; F249P/S/T/W/Y/V/A/R/N/D/C/Q/E/G/H/I/L/K/M/deletion; M250F/P/S/T/W/Y/V/A/R/N/D/C/Q/E/G/H/I/L/K/deletion; G251H/I/L/K/M/F/P/S/T/W/Y/V/A/R/N/D/C/Q/E; and V251A/R/N/D/C/Q/E/G/H/I/L/K/M/F/P/S/T/W/Y/deletion or a combination of two or more mutations.

In one embodiment, for example, an HBV variant may be identified having a particular mutation in its polymerase conferring resistance or decreased sensitivity to a nucleoside analog. This variant may then be mutated to render it defective, i.e. attenuated or unable to cause infection. Such a defective, nucleoside analog-resistant virus may then be used as a therapeutic vaccine against virulent viruses having the same mutation in its polymerase.

The subject invention extends to kits for assays for variant HBV resistant to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV ADV and LMV and FTC, or ADV and FTC and LMV and TFV. Such kits may, for example, contain the reagents from PCR or other nucleic acid hybridization technology or reagents for immunologically based detection techniques. A particularly useful assay includes the reagents and components required for immobilized oligonucleotide- or oligopeptide-mediated detection systems.

Still another aspect of the present invention contemplates a method for determining the potential for an HBV to exhibit reduced sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV and/or optionally other nucleoside or nucleotide analogs or other anti-HBV agents or combination thereof, said method comprising isolating DNA or corresponding mRNA from said HBV and screening for a mutation in the nucleotide sequence encoding HBV DNA polymerase resulting in at least one amino acid substitution, deletion and/or addition in any one or more of domains F and G, and domains A through to E or a region proximal thereto of said DNA polymerase and associated with resistance or decreased sensitivity to ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV, wherein the presence of such a mutation is an indication of the likelihood of resistance to said ADV, LMV, TFV, or FTC, or ADV and LMV, ADV and TFV, LMV and TFV, FTC and ADV, FTC and TFV, FTC and LMV, or ADV and LMV and TFV, or ADV and FTC and TFV, TFV and FTC and LMV, ADV and LMV and FTC, or ADV and FTC and LMV and TFV.

An assessment of a potential viral variant is important for selection of an appropriate therapeutic protocol. Such an assessment is suitably facilitated with the assistance of a computer programmed with software, which inter alia adds index values ($I_{Vs}$) for at least two features associated with the viral variants to provide a potency value ($P_A$) corresponding to the resistance or sensitivity of a viral variant to a particular chemical compound or immunological agent. The $I_{Vs}$ can be selected from (a) the ability to exhibit resistance for reduced sensitivity to a particular compound or immunological agent; (b) an altered DNA polymerase from wild-type HBV; (c) an altered surface antigen from wild-type HBV; or (d) morbidity or recovery potential of a patient. Thus, in accordance with the present invention, $I_{Vs}$ for such features are stored in a machine-readable storage medium, which is capable of processing the data to provide a $P_A$ for a particular viral variant or a biological specimen comprising same.

Thus, in another aspect, the invention contemplates a computer program product for assessing the likely usefulness of a viral variant or biological sample comprising same for determining an appropriate therapeutic protocol in a subject, said product comprising:

(1) code that receives as input $I_{Vs}$ for at least two features associated with said viral agents or biological sample comprising same, wherein said features are selected from:
 (a) the ability to exhibit resistance for reduced sensitivity to a particular compound or immunological agent;
 (b) an altered DNA polymerase from wild-type HBV;
 (c) an altered surface antigen from wild-type HBV;
 (d) morbidity or recovery potential of a patient; or
 (e) altered replication capacity (increased or decreased);
(2) code that adds said $I_{Vs}$ to provide a sum corresponding to a $P_V$ for said viral variants or biological samples; and
(3) a computer readable medium that stores the codes.

In a related aspect, the invention extends to a computer for assessing the likely usefulness of a viral variant or biological sample comprising same in a subject, wherein said computer comprises:

(1) a machine-readable data storage medium comprising a data storage material encoded with machine-readable data, wherein said machine-readable data comprise $I_{Vs}$ for at least two features associated with said viral variant or biological sample; wherein said features are selected from:
 (a) the ability to exhibit resistance for reduced sensitivity to a particular compound or immunological agent;
 (b) an altered DNA polymerase from wild-type HBV;
 (c) an altered surface antigen from wild-type HBV;
 (d) morbidity or recovery potential of a patient; or
 (e) altered replication capacity (increased or decreased);
(2) a working memory for storing instructions for processing said machine-readable data;
(3) a central-processing unit coupled to said working memory and to said machine-readable data storage medium, for processing said machine readable data to provide a sum of said $I_{Vs}$ corresponding to a $P_V$ for said compound(s); and
(4) an output hardware coupled to said central processing unit, for receiving said $P_V$.

Figure 19:
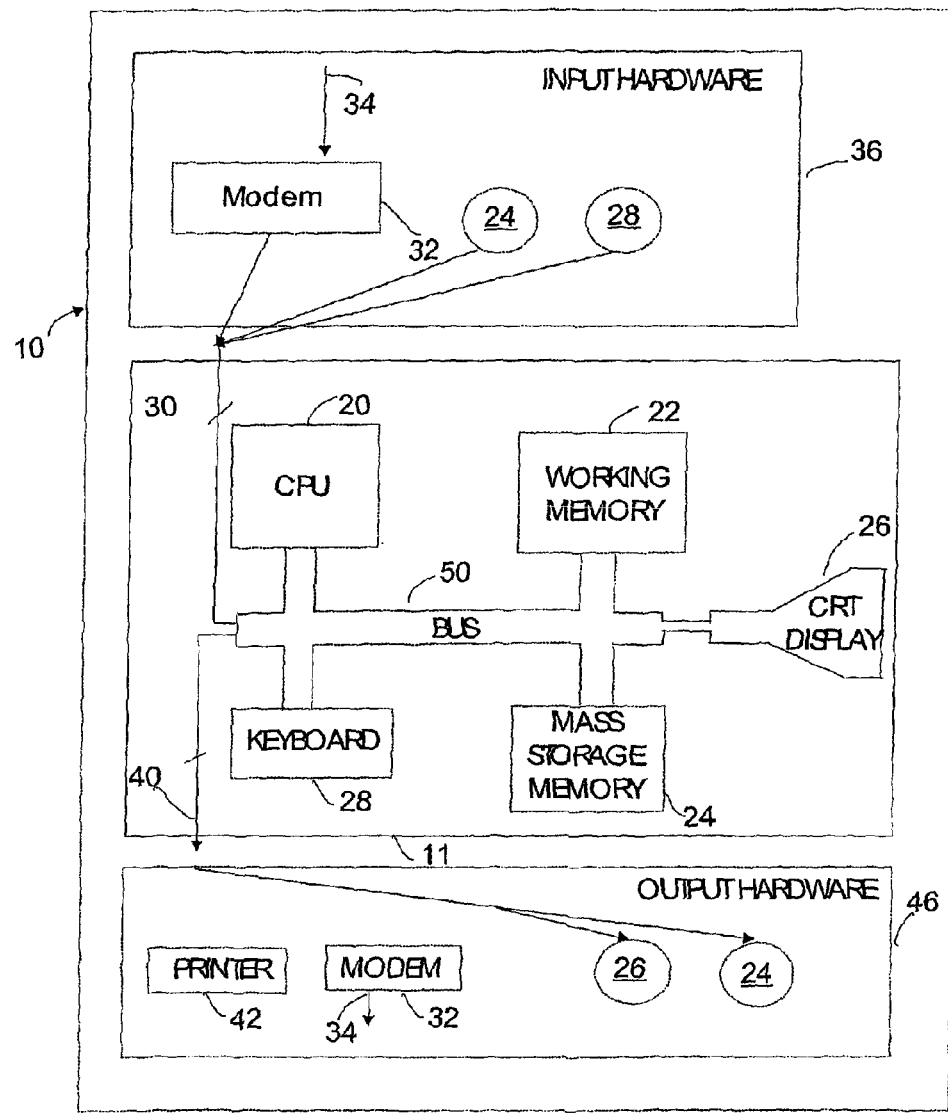
FIG. 19 is a diagrammatic representation of a system used to carry out the instructions encoded by the storage medium.

Any general or special purpose computer system is contemplated by the present invention and includes a processor in electrical communication with both a memory and at least one input/output device, such as a terminal. FIG. 19 shows a generally suitable computer system. Such a system may include, but is not limited to, personal computers, workstations or mainframes. The processor may be a general purpose processor or microprocessor or a specialized processor executing programs located in RAM memory. The programs may be placed in RAM from a storage device, such as a disk or pre-programmed ROM memory. The RAM memory in one embodiment is used both for data storage and program execution. The computer system also embraces systems where the processor and memory reside in different physical entities but which are in electrical communication by means of a network.

In an alternative embodiment, the program screens for a mutation selected from, in one embodiment, rtS21A, rtL122F, rtN124H, rtH126R, rtT28N, rtP130Q, rtD131N and rtY135C; in another embodiment, rt/N/S/T/I/V53D, rtY126Q, rtL180M, rtS202G, rtI204V and rtI235I/M; in a further embodiment, rtN53D, rtY54H, rtS57P, rtL91I, rtS116P, rtF122L, rtY124H, rtV134D, rtY141Y/F, rtL145M, rtF151F/Y, r/A181T, rtK212R, rtL217R, rtS219A, rtN236T and rtN238D; in yet another embodiment, rtS78T, rtV84M, rtY126C, rtV191I, rtM204I and rtV214A; in still another embodiment rtH90D and rtL/F108L; in even yet another embodiment, rtL157L/M, rtA181V and rtV207I; in even still another embodiment, rtL80V, rtP109S, rt1163V, rtL229M and rtN/H/A/S/Q238K; in another embodiment, rtS78S/T, rtN118N/S; rtN139N/K, rtV142E, rtA181A/T, rt1204M, rtQ/P/S/Stop215Q, rtE218K/E and rtN238N/H; in a further embodiment, sP120T, sM125T and sT127A; in yet another embodiment, sT118R, sM133T, SF134V, sI195M, sS207R and sY225Y/C; in still another embodiment, sS126T, sM133L/M, sS143S/T, sD144A, sG145A and sW172Stop; in even yet another embodiment, sN40S, sC69Stop, sM75I, sL88P, sT118A, sW182STOP, sW196L, sY206H and sY225F; in even still another embodiment, s181M and sP214Q; in another embodiment, sF83S, sL173F and SW199L; in a further embodiment, sI126T, sK160R, sS174N, sA184V, sW196L, sS210N, sF/C220L and sY221C; in yet another embodiment, sC69Stop/C, sC76Y sI110V/I, sY134N, sW172Stop/W, sW196Stop and sS207R; in still another embodiment, rtK32, rtN33, rtP34, rtH35 and rtT37; in even yet another embodiment, rtP59, rtK60, rtF61, rtA62 and rtV63; in even still another embodiment, rtD83, rtV84, rtS85, rtA86, rtY89, rtH90 and rtI/L91; in another embodiment, rtP177, rtF178, rtL179, rtL180, rtA181, rtQ182, rtF183 and rtT184; in a further embodiment, rtM204 and rtY203; in yet another embodiment, rt235, rt236, rt237, rt23S and rt239 in still another embodiment, rt247, rt248, rt249, rt250 and rt251; and in even yet another embodiment, K32M/F/P/S/T/W/Y/V/A/R/N/D/C/Q/E/G/H/I/L/deletion; N33D/C/Q/E/G/H/I/L/K/M/F/P/S/T/W/Y/V/A/R/deletion; P34S/T/W/Y/V/A/R/N/D/C/Q/E/G/H/I/L/K/M/F/deletion; H35I/L/K/M/F/P/S/T/W/Y/V/A/R/N/D/C/Q/E/G/deletion; T37W/Y/V/A/R/N/D/C/Q/E/G/H/I/L/K/M/F/P/S/deletion; P59S/T/W/Y/V/A/R/N/D/C/Q/E/G/H/I/L/K/M/F/deletion; K60M/F/P/S/T/W/Y/V/A/R/N/D/C/Q/E/G/H/I/L/deletion; F61P/S/T/W/Y/V/A/R/N/D/C/Q/E/G/H/I/L/K/M/deletion; A62R/N/D/C/Q/E/G/H/I/L/K/M/F/P/S/T/W/Y/V/deletion; V63A/R/N/D/C/Q/E/G/H/I/L/K/M/F/P/S/T/W/Y/deletion; D83C/Q/E/G/H/I/L/K/M/F/P/S/T/W/Y/V/A/R/N/deletion; V84A/R/N/D/C/Q/E/G/H/I/L/K/M/F/P/S/T/W/Y/deletion; S85T/W/Y/V/A/R/N/D/C/Q/E/G/H/I/L/K/M/F/P/deletion; A86R/N/D/C/Q/E/G/H/I/L/K/M/F/P/S/T/W/Y/V/deletion;

Y89V/A/R/N/D/C/Q/E/G/H/I/L/K/M/F/P/S/T/W/deletion;
H90I/L/K/M/F/P/S/T/W/Y/V/A/R/N/D/C/Q/E/G/deletion;
I/L91K/M/F/P/S/T/W/Y/V/A/R/N/D/C/Q/E/G/H/deletion;
P177S/T/W/Y/V/A/R/N/D/C/Q/E/G/H/I/L/K/M/F/deletion;
F178P/S/T/W/Y/V/A/R/N/D/C/Q/E/G/H/I/L/K/M/deletion;
L179K/M/F/P/S/T/W/Y/V/A/R/N/D/C/Q/E/G/H/I/deletion;
L180K/M/F/P/S/T/W/Y/V/A/R/N/D/C/Q/E/G/H/I/deletion;
A181R/N/D/C/Q/E/G/H/I/L/K/M/F/P/S/T/W/Y/V/deletion;
Q183E/G/H/I/L/K/M/F/P/S/T/W/Y/V/A/R/N/D/C/deletion;
F183P/S/T/W/Y/V/A/R/N/D/C/Q/E/G/H/I/L/K/M/deletion;
T184W/Y/V/A/R/N/D/C/Q/E/G/H/I/L/K/M/F/P/S/deletion;
Y203V/A/R/N/D/C/Q/E/G/H/I/L/K/M/F/P/S/T/W/deletion;
M204F/P/S/T/W/Y/V/A/R/N/D/C/Q/E/G/H/I/L/K/deletion;
L235K/M/F/P/S/T/W/Y/V/A/R/N/D/C/Q/E/G/H/I/deletion;
N236D/C/Q/E/G/H/I/L/K/M/F/P/S/T/W/Y/V/A/R/deletion;
T237W/Y/V/A/R/N/D/C/Q/E/G/H/I/L/K/M/F/P/S/deletion;
P237S/T/W/Y/V/A/R/N/D/C/Q/E/G/H/I/L/K/M/F/deletion;
N238D/C/Q/E/G/H/I/L/K/M/F/P/S/T/W/Y/V/A/R/deletion;
H238I/L/K/M/F/P/S/T/W/Y/V/A/R/N/D/C/Q/E/G/deletion;
A238R/N/D/C/Q/E/G/H/I/L/K/M/F/P/S/T/W/Y/V/deletion;
S239T/W/Y/V/A/R/N/D/C/Q/E/G/H/I/L/K/M/F/P/deletion;
Q238E/G/H/I/L/K/M/F/P/S/T/W/Y/V/A/R/N/D/C/deletion; K239M/F/P/S/T/W/Y/V/A/R/N/D/C/Q/E/G/H/I/L/deletion; L247K/M/F/P/S/T/W/Y/V/A/R/N/D/C/Q/E/G/H/I/deletion; N248D/C/Q/E/G/H/I/L/K/M/F/P/S/T/W/Y/V/A/R/deletion; H248I/L/K/M/F/P/S/T/W/Y/V/A/R/N/D/C/Q/E/G/deletion; F249P/S/T/W/Y/V/A/R/N/D/C/Q/E/G/H/I/L/K/M/deletion; M250F/P/S/T/W/Y/V/A/R/N/D/C/Q/E/G/H/I/L/K/deletion; G251H/I/L/K/M/F/P/S/T/W/Y/V/A/R/N/D/C/Q/E; and V251A/R/N/D/C/Q/E/G/H/I/L/K/M/F/P/S/T/W/Y/deletion or a combination of two or more mutations.

The present invention is further described by the following non-limiting Examples.

Example 1

Overlapping Genome of HBV

The overlapping genome of HBV is represented in FIG. 1. The gene encoding DNA polymerase (P), overlaps the viral envelope genes, Pre-S 1 and Pre-S2, and partially overlaps the X and core (C) genes. The HBV envelope comprises small, middle and large proteins HBV surface antigens. The large protein component is referred to as the HBV surface antigen (HBsAg) and is encoded by the S gene sequence. The Pre-S1 and Pre-S2 gene sequences encode the other envelope components.

Example 2

Patients and Treatment

Patient A, a 48 year old Lebanese woman was initially referred for evaluation of thrombocytopenia and hepatosplenomegaly. At this time the patient had abnormal LFT's (ALT 67 U/L, normal <55) and the HBV DNA was 61 pg/ml (231 days prior to the start of treatment). The patient was HBsAg and HBeAg positive. The ALT's fluctuated between 50-70 IU/L from (−231 to −35 days pretreatment). ADV was commenced on Day 0 in a clinical trial on 30 mg/day. HBV DNA levels were reduced with ADV treatment. The ADV treatment was reduced to 10 mg/day (144 days post-treatment). There was a problem with the randomization treatment protocol. The patient was on antiviral treatment for 1 month only during the second year of the treatment period. The study was completed on Day 679 post ADV treatment. The patient was not on ADV treatment until the open label ADV was recommenced on Day 875 from the start of the initial ADV treatment. This second period of ADV treatment was given for 108 days (day 983 post initial ADV treatment). The HBV DNA levels remained at 7-10 pg/ml ($1.96\times10^5$ to $2.8\times10^5$ copies/ml). At Day 983, ADV treatment was stopped and the patient was treated with LMV.

Patient B is a male liver transplant patient. The patient has been on both sequential and combination antiviral therapy including HBIG, FCV+HBIG, LMV+HBIG, LMV, LMV+GCV, LMV+FCV+GCV, LMV+GCV and finally LMV+ADV. The patient has been on long term ADV+LMV treatment for over 795 days. Patient C, is a 58 year old male. Prior to ADV treatment the patient had abnormal LFT's (ALT 240 IU/L, normal <55) and the HBV DNA was $2\times10^7$ copies/ml. ADV was commenced on Day 0 in a clinical trial on 10 mg/day for two years. The average ALT during the two year clinical trial period ws 114 IU/L. However, the ALT was rising and at 630 days after the start of ADV treatment the ALT remained high 407 IU/L. Open label ADV was commenced on Day 668 from the start of the initial ADV treatment. This second period of ADV treatment was given for 71' days. The HBV DNA levels remained high during open label ADV treatment ($3.7\times10^6$ to 1.5 $10^7$ copies/ml). The peak ALT during open label ADV treatment was 517 IU/L (Day 738). The next day (Day 739), ADV treatment was stopped and the patient was treated with LMV.

Example 3

Detection of Viral Markers

Hepatitis B surface antigen (HBsAg), hepatitis B e antigen (HBeAg), anti-HBe and hepatitis B core antigen (HBcAg) specific IgG and IgM were measured using commercially available immunoassays (Abbott Laboratories, North Chicago, Ill., USA). Hepatitis B viral DNA levels were measured using a capture hybridization assay according to the manufacturer's directions (Digene Hybrid Capture II, Digene Diagnostics Inc., Beltsville, Md.). The manufacturers stated cut-off for detecting HBV viremia in clinical specimens was $0.7\times10^6$ copies/ml or 2.5 pg/ml, [Hendricks et al., Am J Clin Pathol 104: 537-46, 1995]. HBV DNA levels can also be quantitated using other commercial kits such as Cobas amplification HBV monitor kit (Roche).

Example 4

Sequencing of HBV DNA

HBV DNA was extracted from 100 μl of serum as described previously by Aye et al., J. Hepatol. 26: 1148-1153, 1997. Oligonucleotides were synthesized by Geneworks, Adelaide, Australia. Amplification of the HBV polymerase gene has been described by Aye et al., 1997, supra.

The specific amplified products were purified using PCR purification columns from MO BIO Laboratories Inc (La Jolla, Calif.) and directly sequenced using Big Dye terminator Cycle sequencing Ready Reaction Kit (Perkin Elmer, Cetus Norwalk, Conn.). The PCR primers were used as sequencing primers, OS1 5'-GCC TCA TTT TGT GGG TCA CCA TA-3' (nt 1408-1430) [SEQ ID NO:3], TTA3 5'-AAA. TTC GCA GTC CCC AAA-3'(nt2128-2145) [SEQ ID NO:4], JM 5'-TTG GGG TGG AGC CCT CAG GCT-3' (nt1676-1696) [SEQ ID NO:5], TTA4 5'-GAA AAT TGG TAA CAG CGG-3' (nt 2615-2632) [SEQ ID NO:6], OS2 5'

TCT CTG ACA TAC TTT CCA AT 3' (nt 2798-2817) [SEQ ID NO:7], to sequence the internal regions of the PCR products.

Example 5

Analysis of HBV DNA

Figure 4:
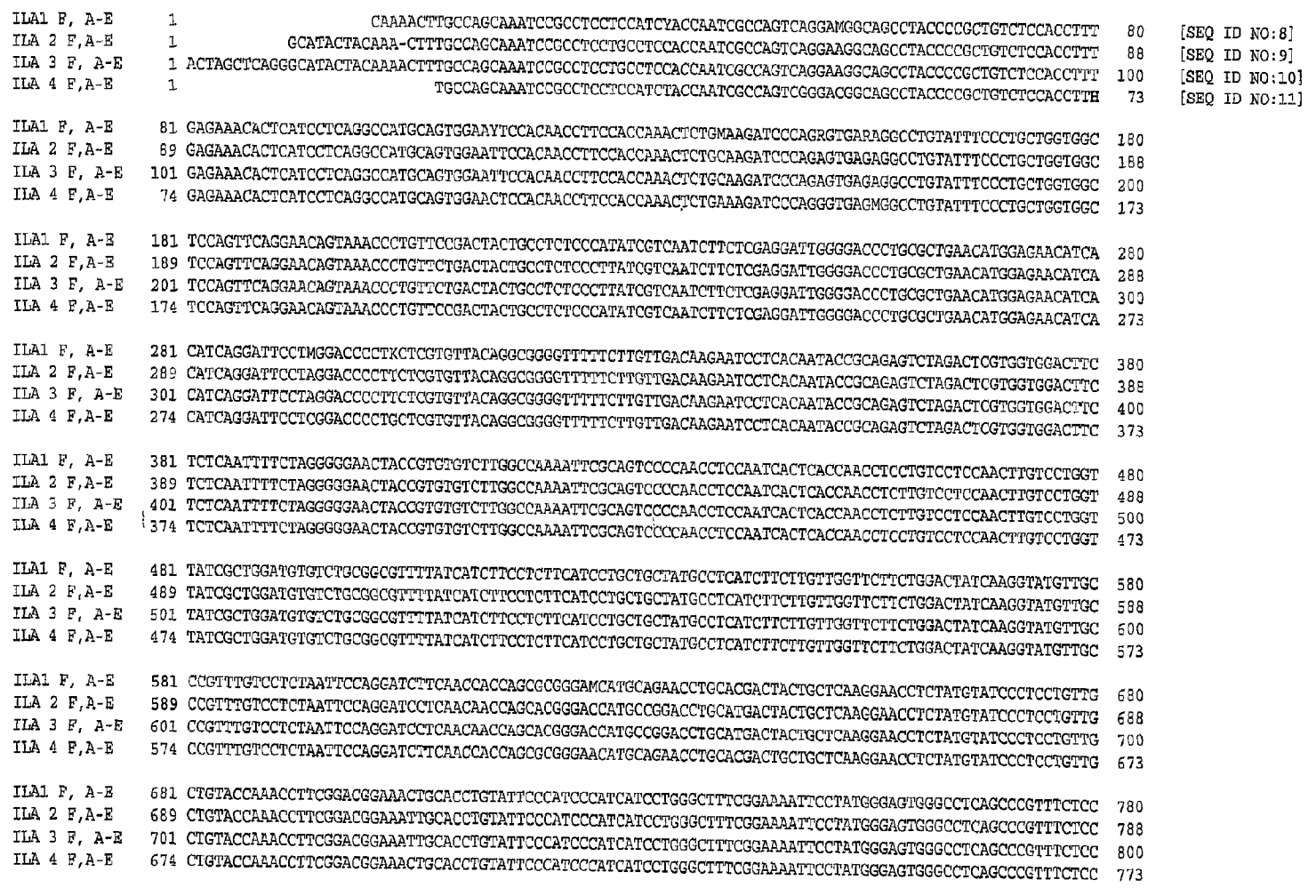

Patient A: During ADV treatment, unique HBV mutations were detected by sequencing (Tables 4 and 5) This includes the unique mutation at rtY135C in addition to the mutation at rtT128N that was present prior to ADV treatment. A number of other unique changes were also detected in the polymerase and in the overlapping envelope gene (Table 5, FIGS. 4, 5 and 6). The unique change in the HBsAg include sP120T. These unique changes were compared to reference sequences from each of the seven genotypes A-G as well as a consensus sequence from pretreatment samples to determine unique changes.

Patient B: The HBV mutations prior to ADV treatment and during ADV treatment are listed in Table 6 and 7 and FIGS. 7, 8, and 9. The unique changes in the rt region of the HBV DNA polymerase include rtN/S/T/I/V53D, rtY126Q, rtL180M, rtS202G, rtI204V and rtI235I/M. The unique changes in the HBsAg include sT118R, sM133T, sF134V, sI195M, sS207R, sY225Y/C.

Patient C: The HBV mutations prior to ADV treatment and during ADV treatment are listed in Tables 8 and 9 and FIGS. 10, 11 and 12. The unique changes in the rt region of the HBV DNA polymerase include rtN53D, rtS116P, rtF151F/T, rtN236T and rtN238D. The unique changes in the HBsAg include sG145A and sW172stop.

Patient D: The HBV mutations during ADV treatment is listed in Table 10 and FIGS. 13, 14 and 15. The unique changes in the HBV DNA polymerase include rtS78T, rtV84M, rtY126C, rtV191I, rtM204I and rtV214A. The unique changes in the surface include sN40S and sC69 Stop. A number of unique changes were detected after the stop codon mutation at codon 69 of the S gene including sM75I, sL88P, sT118A, sW182stop, sW196L, sY206H and sY225F.

Patient E: The HBV mutations during ADV treatment is listed in Table 11 and FIGS. 16, 17 and 18. The unique changes in the HBV DNA polymerase include rtH90D and rtL/F108L. The unique changes in the surface include sI81M and sP214Q. A six nucleotide insertion was also detected resulting in a two amino acid insertion in the HBV polymerase and envelope gene at codons rt131 and s122, respectively. This insertion was previously detected in pre-ADV samples.

Example 6

Adefovir Dipivoxil (ADV)

Figure 2:
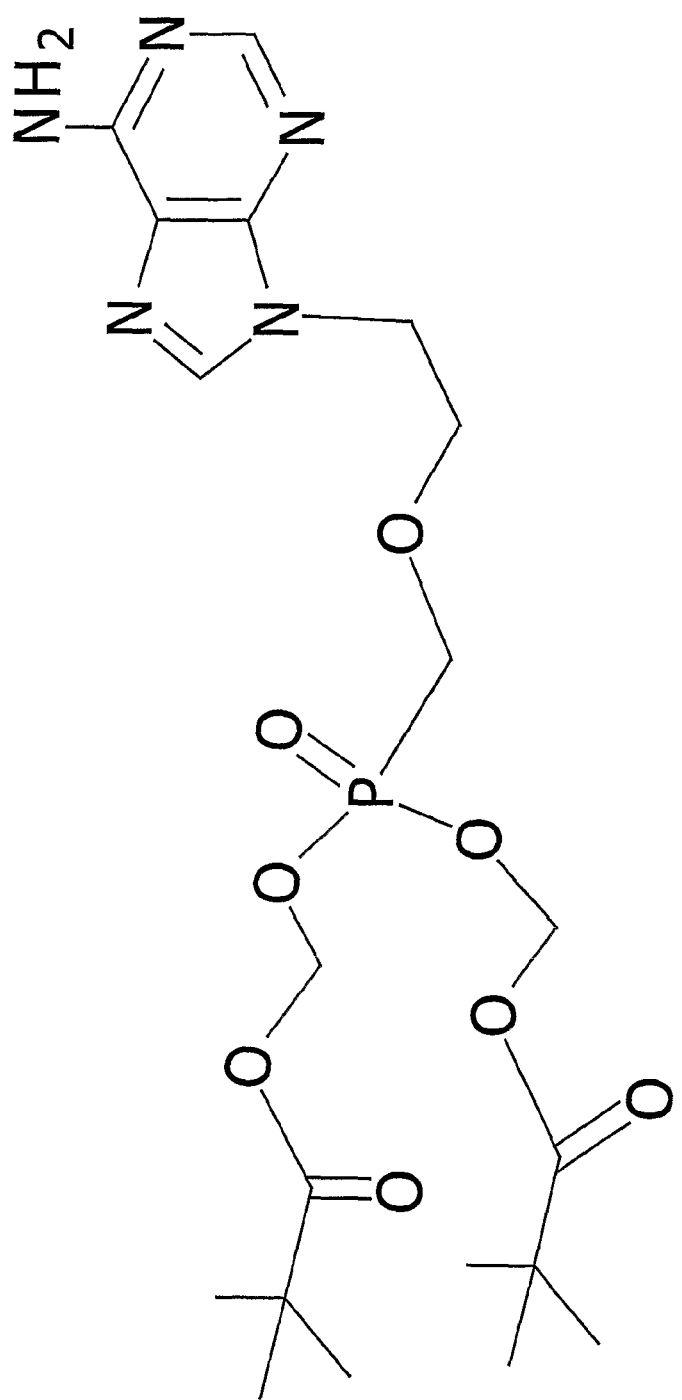
FIG. 2 is a diagrammatic representation of the chemical structure of ADV.
Figure 3:
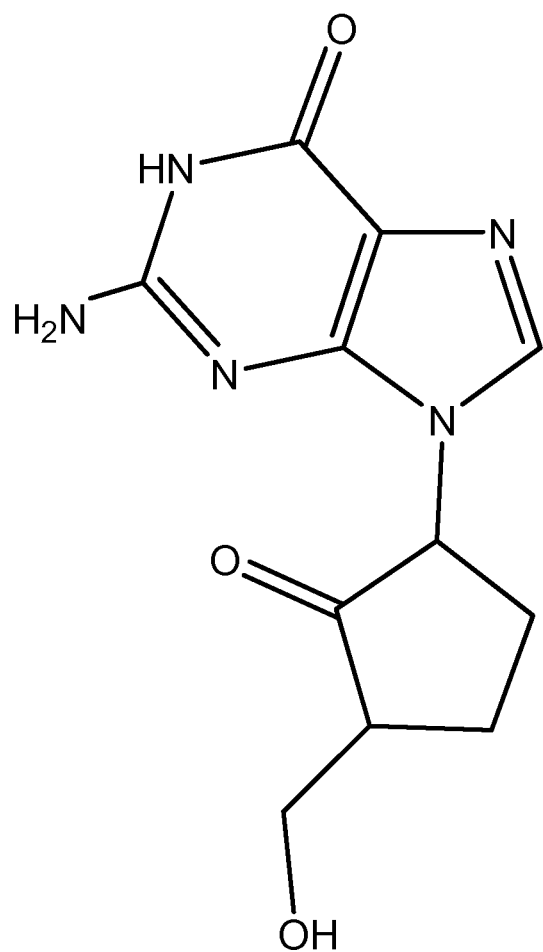
FIG. 3 is a diagrammatic representation of a computer system for determining the potency value ($P_A$) of a variant HBV.

ADV (formerly Bis-pom PMEA)) is a potent inhibitor of HBV replication. The structure of ADV is shown in FIG. 2 and its synthesis is described by Benzaria et al., J Med. Chem. 39: 4958-4965, 1996).

Example 7

HBV Rt Mutants

The HBV polymerase has similarities to other polymerases including HIV. Thus, mutations associated with resistance to antiviral agents may occur within the polymerase in functionally important regions such as the nucleotide triphosphate binding pocket that may also include the interaction between the DNA primer and template strand, magnesium ions and nucleoside triphosphates or nucleoside/nucleotide analogs (and there various phosphorylated forms). Codons which are proposed to be mutated during anti-viral selection pressure are rtK32, rt N33, rtP34, rtH35 and rtT37 (that are upstream from the F domain); rt P59, rtK60, rtF61, rtA62 and rtV63 (between the F and A domains), rtD83, rtVS4, rtS85, rtA86, rt Y89, rt H90 and rtI/L91 (within the A domain and the region immediately prior to and after), rtP177, rtF178, rt L179, rtL180, rtA181, rtQ182, rtF183 and rtT184 (B domain); rtM204 and rtY203 (C Domain), rtL235, rtN236, rtP/T237, rtN/H/A/S/Q238 and rtK239 (D Domain), rLt247, rtN/H248, rtF249, rtM250 and rtG251 (E Domain). The codons are defined in Table 12 and examples of various mutants are given in Tables 13 and 14.

Example 8

Patient F

The HBV mutations during ADV treatment of Patient F are listed in Table 15 and FIGS. 20, 21 and 22. The unique changes in the HBV DNA polymerase includes rtL157L/M, rtA181V, rtV207I, and rtN236T. The unique changes in the surface includes sF83S, sL173F and sW199L.

Example 9

Patient G

The HBV mutations during ADV treatment of Patient G are listed in Table 16 and FIGS. 23, 24 and 25. The unique changes in the HBV DNA polymerase includes rtL80V, rtP109S, rtI163V, rtM204I, rtL229M and rtN/H/A/S/Q238K. The unique changes in the surface includes sI126T, sK160R, sS174N, sA184V, sW196L, sS210N, sF/C220L and sY221C.

Example 10

Patient H

The HBV mutations during ADV treatment in Patient H are listed in Table 17 and FIGS. 26, 27 and 28. The unique changes in the HBV DNA polymerase includes rtS78S/T, rtN118N/S, rtN139N/K, rtV142E, rtA181A/T, rtI204M, rtQ/P/S/Stop215Q, rtE218K/E, and rtN238N/H. The unique changes in the surface include sC69Stop/C, sC76Y sI110V/I, sY134N, sW172Stop/W, sW196Stop and sS207R.

Example 11

In Vitro Analysis of ADV Resistance

The sensitivity/resistance profile of HBV mutants to ADV was examined in vitro using recombinant HBV/baculovirus. The procedure for analyzing the resistance profile is outlined in the following Examples 12-20.

Example 12

Cell Culture

Sf21 insect cells were maintained in supplemented Grace's insect medium further supplemented with 10% v/v heat-inactivated fetal bovine serum (Gibco BRL, Gaithersburg, Md.) in humidified incubator at 28° C. with $CO_2$. HepG2 cells were maintained in minimal essential medium supplemented with 10% v/v heat-inactivated fetal bovine serum (MEM-FBS). HepG2 cells were grown in humidified 37° C. incubators at 5% v/v $CO_2$.

Example 13

Preparation of HBV/Baculovirus Transfer Vector with Specific Point Mutations

The recombinant HBV/baculovirus system used for antiviral testing has been previously described (Delaney et al., Antimicrob Agents Chemother 45(6): 17054013, 2001). In brief, the recombinant transfer vector was created by excising a fragment containing the 1.3X HBV genome construct and cloning it into the multiple cloning region of a baculovirus vector pBlueBac4.5 (Invitrogen, Carlsbad, Calif.). Point mutations were created by site directed mutagenesis using the commercial kits according to the manufacturer's specifications (QuikChange, Stratagene). HBV/baculovirus recombinant clones encoding the reverse transcriptase mutations rtA181T/N236T/N238D and rtN236T/N236D in combination with the precore mutation at G1896A (pcW28 stop) or wild-type with respect to codon pcW28, were prepared by site-directed mutagenesis. The nucleotide sequence of the plasmid and the point mutations generated by site directed mutagenesis were confirmed by sequencing using the ABI Prism Big Dye Terminator Cycle Sequencing Ready Reaction Kit according to the manufacturer's specifications (Perkin Elmer, Cetus Norwalk, Conn.).

Example 14

Generation of Recombinant Baculoviruses Containing the 1.3 HBV Construct

Purified recombinant transfer vector and linear AcMNPV baculovirus DNA were co-transfected into Sf21 cells using the BacNBlue transfection kit from Invitrogen (Carlsbad, Calif.); recombinant viruses were isolated by plaque assay according to the manufacturer's instructions. A series of recombinant viruses were amplified from isolated plaques by infecting 100-mm dishes of Sf21 cells. Viral DNA was extracted from amplified viruses using standard procedures. Purified viral DNA was digested with restriction enzymes and then fractionated by electrophoresis in a 1% v/v agarose gel. Southern blotting was performed to determine which virus isolates contained the intact 1.3 HBV construct. A Boehringer Mannheim Random Prime DNA Labeling kit (Indianapolis, Ind.) was used to generate [$P^{32}$]-radiolabeled probes. A full-length double-stranded HBV genome was used as a template for all radiolabeled probes. Viral DNA sequence was confirmed by PCR amplification of the polymerase catalytic region using the sense primer 5'-GCC TCA TTT TGT GGG TCA CCA TA-3' [SEQ ID NO:8], (nucleotide 1408 to 1430 according to HBV Genebank Accession number M38454) and the antisense primer 5'-TCT CTG ACA TAC TTT CCA AT-3' [SEQ ID NO:9] (nucleotides 2817 to 2798 according to HBV Genebank Accession number M38454). The following primers were utilized for the sequencing of internal regions 5'-TGC ACG ATT CCT GCT CAA-3' [SEQ ID NO:10] (nucleotides 2345-2362 according to HBV Genebank Accession number M38454) and 5'-TTT CTC AAA GGT GGA GAC AG-3' [SEQ ID NO:11] (nucleotides 1790-1810 according to HBV Genebank Accession number M38454).

Example 15

Preparative Baculovirus Amplification and Purification

Baculoviruses were amplified by infecting suspension cultures of Sf21 cells in log phase at a multiplicity of infection (moi) of 0.5 pfu/cell. Infections were allowed to proceed until a majority of the cells in the flasks showed visible signs of infection (four to five days). Virions were concentrated from infected Sf21 medium by centrifugation at 80,000×g and purified through a 20-60% w/v sucrose gradient. Purified virus was titrated in quadruplicate in Sf21 cells by end-point dilution. An aliquot of each high titer stock was used for DNA extraction. The polymerase gene was amplified and sequenced to confirm the presence of the site-directed mutagenesis as in Example 14.

Example 16

Infection of HepG2 Cells with Recombinant HBV Expressing Baculovirus

HepG2 cells were seeded at approximately 20-40% confluency and then were grown for 16-24 hours before infection. On the day of infection, triplicate plates of cells were trypsinized, and viable cell number was determined with a hemocytometer using Trypan blue exclusion. Average cell counts were calculated and used to determine the volume of high-titer viral stock necessary to infect cells at the indicated moi. HepG2 cells were washed one time with serum-free MEM to remove traces of serum. Baculovirus was diluted into MEM without serum to achieve the appropriate moi using volumes of 1.0, 0.5, and 0.25 ml to infect 100-mm, 60 mm, and 35-mm dishes, respectively. Baculovirus was adsorbed to HepG2 cells for one hour at 37° C. with gentle rocking every 15 minutes to ensure that the inoculum was evenly distributed. The inoculum was then aspirated and HepG2 cells were washed two times with phosphate-buffered saline and refed MEM-FBS with or without various concentrations of agents.

Example 17

Detection of Intracellular Replicative Intermediates

HBV core particles were isolated from the cytoplasmic fraction of HepG2 cells lysed in 0.5% w/v NP-40. Cytoplasmic extracts were adjusted to 10 mmol/l McC12 and unprotected DNA was removed by an incubation to 500 g/ml Proteinase K for 1.5 hours at 37° C. 1113V DNA in the samples were then extracted using commercial DNA extraction kits such as Qiagen (DNA extraction) or in-house methods using sequential phenol and chloroform extractions, and the nucleic acids were recovered by ethanol precipitation. Nucleic acids were resuspended in 50 µl/l TE (10 mmol/l Tris, 1 mmol/l ethylenediaminetetraacetic acid), normalized by OD260, and digested with 100 g/ml. RNase (Boehringer Mannheim, Indianapolis, Ind.) for one hour at 37° C. before analysis by real-time PCR or electrophoresis and Southern blotting. After southern blot analysis a BioRad GS-670 imaging densitometer and the Molecular Analyst software (BioRad, Hecules Calif.) was used to analyze suitable exposures of Southern blots. Densitometry data was fitted to logistic dose response curves using the TableCurve 2D software package from Jandel Scientific. Logistic dose response equations were used to calculate $IC_{50}$ and $IC_{90}$ values and co-efficients of variation.

Example 18

Real-Time PCR

For the real-time PCR based assay for HBV, HBV DNA was extracted from 200 μl of serum using the QIAamp DNA Mini Kit according to the manufacturer's instructions (QIAGEN GmbH, lindens, Germany). Primers and a molecular beacon were designed for conserved nucleic acid sequences within the precore domain of the HBV genome to amplify and detect a 216-nucleotide product. Amplification was performed in a 50-μl reaction mixture containing 1.0 Taqman buffer A (Applied Biosystems, Foster City, Calif.), 3.0 mM MgCl, 0.4 pmol of each primer per μl, forward primer, PC1 (5'-GGGAGGAGATTAGGTTAA-3' [SEQ ID NO:12]) and reverse primer, PC2 (5'-GGCAAAAACGAGAG-TAACTC-3' [SEQ ID NO:13]), 0.4 μmol of the HBV-specific molecular beacon per μL, (5'-FAM-CGCGTC-CTACTGTTCAAGCCTCCAAGCTGT GACGCG-DABCYL-3' [SEQ ID NO:14]; where FAM represents fluorophore 6-carboxyfluorescein and DABCYL, 4-dimethylaminophenylazobenzoic acid, a quenching chromophore) and 1.25 U of AmpliTaq Gold DNA polymerase (Perkin-Elmer). PCR was performed using the ABI PRISM 7700 spectrofluorometric thermocycler (Applied Biosystems). The PCR program consisted of an initial cycle (95° C. for 10 minutes) followed by 45 amplification cycles (94° C. for 15 secs, 50° C. for 30 secs, 72° C. for 30 secs). The instrument detected and recorded the fluorescence spectrum of each reaction tube during the annealing phase.

An external standard was constructed by ligation of a 1.3 kB wild-type HBV plasmid (genotype D) into the pBlueBac plasmid vector (Hershey Medical Center, Hershey, Pa.). Quantification of the DNA concentration of the plasmid was determined by spectrophotometry. Duplicates of serial 10-fold dilutions of the plasmid ranging from $10^8$ copies/ml to 100 copies/ml were included in each run in order to generate a standard curve.

The copy number in each experimental reaction was determined by interpolation of the derived threshold cycle ($C_T$).

Example 19

ADV Treatments

ADV was resuspended in sterile water, aliquoted, and frozen at −20° C. to avoid repeated freezing and thawing of the drug. Medium containing ADV was prepared daily as needed using fresh aliquots of 3TC. In experiments in which ADV treatment was initiated after viral infection, HepG2 cells were exposed to the indicated concentration of ADV immediately after infection with HBV baculovirus. In experiments utilizing pretreatment with ADV, cells were fed medium containing ADV 16 hours prior to HBV baculovirus infection, HBV baculovirus infection was also carried out in medium containing ADV, and cells were refed fresh medium containing ADV immediately after completion of the infection and washing procedures.

Example 20

Antiviral Testing Performed with Wild-Type and HBV/Baculovirus Encoding rtA181T/N236T/N238D and rtN236T/N236D The in vitro antiviral drug cross-resistance testing of the HBV mutants is shown in Table 18. The laboratory reference strain of HBV (genotype D subtype ayw) containing the introduced D domain mutations demonstrated increased $IC_{50}$ values against ADV (Table 18). The rt N236T/N238D mutation was associated with a twenty-three fold increase in $IC_{50}$ against ADV. This was reduced to a five-fold increase when the rtA181T was also present and this triple HBV polymerase mutant was resistant to LMV.

TABLE 4

Clinical, virological and HBV sequencing data summary for Patient A while on open label ADV.

| Days post-ADV treatment | HBV DNA copies/ml (pg/ml) | ALT IU/L | Treatment protocol | Key polymerase mutations detected by sequencing[1] |
|---|---|---|---|---|
| −230 | 1.7 $10^6$ (61) | 67 U/L | pre-therapy | rtT/N128T/N<br>rtQ/H/R215Q/stop |
| 875 | | | ADV recommenced | |
| 904 | 1.55 × $10^6$ | | | |
| 932 | 2.97 × $10^6$ | | | |
| 959 | 1.76 × $10^6$ | | | |
| 983 | 1.64 × $10^6$ | 65 | end ADV | rtT128N<br>rtY135C |

[1]Nomenclature according to Stuyver et al., 2001, supra

TABLE 5

Summary of HBV mutations in patient A treated with ADV Days Sample post-ADV

| Sample name | Days post-ADV treatment | Genotype | Polymerase* | Surface |
|---|---|---|---|---|
| ILA1 | −230 | D | rtA/S21A/S<br>rtT/N128T/N**<br>rtQ/H/R215Q/stop | sP120P/T<br>sI208I/L |
| ILA2 | 904 | D | rtA/S21S<br>rtF122L<br>rtR126H<br>rtT/N128T/N<br>rtQ130P<br>rtN131D<br>rtQstop/215Q<br>rtH248N | sP/T120P<br>sT125M<br>sI/1208I/L |
| ILA3 | 932 | D | rtA/S21S<br>rtF122L<br>rtR126H<br>rtT/N128T/N<br>rtQ130P<br>rtN131D<br>rtQstop/215Q<br>rtH248N | sP/T120P<br>sT125M<br>sI/1208I/L |
| ILA4 | 983 | D | rtS21A<br>rtL122F<br>rtN124H<br>rtH126R<br>rtT128N<br>rtP130Q<br>rtD131N<br>rtY135C | sP120T<br>sM125T<br>sT127A |

*Nomenclature according to Stuyver et al., 2001, supra.

**Mutations in bold have not been detected in reference HBV genotypes, mutations not in bold are changes from the previous sample that are present in reference genotypes.

TABLE 6

Clinical, virological and HBV sequencing data summary for Patient B while on open label ADV.

| Days post-ADV treatment | HBV DN copies/ml (pg/ml) | ALT IU/L | Treatment protocol | Key polymerase mutations detected by sequencing[1] |
|---|---|---|---|---|
| −867(S0) | 183 | 298 | pre-therapy | rtN/S/T/I/V53D<br>rtV153G<br>rtQ/E215S<br>rtN248H |
| −8(S6) | 955 | 427 | pre-ADV on LMV | rtI/L80L<br>rtY126Q<br>rtL180M<br>rtS202G<br>rtI204V |
| 76(S8) | not detected | 150 | on ADV (20 mg) and LMV | rtN/S/T/I/V53D<br>rtY126Q<br>rtL180M<br>rtS202G<br>rtI204V |
| 637(S12) | not detected | 36 | on ADV (5 mg) and LMV | rtN/S/T/I/V53D<br>rtY126Q<br>rtL180M<br>rtS202G<br>rtI204V |
| 872(S15) | not detected | 67 | on ADV (5 mg) and LMV | rtN/S/T/I/V53D<br>rtY126Q<br>rtL180M<br>rtS202G<br>rtI204V<br>rtI235I/M |

[1]Nomenclature according to Stuyver et al., 2001, supra

TABLE 7

Summary of HBV mutations in Patient B treated with ADV

| Sample name | Days post-ADV treatment | Genotype | Polymerase* | Surface |
|---|---|---|---|---|
| S0 | −867 | D | rtN/S/T/I/V53D<br>rtV153G<br>rtQ/E215S<br>rtN248H | sM/K/L133T<br>sF134V<br>sS207R<br>sL21V/L |
| S6 | −8 | D | rtI/L80L<br>rtY126Q<br>rtL180M<br>rtS202G<br>rtI204V | sT118R<br>sM133T<br>sF134V<br>sI195M<br>sS207R |
| S8 | 76 | D | rtN/S/T/I/V53D<br>rtY126Q<br>rtL180M<br>rtS202G<br>rtI204V | sT118R<br>sM133T<br>sF134V<br>sI195M<br>sS207R |
| S12 | 637 | D | rtN/S/T/I/V53D<br>rtY126Q<br>rtL180M<br>rtS202G<br>I204V | sT118R<br>sM133T<br>sF134V<br>sI195M<br>sS207R |
| S15 | 872 | D | rtN/S/T/I/V53D<br>rtY126Q<br>rtL180M<br>rtS202G<br>rtI204V<br>rtI235I/M | sT118R<br>sM133T<br>sF134V<br>sI195M<br>sS207R<br>sY225Y/C |

*Nomenclature according to Stuyver et al., 2001, supra
**Mutations in bold have not been detected in reference HBV genotypes, mutations not in bold are changes from the previous sample that are present in reference genotypes.

TABLE 8

Clinical, virological and HBV sequencing data summary for Patient C while on open label ADV.

| Days post-ADV treatment | HBV DNA copies/ml (pg/ml) | ALT IU/L | Treatment protocol | Key polymerase mutations detected by sequencing[1] |
|---|---|---|---|---|
| −26 | 2 × 10⁷ | | pre-therapy | rtN53D<br>rtS116P<br>rtD/N/S134V<br>rtN238D |
| 0 | | 240 | ADV commenced clinical trial | |
| 29 | | 160 | | |
| 630 | | 407 | | |
| 668 | | | Open label ADV | |
| 701 | 1.5 × 10⁷ | 226 | | |
| 730 | 3.7 × 10⁶ | 361 | | rtN53D<br>rtS116P<br>rtF151S/T<br>rtA181T<br>rtN236T<br>rtN238D |
| 738 | | 517 | | |
| 739 | | | end ADV, start LMV | |

[1]Nomenclature according to Stuyver et al., 2001, supra

TABLE 9

Summary of HBV mutations in Patient C treated with ADV Days Sample post-ADV

| Sample name | Days post-ADV treatment | Genotype | Polymerase* | Surface |
|---|---|---|---|---|
| DRJ1299 | −26 | D | rtN53D\*\*<br>rtY54H<br>rtS57P<br>rtL91I<br>rtS116P<br>rtF122L<br>rtY124H<br>rtD/N/S134V<br>rtK212R<br>rtL217R<br>rtS219A<br>rtN238D | T126S<br>S204G<br>L209V<br>S210R |
| DRJ1 | 730 | D | rtN53D<br>rtY54H<br>rtS57P<br>rtL91I<br>rtS116P<br>rtF122L<br>rtY124H<br>rtV134D<br>rtY141Y/F<br>rtL145M<br>rtF151T/F<br>rtA181T<br>rtK12R<br>rtL217R<br>rtS219A<br>rtN236T<br>rtN238D | sS126T<br>sM133L/M<br>sS143S/T<br>sD144A<br>sG145A<br>sW172Stop |

*Nomenclature according to Stuyver et al., 2001, supra.
**Mutations in bold have not been detected in reference HBV genotypes, mutations not in bold are changes from the previous sample that are present in reference genotypes.

TABLE 10

Summary of HBV mutations in Patient D treated with ADV

| Sample Name | Genotype | Polymerase* | Surface |
|---|---|---|---|
| 02575908 | D | rtS78T | sN40S |
| | | rtV84M | sC69stop |
| | | rtY126C | sM75I |
| | | rtV191I | sL88P |
| | | rtM204I | sT118A |
| | | rtV214A | sW182STOP |
| | | | sW196L |
| | | | sY206H |
| | | | sY225F |

*Nomenclature according to Stuyver et al., 2001, supra.
**Mutations in bold have not been detected in reference HBV genotypes, mutations not in bold are changes from the previous sample that are present in reference genotypes.

TABLE 11

Summary of HBV mutations in Patient E treated with ADV

| Sample Name | Genotype | Polymerase* | Surface |
|---|---|---|---|
| 8123/02 | A | rtH90D | sI81M |
| | | rtI/F108L | sY/S100Y |
| | | 6nt insertion/duplication after codon rt131(aaQ&N) | 6nt insertion/duplication after codon s122 (aaT & K) |
| | | | sP214Q |

*Nomenclature according to Stuyver et al., 2001, supra.
**Mutations in bold have not been detected in reference HBV genotypes, mutations not in bold are changes from the previous sample that are present in reference genotypes.

TABLE 12

Codons where mutations occur following exposure to nucleoside or nucleotide analogs

| Region/Domain | Original amino acid in reverse transcriptase (rt) and codon position | Nucleotide | | | | |
|---|---|---|---|---|---|---|
| prior to F | K32 | AAG | AAA | | | |
| | N33 | AAT | | | | |
| | P34 | CCT | | | | |
| | H35 | CAC | | | | |
| | T37 | ACC | | | | |
| F TO A | P59 | CCA | | | | |
| | K60 | AAA | | | | |
| | F61 | TTC | | | | |
| | A62 | GCA | | | | |
| | V63 | GTC | | | | |
| A | D83 | GAT | | | | |
| | V84 | GTG | | | | |
| | S85 | TCT | | | | |
| | A86 | GCG | | | | |
| | Y89 | TAT | | | | |
| | H90 | CAT | | | | |
| | I/L91 | ATT | CTT | | | |
| B | P177 | CCG | | | | |
| | F178 | TTT | | | | |
| | L179 | CTC | | | | |
| | L180 | CTG | | | | |
| | A181 | TTG | | | | |
| | Q182 | CAG | | | | |
| | F183 | TTT | | | | |
| | T184 | ACT | | | | |
| C | Y203 | TAT | | | | |
| | M204 | ATG | | | | |
| D | L235 | TTG | TTA | | | |
| | N236 | AAC | AAT | | | |
| | T237 | ACT | ACC | | | |
| | P237 | CCT | CCC | | | |
| | N238 | AAT | AAC | | | |
| | H238 | CAC | | | | |
| | A238 | GCT | | | | |
| | S238 | TCT | | | | |
| | Q238 | CAG | | | | |
| | K239 | AAA | AAG | | | |
| E | L247 | CTT | TTA | CTA | CTC | CTG |
| | N248 | AAC | AAT | | | |
| | H248 | CAT | CAC | | | |
| | F249 | TTC | TTT | | | |
| | M250 | ATG | | | | |
| | G251 | GGT | GGA | GGC | GGG | |
| | V251 | GTC | | | | |

TABLE 13

Target amino acid sites in rt with codons and mutations leading to amino acid changes.

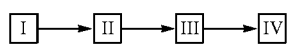

| Title | Codon | Amino Acid | Codon | Amino Acid | Codon | Amino Acid | Codon | Amino Acid | Codon | Amino Acid | Codon | Amino Acid | Codon | Amino Acid |
|---|---|---|---|---|---|---|---|---|---|---|---|---|---|---|
| K32 | AAG | Lys | AAG | Lys | GAG | Glu | CAG | Gln | TAG | Stop | AAG | Lys | AGG | Arg |
| N33 | AAT | Asn | AAT | Asn | GAT | Asp | CAT | His | TAT | Tyr | AAT | Asn | AGT | Ser |
| P34 | CCT | Pro | ACT | Thr | GCT | Ala | CCT | Pro | TCT | Ser | CAT | His | CGT | Arg |
| H35 | CAC | His | AAC | Asn | GAC | Asp | CAC | His | TAC | Tyr | CAC | His | CGC | Arg |
| T37 | ACC | Thr | ACC | Thr | GCC | Ala | CCC | Pro | TCC | Ser | AAC | Asn | AGC | Ser |
| P59 | CCA | Pro | ACA | Thr | GCA | Ala | CCA | Pro | TCA | Ser | CAA | Gln | CGA | Arg |
| K60 | AAA | Lys | AAA | Lys | GAA | Glu | CAA | Gln | TAA | Stop | AAA | Lys | AGA | Arg |
| F61 | TTC | Phe | ATC | Ile | GTC | Val | CTC | Leu | TTC | Phe | TAC | Tyr | TGC | Cys |
| A62 | GCA | Ala | ACA | Thr | GCA | Ala | CCA | Pro | TCA | Ser | GAA | Glu | GGA | Gly |
| V63 | GTC | Val | ATC | Ile | GTC | Val | CTC | Leu | TTC | Phe | GAC | Asp | GGC | Gly |
| D83 | GAT | Asp | AAT | Asn | GAT | Asp | CAT | His | TAT | Tyr | GAT | Asp | GGT | Gly |
| V84 | GTG | Val | ATG | Met | GTG | Val | CTG | Leu | TTG | Leu | GAG | Glu | GGG | Gly |
| S85 | TCT | Ser | ACT | Thr | GCT | Ala | CCT | Pro | TCT | Ser | TAT | Tyr | TGT | Cys |
| A86 | GCG | Ala | ACG | Thr | GCG | Ala | CCG | Pro | TCG | Ser | GAG | Glu | GGG | Gly |
| Y89 | TAT | Tyr | AAT | Asn | GAT | Asp | CAT | His | TAT | Tyr | TAT | Tyr | TGT | Cys |

TABLE 13-continued

Target amino acid sites in rt with codons and mutations leading to amino acid changes.

I → II → III → IV

| Title | Codon | Amino Acid | Codon | Amino Acid | Codon | Amino Acid | Codon | Amino Acid | Codon | Amino Acid | Codon | Amino Acid |
|---|---|---|---|---|---|---|---|---|---|---|---|---|
| H90 | CAT | His | AAT | Asn | GAT | Asp | CAT | His | TAT | Tyr | CAT | His | CGT | Arg |
| I/L91 | ATT | Ile | ATT | Ile | GTT | Val | CTT | Leu | TTT | Phe | AAT | Asn | AGT | Ser |
| P177 | CCG | Pro | ACG | Thr | GCG | Ala | CCG | Pro | TCG | Ser | CAG | Gln | CGG | Arg |
| F178 | TTT | Phe | ATT | Ile | GTT | Val | CTT | Leu | TTT | Phe | TAT | Tyr | TGT | Cys |
| L179 | CTC | Leu | ATC | Ile | GTC | Val | CTC | Leu | TTC | Phe | CAC | His | CGC | Arg |
| L180 | CTG | Leu | ATG | Met | GTG | Val | CTG | Leu | TTG | Leu | CAG | Gln | CGG | Arg |
| A181 | TTG | Leu | ATG | Met | GTG | Val | CTG | Leu | TTG | Leu | TAG | Stop | TGG | Trp |
| Q183 | CAG | Gln | AAG | Lys | GAG | Glu | CAG | Gln | TAG | Stop | CAG | Gln | CGG | Arg |
| F183 | TTT | Phe | ATT | Ile | GTT | Val | CTT | Leu | TTT | Phe | TAT | Tyr | TGT | Cys |
| T184 | ACT | Thr | ACT | Thr | GCT | Ala | CCT | Pro | TCT | Ser | AAT | Asn | AGT | Ser |
| Y203 | TAT | Tyr | AAT | Asn | GAT | Asp | CAT | His | TAT | Tyr | TAT | Tyr | TGT | Cys |
| M204 | ATG | Met | ATG | Met | GTG | Val | CTG | Leu | TTG | Leu | AAG | Lys | AGG | Arg |
| L235 | TTG | Leu | ATG | Met | GTG | Val | CTG | Leu | TTG | Leu | TAG | Stop | TGG | Trp |
| N236 | AAC | Asn | AAC | Asn | GAC | Asp | CAC | His | TAC | Tyr | AAC | Asn | AGC | Ser |
| T237 | ACT | Thr | ACT | Thr | GCT | Ala | CCT | Pro | TCT | Ser | AAT | Asn | AGT | Ser |
| P237 | CCT | Pro | ACT | Thr | GCT | Ala | CCT | Pro | TCT | Ser | CAT | His | CGT | Arg |
| N238 | AAT | Asn | AAT | Asn | GAT | Asp | CAT | His | TAT | Tyr | AAT | Asn | AGT | Ser |
| H238 | CAC | His | AAC | Asn | GAC | Asp | CAC | His | TAC | Tyr | CAC | His | CGC | Arg |
| A238 | GCT | Ala | ACT | Thr | GCT | Ala | CCT | Pro | TCT | Ser | GAT | Asp | GGT | Gly |
| S239 | TCT | Ser | ACT | Thr | GCT | Ala | CCT | Pro | TCT | Ser | TAT | Tyr | TGT | Cys |
| Q238 | CAG | Gln | AAG | Lys | GAG | Glu | CAG | Gln | TAG | Stop | CAG | Gln | CGG | Arg |
| K239 | AAA | Lys | AAA | Lys | GAA | Glu | CAA | Gln | TAA | Stop | AAA | Lys | AGA | Arg |
| L247 | CTT | Leu | ATT | Ile | GTT | Val | CTT | Leu | TTT | Phe | CAT | His | CGT | Arg |
| N248 | AAC | Asn | AAC | Asn | GAC | Asp | CAC | His | TAC | Tyr | AAC | Asn | AGC | Ser |
| H248 | CAT | His | AAT | Asn | GAT | Asp | CAT | His | TAT | Tyr | CAT | His | CGT | Arg |
| F249 | TTC | Phe | ATC | Ile | GTC | Val | CTC | Leu | TTC | Phe | TAC | Tyr | TGC | Cys |
| M250 | ATG | Met | ATG | Met | GTG | Val | CTG | Leu | TTG | Leu | AAG | Lys | AGG | Arg |
| G251 | GGT | Gly | AGT | Ser | GGT | Gly | CGT | Arg | TGT | Cys | GAT | Asp | GGT | Gly |
| V251 | GTC | Val | ATC | Ile | GTC | Val | CTC | Leu | TTC | Phe | GAC | Asp | GGC | Gly |

| Title | Codon | Amino Acid | Codon | Amino Acid | Codon | Amino Acid | Codon | Amino Acid | Codon | Amino Acid | Codon | Amino Acid |
|---|---|---|---|---|---|---|---|---|---|---|---|---|
| K32 | ACG | Thr | ATG | Met | AAA | Lys | AAG | Lys | AAC | Asn | AAT | Asn |
| N33 | ACT | Thr | ATT | Ile | AAA | Lys | AAG | Lys | AAC | Asn | AAT | Asn |
| P34 | CCT | Pro | CTT | Leu | CCA | Pro | CCG | Pro | CCC | Pro | CCT | Pro |
| H35 | CCC | Pro | CTC | Leu | CAA | Gln | CAG | Gln | CAC | His | CAT | His |
| T37 | ACC | Thr | ATC | Ile | ACA | Thr | ACG | Thr | ACC | Thr | ACT | Thr |
| P59 | CCA | Pro | CTA | Leu | CCA | Pro | CCG | Pro | CCC | Pro | CCT | Pro |
| K60 | ACA | Thr | ATA | Ile | AAA | Lys | AAG | Lys | AAC | Asn | AAT | Asn |
| F61 | TCC | Ser | TTC | Phe | TTA | Leu | TTG | Leu | TTC | Phe | TTT | Phe |
| A62 | GCA | Ala | GTA | Val | GCA | Ala | GCG | Ala | GCC | Ala | GCT | Ala |
| V63 | GCC | Ala | GTC | Val | GTA | Val | GTG | Val | GTC | Val | GTT | Val |
| D83 | GCT | Ala | GTT | Val | GAA | Glu | GAG | Glu | GAC | Asp | GAT | Asp |
| V84 | GCG | Ala | GTG | Val | GTA | Val | GTG | Val | GTC | Val | GTT | Val |
| S85 | TCT | Ser | TTT | Phe | TCA | Ser | TCG | Ser | TCC | Ser | TCT | Ser |
| A86 | GCG | Ala | GTG | Val | GCA | Ala | GCG | Ala | GCC | Ala | GCT | Ala |
| Y89 | TCT | Ser | TTT | Phe | TAA | Stop | TAG | Stop | TAC | Tyr | TAT | Tyr |
| H90 | CCT | Pro | CTT | Leu | CAA | Gln | CAG | Gln | CAC | His | CAT | His |
| I/L91 | ACT | Thr | ATT | Ile | ATA | Ile | ATG | Met | ATC | Ile | ATT | Ile |
| P177 | CCG | Pro | CTG | Leu | CCA | Pro | CCG | Pro | CCC | Pro | CCT | Pro |
| F178 | TCT | Ser | TTT | Phe | TTA | Leu | TTG | Leu | TTC | Phe | TTT | Phe |
| L179 | CCC | Pro | CTC | Leu | CTA | Leu | CTG | Leu | CTC | Leu | CTT | Leu |
| L180 | CCG | Pro | CTG | Leu | CTA | Leu | CTG | Leu | CTC | Leu | CTT | Leu |
| A181 | TCG | Ser | TTG | Leu | TTA | Leu | TTG | Leu | TTC | Phe | TTT | Phe |
| Q183 | CCG | Pro | CTG | Leu | CAA | Gln | CAG | Gln | CAC | His | CAT | His |
| F183 | TCT | Ser | TTT | Phe | TTA | Leu | TTG | Leu | TTC | Phe | TTT | Phe |
| T184 | ACT | Thr | ATT | Ile | ACA | Thr | ACG | Thr | ACC | Thr | ACT | Thr |
| Y203 | TCT | Ser | TTT | Phe | TAA | Stop | TAG | Stop | TAC | Tyr | TAT | Tyr

TABLE 13-continued

Target amino acid sites in rt with codons and mutations leading to amino acid changes.

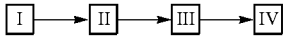

| G251 | GCT | Ala | GTT | Val | GGA | Gly | GGG | Gly | GGC | Gly | GGT | Gly |
| V251 | GCC | Ala | GTC | Val | GTA | Val | GTG | Val | GTC | Val | GTT | Val |

TABLE 14

Amino acid mutations at target sites in rt
Target Mutation K32

| Target | Mutation |
|---|---|
| K32 | M/F/P/S/T/W/Y/V/A/R/N/D/C/Q/E/G/H/I/L |
| N33 | D/C/Q/E/G/H/I/L/K/M/F/P/S/T/W/Y/V/A/R |
| P34 | S/T/W/Y/V/A/R/N/D/C/Q/E/G/H/I/L/K/M/F |
| H35 | I/L/K/M/F/P/S/T/W/Y/V/A/R/N/D/C/Q/E/G |
| T37 | W/Y/V/A/R/N/D/C/Q/E/G/H/I/L/K/M/F/P/S |
| P59 | S/T/W/Y/V/A/R/N/D/C/Q/E/G/H/I/L/K/M/F |
| K60 | M/F/P/S/T/W/Y/V/A/R/N/D/C/Q/E/G/H/I/L |
| F61 | P/S/T/W/Y/V/A/R/N/D/C/Q/E/G/H/I/L/K/M |
| A62 | R/N/D/C/Q/E/G/H/I/L/K/M/F/P/S/T/W/Y/V |
| V63 | A/R/N/D/C/Q/E/G/H/I/L/K/M/F/P/S/T/W/Y |
| D83 | C/Q/E/G/H/I/L/K/M/F/P/S/T/W/Y/V/A/R/N |
| V84 | A/R/N/D/C/Q/E/G/H/I/L/K/M/F/P/S/T/W/Y |
| S85 | T/W/Y/V/A/R/N/D/C/Q/E/G/H/I/L/K/M/F/P |
| A86 | R/N/D/C/Q/E/G/H/I/L/K/M/F/P/S/T/W/Y/V |
| Y89 | V/A/R/N/D/C/Q/E/G/H/I/L/K/M/F/P/S/T/W |
| H90 | I/L/K/M/F/P/S/T/W/Y/V/A/R/N/D/C/Q/E/G |
| I/L91 | K/M/F/P/S/T/W/Y/V/A/R/N/D/C/Q/E/G/H |
| P177 | S/T/W/Y/V/A/R/N/D/C/Q/E/G/H/I/L/K/M/F |
| F178 | P/S/T/W/Y/V/A/R/N/D/C/Q/E/G/H/I/L/K/M |
| L179 | K/M/F/P/S/T/W/Y/V/A/R/N/D/C/Q/E/G/H/I |
| L180 | K/M/F/P/S/T/W/Y/V/A/R/N/D/C/Q/E/G/H/I |
| A181 | R/N/D/C/Q/E/G/H/I/L/K/M/F/P/S/T/W/Y/V |
| Q183 | E/G/H/I/L/K/M/F/P/S/T/W/Y/V/A/R/N/D/C |
| F183 | P/S/T/W/Y/V/A/R/N/D/C/Q/E/G/H/I/L/K/M |
| T184 | W/Y/V/A/R/N/D/C/Q/E/G/H/I/L/K/M/F/P/S |
| Y203 | V/A/R/N/D/C/Q/E/G/H/I/L/K/M/F/P/S/T/W |
| M204 | F/P/S/T/W/Y/V/A/R/N/D/C/Q/E/G/H/I/L/K |
| L235 | K/M/F/P/S/T/W/Y/V/A/R/N/D/C/Q/E/G/H/I |
| N236 | D/C/Q/E/G/H/I/L/K/M/F/P/S/T/W/Y/V/A/R |
| T237 | W/Y/V/A/R/N/D/C/Q/E/G/H/I/L/K/M/F/P/S |
| P237 | S/T/W/Y/V/A/R/N/D/C/Q/E/G/H/I/L/K/M/F |
| N238 | D/C/Q/E/G/H/I/L/K/M/F/P/S/T/W/Y/V/A/R |
| H238 | I/L/K/M/F/P/S/T/W/Y/V/A/R/N/D/C/Q/E/G |
| A238 | R/N/D/C/Q/E/G/H/I/L/K/M/F/P/S/T/W/Y/V |
| S239 | T/W/Y/V/A/R/N/D/C/Q/E/G/H/I/L/K/M/F/P |
| Q238 | E/G/H/I/L/K/M/F/P/S/T/W/Y/V/A/R/N/D/C |
| K239 | M/F/P/S/T/W/Y/V/A/R/N/D/C/Q/E/G/H/I/L |
| L247 | K/M/F/P/S/T/W/Y/V/A/R/N/D/C/Q/E/G/H/I |
| N248 | D/C/Q/E/G/H/I/L/K/M/F/P/S/T/W/Y/V/A/R |
| H248 | I/L/K/M/F/P/S/T/W/Y/V/A/R/N/D/C/Q/E/G |
| F249 | P/S/T/W/Y/V/A/R/N/D/C/Q/E/G/H/I/L/K/M |
| M250 | F/P/S/T/W/Y/V/A/R/N/D/C/Q/E/G/H/I/L/K |
| G251 | H/I/L/K/M/F/P/S/T/W/Y/V/A/R/N/D/C/Q/E |
| V251 | A/R/N/D/C/Q/E/G/H/I/L/K/M/F/P/S/T/W/Y |

TABLE 15

Summary of HBV mutations in
Patient F treated with ADV

| Sample Name | Genotype | Polymerase* | Surface |
|---|---|---|---|
| CAP 01564808 | A | rtL157L/M | sF83S |
| | | rtA181V | sL173F |
| | | rtV207I | sW199L |
| | | rtN236T | |

*Nomenclature according to Stuyver et al., 2001, supra.
**Mutations in bold have not been detected in reference HBV genotypes, mutations not in bold are changes from the previous sample that are present in reference genotypes.

TABLE 16

Summary of HBV mutations in
Patient G treated with ADV

| Sample Name | Genotype | Polymerase* | Surface |
|---|---|---|---|
| KAN 02510355 | C | rtL80V | sI126T |
| | | rtP109S | sK160R |
| | | rtI163V | sS174N |
| | | rtM204I | sA184V |
| | | rtL229M | sW196L |
| | | rtN/H/A/S/Q238K | sS210N |
| | | | sF/C220L |
| | | | sY221C |

*Nomenclature according to Stuyver et al., 2001, supra.
**Mutations in bold have not been detected in reference HBV genotypes, mutations not in bold are changes from the previous sample that are present in reference genotypes.

TABLE 17

Summary of HBV mutations in
Patient H treated with ADV

| Sample Name | Genotype | Polymerase* | Surface |
|---|---|---|---|
| LAV0303 | D | rtS78S/T | sC69Stop/C |
| | | rtN118N/S | sC76Y |
| | | rtN139N/K | sI110V/I |
| | | rtV142E | sY134N |
| | | rtA181A/T | sW172Stop/W |
| | | rtI204M | sW196Stop |
| | | rtQ/P/S/Stop215Q | sS207R |
| | | rtE218K/E | |
| | | rtN238N/H | |

*Nomenclature according to Stuyver et al., 2001, supra.
**Mutations in bold have not been detected in reference HBV genotypes, mutations not in bold are changes from the previous sample that are present in reference genotypes.

TABLE 18

In vitro drug susceptibility of the HBV reference
laboratory strain and patient-derived HBV isolate

| | In vitro Susceptibility IC$_{50}$ (fold change from wild-type) | | |
|---|---|---|---|
| | Real-time PCR | Southern Blot | |
| Mutation | Adefovir | Adefovir | Lamivudine |
| Wild-type (pPC) | 1 | 1 | 1 |
| rt N236T/N238D | 23 | NA$^1$ | NA$^1$ |
| rt A181T/N236T/N238D | 5.1 | 7.3 | >100 |
| rt L180M/M204V$^2$ | NT$^5$ | 0.9 | >2500 |

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features

BIBLIOGRAPHY

Allen et al., Hepatology 27(6): 1670-1677, 1998
Aye et al., J. Hepatol. 26: 1148-1153, 1997
Bartholomeusz et al., Intervirology 40(5-6): 337-342 1997
Benhamou et al., Lancet 358: 718-723, 2001
Benzaria et al., J Med Chem. 39: 4958-4965, 1996
Boyd et al., Antiviral Chem Chemother. 32: 358-363, 1987
Calio et al., Antiviral Res. 23: 77-89, 1994
Das et al., J. Virol. 75(10): 4771-4779, 2001
Delaney et al., Antimicrob Agents Chemother 45(6): 1705-1013, 2001
Dienstag et al., New England J Med 333: 1657-1661, 1995
Frick et al., Antimicrob. Agents Chemother. 37: 2285-2292, 1993
Gaillard et al., Antimicrob Agents Chemother. 46(4): 1005-1013, 2002
Gilson et al., J Viral Hepat 6: 387-395, 1999
Heathcote et al., Hepatology 28: A620, 1998
Hendricks et al., Am J Clin Pathol 104: 537-46, 1995
Kruger et al. Hepatology 22: 219A, 1994
Main et al., J. Viral Hepatitis 3: 211-215, 1996
Norder et al., (J. Gen. Virol. 74: 341-1348, 1993
Perrino et al., Hepatology 32: 129-134, 2000
Peters et al., Transplantation 68: 1912-1914, 1999
Price et al., Proc. Natl. Acad. Sci. USA 86(21): 8541-8544, 1989
Ren and Nassal, J. Virol. 75(3): 1104-1116, 2001
Severini et al., Antimicrobial Agents Chemother. 39: 430-435, 1995
Stuyver et al., Hepatology 33: 751-757, 2001
Summers and Mason, Cell 29: 403-415, 1982
Suo et al., J Biol Chem. 273(42): 27250-27258. 1998
Vere Hodge, Antiviral Chem Chemother 4: 67-84, 1993
Xiong et al., Hepatology. 28(6): 1669-73, 1998
Ying et al., J Viral Hepat. 7(2): 161-165, 2000
Ying et al., J. Viral Hepat. 7(1): 79-83, 2000
Ying et al., Viral Hepat. 7(2): 161-165, 2000

```
Sequence CWU 1 (SEQ ID NO.: 1)
1

59176PRT artificial sequence synthetic - Formula I 1
Leu XAa XAA asp Trp Gly Pro Cys XAa XAa His Gly XAa His XAa Ile
1               5                   10                  15

Arg XAa Pro Arg Thr Pro XAAarg Val XAa Gly Gly Val Phe Leu Val
            20                  25                  30

Asp Lys Asn Pro His Asn Thr XAa Glu Ser XAa Leu XAa Val Asp Phe
        35                  40                  45

Ser Gln Phe Ser Arg Gly XAa XAa XAa Val Ser Trp Pro Lys Phe Ala
    50                  55                  60

Val Pro Asn Leu XAa Ser Leu Thr Asn Leu Leu Ser
65              70                  75

2181PRT artificial sequence synthetic - Formula II 2 (SEQ ID NO.: 2)
Ser XAa Leu Ser Trp Leu Ser Leu Asp Val Ser AlAala Phe Tyr His
1               5                   10                  15

XAa Pro Leu His Pro AlAala Met Pro His Leu Leu XAa Gly Ser Ser
            20                  25                  30

Gly Leu XAAarg Tyr Val AlAarg Leu Ser Ser XAa Ser XAa XAa XAa
            35                  40                  45

Asn XAa Gln XAa XAa XAa XAa XAa XAa Leu His XAa XAa Cys Ser Arg
        50                  55                  60

XAa Leu Tyr Val Ser Leu XAa Leu Leu Tyr XAa Thr XAa Gly XAa Lys
65              70                  75                  80

Leu His Leu XAa XAa His Pro Ile XAa Leu Gly Phe Arg Lys XAa Pro
            85                  90                  95

Met Gly XAa Gly Leu Ser Pro Phe Leu Leu Ala Gln Phe Thr Ser Ala
            100                 105                 110

Ile XAa XAa XAa XAa XAAarg Ala Phe XAa His Cys XAa XAa Phe XAa
            115                 120                 125

Tyr Met Asp Asp XAa Val Leu Gly Ala XAa XAa XAa XAa His XAa Glu
            130                 135                 140

XAa Leu XAa XAa XAa XAa XAa XAa XAa Leu Leu XAa XAa Gly Ile His
145                 150                 155                 160
```

```
Leu Asn Pro XAa Lys Thr Lys Arg Trp Gly Tyr Ser Leu Asn Phe Met
            165                 170                 175

Gly Tyr XAa Ile Gly
            180

323DNA artificial sequenceOS1 primer 3 (SEQ ID NO.: 3)
gcctcatttt gtgggtcacc ata                                              23

418DNA artificial sequenceTTA3 primer 4 (SEQ ID NO.: 4)
Aaattcgcag tccccAaa                                                    18

521DNA artificial sequenceJM primer 5 (SEQ ID NO.: 5)
ttggggtgga gccctcaggc t                                                21

618DNA artificial sequenceTTA4 primer 6 (SEQ ID NO.: 6)
gAaAattggt Aacagcgg                                                    18

720DNA artificial sequenceOS2 primer 7 (SEQ ID NO.: 7)
tctctgacat actttccAat                                                  20

823DNA artificial sequencesense primer 8 (SEQ ID NO.: 8)
gcctcatttt gtgggtcacc ata                                              23

920DNA artificial sequenceantisense primer 9 (SEQ ID NO.: 9)
tctctgacat actttccAat                                                  20

1018DNA artificial sequenceinternal regions primer 10 (SEQ ID NO.: 10)
tgcacgattc ctgctcAa                                                    18

1120DNA artificial sequenceinternal regions primer 11 (SEQ ID NO.: 11)
tttctcAaag gtggagacag                                                  20

1218DNA artificial sequencePC1 forward primer 12 (SEQ ID NO.: 12)
gggaggagat taggttAa                                                    18

1320DNA artificial sequencePC2 reverse primer 13 (SEQ ID NO.: 13)
ggcAaAaacg agagtAactc                                                  20

1436DNA artificial sequenceHBV-specific molecular beacon primer 14 (SEQ ID NO.: 14)
cgcgtcctac tgttcAagcc tccAagctgt gacgcg                                36

15280DNA artificial sequenceSynthetic oligonucleotide 15 (SEQ ID NO.: 15)
tggctcagtt tactagtgcc atttgttcag tggttcgtag ggctttcccc cactgtttgg      60
ctttcagtta tatggatgat gtggtattgg gggccAagtc tgtayagcay cttgagtccc     120
tttttaccgc tgttaccAat tttcttttgt ctttgggtat acatttAaac cctAacAaAa    180
ctAaAagatg gggttactct ttacatttca tgggntatgt cattggatgt tatgggtcat    240
tgccacAaga tcacatcata cagAaAatcAa agatggttt                          280

16242DNA artificial sequenceSynthetic oligonucleotide 16 (SEQ ID NO.: 16)
tggctcagtt tactagtgcc atttgttcag tggttcgtag ggctttcccc cactgtttgg      60
ctttcagtta tatggatgat gtggtattgg gggccAagtc tgtacagcat cttgagtccc    120
tttttaccgc tgttaccAat tttcttttgt ctttgggtat acatttAaac cctAacAaAa    180
cAaagagatg gggttactct ctAaattta tgggttatgt cattggatgt tatgggtcct     240
tg                                                                   242

17277DNA artificial sequence Synthetic oligonucleotide 17 (SEQ ID NO.: 17)
tggctcagtt tactagtgcc atttgttcag tggttcgtag ggctttcccc cactgtttgg      60
ctttcagtta tatggatgat gtggtattgg gggccAagtc tgtacagcat cttgagtccc    120
tttttaccgc tgttaccAat tttcttttgt ctttgggtat acatttAaac cctAacAaAa    180
cAaagagatg gggttactct ctAaattta tgggttatgt cattggatgt tatgggtcct     240 tgccacAagAacacatcata cAaAaAatcAa agAatg                              277

18237DNA artificial sequenceSynthetic oligonucleotide 18 (SEQ ID NO.: 18)
tggctcagtt tactagtgcc atttgttcag tggttcgtag ggctttcccc cactgtttgg      60
ctttcagtta tatggatgat gtggtattgg gggccAagtc tgtacagcat cttgagtccc    120
```

```
tttttaccgc tgttaccAat tttcttttgt ctttgggcat acatttAaac cctAacAaAa      180
ctAaAagatg ggggtactct ttAaatttca tgggatatgt cattggatgg tatgggg        237
```

19 336 PRT artificial sequence Synthetic polypeptide 19 (SEQ ID NO.: 19)

```
Lys Leu Ala Ser Lys Ser Ala Ser Ser Ile XAa Gln Ser Pro Val Arg
1               5                   10                  15

XAAalAala Tyr Pro Ala Val Ser Thr Phe Glu Lys His Ser Ser Ser
            20                  25                  30

Gly His Ala Val Glu XAa His Asn Leu Pro Pro Asn Ser XAAarg Ser
            35                  40                  45

Gln XAa Glu Arg Pro Val Phe Pro Cys Trp Trp Leu Gln Phe Arg Asn
    50                  55                  60

Ser Lys Pro Cys Ser Asp Tyr Cys Leu Ser His Ile Val Asn Leu Leu
65                  70                  75                  80

Glu Asp Trp Gly Pro Cys Ala Glu His Gly Glu His His Ile Arg Ile
                85                  90                  95

Pro Arg Thr Pro XAA arg Val Thr Gly Gly Val Phe Leu Val Asp Lys
            100                 105                 110

Asn Pro His Asn Thr Ala Glu Ser Arg Leu Val Val Asp Phe Ser Gln
            115                 120                 125

Phe Ser Arg Gly Asn Tyr Arg Val Ser Trp Pro Lys Phe Ala Val Pro
130                 135                 140

Asn Leu Gln Ser Leu Thr Asn Leu Leu Ser Ser Asn Leu Ser Trp Leu
145                 150                 155                 160

Ser Leu Asp Val Ser AlA ala Phe Tyr His Leu Pro Leu His Pro Ala
                165                 170                 175

Ala Met Pro His Leu Leu Val Gly Ser Ser Gly Leu Ser Arg Tyr Val
            180                 185                 190

AlAarg Leu Ser Ser Asn Ser Arg Ile Phe Asn His Gln Arg Gly XAa
            195                 200                 205

Met Gln Asn Leu His Asp Tyr Cys Ser Arg Asn Leu Tyr Val Ser Leu
    210                 215                 220

Leu Leu Leu Tyr Gln Thr Phe Gly Arg Lys Leu His Leu Tyr Ser His
225                 230                 235                 240

Pro Ile Ile Leu Gly Phe Arg Lys Ile Pro Met Gly Val Gly Leu Ser
                245                 250                 255

Pro Phe Leu Leu Ala Gln Phe Thr Ser Ala Ile Cys Ser Val Val Arg
            260                 265                 270

Arg Ala Phe Pro His Cys Leu Ala Phe Ser Tyr Met Asp Asp Val Val
            275                 280                 285

Leu Gly Ala Lys Ser Val XAa His Leu Glu Ser Leu Phe Thr Ala Val
    290                 295                 300

Thr Asn Phe Leu Leu Ser Leu Gly Ile His Leu Asn Pro Asn Lys Thr
305                 310                 315                 320

Lys Arg Trp Gly Tyr Ser Leu His Phe Met Gly Tyr Val Ile Gly Cys
                325                 330                 335
```

20 340 PRT artificial sequence Synthetic polypeptide 20 (SEQ ID NO.: 20)

```
His Thr Thr Asn Phe Ala Ser Lys Ser Ala Ser Cys Leu His Gln Ser
1               5                   10                  15

Pro Val Arg Lys AlAala Tyr Pro Ala Val Ser Thr Phe Glu Lys His
            20                  25                  30

Ser Ser Ser Gly His Ala Val Glu Phe His Asn Leu Pro Pro Asn Ser
            35                  40                  45

AlAarg Ser Gln Ser Glu Arg Pro Val Phe Pro Cys Trp Trp Leu Gln
    50                  55                  60
```

```
Phe Arg Asn Ser Lys Pro Cys Ser Asp Tyr Cys Leu Ser Leu Ile Val
 65                  70                  75                  80

Asn Leu Leu Glu Asp Trp Gly Pro Cys Ala Glu His Gly Glu His His
                 85                  90                  95

Ile Arg Ile Pro Arg Thr Pro Ser Arg Val Thr Gly Gly Val Phe Leu
            100                 105                 110

Val Asp Lys Asn Pro His Asn Thr Ala Glu Ser Arg Leu Val Val Asp
        115                 120                 125

Phe Ser Gln Phe Ser Arg Gly Asn Tyr Arg Val Ser Trp Pro Lys Phe
    130                 135                 140

Ala Val Pro Asn Leu Gln Ser Leu Thr Asn Leu Leu Ser Ser Asn Leu
145                 150                 155                 160

Ser Trp Leu Ser Leu Asp Val Ser AlAala Phe Tyr His Leu Pro Leu
                165                 170                 175

His Pro AlAala Met Pro His Leu Leu Val Gly Ser Ser Gly Leu Ser
            180                 185                 190

Arg Tyr Val AlAarg Leu Ser Ser Asn Ser Arg Ile Leu Asn Asn Gln
        195                 200                 205

His Gly Thr Met Pro Asp Leu His Asp Tyr Cys Ser Arg Asn Leu Tyr
    210                 215                 220

Val Ser Leu Leu Leu Leu Tyr Gln Thr Phe Gly Arg Lys Leu His Leu
225                 230                 235                 240

Tyr Ser His Pro Ile Ile Leu Gly Phe Arg Lys Ile Pro Met Gly Val
                245                 250                 255

Gly Leu Ser Pro Phe Leu Leu Ala Gln Phe Thr Ser Ala Ile Cys Ser
            260                 265                 270

Val Val Arg Arg Ala Phe Pro His Cys Leu Ala Phe Ser Tyr Met Asp
        275                 280                 285

Asp Val Val Leu Gly Ala Lys Ser Val Gln His Leu Glu Ser Leu Phe
    290                 295                 300

Thr Ala Val Thr Asn Phe Leu Leu Ser Leu Gly Ile His Leu Asn Pro
305                 310                 315                 320

Asn Lys Thr Lys Arg Trp Gly Tyr Ser Leu Asn Phe Met Gly Tyr Val
                325                 330                 335

Ile Gly Cys Tyr
            340

21344PRTartificial sequenceSynthetic polypeptide 21 (SEQ ID NO.: 21)
Leu Ala Gln Gly Ile Leu Gln Asn Phe Ala Ser Lys Ser Ala Ser Cys
 1               5                  10                  15

Leu His Gln Ser Pro Val Arg Lys AlAala Tyr Pro Ala Val Ser Thr
                20                  25                  30

Phe Glu Lys His Ser Ser Ser Gly His Ala Val Glu Phe His Asn Leu
            35                  40                  45

Pro Pro Asn Ser AlAarg Ser Gln Ser Glu Arg Pro Val Phe Pro Cys
        50                  55                  60

Trp Trp Leu Gln Phe Arg Asn Ser Lys Pro Cys Ser Asp Tyr Cys Leu
 65                  70                  75                  80

Ser Leu Ile Val Asn Leu Leu Glu Asp Trp Gly Pro Cys Ala Glu His
                85                  90                  95

Gly Glu His His Ile Arg Ile Pro Arg Thr Pro Ser Arg Val Thr Gly
            100                 105                 110

Gly Val Phe Leu Val Asp Lys Asn Pro His Asn Thr Ala Glu Ser Arg
        115                 120                 125

Leu Val Val Asp Phe Ser Gln Phe Ser Arg Gly Asn Tyr Arg Val Ser
    130                 135                 140
```

```
Trp Pro Lys Phe Ala Val Pro Asn Leu Gln Ser Leu Thr Asn Leu Leu
145                 150                 155                 160

Ser Ser Asn Leu Ser Trp Leu Ser Leu Asp Val Ser AlaAla Phe Tyr
                165                 170                 175

His Leu Pro Leu His Pro AlAala Met Pro His Leu Leu Val Gly Ser
            180                 185                 190

Ser Gly Leu Ser Arg Tyr Val AlAarg Leu Ser Ser Asn Ser Arg Ile
        195                 200                 205

Leu Asn Asn Gln His Gly Thr Met Pro Asp Leu His Asp Tyr Cys Ser
    210                 215                 220

Arg Asn Leu Tyr Val Ser Leu Leu Leu Tyr Gln Thr Phe Gly Arg
225                 230                 235                 240

Lys Leu His Leu Tyr Ser His Pro Ile Ile Leu Gly Phe Arg Lys Ile
                245                 250                 255

Pro Met Gly Val Gly Leu Ser Pro Phe Leu Leu Ala Gln Phe Thr Ser
            260                 265                 270

Ala Ile Cys Ser Val Val Arg Arg Ala Phe Pro His Cys Leu Ala Phe
        275                 280                 285

Ser Tyr Met Asp Asp Val Val Leu Gly Ala Lys Ser Val Gln His Leu
    290                 295                 300

Glu Ser Leu Phe Thr Ala Val Thr Asn Phe Leu Leu Ser Leu Gly Ile
305                 310                 315                 320

His Leu Asn Pro Asn Lys Thr Lys Arg Trp Gly Tyr Ser Leu Asn Phe
                325                 330                 335

Met Gly Tyr Val Ile Gly Cys Tyr
            340

22336PRTartificial sequenceSynthetic polypeptide 22 (SEQ ID NO.: 22)
Ala Ser Lys Ser Ala Ser Ser Ile Tyr Gln Ser Pro Val Gly Thr Ala
1               5                   10                  15

Ala Tyr Pro Ala Val Ser Thr XAa Glu Lys His Ser Ser Gly His
                20                  25                  30

Ala Val Glu Leu His Asn Leu Pro Pro Asn Ser Glu Arg Ser Gln Gly
            35                  40                  45

Glu Arg Pro Val Phe Pro Cys Trp Trp Leu Gln Phe Arg Asn Ser Lys
        50                  55                  60

Pro Cys Ser Asp Tyr Cys Leu Ser His Ile Val Asn Leu Leu Glu Asp
65                  70                  75                  80

Trp Gly Pro Cys Ala Glu His Gly Glu His His Ile Arg Ile Pro Arg
                85                  90                  95

Thr Pro AlAarg Val Thr Gly Gly Val Phe Leu Val Asp Lys Asn Pro
            100                 105                 110

His Asn Thr Ala Glu Ser Arg Leu Val Val Asp Phe Ser Gln Phe Ser
        115                 120                 125

Arg Gly Asn Tyr Arg Val Ser Trp Pro Lys Phe Ala Val Pro Asn Leu
    130                 135                 140

Gln Ser Leu Thr Asn Leu Leu Ser Ser Asn Leu Ser Trp Leu Ser Leu
145                 150                 155                 160

Asp Val Ser AlAala Phe Tyr His Leu Pro Leu His Pro AlAala Met
                165                 170                 175

Pro His Leu Leu Val Gly Ser Ser Gly Leu Ser Arg Tyr Val AlAarg
            180                 185                 190

Leu Ser Ser Asn Ser Arg Ile Phe Asn His Gln Arg Gly Asn Met Gln
        195                 200                 205

Asn Leu His Asp Cys Cys Ser Arg Asn Leu Tyr Val Ser Leu Leu Leu
```

-continued

```
                210                 215                 220
Leu Tyr Gln Thr Phe Gly Arg Lys Leu His Leu Tyr Ser His Pro Ile
225                 230                 235                 240

Ile Leu Gly Phe Arg Lys Ile Pro Met Gly Val Gly Leu Ser Pro Phe
                245                 250                 255

Leu Leu Ala Gln Phe Thr Ser Ala Ile Cys Ser Val Val Arg Arg Ala
                260                 265                 270

Phe Pro His Cys Leu Ala Phe Ser Tyr Met Asp Asp Val Val Leu Gly
                275                 280                 285

Ala Lys Ser Val Gln His Leu Glu Ser Leu Phe Thr Ala Val Thr Asn
                290                 295                 300

Phe Leu Leu Ser Leu Gly Ile His Leu Asn Pro Asn Lys Thr Lys Arg
305                 310                 315                 320

Trp Gly Tyr Ser Leu Asn Phe Met Gly Tyr Val Ile Gly Trp Tyr Gly
                325                 330                 335

23226PRT artificial sequence Synthetic polypeptide 23 (SEQ ID NO.: 23)
Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
                20                  25                  30

Asp Ser Trp Trp Thr Ser Leu Asn Phe Leu Gly Gly Thr Thr Val Cys
                35                  40                  45

Leu Gly Gln Asn Ser Gln Ser Pro Thr Ser Asn His Ser Pro Thr Ser
50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Cys Leu Ile Phe Leu Leu Val
                85                  90                  95

Leu Leu Asp Tyr Gln Gly Met Leu Pro Val Cys Pro Leu Ile Pro Gly
                100                 105                 110

Ser Ser Thr Thr Ser Ala Gly XAa Cys Arg Thr Cys Thr Thr Thr Ala
                115                 120                 125

Gln Gly Thr Ser Met Tyr Pro Ser Cys Cys Cys Thr Lys Pro Ser Asp
                130                 135                 140

Gly Asn Cys Thr Cys Ile Pro Ile Pro Ser Ser Trp Ala Phe Gly Lys
145                 150                 155                 160

Phe Leu Trp Glu Trp Ala Ser AlaArg Phe Ser Trp Leu Ser Leu Leu
                165                 170                 175

Val Pro Phe Val Gln Trp Phe Val Gly Leu Ser Pro Thr Val Trp Leu
                180                 185                 190

Ser Val Ile Trp Met Met Trp Tyr Trp Gly Pro Ser Leu Tyr Ser XAa
                195                 200                 205

Leu Ser Pro Phe Leu Pro Leu Leu Pro Ile Phe Phe Cys Leu Trp Val
        210                 215                 220

Tyr Ile
225

24309PRTartificial sequenceSynthetic polypeptide 24 (SEQ ID NO.: 24)
Pro Pro Pro Ala Ser Thr Asn Arg Gln Ser Gly Arg Gln Pro Thr Pro
1               5                   10                  15

Leu Ser Pro Pro Leu Arg Asn Thr His Pro Gln Ala Met Gln Trp Asn
                20                  25                  30

Ser Thr Thr Phe His Gln Thr Leu Gln Asp Pro Arg Val Arg Gly Leu
        35                  40                  45

Tyr Phe Pro Ala Gly Gly Ser Ser Gly Thr Val Asn Pro Val Leu
50                  55                  60
```

```
Thr Thr Ala Ser Pro Leu Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
            115                 120                 125

Thr Val Cys Leu Gly Gln Asn Ser Gln Ser Pro Thr Ser Asn His Ser
            130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Thr Gly Pro Cys Arg Thr Cys Met
            195                 200                 205

Thr Thr Ala Gln Gly Thr Ser Met Tyr Pro Ser Cys Cys Cys Thr Lys
            210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270

Val Trp Leu Ser Val Ile Trp Met Met Trp Tyr Trp Gly Pro Ser Leu
            275                 280                 285

Tyr Ser Ile Leu Ser Pro Phe Leu Pro Leu Leu Pro Ile Phe Phe Cys
            290                 295                 300

Leu Trp Val Tyr Ile
305

25309PRTartificial sequenceSynthetic polypeptide 25 (SEQ ID NO.: 25)
Pro Pro Pro Ala Ser Thr Asn Arg Gln Ser Gly Arg Gln Pro Thr Pro
1               5                   10                  15

Leu Ser Pro Pro Leu Arg Asn Thr His Pro Gln Ala Met Gln Trp Asn
            20                  25                  30

Ser Thr Thr Phe His Gln Thr Leu Gln Asp Pro Arg Val Arg Gly Leu
            35                  40                  45

Tyr Phe Pro Ala Gly Gly Ser Ser Gly Thr Val Asn Pro Val Leu
    50                  55                  60

Thr Thr Ala Ser Pro Leu Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
            115                 120                 125

Thr Val Cys Leu Gly Gln Asn Ser Gln Ser Pro Thr Ser Asn His Ser
            130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
```

```
            165                 170                 175
Leu Leu Val Leu Leu Asp Tyr Gln Gly Met Leu Pro Val Cys Pro Leu
            180                 185                 190

Ile Pro Gly Ser Ser Thr Thr Ser Thr Gly Pro Cys Arg Thr Cys Met
            195                 200                 205

Thr Thr Ala Gln Gly Thr Ser Met Tyr Pro Ser Cys Cys Cys Thr Lys
        210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser AlaArg Phe Ser Trp Leu
            245                 250                 255

Ser Leu Leu Val Pro Phe Val Gln Trp Phe Val Gly Leu Ser Pro Thr
            260                 265                 270

Val Trp Leu Ser Val Ile Trp Met Met Trp Tyr Trp Gly Pro Ser Leu
            275                 280                 285

Tyr Ser Ile Leu Ser Pro Phe Leu Pro Leu Leu Pro Ile Phe Phe Cys
        290                 295                 300

Leu Trp Val Tyr Ile
305

26309PRTartificial sequenceSynthetic polypeptide 26 (SEQ ID NO.: 26)
Pro Pro Pro Pro Ser Thr Asn Arg Gln Ser Gly Arg Gln Pro Thr Pro
1               5                   10                  15

Leu Ser Pro Pro XAa Arg Asn Thr His Pro Gln Ala Met Gln Trp Asn
            20                  25                  30

Ser Thr Thr Phe His Gln Thr Leu Lys Asp Pro Arg Val XAa Gly Leu
        35                  40                  45

Tyr Phe Pro Ala Gly Gly Ser Ser Gly Thr Val Asn Pro Val Pro
    50                  55                  60

Thr Thr Ala Ser Pro Ile Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
            85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
            115                 120                 125

Thr Val Cys Leu Gly Gln Asn Ser Gln Ser Pro Thr Ser Asn His Ser
        130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
            165                 170                 175

Leu Leu Val Leu Leu Asp Tyr Gln Gly Met Leu Pro Val Cys Pro Leu
            180                 185                 190

Ile Pro Gly Ser Ser Thr Thr Ser Ala Gly Thr Cys Arg Thr Cys Thr
            195                 200                 205

Thr AlaAla Gln Gly Thr Ser Met Tyr Pro Ser Cys Cys Cys Thr Lys
        210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser AlaArg Phe Ser Trp Leu
            245                 250                 255

Ser Leu Leu Val Pro Phe Val Gln Trp Phe Val Gly Leu Ser Pro Thr
            260                 265                 270
```

Val Trp Leu Ser Val Ile Trp Met Met Trp Tyr Trp Gly Pro Ser Leu
    275                 280                 285

Tyr Ser Ile Leu Ser Pro Phe Leu Pro Leu Leu Pro Ile Phe Phe Cys
    290                 295                 300

Leu Trp Ala Tyr Ile
305

27656DNA artificial sequenceSynthetic oligonucleotide 27 (SEQ ID NO.: 27)

```
cgcagagtct agactcgtgg tggacttctc tcAattttcg aggggggact accgtgtgtc      60
ttggccAaAa ttcgcagtcc ccAacctccAatcactcacc Aacctcctgt cctccAactt     120
gtcctggtta tcgctggatg tgtctgcggc gttttatcat cttcctcttc atcctgctgc    180
tatgcctcat cttcttgttg gttcttctgg actgtcAagg tatgttgccc gtttgtcctc    240
tAattccagg atcctcAacc accagcacgg gaccatgccg Aacctgcacg actcctgctc    300

AaggAacctc tacggttccc tcatgttgct gtaccAaacc ttcggacggAa attgcacct    360 gtattcccat cccatcatcc tgggctttcg gAaAattcct atgggagtgg gcctcagccc    420
gtttctcctg gctcagttta ctagtgccat tgttcagtg gttcgtaggg cttccccca    480 ctgtctggct tttagttata tggatgatgt ggtattgggg gccAagtctg tatcgcatct    540
tgagtccctt tttaccgctg ntaccAattt tcttttgtct tgggtatac atttAaaccc    600 tAacAaAacAa aAagatggg gttactcccct acattttatg ggctatgtca ttggat      656
```

28625DNA artificial sequenceSynthetic oligonucleotide 28 (SEQ ID NO.: 28)

```
ttactcaccn acctcctgtc ctccAacttg tcctggttat cgctggatgt gtctgcggcg     60
ttttatcatc ttcctcttca tcctgctgct atgcctcatc ttcttgttgg ttcttctgga    120
ctgtcAaggt atgttgcccg tttgtcctct AattccaggA tcctcAacca ccagcagggg    180 accatgccgAacctgcacga ctcctgctcAaggAacctct acggttccct catgttgctg    240
taccAaacct tcggacggAa attgcacctg tattcccatc ccatcatcct gggctttcgg    300

AaAattccta tgggagtggg cctcagcccg tttctcatgg ctcagtttac tagtgccatt    360
tgttcagtgg ttcgtagggc ttccccccac tgtctggctt ttggttatgt ggatgatgtg    420
gtattggggg ccAagtctgt atcgcatctt gagtccctt ttaccgctgt taccAatttt    480
cttttgtctt gggtataca tttAaatcct AacAaAacAa Aaagatgggg ttactccta    540 cattttatgg gctatgtcat tggatgtcat gggtccttgc cacAagAaca catcagacAa    600

AaAatcAaag Aatgttttag AaAac                                         625
```

291033DNA artificial sequenceSynthetic oligonucleotide 29 (SEQ ID NO.: 29)

```
tgccccttct gcctccaccAatcgccagtc aggAaggcag cctaccccgc tgtctccacc      60
tttgagagac actcatcctc aggccatgca gtggAactcAacAaccttcc accAaactct    120 gcAagatccc agagtgAaag gcctgtattt ccctgctggt ggctccagtt caggAacagt    180

Aaaccctgtt ccgactactg cctctcactc atcgtcAatc ttctcgagga ttggggtccc    240
tgcgctgAac atgagAacaa tcacatcagg actcctagga ccccttctcg tgttacaggc    300
ggggtttttc ttgttgacAa gAatcctcac Aataccgcag agtctagact cgtggtggac    360
ttctctcAat tttcgagggg ggactaccgt gtgtcttggc cAaAattcgc agtccccAac    420
ctccAatcac tcaccAacct cctgtcctcc Aacttgtcct ggttatcgct ggatgtgtct    480
gcggcgtttt atcatcttcc tcttcatcct gctgctatgc ctcatcttct gttggttct    540 tctggactgt cAaggtatgt tgcccgtttg tcctctAatt ccaggatcct cAaccaccag    600
caggggacca tgccgAacct gcacgactcc tgctcAaggAacctctacgg ttccctcatg    660 ttgctgtacc AaaccttcggAacggAaattg cacctgtatt cccatccat catcctgggc    720 tttcggAaAa ttcctatggg agtgggcctc agcccgtttc tcatggctca gtttactagt    780
```

```
gccatttgtt cagtggttcg tagggctttc ccccactgtc tggcttttgg ttatgtggat        840
gatgtggtat tgggggccAa gtctgtatcg catcttgagt cccttttac cgctgttacc         900

AattttctttΒ tgtctttggg tatacatttAa atcctAacAa aacAaAaaag atggggttac      960
tccctacatt ttatgggcta tgtcattgga tgtcatgggt ccttgccacAagAacacatc        1020 agacAaAaAa tca                                                          1033
```

301100DNA artificial sequence Synthetic oligonucleotide 30 (SEQ ID NO.: 30)
```
ttttggggag ccctcaggct cagggcatat tacAaactct gccagcAaat ccacctcctg         60
cctccaccAa tcgccagtca ggAaggcagc ctaccccgct gtctccacct ttgagagaca       120
ctcatcctca ggccatgcag tggAactcAa cAaccttcca ccAaactctg cAagatccca       180
gagtgAaagg cctgtatttc cctgctggtg gctccagttc aggAacagtAa accctgttc      240 cgactactgc ctctcactca tcgtcAatct tctcgaggat tggggtccct gcgctgAaca       300
tggagAacat cacatcagga ctcctaggac cccttctcgt gttacaggcg ggttttttct      360
tgttgacAag AatcctcacAataccgcaga gtctagactc gtggtggact tctctcAatt        420 ttcgagggggg gactaccgtg tgtcttggcc AaAattcgca gtccccAacc tccAatcact      480
caccAacctc ctgtcctccAacttgtcctg gttatcgctg atgtgtctg cggcgtttta       540 tcatcttcct cttcatcctg ctgctatgcc tcatcttctt gttggttctt ctggactgtc      600

Aaggtatgtt gcccgtttgt cctctAattc caggatcctc AaccaccagcΒ agggggaccat    660 gccgAacctg cacgactcct gctcAaggAa cctctacggt tccctcatgt tgctgtacca      720

AaccttcggaΒ cggAaattgc acctgtattc ccatcccatc atcctgggct ttcggAaAat    780
tcctatggga gtgggcctca gcccgtttct catggctcag tttactagtg ccatttgttc      840
agtggttcgt agggctttccΒ cccactgtct ggcttttggt tatgtggatg atgtggtatt   900 ggggggccAag tctgtatcgc atcttgagtc ccttttacc gctgttaccAattttcttttΒ   960 gtctttgggt atacatttAa atcctAacAa AacAaAaaga tggggttact ccctacattt    1020
tatgggctat gtcattggat gtcatgggtc cttgccacAa gAacacatca gacAaAaAat    1080
cAaagAatgt tttagAaAac                                                1100
```

31987DNA artificial sequenceSynthetic oligonucleotide 31 (SEQ ID NO.: 31)
```
tacAaactttΒ gccagcAaatΒ ccacctcctgΒ cctccaccAaΒ tcgccagtcaΒ ggAaggcagc     60 ctaccccgct gtctccacct ttgagagaca ctcatcctca ggccatgcag tggAactcAa        120
cAaccttcca ccAaactctg cAagatccca gagtgAaagg cctgtatttc cctgctggtg       180
gctccagttc aggAacagtAa accctgttc cgactactgc ctctcactca tcgtcAatct      240
tctcgaggat tggggtccct gcgctgAaca tggagAacat cacatcagga ctcctaggac       300
cccttctcgt gttacaggcg ggtttttnt tgttgacAag AatcctcacAataccgcaga       360 gtctagactc gtggtggact tctctcAatt ttcgagggggg gactaccgtg tgtcttggcc      420

AaAattcgca gtccccAacc tccAatcact caccAacctc ctgtcctccAacttgtcctg      480 gttatcgctg atgtgtctg cggcgtttta tcatcttcct cttcatcctg ctgctatgcc      540
tcatcttctt gttggctcta ctggactgtc Aaggtatgtt gcccgtttgt cctctAattc      600
caggatcctc AaccaccagcΒ agggggaccat gccgAacctg cacgactcct gctcAaggAa    660
cctctacggt tccctcatgt tgctgtaccAa accttcgga cggAaattgc acctgtattc      720
ccatcccatc atcctgggct ttcggAaAat tcctatggga gtgggcctca gcccgtttct      780
catggctcag tttactagtg ccatttgttc agtggttcgt agggctttcc cccactgtct     840
ggcttttggt tatgtggatg atgtggtatt ggggggccAag tctgtatcgc atcttgagtc   900
```

-continued

```
ccttttacc gctgttaccAattttctttt gtctttgggt atncatttAa atcctAacAa        960

AacAaAaaga tggggttact ccctaca                                          987
```

32350PRTartificial sequenceSynthetic polypeptide 32 (SEQ ID NO.: 32)

Ser Gly His Thr Thr Asn Phe Ala Ser Lys Ser Thr Ser Cys Leu His
1               5                   10                  15

Gln Ser Pro Val Arg Lys AlAala Tyr Pro Ala Val Ser Thr Phe Glu
            20                  25                  30

Arg His Ser Ser Ser Gly His Ala Val Glu Leu Asn Asn Leu Pro Pro
        35                  40                  45

Asn Ser AlAarg Ser Gln Ser Glu Arg Pro Val Phe Pro Cys Trp Trp
50                  55                  60

Leu Gln Phe Arg Asn Ser Lys Pro Cys Ser Asp Tyr Cys Leu Ser Leu
65                  70                  75                  80

Ile Val Asn Leu Leu Glu Asp Trp Gly Pro Cys Ala Glu His Gly Glu
                85                  90                  95

His His Ile Arg Thr Pro Arg Thr Pro Ser Arg Val Thr Gly Gly Val
            100                 105                 110

Phe Leu Val Asp Lys Asn Pro His Asn Thr Ala Glu Ser Arg Leu Val
        115                 120                 125

Val Asp Phe Ser Gln Phe Ser Arg Gly Asp Tyr Arg Val Ser Trp Pro
130                 135                 140

Lys Phe Ala Val Pro Asn Leu Gln Ser Leu Thr Asn Leu Leu Ser Ser
145                 150                 155                 160

Asn Leu Ser Trp Leu Ser Leu Asp Val Ser AlAala Phe Tyr His Leu
                165                 170                 175

Pro Leu His Pro AlAala Met Pro His Leu Leu Val Gly Ser Ser Gly
            180                 185                 190

Leu Ser Arg Tyr Val AlAarg Leu Ser Ser Asn Ser Arg Ile Leu Asn
        195                 200                 205

His Gln His Gly Thr Met Pro Asn Leu His Asp Ser Cys Ser Arg Asn
210                 215                 220

Leu Tyr Gly Ser Leu Met Leu Leu Tyr Gln Thr Phe Gly Arg Lys Leu
225                 230                 235                 240

His Leu Tyr Ser His Pro Ile Ile Leu Gly Phe Arg Lys Ile Pro Met
                245                 250                 255

Gly Val Gly Leu Ser Pro Phe Leu Leu Ala Gln Phe Thr Ser Ala Ile
            260                 265                 270

Cys Ser Val Val Arg Arg Ala Phe Pro His Cys Leu Ala Phe Ser Tyr
        275                 280                 285

Met Asp Asp Val Val Leu Gly Ala Lys Ser Val Ser His Leu Glu Ser
290                 295                 300

Leu Phe Thr Ala XAa Thr Asn Phe Leu Leu Ser Leu Gly Ile His Leu
305                 310                 315                 320

Asn Pro Asn Lys Thr Lys Arg Trp Gly Tyr Ser Leu His Phe Met Gly
                325                 330                 335

Tyr Val Ile Gly Cys His Gly Ser XAa Pro Gln Glu His Ile
            340                 345                 350

33181PRT artificial sequence Synthetic polypeptide 33 (SEQ ID NO.: 33)

Ser Asn Leu Ser Trp Leu Ser Leu Asp Val Ser AlAala Phe Tyr His
1               5                   10                  15

Leu Pro Leu His Pro AlAala Met Pro His Leu Leu Val Gly Ser Ser
            20                  25                  30

Gly Leu Ser Arg Tyr Val AlAarg Leu Ser Ser Asn Ser Arg Ile Leu
        35                  40                  45

```
Asn His Gln Gln Gly Thr Met Pro Asn Leu His Asp Ser Cys Ser Arg
 50                  55                  60
Asn Leu Tyr Gly Ser Leu Met Leu Tyr Gln Thr Phe Gly Arg Lys
 65                  70                  75                  80
Leu His Leu Tyr Ser His Pro Ile Ile Leu Gly Phe Arg Lys Ile Pro
                 85                  90                  95
Met Gly Val Gly Leu Ser Pro Phe Leu Met Ala Gln Phe Thr Ser Ala
                100                 105                 110
Ile Cys Ser Val Val Arg Arg Ala Phe Pro His Cys Leu Ala Phe Gly
                115                 120                 125
Tyr Val Asp Asp Val Val Leu Gly Ala Lys Ser Val Ser His Leu Glu
                130                 135                 140
Ser Leu Phe Thr Ala Val Thr Asn Phe Leu Leu Ser Leu Gly Ile His
145                 150                 155                 160
Leu Asn Pro Asn Lys Thr Lys Arg Trp Gly Tyr Ser Leu His Phe Met
                165                 170                 175
Gly Tyr Val Ile Gly
                180

34340PRT artificial sequence Synthetic polypeptide 34 (SEQ ID NO.: 34)
Cys Pro Phe Cys Leu His Gln Ser Pro Val Arg Lys AlAala Tyr Pro
1               5                   10                  15
Ala Val Ser Thr Phe Glu Arg His Ser Ser Gly His Ala Val Glu
                20                  25                  30
Leu Asn Asn Leu Pro Pro Asn Ser AlAarg Ser Gln Ser Glu Arg Pro
                35                  40                  45
Val Phe Pro Cys Trp Trp Leu Gln Phe Arg Asn Ser Lys Pro Cys Ser
 50                  55                  60
Asp Tyr Cys Leu Ser Leu Ile Val Asn Leu Leu Glu Asp Trp Gly Pro
 65                  70                  75                  80
Cys Ala Glu His Gly Glu His His Ile Arg Thr Pro Arg Thr Pro Ser
                 85                  90                  95
Arg Val Thr Gly Gly Val Phe Leu Val Asp Lys Asn Pro His Asn Thr
                100                 105                 110
Ala Glu Ser Arg Leu Val Val Asp Phe Ser Gln Phe Ser Arg Gly Asp
                115                 120                 125
Tyr Arg Val Ser Trp Pro Lys Phe Ala Val Pro Asn Leu Gln Ser Leu
                130                 135                 140
Thr Asn Leu Leu Ser Ser Asn Leu Ser Trp Leu Ser Leu Asp Val Ser
145                 150                 155                 160
AlAala Phe Tyr His Leu Pro Leu His Pro AlAala Met Pro His Leu
                165                 170                 175
Leu Val Gly Ser Ser Gly Leu Ser Arg Tyr Val AlAarg Leu Ser Ser
                180                 185                 190
Asn Ser Arg Ile Leu Asn His Gln Gln Gly Thr Met Pro Asn Leu His
                195                 200                 205
Asp Ser Cys Ser Arg Asn Leu Tyr Gly Ser Leu Met Leu Tyr Gln
                210                 215                 220
Thr Phe Gly Arg Lys Leu His Leu Tyr Ser His Pro Ile Ile Leu Gly
225                 230                 235                 240
Phe Arg Lys Ile Pro Met Gly Val Gly Leu Ser Pro Phe Leu Met Ala
                245                 250                 255
Gln Phe Thr Ser Ala Ile Cys Ser Val Val Arg Arg Ala Phe Pro His
                260                 265                 270
Cys Leu Ala Phe Gly Tyr Val Asp Asp Val Val Leu Gly Ala Lys Ser
                275                 280                 285
```

```
Val Ser His Leu Glu Ser Leu Phe Thr Ala Val Thr Asn Phe Leu Leu
            290                 295                 300

Ser Leu Gly Ile His Leu Asn Pro Asn Lys Thr Lys Arg Trp Gly Tyr
305                 310                 315                 320

Ser Leu His Phe Met Gly Tyr Val Ile Gly Cys His Gly Ser Leu Pro
                325                 330                 335
Gln Glu His Ile
            340

35340PRT artificial sequence Synthetic polypeptide 35 (SEQ ID NO.: 35)
Ser Gly His Ile Thr Asn Ser Ala Ser Lys Ser Thr Ser Cys Leu His
1               5                   10                  15

Gln Ser Pro Val Arg Lys AlAala Tyr Pro Ala Val Ser Thr Phe Glu
            20                  25                  30

Arg His Ser Ser Ser Gly His Ala Val Glu Leu Asn Asn Leu Pro Pro
            35                  40                  45

Asn Ser AlAarg Ser Gln Ser Glu Arg Pro Val Phe Pro Cys Trp Trp
            50                  55                  60

Leu Gln Phe Arg Asn Ser Lys Pro Cys Ser Asp Tyr Cys Leu Ser Leu
65                  70                  75                  80

Ile Val Asn Leu Leu Glu Asp Trp Gly Pro Cys Ala Glu His Gly Glu
                85                  90                  95

His His Ile Arg Thr Pro Arg Thr Pro Ser Arg Val Thr Gly Gly Val
            100                 105                 110

Phe Leu Val Asp Lys Asn Pro His Asn Thr Ala Glu Ser Arg Leu Val
            115                 120                 125

Val Asp Phe Ser Gln Phe Ser Arg Gly Asp Tyr Arg Val Ser Trp Pro
130                 135                 140

Lys Phe Ala Val Pro Asn Leu Gln Ser Leu Thr Asn Leu Leu Ser Ser
145                 150                 155                 160

Asn Leu Ser Trp Leu Ser Leu Asp Val Ser AlAala Phe Tyr His Leu
                165                 170                 175

Pro Leu His Pro AlAala Met Pro His Leu Leu Val Gly Ser Ser Gly
            180                 185                 190

Leu Ser Arg Tyr Val AlAarg Leu Ser Ser Asn Ser Arg Ile Leu Asn
            195                 200                 205

His Gln Gln Gly Thr Met Pro Asn Leu His Asp Ser Cys Ser Arg Asn
            210                 215                 220

Leu Tyr Gly Ser Leu Met Leu Leu Tyr Gln Thr Phe Gly Arg Lys Leu
225                 230                 235                 240

His Leu Tyr Ser His Pro Ile Ile Leu Gly Phe Arg Lys Ile Pro Met
                245                 250                 255

Gly Val Gly Leu Ser Pro Phe Leu Met Ala Gln Phe Thr Ser Ala Ile
            260                 265                 270

Cys Ser Val Val Arg Arg Ala Phe Pro His Cys Leu Ala Phe Gly Tyr
            275                 280                 285

Val Asp Asp Val Val Leu Gly Ala Lys Ser Val Ser His Leu Glu Ser
            290                 295                 300

Leu Phe Thr Ala Val Thr Asn Phe Leu Leu Ser Leu Gly Ile His Leu
305                 310                 315                 320

Asn Pro Asn Lys Thr Lys Arg Trp Gly Tyr Ser Leu His Phe Met Gly
                325                 330                 335

Tyr Val Ile Gly
            340
```

36328PRTartificial sequenceSynthetic polypeptide 36 (SEQ ID NO.: 36)
```
Thr Asn Phe Ala Ser Lys Ser Thr Ser Cys Leu His Gln Ser Pro Val
1               5                   10                  15

Arg Lys AlAala Tyr Pro Ala Val Ser Thr Phe Glu Arg His Ser Ser
            20                  25                  30

Ser Gly His Ala Val Glu Leu Asn Asn Leu Pro Pro Asn Ser AlAarg
        35                  40                  45

Ser Gln Ser Glu Arg Pro Val Phe Pro Cys Trp Trp Leu Gln Phe Arg
50                  55                  60

Asn Ser Lys Pro Cys Ser Asp Tyr Cys Leu Ser Leu Ile Val Asn Leu
65                  70                  75                  80

Leu Glu Asp Trp Gly Pro Cys Ala Glu His Gly Glu His His Ile Arg
                85                  90                  95

Thr Pro Arg Thr Pro Ser Arg Val Thr Gly Gly Val Phe Xaa Val Asp
            100                 105                 110

Lys Asn Pro His Asn Thr Ala Glu Ser Arg Leu Val Val Asp Phe Ser
        115                 120                 125

Gln Phe Ser Arg Gly Asp Tyr Arg Val Ser Trp Pro Lys Phe Ala Val
130                 135                 140

Pro Asn Leu Gln Ser Leu Thr Asn Leu Leu Ser Ser Asn Leu Ser Trp
145                 150                 155                 160

Leu Ser Leu Asp Val Ser AlAala Phe Tyr His Leu Pro Leu His Pro
                165                 170                 175

AlAala Met Pro His Leu Leu Val Gly Ser Thr Gly Leu Ser Arg Tyr
            180                 185                 190

Val AlAarg Leu Ser Ser Asn Ser Arg Ile Leu Asn His Gln Gln Gly
        195                 200                 205

Thr Met Pro Asn Leu His Asp Ser Cys Ser Arg Asn Leu Tyr Gly Ser
210                 215                 220

Leu Met Leu Leu Tyr Gln Thr Phe Gly Arg Lys Leu His Leu Tyr Ser
225                 230                 235                 240

His Pro Ile Ile Leu Gly Phe Arg Lys Ile Pro Met Gly Val Gly Leu
                245                 250                 255

Ser Pro Phe Leu Met Ala Gln Phe Thr Ser Ala Ile Cys Ser Val Val
            260                 265                 270

Arg Arg Ala Phe Pro His Cys Leu Ala Phe Gly Tyr Val Asp Asp Val
        275                 280                 285

Val Leu Gly Ala Lys Ser Val Ser His Leu Glu Ser Leu Phe Thr Ala
290                 295                 300

Val Thr Asn Phe Leu Leu Ser Leu Gly Xaa His Leu Asn Pro Asn Lys
305                 310                 315                 320

Thr Lys Arg Trp Gly Tyr Ser Leu
                325

37197PRTartificial sequenceSynthetic polypeptide 37 (SEQ ID NO.: 37)
Gln Ser Leu Asp Ser Trp Trp Thr Ser Leu Asn Phe Arg Gly Gly Thr
1               5                   10                  15

Thr Val Cys Leu Gly Gln Asn Ser Gln Ser Pro Thr Ser Asn His Ser
            20                  25                  30

Pro Thr Ser Cys Pro Pro Thr Cys Pro Gly Tyr Arg Trp Met Cys Leu
        35                  40                  45

Arg Arg Phe Ile Ile Phe Leu Phe Ile Leu Leu Leu Cys Leu Ile Phe
50                  55                  60

Leu Leu Val Leu Leu Asp Cys Gln Gly Met Leu Pro Val Cys Pro Leu
65                  70                  75                  80
```

-continued

```
Ile Pro Gly Ser Ser Thr Thr Ser Thr Gly Pro Cys Arg Thr Cys Thr
                 85                  90                  95

Thr Pro Ala Gln Gly Thr Ser Val Pro Ser Cys Cys Cys Thr Lys
            100                 105                 110

Pro Ser Asp Gly Asn Cys Thr Cys Ile Pro Ile Pro Ser Ser Trp Ala
            115                 120                 125

Phe Gly Lys Phe Leu Trp Glu Trp Ala Ser AlAarg Phe Ser Trp Leu
        130                 135                 140

Ser Leu Leu Val Pro Phe Val Gln Trp Phe Val Gly Leu Ser Pro Thr
145                 150                 155                 160

Val Trp Leu Leu Val Ile Trp Met Met Trp Tyr Trp Gly Pro Ser Leu
                165                 170                 175

Tyr Arg Ile Leu Ser Pro Phe Leu Pro Leu XAa Pro Ile Phe Phe Cys
            180                 185                 190

Leu Trp Val Tyr Ile
            195

38161PRTartificial sequenceSynthetic polypeptide 38 (SEQ ID NO.: 38)
Pro Pro Thr Cys Pro Gly Tyr Arg Trp Met Cys Leu Arg Arg Phe Ile
1               5                   10                  15

Ile Phe Leu Phe Ile Leu Leu Leu Cys Leu Ile Phe Leu Leu Val Leu
                20                  25                  30

Leu Asp Cys Gln Gly Met Leu Pro Val Cys Pro Leu Ile Pro Gly Ser
            35                  40                  45

Ser Thr Thr Ser Arg Gly Pro Cys Arg Thr Cys Thr Thr Pro Ala Gln
50                  55                  60

Gly Thr Ser Thr Val Pro Ser Cys Cys Cys Thr Lys Pro Ser Asp Gly
65                  70                  75                  80

Asn Cys Thr Cys Ile Pro Ile Pro Ser Ser Trp Ala Phe Gly Lys Phe
                85                  90                  95

Leu Trp Glu Trp Ala Ser AlAarg Phe Ser Trp Leu Ser Leu Leu Val
            100                 105                 110

Pro Phe Val Gln Trp Phe Val Gly Leu Ser Pro Thr Val Trp Leu Leu
        115                 120                 125

Val Met Trp Met Met Trp Tyr Trp Gly Pro Ser Leu Tyr Arg Ile Leu
    130                 135                 140

Ser Pro Phe Leu Pro Leu Leu Pro Ile Phe Phe Cys Leu Trp Val Tyr
145                 150                 155                 160

Ile

39160PRT artificial sequenceSynthetic polypeptide 39 (SEQ ID NO.: 39)
Pro Thr Cys Pro Gly Tyr Arg Trp Met Cys Leu Arg Arg Phe Ile Ile
1               5                   10                  15

Phe Leu Phe Ile Leu Leu Leu Cys Leu Ile Phe Leu Leu Val Leu Leu
                20                  25                  30

Asp Cys Gln Gly Met Leu Pro Val Cys Pro Leu Ile Pro Gly Ser Ser
            35                  40                  45

Thr Thr Ser Arg Gly Pro Cys Arg Thr Cys Thr Thr Pro Ala Gln Gly
        50                  55                  60

Thr Ser Thr Val Pro Ser Cys Cys Cys Thr Lys Pro Ser Asp Gly Asn
65                  70                  75                  80

Cys Thr Cys Ile Pro Ile Pro Ser Ser Trp Ala Phe Gly Lys Phe Leu
                85                  90                  95

Trp Glu Trp Ala Ser AlAarg Phe Ser Trp Leu Ser Leu Leu Val Pro
            100                 105                 110

Phe Val Gln Trp Phe Val Gly Leu Ser Pro Thr Val Trp Leu Leu Val
        115                 120                 125
```

```
Met Trp Met Met Trp Tyr Trp Gly Pro Ser Leu Tyr Arg Ile Leu Ser
        130                 135                 140
Pro Phe Leu Pro Leu Leu Pro Ile Phe Phe Cys Leu Trp Val Tyr Ile
145                 150                 155                 160
```

40325PRTartificial sequenceSynthetic polypeptide 40 (SEQ ID NO.: 40)
```
Leu Gly Ser Pro Gln Ala Gln Gly Ile Leu Gln Thr Leu Pro AlAasn
1               5                   10                  15
Pro Pro Pro Ala Ser Thr Asn Arg Gln Ser Gly Arg Gln Pro Thr Pro
                20                  25                  30
Leu Ser Pro Pro Leu Arg Asp Thr His Pro Gln Ala Met Gln Trp Asn
            35                  40                  45
Ser Thr Thr Phe His Gln Thr Leu Gln Asp Pro Arg Val Lys Gly Leu
        50                  55                  60
Tyr Phe Pro Ala Gly Gly Ser Ser Gly Thr Val Asn Pro Val Pro
65                  70                  75                  80
Thr Thr Ala Ser His Ser Ser Ser Ile Phe Ser Arg Ile Gly Val Pro
                85                  90                  95
Ala Leu Asn Met Glu Asn Ile Thr Ser Gly Leu Leu Gly Pro Leu Leu
                100                 105                 110
Val Leu Gln Ala Gly Phe Phe Leu Leu Thr Arg Ile Leu Thr Ile Pro
            115                 120                 125
Gln Ser Leu Asp Ser Trp Trp Thr Ser Leu Asn Phe Arg Gly Gly Thr
        130                 135                 140
Thr Val Cys Leu Gly Gln Asn Ser Gln Ser Pro Thr Ser Asn His Ser
145                 150                 155                 160
Pro Thr Ser Cys Pro Pro Thr Cys Pro Gly Tyr Arg Trp Met Cys Leu
                165                 170                 175
Arg Arg Phe Ile Ile Phe Leu Phe Ile Leu Leu Leu Cys Leu Ile Phe
                180                 185                 190
Leu Leu Val Leu Leu Asp Cys Gln Gly Met Leu Pro Val Cys Pro Leu
            195                 200                 205
Ile Pro Gly Ser Ser Thr Thr Ser Arg Gly Pro Cys Arg Thr Cys Thr
        210                 215                 220
Thr Pro Ala Gln Gly Thr Ser Thr Val Pro Ser Cys Cys Cys Thr Lys
225                 230                 235                 240
Pro Ser Asp Gly Asn Cys Thr Cys Ile Pro Ile Pro Ser Ser Trp Ala
                245                 250                 255
Phe Gly Lys Phe Leu Trp Glu Trp Ala Ser Ala lAarg Phe Ser Trp Leu
                260                 265                 270
Ser Leu Leu Val Pro Phe Val Gln Trp Phe Val Gly Leu Ser Pro Thr
            275                 280                 285
Val Trp Leu Leu Val Met Trp Met Met Trp Tyr Trp Gly Pro Ser Leu
            290                 295                 300
Tyr Arg Ile Leu Ser Pro Phe Leu Pro Leu Leu Pro Ile Phe Phe Cys
305                 310                 315                 320
Leu Trp Val Tyr Ile
            325
```

41309PRTartificial sequenceSynthetic polypeptide 41 (SEQ ID NO.: 41)
```
Pro Pro Pro Ala Ser Thr Asn Arg Gln Ser Gly Arg Gln Pro Thr Pro
1               5                   10                  15
Leu Ser Pro Pro Leu Arg Asp Thr His Pro Gln Ala Met Gln Trp Asn
                20                  25                  30
Ser Thr Thr Phe His Gln Thr Leu Gln Asp Pro Arg Val Lys Gly Leu
            35                  40                  45
```

-continued

```
Tyr Phe Pro Ala Gly Gly Ser Ser Gly Thr Val Asn Pro Val Pro
 50                  55                  60

Thr Thr Ala Ser His Ser Ser Ile Phe Ser Arg Ile Gly Val Pro
 65                  70                  75                  80

Ala Leu Asn Met Glu Asn Ile Thr Ser Gly Leu Leu Gly Pro Leu Leu
                 85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Arg Gly Gly Thr
            115                 120                 125

Thr Val Cys Leu Gly Gln Asn Ser Gln Ser Pro Thr Ser Asn His Ser
        130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Ala Leu Leu Asp Cys Gln Gly Met Leu Pro Val Cys Pro Leu
            180                 185                 190

Ile Pro Gly Ser Ser Thr Thr Ser Arg Gly Pro Cys Arg Thr Cys Thr
            195                 200                 205

Thr Pro Ala Gln Gly Thr Ser Thr Val Pro Ser Cys Cys Cys Thr Lys
        210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser AlAarg Phe Ser Trp Leu
                245                 250                 255

Ser Leu Leu Val Pro Phe Val Gln Trp Phe Val Gly Leu Ser Pro Thr
            260                 265                 270

Val Trp Leu Leu Val Met Trp Met Met Trp Tyr Trp Gly Pro Ser Leu
        275                 280                 285

Tyr Arg Ile Leu Ser Pro Phe Leu Pro Leu Leu Pro Ile Phe Phe Cys
        290                 295                 300

Leu Trp Val XAa Ile
305
```

421031DNA artificial sequenceSynthetic oligonucleotide 42 (SEQ ID NO.: 42)

```
tactacAaac cttgccagcAa atccgcctc ctgcctctac cAatcgccag tcaggAaggc        60
agcctacccc tctgactcca cctttgagAa acactcatcc tcaggccatg cagtggAact       120
ccacAaactt ccaccgAact ctacAagatc ccagagtgAa aggcctgtat ctccctgctg       180
gtggctccag ttcaggAaca gtAaaccctg ttccgactac tgtctctcac acatcgtcAa       240
tcttatcgag gattggggac cctgcactgA acatggagAa catcacatca ggattcctag       300
gaccccctgct cgtgttacag gcggggtttt tcttgttgac AagAatcctc acAataccgc       360
agagtctaga ctcgtggtgg acttctctcA atttctctagg ggggaccacc gtgtgccttg       420
gccAaAattc gcagtccccA acctccAatc actcaccAac ctcctgtcct ccAacttgtc       480
ctggttatcg ctggatgtgt ctgcggcgtt ttatcatatt cctcttcatc ctgctgctat       540
gcctcatctt cttgttggtt cttctggact atcAaggtat gttgcccgtt tgccctctAa       600
ttccaggatc ctcAaccacc agcacgggac catgcagAac ctgcacgact cctgctcAag       660
gAacctctwt gtatccctca tgttgctgta ccAaaccctwc ggmcgsAaat tgcacctgta       720
ttcccatccc atcatcctgg gctttcggAa Aattcctatg ggagtgggcc tcagcccgtt       780
tctcctgact cagtttacta gtgccatttg ttcagtggtt cgtagggctt ccccccactg       840
tttggctttc agttatatgg atgatgtggt attgggggcc aggtctgtac agcatcgtga       900
```

```
ggcccttttt accgctgtta ccAattttct tttgtctctg ggtatacatt tAaccccgga      960
cAaAacAaAa agatgggggtt actctttaca tttcatgggc tatgtcattg gatgttatgg    1020
gtcattgcca c                                                          1031
```

43345PRTartificial sequenceSynthetic polypeptide 43 (SEQ ID NO.: 43)

Thr Thr Asn Leu Ala Ser Lys Ser Ala Ser Cys Leu Tyr Gln Ser Pro
1               5                   10                  15

Val Arg Lys AlAaala Tyr Pro Ser Asp Ser Thr Phe Glu Lys His Ser
            20                  25                  30

Ser Ser Gly His Ala Val Glu Leu His Lys Leu Pro Pro Asn Ser Thr
        35                  40                  45

Arg Ser Gln Ser Glu Arg Pro Val Ser Pro Cys Trp Trp Leu Gln Phe
    50                  55                  60

Arg Asn Ser Lys Pro Cys Ser Asp Tyr Cys Leu Ser His Ile Val Asn
65                  70                  75                  80

Leu Ile Glu Asp Trp Gly Pro Cys Thr Glu His Gly Glu His His Ile
                85                  90                  95

Arg Ile Pro Arg Thr Pro AlAarg Val Thr Gly Gly Val Phe Leu Val
            100                 105                 110

Asp Lys Asn Pro His Asn Thr Ala Glu Ser Arg Leu Val Val Asp Phe
        115                 120                 125

Ser Gln Phe Ser Arg Gly Asp His Arg Val Pro Trp Pro Lys Phe Ala
    130                 135                 140

Val Pro Asn Leu Gln Ser Leu Thr Asn Leu Leu Ser Ser Asn Leu Ser
145                 150                 155                 160

Trp Leu Ser Leu Asp Val Ser AlAaala Phe Tyr His Ile Pro Leu His
                165                 170                 175

Pro AlAaala Met Pro His Leu Leu Val Gly Ser Ser Gly Leu Ser Arg
            180                 185                 190

Tyr Val AlAarg Leu Pro Ser Asn Ser Arg Ile Leu Asn His Gln His
            195                 200                 205

Gly Thr Met Gln Asn Leu His Asp Ser Cys Ser Arg Asn Leu Tyr Phe
        210                 215                 220

Val Ser Leu Met Leu Leu Tyr Gln Thr Phe Thr Gly Arg Lys Leu His
225                 230                 235                 240

Leu Tyr Ser His Pro Ile Ile Leu Gly Phe Arg Lys Ile Pro Met Gly
                245                 250                 255

Val Gly Leu Ser Pro Phe Leu Leu Thr Gln Phe Thr Ser Ala Ile Cys
            260                 265                 270

Ser Val Val Arg Arg Ala Phe Pro His Cys Leu Ala Phe Ser Tyr Met
        275                 280                 285

Asp Asp Val Val Leu Gly AlAarg Ser Val Gln His Arg Glu Ala Leu
    290                 295                 300

Phe Thr Ala Val Thr Asn Phe Leu Leu Ser Leu Gly Ile His Leu Thr
305                 310                 315                 320

Pro Asp Lys Thr Lys Arg Trp Gly Tyr Ser Leu His Phe Met Gly Tyr
                325                 330                 335

Val Ile Gly Cys Tyr Gly Ser Leu Pro
            340                 345

44317PRT artificial sequence Synthetic polypeptide 44 (SEQ ID NO.: 44)

Leu Gln Thr Leu Pro AlAasn Pro Pro Pro Ala Ser Thr Asn Arg Gln
1               5                   10                  15

Ser Gly Arg Gln Pro Thr Pro Leu Thr Pro Pro Leu Arg Asn Thr His
            20                  25                  30

```
Pro Gln Ala Met Gln Trp Asn Ser Thr Asn Phe His Arg Thr Leu Gln
            35                  40                  45

Asp Pro Arg Val Lys Gly Leu Tyr Leu Pro Ala Gly Gly Ser Ser Ser
 50                  55                  60

Gly Thr Val Asn Pro Val Pro Thr Thr Val Ser His Thr Ser Ser Ile
 65                  70                  75                  80

Leu Ser Arg Ile Gly Asp Pro Ala Leu Asn Met Glu Asn Ile Thr Ser
                 85                  90                  95

Gly Phe Leu Gly Pro Leu Leu Val Leu Gln Ala Gly Phe Phe Leu Leu
            100                 105                 110

Thr Arg Ile Leu Thr Ile Pro Gln Ser Leu Asp Ser Trp Trp Thr Ser
            115                 120                 125

Leu Asn Phe Leu Gly Gly Thr Thr Val Cys Leu Gly Gln Asn Ser Gln
 130                 135                 140

Ser Pro Thr Ser Asn His Ser Pro Thr Ser Cys Pro Pro Thr Cys Pro
145                 150                 155                 160

Gly Tyr Arg Trp Met Cys Leu Arg Arg Phe Ile Ile Phe Leu Phe Ile
                165                 170                 175

Leu Leu Leu Cys Leu Ile Phe Leu Leu Val Leu Leu Asp Tyr Gln Gly
            180                 185                 190

Met Leu Pro Val Cys Pro Leu Ile Pro Gly Ser Ser Thr Thr Ser Thr
            195                 200                 205

Gly Pro Cys Arg Thr Cys Thr Thr Pro Ala Gln Gly Thr Ser Met Leu
210                 215                 220

Tyr Pro Ser Cys Cys Cys Thr Lys Pro Ser Thr AlaAlaAasn Cys Thr
225                 230                 235                 240

Cys Ile Pro Ile Pro Ser Ser Trp Ala Phe Gly Lys Phe Leu Trp Glu
                245                 250                 255

Trp Ala Ser AlAarg Phe Ser Leu Ser Leu Leu Val Pro Phe Val Gln
            260                 265                 270

Trp Phe Val Gly Leu Ser Pro Thr Val Trp Leu Ser Val Ile Trp Met
            275                 280                 285

Met Trp Tyr Trp Gly Pro Gly Leu Tyr Ser Ile Val Arg Pro Phe Leu
            290                 295                 300

Pro Leu Leu Pro Ile Phe Phe Cys Leu Trp Val Tyr Ile
305                 310                 315

45888DNA artificial sequenceSynthetic oligonucleotide 45 (SEQ ID NO.: 45)
tggtcacagt gccAacagtt cctcctcctg cctccaccAa tcggcagtca gggaggcagc      60
ctactcccat ctctccacct ctAagagaca gtcatcctca ggccatggtg gctcagcctg     120
ctggtggctc cagttcaggA acactcAacc ctgttcccAa tattgcctct cacatctcgt     180
cAatctcctt gaggactggg gaccctgcgc cgAacatgga gAacatcaca tcaggattcc     240 taggaccct gctcgtgtta caggcggggt ttttcttgtt gacAagAatc ctcacAatac      300
cgcagagtct agactcgtgg tggacttctc tcagttttct aggggatca cccgtgtgtc      360 ttggccAaAa ttcgcagtcc ccAacctccAatcactcacc AacctcctgT cctccAattt     420
gacctggtta tcgctggata tgtctgcggc gttttatcat attcctcttc atcctgccgc    480
tatgcctcat cttcttattg gttcttctgg attatcAagg tatgttgccc gtttgtcctc    540
tAattccagg atccacAacAaccagtgcgg gaccctgcAa AacctgcAcg actcctgctc    600

AaggcAactc tatgtttccc tcatgttgct gtacAaAacc tacggatggAa attgcacct    660 gtattcccat cccatcatct tgggctttcg cAaAataccT atgggagtgg gcctcagtcc    720
gtttctcttg gctcagttta ctagtgccat tgttcagtg attcgtaggg ctttcccccca    780
```

```
ctgtttggct tcagctata ttgatgatgt ggtactgggg gccAagtctg cacAacatct      840 tgagtcccctt tataccgctg ttaccAattt tcttttgtct ttgggtat                 888
```

46 295PRT artificial sequence Synthetic polypeptide 46 (SEQ ID NO.: 46)

```
Gly His Ser AlAasn Ser Ser Ser Ser Cys Leu His Gln Ser Ala Val
1               5                   10                  15

Arg Glu AlAala Tyr Ser His Leu Ser Thr Ser Lys Arg Gln Ser Ser
            20                  25                  30

Ser Gly His Gly Gly Ser Ala Cys Trp Trp Leu Gln Phe Arg Asn Thr
        35                  40                  45

Gln Pro Cys Ser Gln Tyr Cys Leu Ser His Leu Val Asn Leu Leu Glu
    50                  55                  60

Asp Trp Gly Pro Cys Ala Glu His Gly Glu His His Ile Arg Ile Pro
65                  70                  75                  80

Arg Thr Pro AlAarg Val Thr Gly Gly Val Phe Leu Val Asp Lys Asn
                85                  90                  95

Pro His Asn Thr Ala Glu Ser Arg Leu Val Val Asp Phe Ser Gln Phe
            100                 105                 110

Ser Arg Gly Ile Thr Arg Val Ser Trp Pro Lys Phe Ala Val Pro Asn
        115                 120                 125

Leu Gln Ser Leu Thr Asn Leu Leu Ser Ser Asn Leu Thr Trp Leu Ser
    130                 135                 140

Leu Asp Met Ser AlAala Phe Tyr His Ile Pro Leu His Pro AlAala
145                 150                 155                 160

Met Pro His Leu Leu Ile Gly Ser Ser Gly Leu Ser Arg Tyr Val Ala
                165                 170                 175

Arg Leu Ser Ser Asn Ser Arg Ile His Asn Asn Gln Cys Gly Thr Leu
            180                 185                 190

Gln Asn Leu His Asp Ser Cys Ser Arg Gln Leu Tyr Val Ser Leu Met
        195                 200                 205

Leu Leu Tyr Lys Thr Tyr Gly Trp Lys Leu His Leu Tyr Ser His Pro
    210                 215                 220

Ile Ile Leu Gly Phe Arg Lys Ile Pro Met Gly Val Gly Leu Ser Pro
225                 230                 235                 240

Phe Leu Leu Ala Gln Phe Thr Ser Ala Ile Cys Ser Val Ile Arg Arg
                245                 250                 255

Ala Phe Pro His Cys Leu Ala Phe Ser Tyr Ile Asp Asp Val Val Leu
            260                 265                 270

Gly Ala Lys Ser Ala Gln His Leu Glu Ser Leu Tyr Thr Ala Val Thr
        275                 280                 285

Asn Phe Leu Leu Ser Leu Gly
    290                 295
```

47 293PRT artificial sequence Synthetic polypeptide 47 (SEQ ID NO.: 47)

```
Val Thr Val Pro Thr Val Pro Pro Pro Ala Ser Thr Asn Arg Gln Ser
1               5                   10                  15

Gly Arg Gln Pro Thr Pro Ile Ser Pro Pro Leu Arg Asp Ser His Pro
            20                  25                  30

Gln Ala Met Val Ala Gln Pro Ala Gly Gly Ser Ser Ser Gly Thr Leu
        35                  40                  45

Asn Pro Val Pro Asn Ile Ala Ser His Ile Ser Ser Ile Ser Leu Arg
    50                  55                  60

Thr Gly Asp Pro Ala Pro Asn Met Glu Asn Ile Thr Ser Gly Phe Leu
65                  70                  75                  80

Gly Pro Leu Leu Val Leu Gln Ala Gly Phe Phe Leu Leu Thr Arg Ile
                85                  90                  95
```

```
Leu Thr Ile Pro Gln Ser Leu Asp Ser Trp Trp Thr Ser Leu Ser Phe
            100                 105                 110

Leu Gly Gly Ser Pro Val Cys Leu Gly Gln Asn Ser Gln Ser Pro Thr
            115                 120                 125

Ser Asn His Ser Pro Thr Ser Cys Pro Pro Ile Pro Gly Tyr Arg Trp
            130                 135                 140

Ile Cys Leu Arg Arg Phe Ile Ile Phe Leu Phe Ile Leu Pro Leu Cys
145                 150                 155                 160

Leu Ile Phe Leu Leu Val Leu Leu Asp Tyr Gln Gly Met Leu Pro Val
            165                 170                 175

Cys Pro Leu Ile Pro Gly Ser Thr Thr Thr Ser Ala Gly Pro Cys Lys
            180                 185                 190

Thr Cys Thr Thr Pro Ala Gln Gly Asn Ser Met Phe Pro Ser Cys Cys
            195                 200                 205

Cys Thr Lys Pro Thr Asp Gly Asn Cys Thr Cys Ile Pro Ile Pro Ser
            210                 215                 220

Ser Trp Ala Phe Ala Lys Tyr Leu Trp Glu Trp Ala Ser Val Arg Phe
225                 230                 235                 240

Ser Trp Leu Ser Leu Leu Val Pro Phe Val Gln Phe Val Gly Leu Ser
            245                 250                 255

Pro Thr Val Trp Leu Ser Ala Ile Leu Met Met Trp Tyr Trp Gly Pro
            260                 265                 270

Ser Leu His Asn Ile Leu Ser Pro Phe Ile Pro Leu Leu Pro Ile Phe
            275                 280                 285

Phe Cys Leu Trp Val
            290

48591DNA artificial sequenceSynthetic oligonucleotide 48 (SEQ ID NO.: 48)
tcctgtcctc cAatttgtcc tggttatcgc tggatgtgtc tgcggcgttt tatgatattc        60
ctcttcatcc tgctgctatg cctcatcttc ttattggttc ttctggatta tcAaggtatg       120
ttgcccgtct gtcctctAat tccaggatcA acAacAacca gtacgggacc atgcAaAacc       180

AaAacctgca cgactcctgc tcAaggcAac tctatgtttc cctcatgttg ctgtacAaAa       240
cctacggatg gAaattgcac ctgtattccc atcccatcgt cctgggcttt cgcAaAattc       300
ctatgggagt gggcctcagt ccgtttctct ggctcagtt tactagtgcc atttgttcag        360
tggttcgtag gctttccccc cactgtttgg ctttcagcta tggatgat gtggtattgg         420 gggccAagtc tgtacagcat cgtgaggccc tttatacagc tgttaccAat tttcttttgt       480
ctctgggtat acatttAaac cctAacAaAa cAaAaagatg gggttattcc ctAaacttca       540
tgggttacat AattggAagt tggggAacat tgccacagga tcatattgta c               591

49186PRT artificial sequence Synthetic polypeptide 49 (SEQ ID NO.: 49)
Ser Asn Leu Ser Trp Leu Ser Leu Asp Val Ser AlAala Phe Tyr Asp
1               5                   10                  15

Ile Pro Leu His Pro AlAala Met Pro His Leu Leu Ile Gly Ser Ser
            20                  25                  30

Gly Leu Ser Arg Tyr Val AlAarg Leu Ser Ser Asn Ser Arg Ile Asn
            35                  40                  45

Asn Asn Gln Tyr Gly Thr Met Gln Asn Gln Asn Leu His Asp Ser Cys
    50                  55                  60

Ser Arg Gln Leu Tyr Val Ser Leu Met Leu Leu Tyr Lys Thr Tyr Gly
65                  70                  75                  80

Trp Lys Leu His Leu Tyr Ser His Pro Ile Val Leu Gly Phe Arg Lys
            85                  90                  95

Ile Pro Met Gly Val Gly Leu Ser Pro Phe Leu Leu Ala Gln Phe Thr
            100                 105                 110
```

```
Ser Ala Ile Cys Ser Val Val Arg Arg Ala Phe Pro His Cys Leu Ala
        115                 120                 125
Phe Ser Tyr Met Asp Asp Val Val Leu Gly Ala Lys Ser Val Gln His
    130                 135                 140
Arg Glu Ala Leu Tyr Thr Ala Val Thr Asn Phe Leu Leu Ser Leu Gly
145                 150                 155                 160
Ile His Leu Asn Pro Asn Lys Thr Lys Arg Trp Gly Tyr Ser Leu Asn
                165                 170                 175
Phe Met Gly Tyr Ile Ile Gly Ser Trp Gly
            180                 185

50165PRTartificial sequenceSynthetic polypeptide 50 (SEQ ID NO.: 50)
Ser Cys Pro Pro Ile Cys Pro Gly Tyr Arg Trp Met Cys Leu Arg Arg
1               5                   10                  15
Phe Met Ile Phe Leu Phe Ile Leu Leu Leu Cys Leu Ile Phe Leu Leu
            20                  25                  30
Val Leu Leu Asp Tyr Gln Gly Met Leu Pro Val Cys Pro Leu Ile Pro
        35                  40                  45
Gly Ser Thr Thr Thr Ser Thr Gly Pro Cys Lys Thr Lys Thr Cys Thr
    50                  55                  60
Thr Pro Ala Gln Gly Asn Ser Met Phe Pro Ser Cys Cys Cys Thr Lys
65                  70                  75                  80
Pro Thr Asp Gly Asn Cys Thr Cys Ile Pro Ile Pro Ser Ser Trp Ala
                85                  90                  95
Phe Ala Lys Phe Leu Trp Glu Trp Ala Ser Val Arg Phe Ser Trp Leu
            100                 105                 110
Ser Leu Leu Val Pro Phe Val Gln Trp Phe Val Gly Leu Ser Pro Thr
        115                 120                 125
Val Trp Leu Ser Ala Ile Trp Met Met Trp Tyr Trp Gly Pro Ser Leu
    130                 135                 140
Tyr Ser Ile Val Arg Pro Phe Ile Gln Leu Leu Pro Ile Phe Phe Cys
145                 150                 155                 160
Leu Trp Val Tyr Ile
                165

51669DNA artificial sequenceSynthetic oligonucleotide 51 (SEQ ID NO.: 51)
Aatcctcacaataccgcaga gtctagactt cgtggtgact tctctcaatt ttctagggga     60
ccacccgtgt gtcttggcca aaattgcag tccccaacct ccaatcactc accaacctct   120
tgtcctccaa tttgtcctgg ttatcgctgg atgtgtctgc ggcgttttat catatccctc   180
ttcatcctgc tgctatgcct catcttctta ttggttcttc tggattatca aggtatgttg   240
cccgtttgtc ctctaattcc aggatccaca acaaccagta cgggaccctg caaaacctgc   300
acgactcctg ctcaaggcaa ctctatgttt ccctcatgtt gctgtacaaa acctacggat   360
ggaaattgca cmtgtattcc catcccatca tcttgggctt tcgcaaaata cctatgggag   420
tgggcctcag tccgtttctc ttggttcagt ttactagtgc catttgttca gtggttcgta   480
gggctttccc ccactgtttg gctttcagct atatggatga tattgtactg ggggccaagt   540
ctgtacaaca tcttgagtcc ctttataccg ctgttaccaa ttttcttttg tctttgggta   600
tacatttaac ccctaacaaa acaaagagat ggggttattc cctgaatttc atgggttatg   660
taattggaa                                                           669

52181PRTartificial sequenceSynthetic polypeptide 52 (SEQ ID NO.: 52)
Ser Asn Leu Ser Trp Leu Ser Leu Asp Val Ser Alaala Phe Tyr His
1               5                   10                  15
Ile Pro Leu His Pro Alaala Met Pro His Leu Leu Ile Gly Ser Ser
            20                  25                  30
```

```
Gly Leu Ser Arg Tyr Val AlaArg Leu Ser Ser Asn Ser Arg Ile His
         35                  40                  45

Asn Asn Gln Tyr Gly Thr Leu Gln Asn Leu His Asp Ser Cys Ser Arg
 50                  55                  60

Gln Leu Tyr Val Ser Leu Met Leu Leu Tyr Lys Thr Tyr Gly Trp Lys
 65                  70                  75                  80

Leu His XAa Tyr Ser His Pro Ile Ile Leu Gly Phe Arg Lys Ile Pro
                 85                  90                  95

Met Gly Val Gly Leu Ser Pro Phe Leu Leu Val Gln Phe Thr Ser Ala
                100                 105                 110

Ile Cys Ser Val Val Arg Arg Ala Phe Pro His Cys Leu Ala Phe Ser
            115                 120                 125

Tyr Met Asp Asp Ile Val Leu Gly Ala Lys Ser Val Gln His Leu Glu
        130                 135                 140

Ser Leu Tyr Thr Ala Val Thr Asn Phe Leu Leu Ser Leu Gly Ile His
145                 150                 155                 160

Leu Thr Pro Asn Lys Thr Lys Arg Trp Gly Tyr Ser Leu Asn Phe Met
                165                 170                 175

Gly Tyr Val Ile Gly
            180

53160PRTartificial sequenceSynthetic polypeptide 53 (SEQ ID NO.: 53)
Pro Ile Cys Pro Gly Tyr Arg Trp Met Cys Leu Arg Arg Phe Ile Ile
  1               5                  10                  15

Ser Leu Phe Ile Leu Leu Leu Cys Leu Ile Phe Leu Leu Val Leu Leu
                 20                  25                  30

Asp Tyr Gln Gly Met Leu Pro Val Cys Pro Leu Ile Pro Gly Ser Thr
             35                  40                  45

Thr Thr Ser Thr Gly Pro Cys Lys Thr Cys Thr Thr Pro Ala Gln Gly
 50                  55                  60

Asn Ser Met Phe Pro Ser Cys Cys Cys Thr Lys Pro Thr Asp Gly Asn
 65                  70                  75                  80

Cys Thr Cys Ile Pro Ile Pro Ser Ser Trp Ala Phe Ala Lys Tyr Leu
                 85                  90                  95

Trp Glu Trp Ala Ser Val Arg Phe Ser Trp Phe Ser Leu Leu Val Pro
                100                 105                 110

Phe Val Gln Trp Phe Val Gly Leu Ser Pro Thr Val Trp Leu Ser Ala
            115                 120                 125

Ile Trp Met Ile Leu Tyr Trp Gly Pro Ser Leu Tyr Asn Ile Leu Ser
        130                 135                 140

Pro Phe Ile Pro Leu Leu Pro Ile Phe Phe Cys Leu Trp Val Tyr Ile
145                 150                 155                 160

54554DNA artificial sequenceSynthetic oligonucleotide 54 (SEQ ID NO.: 54)
tccAatttgt cctgggtatc gctggatgtg tctgcggcgt tttatcatat tcctcttcat        60
cctgctgcta tgcctcatct tcttgttggt cttctggac tatcAaggta tgttgcccgt       120
ttgtcctcta cttccaggAa catcAactac cagcacggga ccatgcAaga cctgcacgac       180
tcctgctcAa ggAacctcta tgtttccctc ttgttgctgt acAaAaccct cggacggAaa       240
ttgcacttgt attcccatcc catcgtcttg gctttcgcAa gattccctat gggagtgggc       300
ctcagtccgt ttctcttggc tcartttact agtgccattt gttcagtggt tcgtagggct       360
ttcccccact gtttggcttt cagttatatt gatgatgtgg tattgggggc cAagtctgta       420
cAacatcttg Aatccctttt tacctctatt accAatttc ttatgtcttt gggtatacat        480 ttAaaccctAagAaAaccAa acgttggggc tactcccctt Aacttcatgg atatgtAatt        540
```

-continued ggAagttggg gtac                                          554

55184PRT artificial sequence Synthetic polypeptide 55 (SEQ ID NO.: 55)
Ser Asn Leu Ser Trp Val Ser Leu Asp Val Ser AlAala Phe Tyr His
1               5                   10                  15

Ile Pro Leu His Pro AlAala Met Pro His Leu Val Gly Ser Ser
            20                  25                  30

Gly Leu Ser Arg Tyr Val AlAarg Leu Ser Ser Thr Ser Arg Asn Ile
        35                  40                  45

Asn Tyr Gln His Gly Thr Met Gln Asp Leu His Asp Ser Cys Ser Arg
    50                  55                  60

Asn Leu Tyr Val Ser Leu Leu Leu Tyr Lys Thr Phe Gly Arg Lys
65                  70                  75                  80

Leu His Leu Tyr Ser His Pro Ile Val Leu Gly Phe Arg Lys Ile Pro
                85                  90                  95

Met Gly Val Gly Leu Ser Pro Phe Leu Leu Ala Gln Phe Thr Ser Ala
            100                 105                 110

Ile Cys Ser Val Val Arg Arg Ala Phe Pro His Cys Leu Ala Phe Ser
        115                 120                 125

Tyr Ile Asp Asp Val Val Leu Gly Ala Lys Ser Val Gln His Leu Glu
    130                 135                 140

Ser Leu Phe Thr Ser Ile Thr Asn Phe Leu Met Ser Leu Gly Ile His
145                 150                 155                 160

Leu Asn Pro Lys Lys Thr Lys Arg Trp Gly Tyr Ser Leu Asn Phe Met
                165                 170                 175

Gly Tyr Val Ile Gly Ser Trp Gly
            180

56160PRT artificial sequence Synthetic polypeptide 56 (SEQ ID NO.: 56)
Pro Ile Cys Pro Gly Tyr Arg Trp Met Cys Leu Arg Arg Phe Ile Ile
1               5                   10                  15

Phe Leu Phe Ile Leu Leu Leu Cys Leu Ile Phe Leu Leu Val Leu Leu
            20                  25                  30

Asp Tyr Gln Gly Met Leu Pro Val Cys Pro Leu Leu Pro Gly Thr Ser
        35                  40                  45

Thr Thr Ser Thr Gly Pro Cys Lys Thr Cys Thr Thr Pro Ala Gln Gly
    50                  55                  60

Thr Ser Met Phe Pro Ser Cys Cys Cys Thr Lys Pro Ser Asp Gly Asn
65                  70                  75                  80

Cys Thr Cys Ile Pro Ile Pro Ser Ser Trp Ala Phe AlAarg Phe Leu
                85                  90                  95

Trp Glu Trp Ala Ser Val Arg Phe Ser Trp Leu XAa Leu Leu Val Pro
            100                 105                 110

Phe Val Gln Trp Phe Val Gly Leu Ser Pro Thr Val Trp Leu Ser Val
        115                 120                 125

Ile Leu Met Met Trp Tyr Trp Gly Pro Ser Leu Tyr Asn Ile Leu Asn
    130                 135                 140

Pro Phe Leu Pro Leu Leu Pro Ile Phe Leu Cys Leu Trp Val Tyr Ile
145                 150                 155                 160

571045DNA artificial sequence Synthetic oligonucleotide 57 (SEQ ID NO.: 57)
cagcAaatcc gcctcctgcc tctaccAatc gccagtcagg Aaggcagcct acccctctgt     60
ctccaccttt grgAaacact catcctcagg ccatgcagtg gAactccacAaccttccacc    120

Aaactctgcw agatcccaga gtgagaggcc tgtatttccc tgctggtggc tccagttcag   180
gAacagtAaa ccctgttccg acttctgtct ctcacacatc gtcAatcttc tcgaggattg   240

```
gggwcccctgc gctgAacatg gagAacatca catcaggatt cctaggaccc ctgctcgtgt    300
tacaggcggg gtttttcttg ttgacAagAa tcctcacAat accgcagagt ctagactcgt    360
ggtggacttc tctcAattt ctaggggAa ctaccgtgtg tcttggccAa Aattcgcagt      420
tcccAacctc cAatcactca ccAacctcct gtcctccAac ttgwcctggt tatcgctgga    480
tgtrtctgcg gcgttttatc atcttcctct tcatcctgct gctatgcctc atcttcttgt    540
tggttcttct ggactatcAa ggtatgttgc ccgtttgtcc tctarttcca ggatcttcAa    600
ccaccagcac gggaccatgc agAacctgca cgactcctgc tcAaggAamc tctatgAatc    660
cctcctgttg ctgtaccAaa ccttcggacg gAaattgcac ctgtattccc atcccatcat    720
cctgggcttt cggAaAattc ctatgggagt gggcctcagc ccgtttctcc tgrctcagtt    780
tactagtgcc atttgttcag tggttcgtag ggctttcccc cactgtttgg ctttcagtta    840
tatggatgat gtggtattgg gggccAagtc tgtaymgcat cttragtccc tttttaccgc    900
tgttaccAat tttcttttgt ctytgggtat acatttAaac cctmacAaAa cAaAaagatg    960
gggttactct ttacatttca tgggctatgt cattggatgt tatgggtcat tgccacAaga   1020 tcacatcagacagAaAatcAa agAa                                          1045
```

58348PRT artificial sequence Synthetic polypeptide 58 (SEQ ID NO.: 58)

```
Ser Lys Ser Ala Ser Cys Leu Tyr Gln Ser Pro Val Arg Lys AlAala
1               5                  10                   15

Tyr Pro Ser Val Ser Thr Phe XAa Lys His Ser Ser Gly His Ala
            20                  25                  30

Val Glu Leu His Asn Leu Pro Pro Asn Ser AlAarg Ser Gln Ser Glu
        35                  40                  45

Arg Pro Val Phe Pro Cys Trp Trp Leu Gln Phe Arg Asn Ser Lys Pro
    50                  55                  60

Cys Ser Asp Phe Cys Leu Ser His Ile Val Asn Leu Leu Glu Asp Trp
65                  70                  75                  80

Gly Pro Cys Ala Glu His Gly Glu His His Ile Arg Ile Pro Arg Thr
                85                  90                  95

Pro AlAarg Val Thr Gly Gly Val Phe Leu Val Asp Lys Asn Pro His
            100                 105                 110

Asn Thr Ala Glu Ser Arg Leu Val Val Asp Phe Ser Gln Phe Ser Arg
        115                 120                 125

Gly Asn Tyr Arg Val Ser Trp Pro Lys Phe Ala Val Pro Asn Leu Gln
    130                 135                 140

Ser Leu Thr Asn Leu Leu Ser Ser Asn Leu XAa Trp Leu Ser Leu Asp
145                 150                 155                 160

Val Ser AlAala Phe Tyr His Leu Pro Leu His Pro AlAala Met Pro
                165                 170                 175

His Leu Leu Val Gly Ser Ser Gly Leu Ser Arg Tyr Val AlAarg Leu
            180                 185                 190

Ser Ser XAa Ser Arg Ile Phe Asn His Gln His Gly Thr Met Gln Asn
        195                 200                 205

Leu His Asp Ser Cys Ser Arg XAa Leu Tyr Glu Ser Leu Leu Leu Leu
    210                 215                 220

Tyr Gln Thr Phe Gly Arg Lys Leu His Leu Tyr Ser His Pro Ile Ile
225                 230                 235                 240

Leu Gly Phe Arg Lys Ile Pro Met Gly Val Gly Leu Ser Pro Phe Leu
                245                 250                 255

Leu XAa Gln Phe Thr Ser Ala Ile Cys Ser Val Val Arg Arg Ala Phe
            260                 265                 270
```

```
Pro His Cys Leu Ala Phe Ser Tyr Met Asp Asp Val Val Leu Gly Ala
        275                 280                 285

Lys Ser Val XAa His Leu XAa Ser Leu Phe Thr Ala Val Thr Asn Phe
290             295                 300

Leu Leu Ser Leu Gly Ile His Leu Asn Pro XAa Lys Thr Lys Arg Trp
305             310                 315                 320

Gly Tyr Ser Leu His Phe Met Gly Tyr Val Ile Gly Cys Tyr Gly Ser
                325                 330                 335

Leu Pro Gln Asp His Ile Arg Gln Lys Ile Lys Glu
            340                 345

59311PRTartificial sequenceSynthetic polypeptide 59 (SEQ ID NO.: 59)
AlAasn Pro Pro Pro Ala Ser Thr Asn Arg Gln Ser Gly Arg Gln Pro
1               5                   10                  15

Thr Pro Leu Ser Pro Pro Leu XAa Asn Thr His Pro Gln Ala Met Gln
                20                  25                  30

Trp Asn Ser Thr Thr Phe His Gln Thr Leu XAa Asp Pro Arg Val Arg
                35                  40                  45

Gly Leu Tyr Phe Pro Ala Gly Gly Ser Ser Ser Gly Thr Val Asn Pro
            50                  55                  60

Val Pro Thr Ser Val Ser His Thr Ser Ser Ile Phe Ser Arg Ile Gly
65                  70                  75                  80

XAa Pro Ala Leu Asn Met Glu Asn Ile Thr Ser Gly Phe Leu Gly Pro
                85                  90                  95

Leu Leu Val Leu Gln Ala Gly Phe Phe Leu Leu Thr Arg Ile Leu Thr
            100                 105                 110

Ile Pro Gln Ser Leu Asp Ser Trp Trp Thr Ser Leu Asn Phe Leu Gly
        115                 120                 125

Gly Thr Thr Val Cys Leu Gly Gln Asn Ser Gln Phe Pro Thr Ser Asn
    130                 135                 140

His Ser Pro Thr Ser Cys Pro Pro Thr XAa Pro Gly Tyr Arg Trp Met
145             150                 155                 160

XAa Leu Arg Arg Phe Ile Ile Phe Leu Phe Ile Leu Leu Leu Cys Leu
                165                 170                 175

Ile Phe Leu Leu Val Leu Leu Asp Tyr Gln Gly Met Leu Pro Val Cys
            180                 185                 190

Pro Leu XAa Pro Gly Ser Ser Thr Thr Ser Thr Gly Pro Cys Arg Thr
        195                 200                 205

Cys Thr Thr Pro Ala Gln Gly XAa Ser Met Asn Pro Ser Cys Cys Cys
210                 215                 220

Thr Lys Pro Ser Asp Gly Asn Cys Thr Cys Ile Pro Ile Pro Ser Ser
225                 230                 235                 240

Trp Ala Phe Gly Lys Phe Leu Trp Glu Trp Ala Ser AlAarg Phe Ser
                245                 250                 255

XAa Leu Ser Leu Leu Val Pro Phe Val Gln Trp Phe Val Gly Leu Ser
            260                 265                 270

Pro Thr Val Trp Leu Ser Val Ile Trp Met Met Trp Tyr Trp Gly Pro
        275                 280                 285

Ser Leu Tyr XAa Ile Leu Ser Pro Phe Leu Pro Leu Leu Pro Ile Phe
        290                 295                 300

Phe Cys Leu Trp Val Tyr Ile
305                 310
```

The invention claimed is:

1. A detection kit comprising:
    a) a labeled primer or probe consisting of the sequence cgcgtcctac tgttcaagcc tccaagctgt gacgcg (Sequence ID No. 14), and
    b) an oligonucleotide immobilized to a solid support, wherein the primer or probe is capable of forming an amplicon when used to detect a specific nucleotide variation, and the oligonucleotide immobilized to the solid support is capable of capturing the amplicon by hybridization.
2. A labeled primer or probe consisting of the sequence cgcgtcctac tgttcaagcc tccaagctgt gacgcg (Sequence ID No. 14), wherein the primer or probe comprises a label, and wherein the primer or probe is immobilized on a solid support.
3. The detection kit of claim 1, further comprising one or more primers selected from the group consisting of aaatcgcag tccccaaa (Sequence ID No. 4), ttggggtgga gccctcaggc t (Sequence ID No. 5), gaaaattggt aacagcgg (Sequence ID No. 6), tgcacgattc ctgctcaa (Sequence ID No. 10), tttctcaaag gtggagacag (Sequence ID No. 11), gggaggagat taggttaa (Sequence ID No. 12), and ggcaaaaacg agagtaactc (Sequence ID No. 13).

* * * * *

SEQUENCE LISTING

```
<160> NUMBER OF SEQ ID NOS: 59

<210> SEQ ID NO 1
<211> LENGTH: 76
<212> TYPE: PRT
<213> ORGANISM: artificial sequence
<220> FEATURE:
<223> OTHER INFORMATION: synthetic - Formula I
<220> FEATURE:
<221> NAME/KEY: MISC_FEATURE
<222> LOCATION: (2)..(2)
<223> OTHER INFORMATION: Xaa = L or R or I
<220> FEATURE:
<221> NAME/KEY: MISC_FEATURE
<222> LOCATION: (3)..(3)
<223> OTHER INFORMATION: Xaa = E or D
<220> FEATURE:
<221> NAME/KEY: MISC_FEATURE
<222> LOCATION: (9)..(9)
<223> OTHER INFORMATION: Xaa = T or D or A or N or Y
<220> FEATURE:
<221> NAME/KEY: MISC_FEATURE
<222> LOCATION: (10)..(10)
<223> OTHER INFORMATION: Xaa = E or D
<220> FEATURE:
<221> NAME/KEY: MISC_FEATURE
<222> LOCATION: (13)..(13)
<223> OTHER INFORMATION: Xaa = E or K or Q
<220> FEATURE:
<221> NAME/KEY: MISC_FEATURE
<222> LOCATION: (15)..(15)
<223> OTHER INFORMATION: Xaa = H or R or N
<220> FEATURE:
<221> NAME/KEY: MISC_FEATURE
<222> LOCATION: (18)..(18)
<223> OTHER INFORMATION: Xaa = I or T
<220> FEATURE:
<221> NAME/KEY: MISC_FEATURE
<222> LOCATION: (23)..(23)
<223> OTHER INFORMATION: Xaa = A or S
<220> FEATURE:
<221> NAME/KEY: MISC_FEATURE
<222> LOCATION: (26)..(26)
<223> OTHER INFORMATION: Xaa = T or R
<220> FEATURE:
<221> NAME/KEY: MISC_FEATURE
<222> LOCATION: (40)..(40)
<223> OTHER INFORMATION: Xaa = A or T or S
<220> FEATURE:
<221> NAME/KEY: MISC_FEATURE
<222> LOCATION: (43)..(43)
<223> OTHER INFORMATION: Xaa = R or T
<220> FEATURE:
<221> NAME/KEY: MISC_FEATURE
<222> LOCATION: (45)..(45)
<223> OTHER INFORMATION: Xaa = V or G
<220> FEATURE:
<221> NAME/KEY: MISC_FEATURE
<222> LOCATION: (55)..(55)
<223> OTHER INFORMATION: Xaa = S or I or T or N or V
<220> FEATURE:
<221> NAME/KEY: MISC_FEATURE
<222> LOCATION: (56)..(56)
<223> OTHER INFORMATION: Xaa = T or S or H or Y
<220> FEATURE:
<221> NAME/KEY: MISC_FEATURE
<222> LOCATION: (57)..(57)
<223> OTHER INFORMATION: Xaa = R or H or K or Q
<220> FEATURE:
<221> NAME/KEY: MISC_FEATURE
<222> LOCATION: (69)..(69)
<223> OTHER INFORMATION: Xaa = Q or P

<400> SEQUENCE: 1

Leu Xaa Xaa Asp Trp Gly Pro Cys Xaa Xaa His Gly Xaa His Xaa Ile
1               5                   10                  15
```

-continued

```
Arg Xaa Pro Arg Thr Pro Xaa Arg Val Xaa Gly Gly Val Phe Leu Val
            20                  25                  30

Asp Lys Asn Pro His Asn Thr Xaa Glu Ser Xaa Leu Xaa Val Asp Phe
            35                  40                  45

Ser Gln Phe Ser Arg Gly Xaa Xaa Xaa Val Ser Trp Pro Lys Phe Ala
        50                  55                  60

Val Pro Asn Leu Xaa Ser Leu Thr Asn Leu Leu Ser
65                  70                  75

<210> SEQ ID NO 2
<211> LENGTH: 181
<212> TYPE: PRT
<213> ORGANISM: artificial sequence
<220> FEATURE:
<223> OTHER INFORMATION: synthetic - Formula II
<220> FEATURE:
<221> NAME/KEY: MISC_FEATURE
<222> LOCATION: (2)..(2)
<223> OTHER INFORMATION: Xaa = N or D
<220> FEATURE:
<221> NAME/KEY: MISC_FEATURE
<222> LOCATION: (17)..(17)
<223> OTHER INFORMATION: Xaa = I or P
<220> FEATURE:
<221> NAME/KEY: MISC_FEATURE
<222> LOCATION: (29)..(29)
<223> OTHER INFORMATION: Xaa = I or v
<220> FEATURE:
<221> NAME/KEY: MISC_FEATURE
<222> LOCATION: (35)..(35)
<223> OTHER INFORMATION: Xaa = S or D
<220> FEATURE:
<221> NAME/KEY: MISC_FEATURE
<222> LOCATION: (44)..(44)
<223> OTHER INFORMATION: Xaa = T or N
<220> FEATURE:
<221> NAME/KEY: MISC_FEATURE
<222> LOCATION: (46)..(46)
<223> OTHER INFORMATION: Xaa = R or N
<220> FEATURE:
<221> NAME/KEY: MISC_FEATURE
<222> LOCATION: (47)..(47)
<223> OTHER INFORMATION: Xaa = N or I
<220> FEATURE:
<221> NAME/KEY: MISC_FEATURE
<222> LOCATION: (48)..(48)
<223> OTHER INFORMATION: Xaa = any amino acid
<220> FEATURE:
<221> NAME/KEY: MISC_FEATURE
<222> LOCATION: (50)..(50)
<223> OTHER INFORMATION: Xaa = N or Y or H
<220> FEATURE:
<221> NAME/KEY: MISC_FEATURE
<222> LOCATION: (52)..(52)
<223> OTHER INFORMATION: Xaa = H or Y
<220> FEATURE:
<221> NAME/KEY: MISC_FEATURE
<222> LOCATION: (53)..(53)
<223> OTHER INFORMATION: Xaa = G or R
<220> FEATURE:
<221> NAME/KEY: MISC_FEATURE
<222> LOCATION: (54)..(56)
<223> OTHER INFORMATION: Xaa = any amino acid
<220> FEATURE:
<221> NAME/KEY: MISC_FEATURE
<222> LOCATION: (57)..(57)
<223> OTHER INFORMATION: Xaa = D or N
<220> FEATURE:
<221> NAME/KEY: MISC_FEATURE
<222> LOCATION: (60)..(60)
<223> OTHER INFORMATION: Xaa = D or N
<220> FEATURE:
<221> NAME/KEY: MISC_FEATURE
<222> LOCATION: (61)..(61)
<223> OTHER INFORMATION: Xaa = S or Y
```

```
<220> FEATURE:
<221> NAME/KEY: MISC_FEATURE
<222> LOCATION: (65)..(65)
<223> OTHER INFORMATION: Xaa = N or Q
<220> FEATURE:
<221> NAME/KEY: MISC_FEATURE
<222> LOCATION: (71)..(71)
<223> OTHER INFORMATION: Xaa = L or M
<220> FEATURE:
<221> NAME/KEY: MISC_FEATURE
<222> LOCATION: (75)..(75)
<223> OTHER INFORMATION: Xaa = K or Q
<220> FEATURE:
<221> NAME/KEY: MISC_FEATURE
<222> LOCATION: (77)..(77)
<223> OTHER INFORMATION: Xaa = Y or F
<220> FEATURE:
<221> NAME/KEY: MISC_FEATURE
<222> LOCATION: (79)..(79)
<223> OTHER INFORMATION: Xaa = R or W
<220> FEATURE:
<221> NAME/KEY: MISC_FEATURE
<222> LOCATION: (84)..(84)
<223> OTHER INFORMATION: Xaa = Y or L
<220> FEATURE:
<221> NAME/KEY: MISC_FEATURE
<222> LOCATION: (85)..(85)
<223> OTHER INFORMATION: Xaa = S or A
<220> FEATURE:
<221> NAME/KEY: MISC_FEATURE
<222> LOCATION: (89)..(89)
<223> OTHER INFORMATION: Xaa = I or V
<220> FEATURE:
<221> NAME/KEY: MISC_FEATURE
<222> LOCATION: (95)..(95)
<223> OTHER INFORMATION: Xaa = I or L
<220> FEATURE:
<221> NAME/KEY: MISC_FEATURE
<222> LOCATION: (99)..(99)
<223> OTHER INFORMATION: Xaa = V or G
<220> FEATURE:
<221> NAME/KEY: MISC_FEATURE
<222> LOCATION: (114)..(114)
<223> OTHER INFORMATION: Xaa = C or L
<220> FEATURE:
<221> NAME/KEY: MISC_FEATURE
<222> LOCATION: (115)..(115)
<223> OTHER INFORMATION: Xaa = A or S
<220> FEATURE:
<221> NAME/KEY: MISC_FEATURE
<222> LOCATION: (116)..(116)
<223> OTHER INFORMATION: Xaa = V or M
<220> FEATURE:
<221> NAME/KEY: MISC_FEATURE
<222> LOCATION: (117)..(117)
<223> OTHER INFORMATION: Xaa = V or T
<220> FEATURE:
<221> NAME/KEY: MISC_FEATURE
<222> LOCATION: (118)..(118)
<223> OTHER INFORMATION: Xaa = R or C
<220> FEATURE:
<221> NAME/KEY: MISC_FEATURE
<222> LOCATION: (122)..(122)
<223> OTHER INFORMATION: Xaa = F or P
<220> FEATURE:
<221> NAME/KEY: MISC_FEATURE
<222> LOCATION: (125)..(125)
<223> OTHER INFORMATION: Xaa = L or V
<220> FEATURE:
<221> NAME/KEY: MISC_FEATURE
<222> LOCATION: (126)..(126)
<223> OTHER INFORMATION: Xaa = A or V
<220> FEATURE:
<221> NAME/KEY: MISC_FEATURE
<222> LOCATION: (128)..(128)
<223> OTHER INFORMATION: Xaa = S or A
<220> FEATURE:
<221> NAME/KEY: MISC_FEATURE
<222> LOCATION: (133)..(133)
```

```
<223> OTHER INFORMATION: Xaa = V or L or M
<220> FEATURE:
<221> NAME/KEY: MISC_FEATURE
<222> LOCATION: (138)..(138)
<223> OTHER INFORMATION: Xaa = K or R
<220> FEATURE:
<221> NAME/KEY: MISC_FEATURE
<222> LOCATION: (139)..(139)
<223> OTHER INFORMATION: Xaa = S or T
<220> FEATURE:
<221> NAME/KEY: MISC_FEATURE
<222> LOCATION: (140)..(140)
<223> OTHER INFORMATION: Xaa = V or G
<220> FEATURE:
<221> NAME/KEY: MISC_FEATURE
<222> LOCATION: (141)..(141)
<223> OTHER INFORMATION: Xaa = Q or E
<220> FEATURE:
<221> NAME/KEY: MISC_FEATURE
<222> LOCATION: (143)..(143)
<223> OTHER INFORMATION: Xaa = L or S or R
<220> FEATURE:
<221> NAME/KEY: MISC_FEATURE
<222> LOCATION: (145)..(145)
<223> OTHER INFORMATION: Xaa = S or F
<220> FEATURE:
<221> NAME/KEY: MISC_FEATURE
<222> LOCATION: (147)..(147)
<223> OTHER INFORMATION: Xaa = F or Y
<220> FEATURE:
<221> NAME/KEY: MISC_FEATURE
<222> LOCATION: (148)..(148)
<223> OTHER INFORMATION: Xaa = T or A
<220> FEATURE:
<221> NAME/KEY: MISC_FEATURE
<222> LOCATION: (149)..(149)
<223> OTHER INFORMATION: Xaa = A or S
<220> FEATURE:
<221> NAME/KEY: MISC_FEATURE
<222> LOCATION: (150)..(150)
<223> OTHER INFORMATION: Xaa = V or I
<220> FEATURE:
<221> NAME/KEY: MISC_FEATURE
<222> LOCATION: (151)..(151)
<223> OTHER INFORMATION: Xaa = T or C
<220> FEATURE:
<221> NAME/KEY: MISC_FEATURE
<222> LOCATION: (152)..(152)
<223> OTHER INFORMATION: Xaa = N or S
<220> FEATURE:
<221> NAME/KEY: MISC_FEATURE
<222> LOCATION: (153)..(153)
<223> OTHER INFORMATION: Xaa = F or V
<220> FEATURE:
<221> NAME/KEY: MISC_FEATURE
<222> LOCATION: (156)..(156)
<223> OTHER INFORMATION: Xaa = S or D
<220> FEATURE:
<221> NAME/KEY: MISC_FEATURE
<222> LOCATION: (157)..(157)
<223> OTHER INFORMATION: Xaa = L or V
<220> FEATURE:
<221> NAME/KEY: MISC_FEATURE
<222> LOCATION: (164)..(164)
<223> OTHER INFORMATION: Xaa = N or Q
<220> FEATURE:
<221> NAME/KEY: MISC_FEATURE
<222> LOCATION: (179)..(179)
<223> OTHER INFORMATION: Xaa = V or I

<400> SEQUENCE: 2

Ser Xaa Leu Ser Trp Leu Ser Leu Asp Val Ser Ala Ala Phe Tyr His
  1               5                  10                  15

Xaa Pro Leu His Pro Ala Ala Met Pro His Leu Leu Xaa Gly Ser Ser
             20                  25                  30

Gly Leu Xaa Arg Tyr Val Ala Arg Leu Ser Ser Xaa Ser Xaa Xaa Xaa
```

```
                35                  40                  45
Asn Xaa Gln Xaa Xaa Xaa Xaa Xaa Leu His Xaa Xaa Cys Ser Arg
 50                  55                  60
Xaa Leu Tyr Val Ser Leu Xaa Leu Leu Tyr Xaa Thr Xaa Gly Xaa Lys
 65                  70                  75                  80
Leu His Leu Xaa Xaa His Pro Ile Xaa Leu Gly Phe Arg Lys Xaa Pro
                 85                  90                  95
Met Gly Xaa Gly Leu Ser Pro Phe Leu Leu Ala Gln Phe Thr Ser Ala
            100                 105                 110
Ile Xaa Xaa Xaa Xaa Xaa Arg Ala Phe Xaa His Cys Xaa Xaa Phe Xaa
        115                 120                 125
Tyr Met Asp Asp Xaa Val Leu Gly Ala Xaa Xaa Xaa His Xaa Glu
            130                 135                 140
Xaa Leu Xaa Xaa Xaa Xaa Xaa Xaa Leu Leu Xaa Xaa Gly Ile His
145                 150                 155                 160
Leu Asn Pro Xaa Lys Thr Lys Arg Trp Gly Tyr Ser Leu Asn Phe Met
                165                 170                 175
Gly Tyr Xaa Ile Gly
            180

<210> SEQ ID NO 3
<211> LENGTH: 23
<212> TYPE: DNA
<213> ORGANISM: artificial sequence
<220> FEATURE:
<223> OTHER INFORMATION: OS1 primer

<400> SEQUENCE: 3
gcctcatttt gtgggtcacc ata                                              23

<210> SEQ ID NO 4
<211> LENGTH: 18
<212> TYPE: DNA
<213> ORGANISM: artificial sequence
<220> FEATURE:
<223> OTHER INFORMATION: TTA3 primer

<400> SEQUENCE: 4
aaattcgcag tccccaaa                                                    18

<210> SEQ ID NO 5
<211> LENGTH: 21
<212> TYPE: DNA
<213> ORGANISM: artificial sequence
<220> FEATURE:
<223> OTHER INFORMATION: JM primer

<400> SEQUENCE: 5
ttggggtgga gccctcaggc t                                                21

<210> SEQ ID NO 6
<211> LENGTH: 18
<212> TYPE: DNA
<213> ORGANISM: artificial sequence
<220> FEATURE:
<223> OTHER INFORMATION: TTA4 primer

<400> SEQUENCE: 6
gaaaattggt aacagcgg                                                    18

<210> SEQ ID NO 7
```

```
<211> LENGTH: 20
<212> TYPE: DNA
<213> ORGANISM: artificial sequence
<220> FEATURE:
<223> OTHER INFORMATION: OS2 primer

<400> SEQUENCE: 7
tctctgacat actttccaat                                               20

<210> SEQ ID NO 8
<211> LENGTH: 23
<212> TYPE: DNA
<213> ORGANISM: artificial sequence
<220> FEATURE:
<223> OTHER INFORMATION: sense primer

<400> SEQUENCE: 8
gcctcatttt gtgggtcacc ata                                           23

<210> SEQ ID NO 9
<211> LENGTH: 20
<212> TYPE: DNA
<213> ORGANISM: artificial sequence
<220> FEATURE:
<223> OTHER INFORMATION: antisense primer

<400> SEQUENCE: 9
tctctgacat actttccaat                                               20

<210> SEQ ID NO 10
<211> LENGTH: 18
<212> TYPE: DNA
<213> ORGANISM: artificial sequence
<220> FEATURE:
<223> OTHER INFORMATION: internal regions primer

<400> SEQUENCE: 10
tgcacgattc ctgctcaa                                                 18

<210> SEQ ID NO 11
<211> LENGTH: 20
<212> TYPE: DNA
<213> ORGANISM: artificial sequence
<220> FEATURE:
<223> OTHER INFORMATION: internal regions primer

<400> SEQUENCE: 11
tttctcaaag gtggagacag                                               20

<210> SEQ ID NO 12
<211> LENGTH: 18
<212> TYPE: DNA
<213> ORGANISM: artificial sequence
<220> FEATURE:
<223> OTHER INFORMATION: PC1 forward primer

<400> SEQUENCE: 12
gggaggagat taggttaa                                                 18

<210> SEQ ID NO 13
<211> LENGTH: 20
<212> TYPE: DNA
<213> ORGANISM: artificial sequence
<220> FEATURE:
<223> OTHER INFORMATION: PC2 reverse primer

<400> SEQUENCE: 13
```

-continued

```
ggcaaaaacg agagtaactc                                                    20

<210> SEQ ID NO 14
<211> LENGTH: 36
<212> TYPE: DNA
<213> ORGANISM: artificial sequence
<220> FEATURE:
<223> OTHER INFORMATION: HBV-specific molecular beacon primer
<220> FEATURE:
<221> NAME/KEY: misc_feature
<222> LOCATION: (1)..(1)
<223> OTHER INFORMATION: 5' fluorophore 6-carboxyfluorescein
<220> FEATURE:
<221> NAME/KEY: misc_feature
<222> LOCATION: (36)..(36)
<223> OTHER INFORMATION: 3' 4-dimethylaminophenylazobenzoic acid

<400> SEQUENCE: 14
cgcgtcctac tgttcaagcc tccaagctgt gacgcg                                  36

<210> SEQ ID NO 15
<211> LENGTH: 280
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (215)..(215)
<223> OTHER INFORMATION: n = any nucleotide

<400> SEQUENCE: 15
tggctcagtt tactagtgcc atttgttcag tggttcgtag ggctttcccc cactgtttgg        60
ctttcagtta tatggatgat gtggtattgg gggccaagtc tgtayagcay cttgagtccc       120
tttttaccgc tgttaccaat tttcttttgt ctttgggtat acatttaaac cctaacaaaa       180
ctaaaagatg gggttactct ttacatttca tgggntatgt cattggatgt tatgggtcat       240
tgccacaaga tcacatcata cagaaaatca aagatggttt                             280

<210> SEQ ID NO 16
<211> LENGTH: 242
<212> TYPE: DNA
<213> ORGANISM: artificial sequence
<220> FEATURE:
<223> OTHER INFORMATION: Synthetic oligonucleotide

<400> SEQUENCE: 16
tggctcagtt tactagtgcc atttgttcag tggttcgtag ggctttcccc cactgtttgg        60
ctttcagtta tatggatgat gtggtattgg gggccaagtc tgtacagcat cttgagtccc       120
tttttaccgc tgttaccaat tttcttttgt ctttgggtat acatttaaac cctaacaaaa       180
caaagagatg gggttactct ctaaattta tgggttatgt cattggatgt tatgggtcct       240
tg                                                                     242

<210> SEQ ID NO 17
<211> LENGTH: 277
<212> TYPE: DNA
<213> ORGANISM: artificial sequence
<220> FEATURE:
<223> OTHER INFORMATION: Synthetic oligonucleotide

<400> SEQUENCE: 17
tggctcagtt tactagtgcc atttgttcag tggttcgtag ggctttcccc cactgtttgg        60
```

```
ctttcagtta tatggatgat gtggtattgg gggccaagtc tgtacagcat cttgagtccc    120
tttttaccgc tgttaccaat tttcttttgt ctttgggtat acatttaaac cctaacaaaa    180
caaagagatg gggttactct ctaaatttta tgggttatgt cattggatgt tatgggtcct    240
tgccacaaga acacatcata caaaaaatca aagaatg                             277
```

```
<210> SEQ ID NO 18
<211> LENGTH: 237
<212> TYPE: DNA
<213> ORGANISM: artificial sequence
<220> FEATURE:
<223> OTHER INFORMATION: Synthetic oligonucleotide

<400> SEQUENCE: 18
```

```
tggctcagtt tactagtgcc atttgttcag tggttcgtag ggctttcccc cactgtttgg     60
ctttcagtta tatggatgat gtggtattgg gggccaagtc tgtacagcat cttgagtccc    120
tttttaccgc tgttaccaat tttcttttgt ctttgggcat acatttaaac cctaacaaaa    180
ctaaaagatg ggggtactct ttaaatttca tgggatatgt cattggatgg tatgggg       237
```

```
<210> SEQ ID NO 19
<211> LENGTH: 336
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (11)..(11)
<223> OTHER INFORMATION: Xaa = any amino acid
<220> FEATURE:
<221> NAME/KEY: MISC_FEATURE
<222> LOCATION: (17)..(17)
<223> OTHER INFORMATION: Xaa = any amino acid
<220> FEATURE:
<221> NAME/KEY: MISC_FEATURE
<222> LOCATION: (38)..(38)
<223> OTHER INFORMATION: Xaa = any amino acid
<220> FEATURE:
<221> NAME/KEY: MISC_FEATURE
<222> LOCATION: (46)..(46)
<223> OTHER INFORMATION: Xaa = any amino acid
<220> FEATURE:
<221> NAME/KEY: MISC_FEATURE
<222> LOCATION: (50)..(50)
<223> OTHER INFORMATION: Xaa = any amino acid
<220> FEATURE:
<221> NAME/KEY: MISC_FEATURE
<222> LOCATION: (101)..(101)
<223> OTHER INFORMATION: Xaa = any amino acid
<220> FEATURE:
<221> NAME/KEY: MISC_FEATURE
<222> LOCATION: (208)..(208)
<223> OTHER INFORMATION: Xaa = any amino acid
<220> FEATURE:
<221> NAME/KEY: MISC_FEATURE
<222> LOCATION: (295)..(295)
<223> OTHER INFORMATION: Xaa = any amino acid

<400> SEQUENCE: 19
```

```
Lys Leu Ala Ser Lys Ser Ala Ser Ser Ile Xaa Gln Ser Pro Val Arg
1               5                   10                  15

Xaa Ala Ala Tyr Pro Ala Val Ser Thr Phe Glu Lys His Ser Ser Ser
                20                  25                  30

Gly His Ala Val Glu Xaa His Asn Leu Pro Pro Asn Ser Xaa Arg Ser
            35                  40                  45

Gln Xaa Glu Arg Pro Val Phe Pro Cys Trp Trp Leu Gln Phe Arg Asn
    50                  55                  60
```

-continued

```
Ser Lys Pro Cys Ser Asp Tyr Cys Leu Ser His Ile Val Asn Leu Leu
 65                  70                  75                  80

Glu Asp Trp Gly Pro Cys Ala Glu His Gly Glu His His Ile Arg Ile
                 85                  90                  95

Pro Arg Thr Pro Xaa Arg Val Thr Gly Gly Val Phe Leu Val Asp Lys
            100                 105                 110

Asn Pro His Asn Thr Ala Glu Ser Arg Leu Val Val Asp Phe Ser Gln
        115                 120                 125

Phe Ser Arg Gly Asn Tyr Arg Val Ser Trp Pro Lys Phe Ala Val Pro
130                 135                 140

Asn Leu Gln Ser Leu Thr Asn Leu Leu Ser Ser Asn Leu Ser Trp Leu
145                 150                 155                 160

Ser Leu Asp Val Ser Ala Ala Phe Tyr His Leu Pro Leu His Pro Ala
                165                 170                 175

Ala Met Pro His Leu Leu Val Gly Ser Ser Gly Leu Ser Arg Tyr Val
            180                 185                 190

Ala Arg Leu Ser Ser Asn Ser Arg Ile Phe Asn His Gln Arg Gly Xaa
        195                 200                 205

Met Gln Asn Leu His Asp Tyr Cys Ser Arg Asn Leu Tyr Val Ser Leu
210                 215                 220

Leu Leu Leu Tyr Gln Thr Phe Gly Arg Lys Leu His Leu Tyr Ser His
225                 230                 235                 240

Pro Ile Ile Leu Gly Phe Arg Lys Ile Pro Met Gly Val Gly Leu Ser
                245                 250                 255

Pro Phe Leu Leu Ala Gln Phe Thr Ser Ala Ile Cys Ser Val Val Arg
            260                 265                 270

Arg Ala Phe Pro His Cys Leu Ala Phe Ser Tyr Met Asp Asp Val Val
        275                 280                 285

Leu Gly Ala Lys Ser Val Xaa His Leu Glu Ser Leu Phe Thr Ala Val
290                 295                 300

Thr Asn Phe Leu Leu Ser Leu Gly Ile His Leu Asn Pro Asn Lys Thr
305                 310                 315                 320

Lys Arg Trp Gly Tyr Ser Leu His Phe Met Gly Tyr Val Ile Gly Cys
                325                 330                 335
```

<210> SEQ ID NO 20
<211> LENGTH: 340
<212> TYPE: PRT
<213> ORGANISM: artificial sequence
<220> FEATURE:
<223> OTHER INFORMATION: Synthetic polypeptide

<400> SEQUENCE: 20

```
His Thr Thr Asn Phe Ala Ser Lys Ser Ala Ser Cys Leu His Gln Ser
 1               5                  10                  15

Pro Val Arg Lys Ala Ala Tyr Pro Ala Val Ser Thr Phe Glu Lys His
                20                  25                  30

Ser Ser Ser Gly His Ala Val Glu Phe His Asn Leu Pro Pro Asn Ser
            35                  40                  45

Ala Arg Ser Gln Ser Glu Arg Pro Val Phe Pro Cys Trp Trp Leu Gln
        50                  55                  60

Phe Arg Asn Ser Lys Pro Cys Ser Asp Tyr Cys Leu Ser Leu Ile Val
 65                  70                  75                  80

Asn Leu Leu Glu Asp Trp Gly Pro Cys Ala Glu His Gly Glu His His
                 85                  90                  95
```

```
Ile Arg Ile Pro Arg Thr Pro Ser Arg Val Thr Gly Gly Val Phe Leu
            100                 105                 110

Val Asp Lys Asn Pro His Asn Thr Ala Glu Ser Arg Leu Val Val Asp
        115                 120                 125

Phe Ser Gln Phe Ser Arg Gly Asn Tyr Arg Val Ser Trp Pro Lys Phe
    130                 135                 140

Ala Val Pro Asn Leu Gln Ser Leu Thr Asn Leu Leu Ser Ser Asn Leu
145                 150                 155                 160

Ser Trp Leu Ser Leu Asp Val Ser Ala Ala Phe Tyr His Leu Pro Leu
                165                 170                 175

His Pro Ala Ala Met Pro His Leu Leu Val Gly Ser Ser Gly Leu Ser
            180                 185                 190

Arg Tyr Val Ala Arg Leu Ser Ser Asn Ser Arg Ile Leu Asn Asn Gln
        195                 200                 205

His Gly Thr Met Pro Asp Leu His Asp Tyr Cys Ser Arg Asn Leu Tyr
    210                 215                 220

Val Ser Leu Leu Leu Leu Tyr Gln Thr Phe Gly Arg Lys Leu His Leu
225                 230                 235                 240

Tyr Ser His Pro Ile Ile Leu Gly Phe Arg Lys Ile Pro Met Gly Val
                245                 250                 255

Gly Leu Ser Pro Phe Leu Leu Ala Gln Phe Thr Ser Ala Ile Cys Ser
            260                 265                 270

Val Val Arg Arg Ala Phe Pro His Cys Leu Ala Phe Ser Tyr Met Asp
        275                 280                 285

Asp Val Val Leu Gly Ala Lys Ser Val Gln His Leu Glu Ser Leu Phe
    290                 295                 300

Thr Ala Val Thr Asn Phe Leu Leu Ser Leu Gly Ile His Leu Asn Pro
305                 310                 315                 320

Asn Lys Thr Lys Arg Trp Gly Tyr Ser Leu Asn Phe Met Gly Tyr Val
                325                 330                 335

Ile Gly Cys Tyr
            340

<210> SEQ ID NO 21
<211> LENGTH: 344
<212> TYPE: PRT
<213> ORGANISM: artificial sequence
<220> FEATURE:
<223> OTHER INFORMATION: Synthetic polypeptide

<400> SEQUENCE: 21

Leu Ala Gln Gly Ile Leu Gln Asn Phe Ala Ser Lys Ser Ala Ser Cys
1               5                   10                  15

Leu His Gln Ser Pro Val Arg Lys Ala Ala Tyr Pro Ala Val Ser Thr
            20                  25                  30

Phe Glu Lys His Ser Ser Ser Gly His Ala Val Glu Phe His Asn Leu
        35                  40                  45

Pro Pro Asn Ser Ala Arg Ser Gln Ser Glu Arg Pro Val Phe Pro Cys
    50                  55                  60

Trp Trp Leu Gln Phe Arg Asn Ser Lys Pro Cys Ser Asp Tyr Cys Leu
65                  70                  75                  80

Ser Leu Ile Val Asn Leu Leu Glu Asp Trp Gly Pro Cys Ala Glu His
                85                  90                  95

Gly Glu His His Ile Arg Ile Pro Arg Thr Pro Ser Arg Val Thr Gly
            100                 105                 110
```

```
Gly Val Phe Leu Val Asp Lys Asn Pro His Asn Thr Ala Glu Ser Arg
            115                 120                 125

Leu Val Val Asp Phe Ser Gln Phe Ser Arg Gly Asn Tyr Arg Val Ser
    130                 135                 140

Trp Pro Lys Phe Ala Val Pro Asn Leu Gln Ser Leu Thr Asn Leu Leu
145                 150                 155                 160

Ser Ser Asn Leu Ser Trp Leu Ser Leu Asp Val Ser Ala Ala Phe Tyr
                165                 170                 175

His Leu Pro Leu His Pro Ala Ala Met Pro His Leu Leu Val Gly Ser
            180                 185                 190

Ser Gly Leu Ser Arg Tyr Val Ala Arg Leu Ser Ser Asn Ser Arg Ile
        195                 200                 205

Leu Asn Asn Gln His Gly Thr Met Pro Asp Leu His Asp Tyr Cys Ser
    210                 215                 220

Arg Asn Leu Tyr Val Ser Leu Leu Leu Tyr Gln Thr Phe Gly Arg
225                 230                 235                 240

Lys Leu His Leu Tyr Ser His Pro Ile Ile Leu Gly Phe Arg Lys Ile
                245                 250                 255

Pro Met Gly Val Gly Leu Ser Pro Phe Leu Leu Ala Gln Phe Thr Ser
            260                 265                 270

Ala Ile Cys Ser Val Val Arg Arg Ala Phe Pro His Cys Leu Ala Phe
        275                 280                 285

Ser Tyr Met Asp Asp Val Val Leu Gly Ala Lys Ser Val Gln His Leu
    290                 295                 300

Glu Ser Leu Phe Thr Ala Val Thr Asn Phe Leu Leu Ser Leu Gly Ile
305                 310                 315                 320

His Leu Asn Pro Asn Lys Thr Lys Arg Trp Gly Tyr Ser Leu Asn Phe
                325                 330                 335

Met Gly Tyr Val Ile Gly Cys Tyr
            340

<210> SEQ ID NO 22
<211> LENGTH: 336
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (24)..(24)
<223> OTHER INFORMATION: Xaa =any amino acid

<400> SEQUENCE: 22

Ala Ser Lys Ser Ala Ser Ser Ile Tyr Gln Ser Pro Val Gly Thr Ala
1               5                   10                  15

Ala Tyr Pro Ala Val Ser Thr Xaa Glu Lys His Ser Ser Gly His
            20                  25                  30

Ala Val Glu Leu His Asn Leu Pro Pro Asn Ser Glu Arg Ser Gln Gly
        35                  40                  45

Glu Arg Pro Val Phe Pro Cys Trp Trp Leu Gln Phe Arg Asn Ser Lys
    50                  55                  60

Pro Cys Ser Asp Tyr Cys Leu Ser His Ile Val Asn Leu Leu Glu Asp
65                  70                  75                  80

Trp Gly Pro Cys Ala Glu His Gly Glu His His Ile Arg Ile Pro Arg
                85                  90                  95

Thr Pro Ala Arg Val Thr Gly Gly Val Phe Leu Val Asp Lys Asn Pro
```

100                 105                 110
His Asn Thr Ala Glu Ser Arg Leu Val Val Asp Phe Ser Gln Phe Ser
            115                 120                 125

Arg Gly Asn Tyr Arg Val Ser Trp Pro Lys Phe Ala Val Pro Asn Leu
    130                 135                 140

Gln Ser Leu Thr Asn Leu Leu Ser Ser Asn Leu Ser Trp Leu Ser Leu
145                 150                 155                 160

Asp Val Ser Ala Ala Phe Tyr His Leu Pro Leu His Pro Ala Ala Met
                165                 170                 175

Pro His Leu Leu Val Gly Ser Ser Gly Leu Ser Arg Tyr Val Ala Arg
            180                 185                 190

Leu Ser Ser Asn Ser Arg Ile Phe Asn His Gln Arg Gly Asn Met Gln
        195                 200                 205

Asn Leu His Asp Cys Cys Ser Arg Asn Leu Tyr Val Ser Leu Leu Leu
    210                 215                 220

Leu Tyr Gln Thr Phe Gly Arg Lys Leu His Leu Tyr Ser His Pro Ile
225                 230                 235                 240

Ile Leu Gly Phe Arg Lys Ile Pro Met Gly Val Gly Leu Ser Pro Phe
                245                 250                 255

Leu Leu Ala Gln Phe Thr Ser Ala Ile Cys Ser Val Val Arg Arg Ala
            260                 265                 270

Phe Pro His Cys Leu Ala Phe Ser Tyr Met Asp Asp Val Val Leu Gly
        275                 280                 285

Ala Lys Ser Val Gln His Leu Glu Ser Leu Phe Thr Ala Val Thr Asn
    290                 295                 300

Phe Leu Leu Ser Leu Gly Ile His Leu Asn Pro Asn Lys Thr Lys Arg
305                 310                 315                 320

Trp Gly Tyr Ser Leu Asn Phe Met Gly Tyr Val Ile Gly Trp Tyr Gly
                325                 330                 335

<210> SEQ ID NO 23
<211> LENGTH: 226
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (120)..(120)
<223> OTHER INFORMATION: Xaa = any amino acid
<220> FEATURE:
<221> NAME/KEY: MISC_FEATURE
<222> LOCATION: (208)..(208)
<223> OTHER INFORMATION: Xaa = any amino acid

<400> SEQUENCE: 23

Met Glu Asn Ile Thr Ser Gly Phe Leu Gly Pro Leu Leu Val Leu Gln
1               5                   10                  15

Ala Gly Phe Phe Leu Leu Thr Arg Ile Leu Thr Ile Pro Gln Ser Leu
            20                  25                  30

Asp Ser Trp Trp Thr Ser Leu Asn Phe Leu Gly Gly Thr Thr Val Cys
        35                  40                  45

Leu Gly Gln Asn Ser Gln Ser Pro Thr Ser Asn His Ser Pro Thr Ser
    50                  55                  60

Cys Pro Pro Thr Cys Pro Gly Tyr Arg Trp Met Cys Leu Arg Arg Phe
65                  70                  75                  80

Ile Ile Phe Leu Phe Ile Leu Leu Leu Cys Leu Ile Phe Leu Leu Val
                85                  90                  95

```
Leu Leu Asp Tyr Gln Gly Met Leu Pro Val Cys Pro Leu Ile Pro Gly
            100                 105                 110

Ser Ser Thr Thr Ser Ala Gly Xaa Cys Arg Thr Cys Thr Thr Thr Ala
            115                 120                 125

Gln Gly Thr Ser Met Tyr Pro Ser Cys Cys Thr Lys Pro Ser Asp
130                 135                 140

Gly Asn Cys Thr Cys Ile Pro Ile Pro Ser Ser Trp Ala Phe Gly Lys
145                 150                 155                 160

Phe Leu Trp Glu Trp Ala Ser Ala Arg Phe Ser Trp Leu Ser Leu Leu
            165                 170                 175

Val Pro Phe Val Gln Trp Phe Val Gly Leu Ser Pro Thr Val Trp Leu
            180                 185                 190

Ser Val Ile Trp Met Met Trp Tyr Trp Gly Pro Ser Leu Tyr Ser Xaa
            195                 200                 205

Leu Ser Pro Phe Leu Pro Leu Leu Pro Ile Phe Phe Cys Leu Trp Val
            210                 215                 220

Tyr Ile
225

<210> SEQ ID NO 24
<211> LENGTH: 309
<212> TYPE: PRT
<213> ORGANISM: artificial sequence
<220> FEATURE:
<223> OTHER INFORMATION: Synthetic polypeptide

<400> SEQUENCE: 24

Pro Pro Pro Ala Ser Thr Asn Arg Gln Ser Gly Arg Gln Pro Thr Pro
1               5                   10                  15

Leu Ser Pro Pro Leu Arg Asn Thr His Pro Gln Ala Met Gln Trp Asn
            20                  25                  30

Ser Thr Thr Phe His Gln Thr Leu Gln Asp Pro Arg Val Arg Gly Leu
        35                  40                  45

Tyr Phe Pro Ala Gly Gly Ser Ser Gly Thr Val Asn Pro Val Leu
    50                  55                  60

Thr Thr Ala Ser Pro Leu Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
            115                 120                 125

Thr Val Cys Leu Gly Gln Asn Ser Gln Ser Pro Thr Ser Asn His Ser
        130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Thr Gly Pro Cys Arg Thr Cys Met
            195                 200                 205

Thr Thr Ala Gln Gly Thr Ser Met Tyr Pro Ser Cys Cys Cys Thr Lys
        210                 215                 220
```

```
Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
            245                 250                 255

Ser Leu Leu Val Pro Phe Val Gln Trp Phe Val Gly Leu Ser Pro Thr
            260                 265                 270

Val Trp Leu Ser Val Ile Trp Met Met Trp Tyr Trp Gly Pro Ser Leu
        275                 280                 285

Tyr Ser Ile Leu Ser Pro Phe Leu Pro Leu Leu Pro Ile Phe Phe Cys
        290                 295                 300

Leu Trp Val Tyr Ile
305

<210> SEQ ID NO 25
<211> LENGTH: 309
<212> TYPE: PRT
<213> ORGANISM: artificial sequence
<220> FEATURE:
<223> OTHER INFORMATION: Synthetic polypeptide

<400> SEQUENCE: 25

Pro Pro Pro Ala Ser Thr Asn Arg Gln Ser Gly Arg Gln Pro Thr Pro
1               5                   10                  15

Leu Ser Pro Pro Leu Arg Asn Thr His Pro Gln Ala Met Gln Trp Asn
            20                  25                  30

Ser Thr Thr Phe His Gln Thr Leu Gln Asp Pro Arg Val Arg Gly Leu
        35                  40                  45

Tyr Phe Pro Ala Gly Gly Ser Ser Gly Thr Val Asn Pro Val Leu
    50                  55                  60

Thr Thr Ala Ser Pro Leu Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
        115                 120                 125

Thr Val Cys Leu Gly Gln Asn Ser Gln Ser Pro Thr Ser Asn His Ser
    130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Thr Gly Pro Cys Arg Thr Cys Met
        195                 200                 205

Thr Thr Ala Gln Gly Thr Ser Met Tyr Pro Ser Cys Cys Cys Thr Lys
    210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270
```

```
Val Trp Leu Ser Val Ile Trp Met Met Trp Tyr Trp Gly Pro Ser Leu
            275                 280                 285

Tyr Ser Ile Leu Ser Pro Phe Leu Pro Leu Leu Pro Ile Phe Phe Cys
        290                 295                 300

Leu Trp Val Tyr Ile
305

<210> SEQ ID NO 26
<211> LENGTH: 309
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (21)..(21)
<223> OTHER INFORMATION: Xaa = any amino acid
<220> FEATURE:
<221> NAME/KEY: MISC_FEATURE
<222> LOCATION: (46)..(46)
<223> OTHER INFORMATION: Xaa = any amino acid

<400> SEQUENCE: 26

Pro Pro Pro Pro Ser Thr Asn Arg Gln Ser Gly Arg Gln Pro Thr Pro
1               5                   10                  15

Leu Ser Pro Pro Xaa Arg Asn Thr His Pro Gln Ala Met Gln Trp Asn
            20                  25                  30

Ser Thr Thr Phe His Gln Thr Leu Lys Asp Pro Arg Val Xaa Gly Leu
        35                  40                  45

Tyr Phe Pro Ala Gly Gly Ser Ser Gly Thr Val Asn Pro Val Pro
    50                  55                  60

Thr Thr Ala Ser Pro Ile Ser Ser Ile Phe Ser Arg Ile Gly Asp Pro
65                  70                  75                  80

Ala Leu Asn Met Glu Asn Ile Thr Ser Gly Phe Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Leu Gly Gly Thr
        115                 120                 125

Thr Val Cys Leu Gly Gln Asn Ser Gln Ser Pro Thr Ser Asn His Ser
    130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Val Leu Leu Asp Tyr Gln Gly Met Leu Pro Val Cys Pro Leu
            180                 185                 190

Ile Pro Gly Ser Ser Thr Thr Ser Ala Gly Thr Cys Arg Thr Cys Thr
        195                 200                 205

Thr Ala Ala Gln Gly Thr Ser Met Tyr Pro Ser Cys Cys Cys Thr Lys
    210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270
```

Val Trp Leu Ser Val Ile Trp Met Met Trp Tyr Trp Gly Pro Ser Leu
             275                 280                 285

Tyr Ser Ile Leu Ser Pro Phe Leu Pro Leu Leu Pro Ile Phe Phe Cys
        290                 295                 300

Leu Trp Ala Tyr Ile
305

<210> SEQ ID NO 27
<211> LENGTH: 656
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (561)..(561)
<223> OTHER INFORMATION: n = any nucleotide

<400> SEQUENCE: 27

```
cgcagagtct agactcgtgg tggacttctc tcaattttcg aggggggact accgtgtgtc    60
ttggccaaaa ttcgcagtcc ccaacctcca atcactcacc aacctcctgt cctccaactt   120
gtcctggtta cgctggatgt gtctgcggc gttttatcat cttcctcttc atcctgctgc   180
tatgcctcat cttcttgttg gttcttctgg actgtcaagg tatgttgccc gtttgtcctc   240
taattccagg atcctcaacc accagcacga gaccatgccg aacctgcacg actcctgctc   300
aaggaacctc tacggttccc tcatgttgct gtaccaaacc ttcgacgga aattgcacct   360
gtattcccat cccatcatcc tgggctttcg gaaaattcct atgggagtgg gcctcagccc   420
gtttctcctg gctcagttta ctagtgccat tgttcagtg gttcgtaggg ctttccccca   480
ctgtctggct tttagttata tggatgatgt ggtattgggg gccaagtctg tatcgcatct   540
tgagtccctt tttaccgctg ntaccaattt tcttttgtct tgggtatac atttaaaccc   600
taacaaaaca aaaagatggg gttactccct acattttatg ggctatgtca ttggat      656
```

<210> SEQ ID NO 28
<211> LENGTH: 625
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (10)..(10)
<223> OTHER INFORMATION: n = any nucleotide

<400> SEQUENCE: 28

```
ttactcaccn acctcctgtc ctccaacttg tcctggttat cgctggatgt gtctgcggcg    60
ttttatcatc ttcctcttca tcctgctgct atgcctcatc ttcttgttgg ttcttctgga   120
ctgtcaaggt atgttgcccg tttgtcctct aattccagga tcctcaacca ccagcagggg   180
accatgccga acctgcacga ctcctgctca aggaacctct acggttccct catgttgctg   240
taccaaacct tcggacggaa attgcacctg tattcccatc catcatcct gggctttcgg    300
aaaattccta tgggagtggg cctcagcccg tttctcatgg ctcagtttac tagtgccatt   360
tgttcagtgg ttcgtagggc tttcccccac tgtctggctt ttggttatgt ggatgatgtg   420
gtattggggg ccaagtctgt atcgcatctt gagtcccttt ttaccgctgt taccaatttt   480
cttttgtctt gggtataca tttaaatcct aacaaaacaa aaagatgggg ttactcccta   540
cattttatgg gctatgtcat tggatgtcat gggtccttgc acaagaaca catcagacaa    600
```

```
aaaatcaaag aatgttttag aaaac                                          625

<210> SEQ ID NO 29
<211> LENGTH: 1033
<212> TYPE: DNA
<213> ORGANISM: artificial sequence
<220> FEATURE:
<223> OTHER INFORMATION: Synthetic oligonucleotide

<400> SEQUENCE: 29
tgccccttct gcctccacca atcgccagtc aggaaggcag cctacccgc tgtctccacc      60 tttgagagac actcatcctc aggccatgca gtggaactca acaaccttcc accaaactct    120
gcaagatccc agagtgaaag gcctgtattt ccctgctggt ggctccagtt caggaacagt    180
aaaccctgtt ccgactactg cctctcactc atcgtcaatc ttctcgagga ttggggtccc    240
tgcgctgaac atggagaaca tcacatcagg actcctagga cccttctcg tgttacaggc     300 ggggttttttc ttgttgacaa gaatcctcac aataccgcag agtctagact cgtggtggac    360
ttctctcaat tttcgagggg ggactaccgt gtgtcttggc caaaattcgc agtccccaac    420
ctccaatcac tcaccaacct cctgtcctcc aacttgtcct ggttatcgct ggatgtgtct    480
gcggcgtttt atcatcttcc tcttcatcct gctgctatgc ctcatcttct gttggttct     540 tctggactgt caaggtatgt tgcccgtttg tcctctaatt ccaggatcct caaccaccag    600
caggggacca tgccgaacct gcacgactcc tgctcaagga acctctacgg ttccctcatg    660
ttgctgtacc aaaccttcgg acggaaattg cacctgtatt cccatcccat catcctgggc    720
tttcggaaaa ttcctatggg agtgggcctc agcccgtttc tcatggctca gtttactagt    780
gccatttgtt cagtggttcg tagggctttc ccccactgtc tggcttttgg ttatgtggat    840
gatgtggtat tggggccaa gtctgtatcg catcttgagt ccctttttac cgctgttacc     900
aattttcttt tgtctttggg tatacattta aatcctaaca aaacaaaaag atgggttac    960 tccctacatt ttatgggcta tgtcattgga tgtcatgggt ccttgccaca agaacacatc    1020
agacaaaaaa tca                                                      1033

<210> SEQ ID NO 30
<211> LENGTH: 1100
<212> TYPE: DNA
<213> ORGANISM: artificial sequence
<220> FEATURE:
<223> OTHER INFORMATION: Synthetic oligonucleotide

<400> SEQUENCE: 30
ttttggggag ccctcaggct cagggcatat acaaaactct gccagcaaat ccacctcctg     60
cctccaccaa tcgccagtca ggaaggcagc ctacccgct gtctccacct ttgagagaca     120
ctcatcctca ggccatgcag tggaactcaa caaccttcca ccaaactctg caagatccca    180
gagtgaaagg cctgtatttc cctgctggtg gctccagttc aggaacagta aaccctgttc    240
cgactactgc ctctcactca tcgtcaatct tctcgaggat tggggtccct gcgctgaaca    300
tggagaacat cacatcagga ctcctaggac cccttctcgt gttacaggcg ggttttttct    360
tgttgacaag aatcctcaca ataccgcaga gtctagactc gtggtggact tctctcaatt    420
ttcgaggggg gactaccgtg tgtcttggcc aaaattcgca gtccccaacc tccaatcact    480
caccaacctc ctgtcctcca acttgtcctg gttatcgctg gatgtgtctg cggcgttta    540 tcatcttcct cttcatcctg ctgctatgcc tcatcttctt gttggttctt ctggactgtc    600
aaggtatgtt gcccgtttgt cctctaattc caggatcctc aaccaccagc agggaccat    660
```

```
gccgaacctg cacgactcct gctcaaggaa cctctacggt tccctcatgt tgctgtacca    720
aaccttcgga cggaaattgc acctgtattc ccatcccatc atcctgggct ttcggaaaat    780
tcctatggga gtgggcctca gcccgtttct catggctcag tttactagtg ccatttgttc    840
agtggttcgt agggctttcc cccactgtct ggcttttggt tatgtggatg atgtggtatt    900
gggggccaag tctgtatcgc atcttgagtc ccttttacc gctgttacca attttctttt    960
gtctttgggt atacatttaa atcctaacaa aacaaaaaga tggggttact ccctacattt   1020
tatgggctat gtcattggat gtcatgggtc cttgccacaa gaacacatca gacaaaaaat   1080
caaagaatgt tttagaaaac                                              1100
```

<210> SEQ ID NO 31
<211> LENGTH: 987
<212> TYPE: DNA
<213> ORGANISM: artificial sequence
<220> FEATURE:
<223> OTHER INFORMATION: Synthetic oligonucleotide
<220> FEATURE:
<221> NAME/KEY: misc_feature
<222> LOCATION: (329)..(329)
<223> OTHER INFORMATION: n = any nucleotide
<220> FEATURE:
<221> NAME/KEY: misc_feature
<222> LOCATION: (943)..(943)
<223> OTHER INFORMATION: n = any nucleotide

<400> SEQUENCE: 31

```
tacaaacttt gccagcaaat ccacctcctg cctccaccaa tcgccagtca ggaaggcagc     60
ctaccccgct gtctccacct tgagagaca ctcatcctca ggccatgcag tggaactcaa    120
caaccttcca ccaaactctg caagatccca gagtgaaagg cctgtatttc cctgctggtg    180
gctccagttc aggaacagta aaccctgttc cgactactgc ctctcactca tcgtcaatct    240
tctcgaggat tgggtccct cgctgaaca tggagaacat cacatcagga ctcctaggac    300
cccttctcgt gttacaggcg gggttttnt tgttgacaag aatcctcaca ataccgcaga    360
gtctagactc gtggtggact tctctcaatt ttcgagggg gactaccgtg tgtcttggcc    420
aaaattcgca gtccccaacc tccaatcact caccaacctc ctgtcctcca acttgtcctg    480
gttatcgctg gatgtgtctg cggcgtttta tcatcttcct cttcatcctg ctgctatgcc    540
tcatcttctt gttggctcta ctggactgtc aaggtatgtt gccgtttgt cctctaattc    600 caggatcctc aaccaccagc agggaccat gccgaacctg cacgactcct gctcaaggaa    660
cctctacggt tccctcatgt tgctgtacca aaccttcgga cggaaattgc acctgtattc    720
ccatcccatc atcctgggct ttcggaaaat tcctatggga gtgggcctca gcccgtttct    780
catggctcag tttactagtg ccatttgttc agtggttcgt agggctttcc cccactgtct    840
ggcttttggt tatgtggatg atgtggtatt gggggccaag tctgtatcgc atcttgagtc    900
cctttttacc gctgttacca attttctttt gtctttgggt atncatttaa atcctaacaa    960
aacaaaaaga tggggttact ccctaca                                       987
```

<210> SEQ ID NO 32
<211> LENGTH: 350
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (309)..(309)

<223> OTHER INFORMATION: Xaa = any amino acid
<220> FEATURE:
<221> NAME/KEY: MISC_FEATURE
<222> LOCATION: (345)..(345)
<223> OTHER INFORMATION: Xaa = any amino acid

<400> SEQUENCE: 32

Ser Gly His Thr Thr Asn Phe Ala Ser Lys Ser Thr Ser Cys Leu His
1               5                   10                  15

Gln Ser Pro Val Arg Lys Ala Ala Tyr Pro Ala Val Ser Thr Phe Glu
            20                  25                  30

Arg His Ser Ser Ser Gly His Ala Val Glu Leu Asn Asn Leu Pro Pro
        35                  40                  45

Asn Ser Ala Arg Ser Gln Ser Glu Arg Pro Val Phe Pro Cys Trp Trp
    50                  55                  60

Leu Gln Phe Arg Asn Ser Lys Pro Cys Ser Asp Tyr Cys Leu Ser Leu
65                  70                  75                  80

Ile Val Asn Leu Leu Glu Asp Trp Gly Pro Cys Ala Glu His Gly Glu
                85                  90                  95

His His Ile Arg Thr Pro Arg Thr Pro Ser Arg Val Thr Gly Gly Val
            100                 105                 110

Phe Leu Val Asp Lys Asn Pro His Asn Thr Ala Glu Ser Arg Leu Val
        115                 120                 125

Val Asp Phe Ser Gln Phe Ser Arg Gly Asp Tyr Arg Val Ser Trp Pro
    130                 135                 140

Lys Phe Ala Val Pro Asn Leu Gln Ser Leu Thr Asn Leu Leu Ser Ser
145                 150                 155                 160

Asn Leu Ser Trp Leu Ser Leu Asp Val Ser Ala Ala Phe Tyr His Leu
                165                 170                 175

Pro Leu His Pro Ala Ala Met Pro His Leu Leu Val Gly Ser Ser Gly
            180                 185                 190

Leu Ser Arg Tyr Val Ala Arg Leu Ser Ser Asn Ser Arg Ile Leu Asn
        195                 200                 205

His Gln His Gly Thr Met Pro Asn Leu His Asp Ser Cys Ser Arg Asn
    210                 215                 220

Leu Tyr Gly Ser Leu Met Leu Leu Tyr Gln Thr Phe Gly Arg Lys Leu
225                 230                 235                 240

His Leu Tyr Ser His Pro Ile Ile Leu Gly Phe Arg Lys Ile Pro Met
                245                 250                 255

Gly Val Gly Leu Ser Pro Phe Leu Leu Ala Gln Phe Thr Ser Ala Ile
            260                 265                 270

Cys Ser Val Val Arg Arg Ala Phe Pro His Cys Leu Ala Phe Ser Tyr
        275                 280                 285

Met Asp Asp Val Val Leu Gly Ala Lys Ser Val Ser His Leu Glu Ser
    290                 295                 300

Leu Phe Thr Ala Xaa Thr Asn Phe Leu Leu Ser Leu Gly Ile His Leu
305                 310                 315                 320

Asn Pro Asn Lys Thr Lys Arg Trp Gly Tyr Ser Leu His Phe Met Gly
                325                 330                 335

Tyr Val Ile Gly Cys His Gly Ser Xaa Pro Gln Glu His Ile
            340                 345                 350

<210> SEQ ID NO 33
<211> LENGTH: 181
<212> TYPE: PRT
<213> ORGANISM: artificial sequence
<220> FEATURE:
<223> OTHER INFORMATION: Synthetic polypeptide

<400> SEQUENCE: 33

```
Ser Asn Leu Ser Trp Leu Ser Leu Asp Val Ser Ala Ala Phe Tyr His
1               5                   10                  15

Leu Pro Leu His Pro Ala Ala Met Pro His Leu Leu Val Gly Ser Ser
            20                  25                  30

Gly Leu Ser Arg Tyr Val Ala Arg Leu Ser Ser Asn Ser Arg Ile Leu
        35                  40                  45

Asn His Gln Gln Gly Thr Met Pro Asn Leu His Asp Ser Cys Ser Arg
50                  55                  60

Asn Leu Tyr Gly Ser Leu Met Leu Leu Tyr Gln Thr Phe Gly Arg Lys
65                  70                  75                  80

Leu His Leu Tyr Ser His Pro Ile Ile Leu Gly Phe Arg Lys Ile Pro
                85                  90                  95

Met Gly Val Gly Leu Ser Pro Phe Leu Met Ala Gln Phe Thr Ser Ala
            100                 105                 110

Ile Cys Ser Val Val Arg Arg Ala Phe Pro His Cys Leu Ala Phe Gly
        115                 120                 125

Tyr Val Asp Asp Val Val Leu Gly Ala Lys Ser Val Ser His Leu Glu
    130                 135                 140

Ser Leu Phe Thr Ala Val Thr Asn Phe Leu Leu Ser Leu Gly Ile His
145                 150                 155                 160

Leu Asn Pro Asn Lys Thr Lys Arg Trp Gly Tyr Ser Leu His Phe Met
                165                 170                 175

Gly Tyr Val Ile Gly
            180
```

<210> SEQ ID NO 34
<211> LENGTH: 340
<212> TYPE: PRT
<213> ORGANISM: artificial sequence
<220> FEATURE:
<223> OTHER INFORMATION: Synthetic polypeptide

<400> SEQUENCE: 34

```
Cys Pro Phe Cys Leu His Gln Ser Pro Val Arg Lys Ala Ala Tyr Pro
1               5                   10                  15

Ala Val Ser Thr Phe Glu Arg His Ser Ser Gly His Ala Val Glu
            20                  25                  30

Leu Asn Asn Leu Pro Pro Asn Ser Ala Arg Ser Gln Ser Glu Arg Pro
        35                  40                  45

Val Phe Pro Cys Trp Trp Leu Gln Phe Arg Asn Ser Lys Pro Cys Ser
    50                  55                  60

Asp Tyr Cys Leu Ser Leu Ile Val Asn Leu Leu Glu Asp Trp Gly Pro
65                  70                  75                  80

Cys Ala Glu His Gly Glu His His Ile Arg Thr Pro Arg Thr Pro Ser
                85                  90                  95

Arg Val Thr Gly Gly Val Phe Leu Val Asp Lys Asn Pro His Asn Thr
            100                 105                 110

Ala Glu Ser Arg Leu Val Val Asp Phe Ser Gln Phe Ser Arg Gly Asp
        115                 120                 125

Tyr Arg Val Ser Trp Pro Lys Phe Ala Val Pro Asn Leu Gln Ser Leu
    130                 135                 140

Thr Asn Leu Leu Ser Ser Asn Leu Ser Trp Leu Ser Leu Asp Val Ser
```

```
145                 150                 155                 160
Ala Ala Phe Tyr His Leu Pro Leu His Pro Ala Ala Met Pro His Leu
                165                 170                 175

Leu Val Gly Ser Ser Gly Leu Ser Arg Tyr Val Ala Arg Leu Ser Ser
            180                 185                 190

Asn Ser Arg Ile Leu Asn His Gln Gln Gly Thr Met Pro Asn Leu His
                195                 200                 205

Asp Ser Cys Ser Arg Asn Leu Tyr Gly Ser Leu Met Leu Leu Tyr Gln
        210                 215                 220

Thr Phe Gly Arg Lys Leu His Leu Tyr Ser His Pro Ile Ile Leu Gly
225                 230                 235                 240

Phe Arg Lys Ile Pro Met Gly Val Gly Leu Ser Pro Phe Leu Met Ala
                245                 250                 255

Gln Phe Thr Ser Ala Ile Cys Ser Val Val Arg Arg Ala Phe Pro His
            260                 265                 270

Cys Leu Ala Phe Gly Tyr Val Asp Asp Val Val Leu Gly Ala Lys Ser
        275                 280                 285

Val Ser His Leu Glu Ser Leu Phe Thr Ala Val Thr Asn Phe Leu Leu
    290                 295                 300

Ser Leu Gly Ile His Leu Asn Pro Asn Lys Thr Lys Arg Trp Gly Tyr
305                 310                 315                 320

Ser Leu His Phe Met Gly Tyr Val Ile Gly Cys His Gly Ser Leu Pro
                325                 330                 335

Gln Glu His Ile
            340

<210> SEQ ID NO 35
<211> LENGTH: 340
<212> TYPE: PRT
<213> ORGANISM: artificial sequence
<220> FEATURE:
<223> OTHER INFORMATION: Synthetic polypeptide

<400> SEQUENCE: 35

Ser Gly His Ile Thr Asn Ser Ala Ser Lys Ser Thr Ser Cys Leu His
1               5                   10                  15

Gln Ser Pro Val Arg Lys Ala Ala Tyr Pro Ala Val Ser Thr Phe Glu
            20                  25                  30

Arg His Ser Ser Ser Gly His Ala Val Glu Leu Asn Asn Leu Pro Pro
        35                  40                  45

Asn Ser Ala Arg Ser Gln Ser Glu Arg Pro Val Phe Pro Cys Trp Trp
    50                  55                  60

Leu Gln Phe Arg Asn Ser Lys Pro Cys Ser Asp Tyr Cys Leu Ser Leu
65                  70                  75                  80

Ile Val Asn Leu Leu Glu Asp Trp Gly Pro Cys Ala Glu His Gly Glu
                85                  90                  95

His His Ile Arg Thr Pro Arg Thr Pro Ser Arg Val Thr Gly Gly Val
            100                 105                 110

Phe Leu Val Asp Lys Asn Pro His Asn Thr Ala Glu Ser Arg Leu Val
        115                 120                 125

Val Asp Phe Ser Gln Phe Ser Arg Gly Asp Tyr Arg Val Ser Trp Pro
    130                 135                 140

Lys Phe Ala Val Pro Asn Leu Gln Ser Leu Thr Asn Leu Leu Ser Ser
145                 150                 155                 160

Asn Leu Ser Trp Leu Ser Leu Asp Val Ser Ala Ala Phe Tyr His Leu
```

```
                        165                 170                 175
Pro Leu His Pro Ala Met Pro His Leu Leu Val Gly Ser Ser Gly
            180                 185                 190

Leu Ser Arg Tyr Val Ala Arg Leu Ser Ser Asn Ser Arg Ile Leu Asn
        195                 200                 205

His Gln Gln Gly Thr Met Pro Asn Leu His Asp Ser Cys Ser Arg Asn
    210                 215                 220

Leu Tyr Gly Ser Leu Met Leu Leu Tyr Gln Thr Phe Gly Arg Lys Leu
225                 230                 235                 240

His Leu Tyr Ser His Pro Ile Ile Leu Gly Phe Arg Lys Ile Pro Met
                245                 250                 255

Gly Val Gly Leu Ser Pro Phe Leu Met Ala Gln Phe Thr Ser Ala Ile
            260                 265                 270

Cys Ser Val Val Arg Arg Ala Phe Pro His Cys Leu Ala Phe Gly Tyr
            275                 280                 285

Val Asp Asp Val Val Leu Gly Ala Lys Ser Val Ser His Leu Glu Ser
        290                 295                 300

Leu Phe Thr Ala Val Thr Asn Phe Leu Leu Ser Leu Gly Ile His Leu
305                 310                 315                 320

Asn Pro Asn Lys Thr Lys Arg Trp Gly Tyr Ser Leu His Phe Met Gly
                325                 330                 335

Tyr Val Ile Gly
            340

<210> SEQ ID NO 36
<211> LENGTH: 328
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (110)..(110)
<223> OTHER INFORMATION: Xaa = any amino acid
<220> FEATURE:
<221> NAME/KEY: MISC_FEATURE
<222> LOCATION: (314)..(314)
<223> OTHER INFORMATION: Xaa = any amino acid

<400> SEQUENCE: 36

Thr Asn Phe Ala Ser Lys Ser Thr Ser Cys Leu His Gln Ser Pro Val
1               5                   10                  15

Arg Lys Ala Ala Tyr Pro Ala Val Ser Thr Phe Glu Arg His Ser Ser
            20                  25                  30

Ser Gly His Ala Val Glu Leu Asn Asn Leu Pro Pro Asn Ser Ala Arg
        35                  40                  45

Ser Gln Ser Glu Arg Pro Val Phe Pro Cys Trp Trp Leu Gln Phe Arg
    50                  55                  60

Asn Ser Lys Pro Cys Ser Asp Tyr Cys Leu Ser Leu Ile Val Asn Leu
65                  70                  75                  80

Leu Glu Asp Trp Gly Pro Cys Ala Glu His Gly Glu His His Ile Arg
                85                  90                  95

Thr Pro Arg Thr Pro Ser Arg Val Thr Gly Gly Val Phe Xaa Val Asp
            100                 105                 110

Lys Asn Pro His Asn Thr Ala Glu Ser Arg Leu Val Val Asp Phe Ser
        115                 120                 125

Gln Phe Ser Arg Gly Asp Tyr Arg Val Ser Trp Pro Lys Phe Ala Val
    130                 135                 140
```

```
Pro Asn Leu Gln Ser Leu Thr Asn Leu Leu Ser Ser Asn Leu Ser Trp
145                 150                 155                 160

Leu Ser Leu Asp Val Ser Ala Ala Phe Tyr His Leu Pro Leu His Pro
                165                 170                 175

Ala Ala Met Pro His Leu Leu Val Gly Ser Thr Gly Leu Ser Arg Tyr
            180                 185                 190

Val Ala Arg Leu Ser Ser Asn Ser Arg Ile Leu Asn His Gln Gln Gly
        195                 200                 205

Thr Met Pro Asn Leu His Asp Ser Cys Ser Arg Asn Leu Tyr Gly Ser
    210                 215                 220

Leu Met Leu Leu Tyr Gln Thr Phe Gly Arg Lys Leu His Leu Tyr Ser
225                 230                 235                 240

His Pro Ile Ile Leu Gly Phe Arg Lys Ile Pro Met Gly Val Gly Leu
                245                 250                 255

Ser Pro Phe Leu Met Ala Gln Phe Thr Ser Ala Ile Cys Ser Val Val
                260                 265                 270

Arg Arg Ala Phe Pro His Cys Leu Ala Phe Gly Tyr Val Asp Asp Val
        275                 280                 285

Val Leu Gly Ala Lys Ser Val Ser His Leu Glu Ser Leu Phe Thr Ala
    290                 295                 300

Val Thr Asn Phe Leu Leu Ser Leu Gly Xaa His Leu Asn Pro Asn Lys
305                 310                 315                 320

Thr Lys Arg Trp Gly Tyr Ser Leu
                325

<210> SEQ ID NO 37
<211> LENGTH: 197
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (187)..(187)
<223> OTHER INFORMATION: Xaa = any amino acid

<400> SEQUENCE: 37

Gln Ser Leu Asp Ser Trp Trp Thr Ser Leu Asn Phe Arg Gly Gly Thr
1               5                   10                  15

Thr Val Cys Leu Gly Gln Asn Ser Gln Ser Pro Thr Ser Asn His Ser
                20                  25                  30

Pro Thr Ser Cys Pro Pro Thr Cys Pro Gly Tyr Arg Trp Met Cys Leu
            35                  40                  45

Arg Arg Phe Ile Ile Phe Leu Phe Ile Leu Leu Leu Cys Leu Ile Phe
        50                  55                  60

Leu Leu Val Leu Leu Asp Cys Gln Gly Met Leu Pro Val Cys Pro Leu
65                  70                  75                  80

Ile Pro Gly Ser Ser Thr Thr Ser Thr Gly Pro Cys Arg Thr Cys Thr
                85                  90                  95

Thr Pro Ala Gln Gly Thr Ser Thr Val Pro Ser Cys Cys Thr Lys
            100                 105                 110

Pro Ser Asp Gly Asn Cys Thr Cys Ile Pro Ile Pro Ser Ser Trp Ala
        115                 120                 125

Phe Gly Lys Phe Leu Trp Glu Trp Ala Ser Ala Arg Phe Ser Trp Leu
    130                 135                 140

Ser Leu Leu Val Pro Phe Val Gln Trp Phe Val Gly Leu Ser Pro Thr
```

```
145                 150                 155                 160
Val Trp Leu Leu Val Ile Trp Met Met Trp Tyr Trp Gly Pro Ser Leu
                165                 170                 175
Tyr Arg Ile Leu Ser Pro Phe Leu Pro Leu Xaa Pro Ile Phe Phe Cys
            180                 185                 190
Leu Trp Val Tyr Ile
            195

<210> SEQ ID NO 38
<211> LENGTH: 161
<212> TYPE: PRT
<213> ORGANISM: artificial sequence
<220> FEATURE:
<223> OTHER INFORMATION: Synthetic polypeptide

<400> SEQUENCE: 38

Pro Pro Thr Cys Pro Gly Tyr Arg Trp Met Cys Leu Arg Arg Phe Ile
1               5                   10                  15
Ile Phe Leu Phe Ile Leu Leu Leu Cys Leu Ile Phe Leu Leu Val Leu
            20                  25                  30
Leu Asp Cys Gln Gly Met Leu Pro Val Cys Pro Leu Ile Pro Gly Ser
        35                  40                  45
Ser Thr Thr Ser Arg Gly Pro Cys Arg Thr Cys Thr Thr Pro Ala Gln
    50                  55                  60
Gly Thr Ser Thr Val Pro Ser Cys Cys Cys Thr Lys Pro Ser Asp Gly
65                  70                  75                  80
Asn Cys Thr Cys Ile Pro Ile Pro Ser Ser Trp Ala Phe Gly Lys Phe
                85                  90                  95
Leu Trp Glu Trp Ala Ser Ala Arg Phe Ser Trp Leu Ser Leu Leu Val
            100                 105                 110
Pro Phe Val Gln Trp Phe Val Gly Leu Ser Pro Thr Val Trp Leu Leu
        115                 120                 125
Val Met Trp Met Met Trp Tyr Trp Gly Pro Ser Leu Tyr Arg Ile Leu
    130                 135                 140
Ser Pro Phe Leu Pro Leu Leu Pro Ile Phe Phe Cys Leu Trp Val Tyr
145                 150                 155                 160
Ile

<210> SEQ ID NO 39
<211> LENGTH: 160
<212> TYPE: PRT
<213> ORGANISM: artificial sequence
<220> FEATURE:
<223> OTHER INFORMATION: Synthetic polypeptide

<400> SEQUENCE: 39

Pro Thr Cys Pro Gly Tyr Arg Trp Met Cys Leu Arg Arg Phe Ile Ile
1               5                   10                  15
Phe Leu Phe Ile Leu Leu Leu Cys Leu Ile Phe Leu Leu Val Leu Leu
            20                  25                  30
Asp Cys Gln Gly Met Leu Pro Val Cys Pro Leu Ile Pro Gly Ser Ser
        35                  40                  45
Thr Thr Ser Arg Gly Pro Cys Arg Thr Cys Thr Thr Pro Ala Gln Gly
    50                  55                  60
Thr Ser Thr Val Pro Ser Cys Cys Cys Thr Lys Pro Ser Asp Gly Asn
65                  70                  75                  80
Cys Thr Cys Ile Pro Ile Pro Ser Ser Trp Ala Phe Gly Lys Phe Leu
```

```
                    85                  90                  95
Trp Glu Trp Ala Ser Ala Arg Phe Ser Trp Leu Ser Leu Leu Val Pro
                   100                 105                 110

Phe Val Gln Trp Phe Val Gly Leu Ser Pro Thr Val Trp Leu Leu Val
                   115                 120                 125

Met Trp Met Met Trp Tyr Trp Gly Pro Ser Leu Tyr Arg Ile Leu Ser
                   130                 135                 140

Pro Phe Leu Pro Leu Leu Pro Ile Phe Phe Cys Leu Trp Val Tyr Ile
145                 150                 155                 160

<210> SEQ ID NO 40
<211> LENGTH: 325
<212> TYPE: PRT
<213> ORGANISM: artificial sequence
<220> FEATURE:
<223> OTHER INFORMATION: Synthetic polypeptide

<400> SEQUENCE: 40

Leu Gly Ser Pro Gln Ala Gln Gly Ile Leu Gln Thr Leu Pro Ala Asn
1               5                  10                  15

Pro Pro Pro Ala Ser Thr Asn Arg Gln Ser Gly Arg Gln Pro Thr Pro
                20                  25                  30

Leu Ser Pro Leu Arg Asp Thr His Pro Gln Ala Met Gln Trp Asn
        35                  40                  45

Ser Thr Thr Phe His Gln Thr Leu Gln Asp Pro Arg Val Lys Gly Leu
    50                  55                  60

Tyr Phe Pro Ala Gly Gly Ser Ser Ser Gly Thr Val Asn Pro Val Pro
65                  70                  75                  80

Thr Thr Ala Ser His Ser Ser Ser Ile Phe Ser Arg Ile Gly Val Pro
                85                  90                  95

Ala Leu Asn Met Glu Asn Ile Thr Ser Gly Leu Leu Gly Pro Leu Leu
                100                 105                 110

Val Leu Gln Ala Gly Phe Phe Leu Leu Thr Arg Ile Leu Thr Ile Pro
                115                 120                 125

Gln Ser Leu Asp Ser Trp Trp Thr Ser Leu Asn Phe Arg Gly Gly Thr
130                 135                 140

Thr Val Cys Leu Gly Gln Asn Ser Gln Ser Pro Thr Ser Asn His Ser
145                 150                 155                 160

Pro Thr Ser Cys Pro Pro Thr Cys Pro Gly Tyr Arg Trp Met Cys Leu
                165                 170                 175

Arg Arg Phe Ile Ile Phe Leu Phe Ile Leu Leu Leu Cys Leu Ile Phe
                180                 185                 190

Leu Leu Val Leu Leu Asp Cys Gln Gly Met Leu Pro Val Cys Pro Leu
                195                 200                 205

Ile Pro Gly Ser Ser Thr Thr Ser Arg Gly Pro Cys Arg Thr Cys Thr
210                 215                 220

Thr Pro Ala Gln Gly Thr Ser Val Pro Ser Cys Cys Cys Thr Lys
225                 230                 235                 240

Pro Ser Asp Gly Asn Cys Thr Cys Ile Pro Ile Pro Ser Ser Trp Ala
                245                 250                 255

Phe Gly Lys Phe Leu Trp Glu Trp Ala Ser Ala Arg Phe Ser Trp Leu
                260                 265                 270

Ser Leu Leu Val Pro Phe Val Gln Trp Phe Val Gly Leu Ser Pro Thr
                275                 280                 285

Val Trp Leu Leu Val Met Trp Met Met Trp Tyr Trp Gly Pro Ser Leu
```

Tyr Arg Ile Leu Ser Pro Phe Leu Pro Leu Leu Pro Ile Phe Phe Cys
305                 310                 315                 320

Leu Trp Val Tyr Ile
                325

<210> SEQ ID NO 41
<211> LENGTH: 309
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (308)..(308)
<223> OTHER INFORMATION: Xaa = any amino acid

<400> SEQUENCE: 41

Pro Pro Pro Ala Ser Thr Asn Arg Gln Ser Gly Arg Gln Pro Thr Pro
1               5                   10                  15

Leu Ser Pro Pro Leu Arg Asp Thr His Pro Gln Ala Met Gln Trp Asn
            20                  25                  30

Ser Thr Thr Phe His Gln Thr Leu Gln Asp Pro Arg Val Lys Gly Leu
        35                  40                  45

Tyr Phe Pro Ala Gly Gly Ser Ser Gly Thr Val Asn Pro Val Pro
50                  55                  60

Thr Thr Ala Ser His Ser Ser Ile Phe Ser Arg Ile Gly Val Pro
65              70                  75                  80

Ala Leu Asn Met Glu Asn Ile Thr Ser Gly Leu Leu Gly Pro Leu Leu
                85                  90                  95

Val Leu Gln Ala Gly Phe Phe Leu Leu Thr Arg Ile Leu Thr Ile Pro
            100                 105                 110

Gln Ser Leu Asp Ser Trp Trp Thr Ser Leu Asn Phe Arg Gly Gly Thr
        115                 120                 125

Thr Val Cys Leu Gly Gln Asn Ser Gln Ser Pro Thr Ser Asn His Ser
130                 135                 140

Pro Thr Ser Cys Pro Pro Thr Cys Pro Gly Tyr Arg Trp Met Cys Leu
145                 150                 155                 160

Arg Arg Phe Ile Ile Phe Leu Phe Ile Leu Leu Leu Cys Leu Ile Phe
                165                 170                 175

Leu Leu Ala Leu Leu Asp Cys Gln Gly Met Leu Pro Val Cys Pro Leu
            180                 185                 190

Ile Pro Gly Ser Ser Thr Thr Ser Arg Gly Pro Cys Arg Thr Cys Thr
        195                 200                 205

Thr Pro Ala Gln Gly Thr Ser Thr Val Pro Ser Cys Cys Cys Thr Lys
210                 215                 220

Pro Ser Asp Gly Asn Cys Thr Cys Ile Pro Ile Pro Ser Ser Trp Ala
225                 230                 235                 240

Phe Gly Lys Phe Leu Trp Glu Trp Ala Ser Ala Arg Phe Ser Trp Leu
                245                 250                 255

Ser Leu Leu Val Pro Phe Val Gln Trp Phe Val Gly Leu Ser Pro Thr
            260                 265                 270

Val Trp Leu Leu Val Met Trp Met Met Trp Tyr Trp Gly Pro Ser Leu
        275                 280                 285

Tyr Arg Ile Leu Ser Pro Phe Leu Pro Leu Leu Pro Ile Phe Phe Cys
290                 295                 300

```
Leu Trp Val Xaa Ile
305

<210> SEQ ID NO 42
<211> LENGTH: 1031
<212> TYPE: DNA
<213> ORGANISM: artificial sequence
<220> FEATURE:
<223> OTHER INFORMATION: Synthetic oligonucleotide

<400> SEQUENCE: 42
tactacaaac cttgccagca atccgcctc ctgcctctac caatcgccag tcaggaaggc     60
agcctacccc tctgactcca cctttgagaa acactcatcc tcaggccatg cagtggaact    120
ccacaaactt ccaccgaact ctacaagatc ccagagtgaa aggcctgtat ctccctgctg    180
gtggctccag ttcaggaaca gtaaaccctg ttccgactac tgtctctcac acatcgtcaa    240
tcttatcgag gattggggac cctgcactga acatggagaa catcacatca ggattcctag    300 gaccctgct cgtgttacag gcggggtttt tcttgttgac aagaatcctc acaataccgc    360
agagtctaga ctcgtggtgg acttctctca attttctagg ggggaccacc gtgtgccttg    420
gccaaaattc gcagtcccca acctccaatc actcaccaac ctcctgtcct ccaacttgtc    480
ctggttatcg ctggatgtgt ctgcggcgtt ttatcatatt cctcttcatc ctgctgctat    540
gcctcatctt cttgttggtt cttctggact atcaaggtat gttgcccgtt tgccctctaa    600
ttccaggatc ctcaaccacc agcacgggac catgcagaac ctgcacgact cctgctcaag    660
gaacctctwt gtatccctca tgttgctgta ccaaacctwc ggmcgsaaat tgcacctgta    720
ttcccatccc atcatcctgg gctttcggaa aattcctatg ggagtgggcc tcagcccgtt    780
tctcctgact cagtttacta gtgccatttg ttcagtggtt cgtagggctt ccccccactg    840
tttggctttc agttatatgg atgatgtggt attggggggcc aggtctgtac agcatcgtga    900 ggccctttt accgctgtta ccaatttct tttgtctctg gtatacatt taaccccgga    960 caaaacaaaa agatggggtt actctttaca tttcatgggc tatgtcattg gatgttatgg   1020
gtcattgcca c                                                        1031

<210> SEQ ID NO 43
<211> LENGTH: 345
<212> TYPE: PRT
<213> ORGANISM: artificial sequence
<220> FEATURE:
<223> OTHER INFORMATION: Synthetic polypeptide

<400> SEQUENCE: 43

Thr Thr Asn Leu Ala Ser Lys Ser Ala Ser Cys Leu Tyr Gln Ser Pro
1               5                   10                  15

Val Arg Lys Ala Ala Tyr Pro Ser Asp Ser Thr Phe Glu Lys His Ser
            20                  25                  30

Ser Ser Gly His Ala Val Glu Leu His Lys Leu Pro Pro Asn Ser Thr
        35                  40                  45

Arg Ser Gln Ser Glu Arg Pro Val Ser Pro Cys Trp Trp Leu Gln Phe
    50                  55                  60

Arg Asn Ser Lys Pro Cys Ser Asp Tyr Cys Leu Ser His Ile Val Asn
65                  70                  75                  80

Leu Ile Glu Asp Trp Gly Pro Cys Thr Glu His Gly Glu His His Ile
                85                  90                  95

Arg Ile Pro Arg Thr Pro Ala Arg Val Thr Gly Gly Val Phe Leu Val
            100                 105                 110
```

Asp Lys Asn Pro His Asn Thr Ala Glu Ser Arg Leu Val Val Asp Phe
            115                 120                 125

Ser Gln Phe Ser Arg Gly Asp His Arg Val Pro Trp Pro Lys Phe Ala
130                 135                 140

Val Pro Asn Leu Gln Ser Leu Thr Asn Leu Leu Ser Ser Asn Leu Ser
145                 150                 155                 160

Trp Leu Ser Leu Asp Val Ser Ala Ala Phe Tyr His Ile Pro Leu His
                165                 170                 175

Pro Ala Ala Met Pro His Leu Leu Val Gly Ser Ser Gly Leu Ser Arg
            180                 185                 190

Tyr Val Ala Arg Leu Pro Ser Asn Ser Arg Ile Leu Asn His Gln His
            195                 200                 205

Gly Thr Met Gln Asn Leu His Asp Ser Cys Ser Arg Asn Leu Tyr Phe
210                 215                 220

Val Ser Leu Met Leu Leu Tyr Gln Thr Phe Thr Gly Arg Lys Leu His
225                 230                 235                 240

Leu Tyr Ser His Pro Ile Ile Leu Gly Phe Arg Lys Ile Pro Met Gly
                245                 250                 255

Val Gly Leu Ser Pro Phe Leu Leu Thr Gln Phe Thr Ser Ala Ile Cys
            260                 265                 270

Ser Val Val Arg Arg Ala Phe Pro His Cys Leu Ala Phe Ser Tyr Met
            275                 280                 285

Asp Asp Val Val Leu Gly Ala Arg Ser Val Gln His Arg Glu Ala Leu
290                 295                 300

Phe Thr Ala Val Thr Asn Phe Leu Leu Ser Leu Gly Ile His Leu Thr
305                 310                 315                 320

Pro Asp Lys Thr Lys Arg Trp Gly Tyr Ser Leu His Phe Met Gly Tyr
                325                 330                 335

Val Ile Gly Cys Tyr Gly Ser Leu Pro
            340                 345

<210> SEQ ID NO 44
<211> LENGTH: 317
<212> TYPE: PRT
<213> ORGANISM: artificial sequence
<220> FEATURE:
<223> OTHER INFORMATION: Synthetic polypeptide

<400> SEQUENCE: 44

Leu Gln Thr Leu Pro Ala Asn Pro Pro Ala Ser Thr Asn Arg Gln
1               5                   10                  15

Ser Gly Arg Gln Pro Thr Pro Leu Thr Pro Pro Leu Arg Asn Thr His
                20                  25                  30

Pro Gln Ala Met Gln Trp Asn Ser Thr Asn Phe His Arg Thr Leu Gln
            35                  40                  45

Asp Pro Arg Val Lys Gly Leu Tyr Leu Pro Ala Gly Gly Ser Ser Ser
        50                  55                  60

Gly Thr Val Asn Pro Val Pro Thr Thr Val Ser His Thr Ser Ser Ile
65                  70                  75                  80

Leu Ser Arg Ile Gly Asp Pro Ala Leu Asn Met Glu Asn Ile Thr Ser
                85                  90                  95

Gly Phe Leu Gly Pro Leu Leu Val Leu Gln Ala Gly Phe Phe Leu Leu
            100                 105                 110

Thr Arg Ile Leu Thr Ile Pro Gln Ser Leu Asp Ser Trp Trp Thr Ser
            115                 120                 125

Leu Asn Phe Leu Gly Gly Thr Thr Val Cys Leu Gly Gln Asn Ser Gln
    130                 135                 140

Ser Pro Thr Ser Asn His Ser Pro Thr Ser Cys Pro Pro Thr Cys Pro
145                 150                 155                 160

Gly Tyr Arg Trp Met Cys Leu Arg Arg Phe Ile Ile Phe Leu Phe Ile
                165                 170                 175

Leu Leu Leu Cys Leu Ile Phe Leu Leu Val Leu Leu Asp Tyr Gln Gly
            180                 185                 190

Met Leu Pro Val Cys Pro Leu Ile Pro Gly Ser Ser Thr Thr Ser Thr
        195                 200                 205

Gly Pro Cys Arg Thr Cys Thr Thr Pro Ala Gln Gly Thr Ser Met Leu
    210                 215                 220

Tyr Pro Ser Cys Cys Cys Thr Lys Pro Ser Thr Ala Ala Asn Cys Thr
225                 230                 235                 240

Cys Ile Pro Ile Pro Ser Ser Trp Ala Phe Gly Lys Phe Leu Trp Glu
                245                 250                 255

Trp Ala Ser Ala Arg Phe Ser Leu Ser Leu Leu Val Pro Phe Val Gln
            260                 265                 270

Trp Phe Val Gly Leu Ser Pro Thr Val Trp Leu Ser Val Ile Trp Met
        275                 280                 285

Met Trp Tyr Trp Gly Pro Gly Leu Tyr Ser Ile Val Arg Pro Phe Leu
    290                 295                 300

Pro Leu Leu Pro Ile Phe Phe Cys Leu Trp Val Tyr Ile
305                 310                 315

<210> SEQ ID NO 45
<211> LENGTH: 888
<212> TYPE: DNA
<213> ORGANISM: artificial sequence
<220> FEATURE:
<223> OTHER INFORMATION: Synthetic oligonucleotide

<400> SEQUENCE: 45
tggtcacagt gccaacagtt cctcctcctg cctccaccaa tcggcagtca gggaggcagc      60
ctactcccat ctctccacct ctaagagaca gtcatcctca ggccatggtg gctcagcctg     120
ctggtggctc cagttcagga acactcaacc ctgttcccaa tattgcctct cacatctcgt     180
caatctcctt gaggactggg gaccctgcgc cgaacatgga gaacatcaca tcaggattcc     240
taggacccct gctcgtgtta caggcggggt ttttcttgtt gacaagaatc ctcacaatac     300
cgcagagtct agactcgtgg tggacttctc tcagttttct aggggatcac ccgtgtgtc     360 ttggccaaaa ttcgcagtcc ccaacctcca atcactcacc aacctcctgt cctccaattt     420
gacctggtta tcgctggata tgtctgcggc gttttatcat attcctcttc atcctgccgc     480
tatgcctcat cttcttattg gttcttctgg attatcaagg tatgttgccc gtttgtcctc     540
taattccagg atccacaaca accagtgcgg gaccctgcaa aacctgcacg actcctgctc     600
aaggcaactc tatgtttccc tcatgttgct gtacaaaacc tacggatgga aattgcacct     660
gtattcccat cccatcatct tgggctttcg caaaatacct atgggagtgg gcctcagtcc     720
gtttctcttg gctcagttta ctagtgccat tgttcagtg attcgtaggg ctttccccca     780
ctgtttggct ttcagctata ttgatgatgt ggtactgggg gccaagtctg cacaacatct     840
tgagtcccct tataccgctg ttaccaattt tcttttgtct ttgggtat                  888

<210> SEQ ID NO 46

```
<211> LENGTH: 295
<212> TYPE: PRT
<213> ORGANISM: artificial sequence
<220> FEATURE:
<223> OTHER INFORMATION: Synthetic polypeptide

<400> SEQUENCE: 46

Gly His Ser Ala Asn Ser Ser Ser Cys Leu His Gln Ser Ala Val
1               5                   10                  15

Arg Glu Ala Ala Tyr Ser His Leu Ser Thr Ser Lys Arg Gln Ser Ser
            20                  25                  30

Ser Gly His Gly Gly Ser Ala Cys Trp Trp Leu Gln Phe Arg Asn Thr
        35                  40                  45

Gln Pro Cys Ser Gln Tyr Cys Leu Ser His Leu Val Asn Leu Leu Glu
    50                  55                  60

Asp Trp Gly Pro Cys Ala Glu His Gly Glu His His Ile Arg Ile Pro
65                  70                  75                  80

Arg Thr Pro Ala Arg Val Thr Gly Gly Val Phe Leu Val Asp Lys Asn
                85                  90                  95

Pro His Asn Thr Ala Glu Ser Arg Leu Val Val Asp Phe Ser Gln Phe
            100                 105                 110

Ser Arg Gly Ile Thr Arg Val Ser Trp Pro Lys Phe Ala Val Pro Asn
        115                 120                 125

Leu Gln Ser Leu Thr Asn Leu Leu Ser Ser Asn Leu Thr Trp Leu Ser
    130                 135                 140

Leu Asp Met Ser Ala Ala Phe Tyr His Ile Pro Leu His Pro Ala Ala
145                 150                 155                 160

Met Pro His Leu Leu Ile Gly Ser Ser Gly Leu Ser Arg Tyr Val Ala
                165                 170                 175

Arg Leu Ser Ser Asn Ser Arg Ile His Asn Asn Gln Cys Gly Thr Leu
            180                 185                 190

Gln Asn Leu His Asp Ser Cys Ser Arg Gln Leu Tyr Val Ser Leu Met
        195                 200                 205

Leu Leu Tyr Lys Thr Tyr Gly Trp Lys Leu His Leu Tyr Ser His Pro
    210                 215                 220

Ile Ile Leu Gly Phe Arg Lys Ile Pro Met Gly Val Gly Leu Ser Pro
225                 230                 235                 240

Phe Leu Leu Ala Gln Phe Thr Ser Ala Ile Cys Ser Val Ile Arg Arg
                245                 250                 255

Ala Phe Pro His Cys Leu Ala Phe Ser Tyr Ile Asp Asp Val Val Leu
            260                 265                 270

Gly Ala Lys Ser Ala Gln His Leu Glu Ser Leu Tyr Thr Ala Val Thr
        275                 280                 285

Asn Phe Leu Leu Ser Leu Gly
    290                 295

<210> SEQ ID NO 47
<211> LENGTH: 293
<212> TYPE: PRT
<213> ORGANISM: artificial sequence
<220> FEATURE:
<223> OTHER INFORMATION: Synthetic polypeptide

<400> SEQUENCE: 47

Val Thr Val Pro Thr Val Pro Pro Ala Ser Thr Asn Arg Gln Ser
1               5                   10                  15

Gly Arg Gln Pro Thr Pro Ile Ser Pro Pro Leu Arg Asp Ser His Pro
```

```
            20                  25                  30
Gln Ala Met Val Ala Gln Pro Ala Gly Gly Ser Ser Gly Thr Leu
        35                  40                  45
Asn Pro Val Pro Asn Ile Ala Ser His Ile Ser Ser Ile Ser Leu Arg
    50                  55                  60
Thr Gly Asp Pro Ala Pro Asn Met Glu Asn Ile Thr Ser Gly Phe Leu
65                  70                  75                  80
Gly Pro Leu Leu Val Leu Gln Ala Gly Phe Phe Leu Leu Thr Arg Ile
                85                  90                  95
Leu Thr Ile Pro Gln Ser Leu Asp Ser Trp Trp Thr Ser Leu Ser Phe
            100                 105                 110
Leu Gly Gly Ser Pro Val Cys Leu Gly Gln Asn Ser Gln Ser Pro Thr
        115                 120                 125
Ser Asn His Ser Pro Thr Ser Cys Pro Pro Ile Pro Gly Tyr Arg Trp
    130                 135                 140
Ile Cys Leu Arg Arg Phe Ile Ile Phe Leu Phe Ile Leu Pro Leu Cys
145                 150                 155                 160
Leu Ile Phe Leu Leu Val Leu Leu Asp Tyr Gln Gly Met Leu Pro Val
                165                 170                 175
Cys Pro Leu Ile Pro Gly Ser Thr Thr Thr Ser Ala Gly Pro Cys Lys
            180                 185                 190
Thr Cys Thr Thr Pro Ala Gln Gly Asn Ser Met Phe Pro Ser Cys Cys
        195                 200                 205
Cys Thr Lys Pro Thr Asp Gly Asn Cys Thr Cys Ile Pro Ile Pro Ser
    210                 215                 220
Ser Trp Ala Phe Ala Lys Tyr Leu Trp Glu Trp Ala Ser Val Arg Phe
225                 230                 235                 240
Ser Trp Leu Ser Leu Leu Val Pro Phe Val Gln Phe Val Gly Leu Ser
                245                 250                 255
Pro Thr Val Trp Leu Ser Ala Ile Leu Met Met Trp Tyr Trp Gly Pro
            260                 265                 270
Ser Leu His Asn Ile Leu Ser Pro Phe Ile Pro Leu Leu Pro Ile Phe
        275                 280                 285
Phe Cys Leu Trp Val
    290

<210> SEQ ID NO 48
<211> LENGTH: 591
<212> TYPE: DNA
<213> ORGANISM: artificial sequence
<220> FEATURE:
<223> OTHER INFORMATION: Synthetic oligonucleotide

<400> SEQUENCE: 48
tcctgtcctc caatttgtcc tggttatcgc tggatgtgtc tgcggcgttt tatgatattc      60
ctcttcatcc tgctgctatg cctcatcttc ttattggttc ttctggatta tcaaggtatg     120
ttgcccgtct gtcctctaat tccaggatca acaacaacca gtacgggacc atgcaaaacc     180
aaaacctgca cgactcctgc tcaaggcaac tctatgtttc cctcatgttg ctgtacaaaa     240
cctacggatg gaaattgcac ctgtattccc atcccatcgt cctgggcttt cgcaaaattc     300
ctatgggagt gggcctcagt ccgtttctct ggctcagtt tactagtgcc atttgttcag      360
tggttcgtag gctttccccc actgtttgg ctttcagcta tggatgat gtggtattgg        420 gggccaagtc tgtacagcat cgtgaggccc tttatacagc tgttaccaat tttcttttgt     480
```

```
ctctgggtat acatttaaac cctaacaaaa caaaaagatg gggttattcc ctaaacttca    540
tgggttacat aattggaagt tggggaacat tgccacagga tcatattgta c             591
```

<210> SEQ ID NO 49
<211> LENGTH: 186
<212> TYPE: PRT
<213> ORGANISM: artificial sequence
<220> FEATURE:
<223> OTHER INFORMATION: Synthetic polypeptide

<400> SEQUENCE: 49

```
Ser Asn Leu Ser Trp Leu Ser Leu Asp Val Ser Ala Ala Phe Tyr Asp
1               5                   10                  15

Ile Pro Leu His Pro Ala Ala Met Pro His Leu Leu Ile Gly Ser Ser
            20                  25                  30

Gly Leu Ser Arg Tyr Val Ala Arg Leu Ser Ser Asn Ser Arg Ile Asn
        35                  40                  45

Asn Asn Gln Tyr Gly Thr Met Gln Asn Gln Asn Leu His Asp Ser Cys
50                  55                  60

Ser Arg Gln Leu Tyr Val Ser Leu Met Leu Leu Tyr Lys Thr Tyr Gly
65                  70                  75                  80

Trp Lys Leu His Leu Tyr Ser His Pro Ile Val Leu Gly Phe Arg Lys
                85                  90                  95

Ile Pro Met Gly Val Gly Leu Ser Pro Phe Leu Leu Ala Gln Phe Thr
            100                 105                 110

Ser Ala Ile Cys Ser Val Val Arg Arg Ala Phe Pro His Cys Leu Ala
        115                 120                 125

Phe Ser Tyr Met Asp Asp Val Val Leu Gly Ala Lys Ser Val Gln His
130                 135                 140

Arg Glu Ala Leu Tyr Thr Ala Val Thr Asn Phe Leu Leu Ser Leu Gly
145                 150                 155                 160

Ile His Leu Asn Pro Asn Lys Thr Lys Arg Trp Gly Tyr Ser Leu Asn
                165                 170                 175

Phe Met Gly Tyr Ile Ile Gly Ser Trp Gly
            180                 185
```

<210> SEQ ID NO 50
<211> LENGTH: 165
<212> TYPE: PRT
<213> ORGANISM: artificial sequence
<220> FEATURE:
<223> OTHER INFORMATION: Synthetic polypeptide

<400> SEQUENCE: 50

```
Ser Cys Pro Pro Ile Cys Pro Gly Tyr Arg Trp Met Cys Leu Arg Arg
1               5                   10                  15

Phe Met Ile Phe Leu Phe Ile Leu Leu Cys Leu Ile Phe Leu Leu
            20                  25                  30

Val Leu Leu Asp Tyr Gln Gly Met Leu Pro Val Cys Pro Leu Ile Pro
        35                  40                  45

Gly Ser Thr Thr Thr Ser Thr Gly Pro Cys Lys Thr Lys Thr Cys Thr
50                  55                  60

Thr Pro Ala Gln Gly Asn Ser Met Phe Pro Ser Cys Cys Cys Thr Lys
65                  70                  75                  80

Pro Thr Asp Gly Asn Cys Thr Cys Ile Pro Ile Pro Ser Ser Trp Ala
                85                  90                  95

Phe Ala Lys Phe Leu Trp Glu Trp Ala Ser Val Arg Phe Ser Trp Leu
```

```
             100                 105                 110
Ser Leu Leu Val Pro Phe Val Gln Trp Phe Val Gly Leu Ser Pro Thr
            115                 120                 125

Val Trp Leu Ser Ala Ile Trp Met Met Trp Tyr Trp Gly Pro Ser Leu
        130                 135                 140

Tyr Ser Ile Val Arg Pro Phe Ile Gln Leu Leu Pro Ile Phe Phe Cys
145                 150                 155                 160

Leu Trp Val Tyr Ile
                165

<210> SEQ ID NO 51
<211> LENGTH: 669
<212> TYPE: DNA
<213> ORGANISM: artificial sequence
<220> FEATURE:
<223> OTHER INFORMATION: Synthetic oligonucleotide

<400> SEQUENCE: 51
aatcctcaca ataccgcaga gtctagactt cgtggtgact ctctcaatt tctagggga      60 ccacccgtgt gtcttggcca aaattcgcag tccccaacct ccaatcactc accaacctct   120
tgtcctccaa tttgtcctgg ttatcgctgg atgtgtctgc ggcgttttat catatccctc   180
ttcatcctgc tgctatgcct catcttctta ttggttcttc tggattatca aggtatgttg   240
cccgtttgtc ctctaattcc aggatccaca acaaccagta cgggaccctg caaaacctgc   300
acgactcctg ctcaaggcaa ctctatgttt ccctcatgtt gctgtacaaa acctacggat   360
ggaaattgca cmtgtattcc catcccatca tcttgggctt tcgcaaaata cctatgggag   420
tgggcctcag tccgtttctc ttggttcagt ttactagtgc catttgttca gtggttcgta   480
gggctttccc ccactgtttg gctttcagct atatggatga tattgtactg ggggccaagt   540
ctgtacaaca tcttgagtcc ctttataccg ctgttaccaa ttttcttttg tctttgggta   600
tacatttaac ccctaacaaa acaaagagat ggggttattc cctgaatttc atgggttatg   660
taattggaa                                                          669

<210> SEQ ID NO 52
<211> LENGTH: 181
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (83)..(83)
<223> OTHER INFORMATION: Xaa = any amino acid

<400> SEQUENCE: 52

Ser Asn Leu Ser Trp Leu Ser Leu Asp Val Ser Ala Ala Phe Tyr His
1               5                   10                  15

Ile Pro Leu His Pro Ala Ala Met Pro His Leu Leu Ile Gly Ser Ser
            20                  25                  30

Gly Leu Ser Arg Tyr Val Ala Arg Leu Ser Ser Asn Ser Arg Ile His
        35                  40                  45

Asn Asn Gln Tyr Gly Thr Leu Gln Asn Leu His Asp Ser Cys Ser Arg
    50                  55                  60

Gln Leu Tyr Val Ser Leu Met Leu Leu Tyr Lys Thr Tyr Gly Trp Lys
65                  70                  75                  80

Leu His Xaa Tyr Ser His Pro Ile Ile Leu Gly Phe Arg Lys Ile Pro
                85                  90                  95
```

```
Met Gly Val Gly Leu Ser Pro Phe Leu Leu Val Gln Phe Thr Ser Ala
            100                 105                 110

Ile Cys Ser Val Val Arg Arg Ala Phe Pro His Cys Leu Ala Phe Ser
        115                 120                 125

Tyr Met Asp Asp Ile Val Leu Gly Ala Lys Ser Val Gln His Leu Glu
    130                 135                 140

Ser Leu Tyr Thr Ala Val Thr Asn Phe Leu Leu Ser Leu Gly Ile His
145                 150                 155                 160

Leu Thr Pro Asn Lys Thr Lys Arg Trp Gly Tyr Ser Leu Asn Phe Met
                165                 170                 175

Gly Tyr Val Ile Gly
            180

<210> SEQ ID NO 53
<211> LENGTH: 160
<212> TYPE: PRT
<213> ORGANISM: artificial sequence
<220> FEATURE:
<223> OTHER INFORMATION: Synthetic polypeptide

<400> SEQUENCE: 53

Pro Ile Cys Pro Gly Tyr Arg Trp Met Cys Leu Arg Arg Phe Ile Ile
1               5                   10                  15

Ser Leu Phe Ile Leu Leu Leu Cys Leu Ile Phe Leu Leu Val Leu Leu
            20                  25                  30

Asp Tyr Gln Gly Met Leu Pro Val Cys Pro Leu Ile Pro Gly Ser Thr
        35                  40                  45

Thr Thr Ser Thr Gly Pro Cys Lys Thr Cys Thr Thr Pro Ala Gln Gly
    50                  55                  60

Asn Ser Met Phe Pro Ser Cys Cys Cys Thr Lys Pro Thr Asp Gly Asn
65                  70                  75                  80

Cys Thr Cys Ile Pro Ile Pro Ser Ser Trp Ala Phe Ala Lys Tyr Leu
                85                  90                  95

Trp Glu Trp Ala Ser Val Arg Phe Ser Trp Phe Ser Leu Leu Val Pro
            100                 105                 110

Phe Val Gln Trp Phe Val Gly Leu Ser Pro Thr Val Trp Leu Ser Ala
        115                 120                 125

Ile Trp Met Ile Leu Tyr Trp Gly Pro Ser Leu Tyr Asn Ile Leu Ser
    130                 135                 140

Pro Phe Ile Pro Leu Leu Pro Ile Phe Phe Cys Leu Trp Val Tyr Ile
145                 150                 155                 160

<210> SEQ ID NO 54
<211> LENGTH: 554
<212> TYPE: DNA
<213> ORGANISM: artificial sequence
<220> FEATURE:
<223> OTHER INFORMATION: Synthetic oligonucleotide

<400> SEQUENCE: 54
tccaatttgt cctgggtatc gctggatgtg tctgcggcgt tttatcatat tcctcttcat      60
cctgctgcta tgcctcatct tcttgttggt cttctggac tatcaaggta tgttgcccgt     120
ttgtcctcta cttccaggaa catcaactac cagcacggga ccatgcaaga cctgcacgac    180
tcctgctcaa ggaacctcta tgtttccctc ttgttgctgt acaaaacctt cggacggaaa    240
ttgcacttgt attcccatcc catcgtcttg ggctttcgca agattcctat gggagtgggc    300
```

```
ctcagtccgt ttctcttggc tcartttact agtgccattt gttcagtggt tcgtagggct    360
ttcccccact gtttggcttt cagttatatt gatgatgtgg tattgggggc caagtctgta    420
caacatcttg aatccctttt tacctctatt accaattttc ttatgtcttt gggtatacat    480 ttaaaccta agaaaaccaa acgttggggc tactcccta acttcatggg atatgtaatt    540
ggaagttggg gtac                                                     554
```

<210> SEQ ID NO 55
<211> LENGTH: 184
<212> TYPE: PRT
<213> ORGANISM: artificial sequence
<220> FEATURE:
<223> OTHER INFORMATION: Synthetic polypeptide

<400> SEQUENCE: 55

```
Ser Asn Leu Ser Trp Val Ser Leu Asp Val Ser Ala Ala Phe Tyr His
1               5                   10                  15

Ile Pro Leu His Pro Ala Ala Met Pro His Leu Leu Val Gly Ser Ser
            20                  25                  30

Gly Leu Ser Arg Tyr Val Ala Arg Leu Ser Ser Thr Ser Arg Asn Ile
        35                  40                  45

Asn Tyr Gln His Gly Thr Met Gln Asp Leu His Asp Ser Cys Ser Arg
    50                  55                  60

Asn Leu Tyr Val Ser Leu Leu Leu Tyr Lys Thr Phe Gly Arg Lys
65                  70                  75                  80

Leu His Leu Tyr Ser His Pro Ile Val Leu Gly Phe Arg Lys Ile Pro
                85                  90                  95

Met Gly Val Gly Leu Ser Pro Phe Leu Leu Ala Gln Phe Thr Ser Ala
            100                 105                 110

Ile Cys Ser Val Val Arg Arg Ala Phe Pro His Cys Leu Ala Phe Ser
        115                 120                 125

Tyr Ile Asp Asp Val Val Leu Gly Ala Lys Ser Val Gln His Leu Glu
    130                 135                 140

Ser Leu Phe Thr Ser Ile Thr Asn Phe Leu Met Ser Leu Gly Ile His
145                 150                 155                 160

Leu Asn Pro Lys Lys Thr Lys Arg Trp Gly Tyr Ser Leu Asn Phe Met
                165                 170                 175

Gly Tyr Val Ile Gly Ser Trp Gly
            180
```

<210> SEQ ID NO 56
<211> LENGTH: 160
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (108)..(108)
<223> OTHER INFORMATION: Xaa = any amino acid

<400> SEQUENCE: 56

```
Pro Ile Cys Pro Gly Tyr Arg Trp Met Cys Leu Arg Arg Phe Ile Ile
1               5                   10                  15

Phe Leu Phe Ile Leu Leu Leu Cys Leu Ile Phe Leu Leu Val Leu Leu
            20                  25                  30

Asp Tyr Gln Gly Met Leu Pro Val Cys Pro Leu Leu Pro Gly Thr Ser
        35                  40                  45
```

```
Thr Thr Ser Thr Gly Pro Cys Lys Thr Cys Thr Pro Ala Gln Gly
        50                  55                  60

Thr Ser Met Phe Pro Ser Cys Cys Thr Lys Pro Ser Asp Gly Asn
65                  70                  75                  80

Cys Thr Cys Ile Pro Ile Pro Ser Ser Trp Ala Phe Ala Arg Phe Leu
                85                  90                  95

Trp Glu Trp Ala Ser Val Arg Phe Ser Trp Leu Xaa Leu Leu Val Pro
                100                 105                 110

Phe Val Gln Trp Phe Val Gly Leu Ser Pro Thr Val Trp Leu Ser Val
            115                 120                 125

Ile Leu Met Met Trp Tyr Trp Gly Pro Ser Leu Tyr Asn Ile Leu Asn
        130                 135                 140

Pro Phe Leu Pro Leu Leu Pro Ile Phe Leu Cys Leu Trp Val Tyr Ile
145                 150                 155                 160

<210> SEQ ID NO 57
<211> LENGTH: 1045
<212> TYPE: DNA
<213> ORGANISM: artificial sequence
<220> FEATURE:
<223> OTHER INFORMATION: Synthetic oligonucleotide

<400> SEQUENCE: 57
cagcaaatcc gcctcctgcc tctaccaatc gccagtcagg aaggcagcct accoctctgt      60
ctccaccttt grgaaacact catcctcagg ccatgcagtg gaactccaca accttccacc     120
aaactctgcw agatcccaga gtgagaggcc tgtatttccc tgctggtggc tccagttcag     180
gaacagtaaa ccctgttccg acttctgtct ctcacacatc gtcaatcttc tcgaggattg     240
gggwccctgc gctgaacatg gagaacatca catcaggatt cctaggaccc ctgctcgtgt     300
tacaggcggg gttttcttg ttgacaagaa tcctcacaat accgcagagt ctagactcgt     360
ggtggacttc tctcaatttt ctaggggaa ctaccgtgtg tcttggccaa aattcgcagt      420
tcccaacctc caatcactca ccaacctcct gtcctccaac ttgwcctggt tatcgctgga     480
tgtrtctgcg gcgttttatc atcttcctct tcatcctgct gctatgcctc atcttcttgt     540
tggttcttct ggactatcaa ggtatgttgc ccgtttgtcc tctarttcca ggatcttcaa     600
ccaccagcac gggaccatgc agaacctgca cgactcctgc tcaaggaamc tctatgaatc     660
cctcctgttg ctgtaccaaa ccttcggacg gaaattgcac ctgtattccc atcccatcat     720
cctgggcttt cggaaaattc ctatgggagt gggcctcagc ccgtttctcc tgrctcagtt     780
tactagtgcc atttgttcag tggttcgtag ggctttcccc cactgtttgg ctttcagtta     840
tatggatgat gtggtattgg gggccaagtc tgtaymgcat cttragtccc tttttaccgc     900
tgttaccaat tttcttttgt ctytgggtat acatttaaac cctmacaaaa caaaagatg      960
gggttactct ttacatttca tgggctatgt cattggatgt tatgggtcat tgccacaaga   1020
tcacatcaga cagaaaatca aagaa                                          1045

<210> SEQ ID NO 58
<211> LENGTH: 348
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (24)..(24)
<223> OTHER INFORMATION: Xaa = any amino acid
<220> FEATURE:
```

<220> FEATURE:
<221> NAME/KEY: MISC_FEATURE
<222> LOCATION: (155)..(155)
<223> OTHER INFORMATION: Xaa = any amino acid
<220> FEATURE:
<221> NAME/KEY: MISC_FEATURE
<222> LOCATION: (195)..(195)
<223> OTHER INFORMATION: Xaa = any amino acid
<220> FEATURE:
<221> NAME/KEY: MISC_FEATURE
<222> LOCATION: (216)..(216)
<223> OTHER INFORMATION: Xaa = any amino acid
<220> FEATURE:
<221> NAME/KEY: MISC_FEATURE
<222> LOCATION: (258)..(258)
<223> OTHER INFORMATION: Xaa = any amino acid
<220> FEATURE:
<221> NAME/KEY: MISC_FEATURE
<222> LOCATION: (292)..(292)
<223> OTHER INFORMATION: Xaa = any amino acid
<220> FEATURE:
<221> NAME/KEY: MISC_FEATURE
<222> LOCATION: (295)..(295)
<223> OTHER INFORMATION: Xaa = any amino acid
<220> FEATURE:
<221> NAME/KEY: MISC_FEATURE
<222> LOCATION: (315)..(315)
<223> OTHER INFORMATION: Xaa = any amino acid

<400> SEQUENCE: 58

```
Ser Lys Ser Ala Ser Cys Leu Tyr Gln Ser Pro Val Arg Lys Ala Ala
1               5                   10                  15

Tyr Pro Ser Val Ser Thr Phe Xaa Lys His Ser Ser Gly His Ala
            20                  25                  30

Val Glu Leu His Asn Leu Pro Pro Asn Ser Ala Arg Ser Gln Ser Glu
        35                  40                  45

Arg Pro Val Phe Pro Cys Trp Trp Leu Gln Phe Arg Asn Ser Lys Pro
    50                  55                  60

Cys Ser Asp Phe Cys Leu Ser His Ile Val Asn Leu Leu Glu Asp Trp
65                  70                  75                  80

Gly Pro Cys Ala Glu His Gly Glu His His Ile Arg Ile Pro Arg Thr
                85                  90                  95

Pro Ala Arg Val Thr Gly Gly Val Phe Leu Val Asp Lys Asn Pro His
            100                 105                 110

Asn Thr Ala Glu Ser Arg Leu Val Val Asp Phe Ser Gln Phe Ser Arg
        115                 120                 125

Gly Asn Tyr Arg Val Ser Trp Pro Lys Phe Ala Val Pro Asn Leu Gln
    130                 135                 140

Ser Leu Thr Asn Leu Leu Ser Ser Asn Leu Xaa Trp Leu Ser Leu Asp
145                 150                 155                 160

Val Ser Ala Ala Phe Tyr His Leu Pro Leu His Pro Ala Ala Met Pro
                165                 170                 175

His Leu Leu Val Gly Ser Ser Gly Leu Ser Arg Tyr Val Ala Arg Leu
            180                 185                 190

Ser Ser Xaa Ser Arg Ile Phe Asn His Gln His Gly Thr Met Gln Asn
        195                 200                 205

Leu His Asp Ser Cys Ser Arg Xaa Leu Tyr Glu Ser Leu Leu Leu Leu
    210                 215                 220

Tyr Gln Thr Phe Gly Arg Lys Leu His Leu Tyr Ser His Pro Ile Ile
225                 230                 235                 240

Leu Gly Phe Arg Lys Ile Pro Met Gly Val Gly Leu Ser Pro Phe Leu
                245                 250                 255

Leu Xaa Gln Phe Thr Ser Ala Ile Cys Ser Val Val Arg Arg Ala Phe
```

```
                    260                 265                 270
Pro His Cys Leu Ala Phe Ser Tyr Met Asp Asp Val Val Leu Gly Ala
                275                 280                 285

Lys Ser Val Xaa His Leu Xaa Ser Leu Phe Thr Ala Val Thr Asn Phe
            290                 295                 300

Leu Leu Ser Leu Gly Ile His Leu Asn Pro Xaa Lys Thr Lys Arg Trp
305                 310                 315                 320

Gly Tyr Ser Leu His Phe Met Gly Tyr Val Ile Gly Cys Tyr Gly Ser
                325                 330                 335

Leu Pro Gln Asp His Ile Arg Gln Lys Ile Lys Glu
            340                 345

<210> SEQ ID NO 59
<211> LENGTH: 311
<212> TYPE: PRT
<213> ORGANISM: artificial sequence
<220> FEATURE:
<223> OTHER INFORMATION: Synthetic polypeptide
<220> FEATURE:
<221> NAME/KEY: MISC_FEATURE
<222> LOCATION: (24)..(24)
<223> OTHER INFORMATION: Xaa = any amino acid
<220> FEATURE:
<221> NAME/KEY: MISC_FEATURE
<222> LOCATION: (43)..(43)
<223> OTHER INFORMATION: Xaa = any amino acid
<220> FEATURE:
<221> NAME/KEY: MISC_FEATURE
<222> LOCATION: (81)..(81)
<223> OTHER INFORMATION: Xaa = any amino acid
<220> FEATURE:
<221> NAME/KEY: MISC_FEATURE
<222> LOCATION: (154)..(154)
<223> OTHER INFORMATION: Xaa = any amino acid
<220> FEATURE:
<221> NAME/KEY: MISC_FEATURE
<222> LOCATION: (161)..(161)
<223> OTHER INFORMATION: Xaa = any amino acid
<220> FEATURE:
<221> NAME/KEY: MISC_FEATURE
<222> LOCATION: (195)..(195)
<223> OTHER INFORMATION: Xaa = any amino acid
<220> FEATURE:
<221> NAME/KEY: MISC_FEATURE
<222> LOCATION: (216)..(216)
<223> OTHER INFORMATION: Xaa = any amino acid
<220> FEATURE:
<221> NAME/KEY: MISC_FEATURE
<222> LOCATION: (257)..(257)
<223> OTHER INFORMATION: Xaa = any amino acid
<220> FEATURE:
<221> NAME/KEY: MISC_FEATURE
<222> LOCATION: (292)..(292)
<223> OTHER INFORMATION: Xaa = any amino acid

<400> SEQUENCE: 59

Ala Asn Pro Pro Ala Ser Thr Asn Arg Gln Ser Gly Arg Gln Pro
1               5                   10                  15

Thr Pro Leu Ser Pro Pro Leu Xaa Asn Thr His Pro Gln Ala Met Gln
            20                  25                  30

Trp Asn Ser Thr Thr Phe His Gln Thr Leu Xaa Asp Pro Arg Val Arg
        35                  40                  45

Gly Leu Tyr Phe Pro Ala Gly Gly Ser Ser Ser Gly Thr Val Asn Pro
    50                  55                  60

Val Pro Thr Ser Val Ser His Thr Ser Ser Ile Phe Ser Arg Ile Gly
65                  70                  75                  80

Xaa Pro Ala Leu Asn Met Glu Asn Ile Thr Ser Gly Phe Leu Gly Pro
```

|  |  |  |  |  |  |  | 85 |  |  |  | 90 |  |  |  | 95 |  |  |
|---|---|---|---|---|---|---|---|---|---|---|---|---|---|---|---|---|---|
| Leu | Leu | Val | Leu | Gln | Ala | Gly | Phe | Phe | Leu | Leu | Thr | Arg | Ile | Leu | Thr |
|  |  |  | 100 |  |  |  |  | 105 |  |  |  |  | 110 |  |  |
| Ile | Pro | Gln | Ser | Leu | Asp | Ser | Trp | Trp | Thr | Ser | Leu | Asn | Phe | Leu | Gly |
|  |  | 115 |  |  |  |  | 120 |  |  |  |  | 125 |  |  |  |
| Gly | Thr | Thr | Val | Cys | Leu | Gly | Gln | Asn | Ser | Gln | Phe | Pro | Thr | Ser | Asn |
|  | 130 |  |  |  |  | 135 |  |  |  |  | 140 |  |  |  |  |
| His | Ser | Pro | Thr | Ser | Cys | Pro | Pro | Thr | Xaa | Pro | Gly | Tyr | Arg | Trp | Met |
| 145 |  |  |  |  | 150 |  |  |  |  | 155 |  |  |  |  | 160 |
| Xaa | Leu | Arg | Arg | Phe | Ile | Ile | Phe | Leu | Phe | Ile | Leu | Leu | Leu | Cys | Leu |
|  |  |  | 165 |  |  |  |  | 170 |  |  |  |  | 175 |  |  |
| Ile | Phe | Leu | Leu | Val | Leu | Leu | Asp | Tyr | Gln | Gly | Met | Leu | Pro | Val | Cys |
|  |  |  | 180 |  |  |  |  | 185 |  |  |  |  | 190 |  |  |
| Pro | Leu | Xaa | Pro | Gly | Ser | Ser | Thr | Thr | Ser | Thr | Gly | Pro | Cys | Arg | Thr |
|  |  | 195 |  |  |  |  | 200 |  |  |  |  | 205 |  |  |  |
| Cys | Thr | Thr | Pro | Ala | Gln | Gly | Xaa | Ser | Met | Asn | Pro | Ser | Cys | Cys | Cys |
|  | 210 |  |  |  |  | 215 |  |  |  |  | 220 |  |  |  |  |
| Thr | Lys | Pro | Ser | Asp | Gly | Asn | Cys | Thr | Cys | Ile | Pro | Ile | Pro | Ser | Ser |
| 225 |  |  |  |  | 230 |  |  |  |  | 235 |  |  |  |  | 240 |
| Trp | Ala | Phe | Gly | Lys | Phe | Leu | Trp | Glu | Trp | Ala | Ser | Ala | Arg | Phe | Ser |
|  |  |  | 245 |  |  |  |  | 250 |  |  |  |  | 255 |  |  |
| Xaa | Leu | Ser | Leu | Leu | Val | Pro | Phe | Val | Gln | Trp | Phe | Val | Gly | Leu | Ser |
|  |  | 260 |  |  |  |  | 265 |  |  |  |  | 270 |  |  |  |
| Pro | Thr | Val | Trp | Leu | Ser | Val | Ile | Trp | Met | Met | Trp | Tyr | Trp | Gly | Pro |
|  |  | 275 |  |  |  |  | 280 |  |  |  |  | 285 |  |  |  |
| Ser | Leu | Tyr | Xaa | Ile | Leu | Ser | Pro | Phe | Leu | Pro | Leu | Leu | Pro | Ile | Phe |
|  | 290 |  |  |  |  | 295 |  |  |  |  | 300 |  |  |  |  |
| Phe | Cys | Leu | Trp | Val | Tyr | Ile |
| 305 |  |  |  |  | 310 |  |